US009192623B2

(12) United States Patent
Scott

(10) Patent No.: US 9,192,623 B2
(45) Date of Patent: *Nov. 24, 2015

(54) ARYLAMIDE COMPOUNDS AND COMPOSITIONS AND USES THEREOF

(71) Applicant: Cellceutix Corporation, Beverly, MA (US)

(72) Inventor: Richard W. Scott, Radnor, PA (US)

(73) Assignee: Cellceutix Corporation, Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/661,466

(22) Filed: Oct. 26, 2012

(65) Prior Publication Data

US 2013/0065818 A1    Mar. 14, 2013

Related U.S. Application Data

(63) Continuation of application No. 11/965,194, filed on Dec. 27, 2007, now abandoned.

(60) Provisional application No. 60/882,800, filed on Dec. 29, 2006.

(51) Int. Cl.

| | | |
|---|---|---|
| *A61K 31/74* | (2006.01) | |
| *A61K 31/506* | (2006.01) | |
| *C07D 239/02* | (2006.01) | |
| *C07D 239/24* | (2006.01) | |
| *C07D 239/28* | (2006.01) | |
| *C07D 403/14* | (2006.01) | |
| *A61K 47/06* | (2006.01) | |
| *A61K 47/18* | (2006.01) | |
| *A61K 47/38* | (2006.01) | |
| *A61K 9/00* | (2006.01) | |

(52) U.S. Cl.
CPC .............. *A61K 31/74* (2013.01); *A61K 9/0046* (2013.01); *A61K 9/0048* (2013.01); *A61K 9/0051* (2013.01); *A61K 31/506* (2013.01); *A61K 47/06* (2013.01); *A61K 47/183* (2013.01); *A61K 47/186* (2013.01); *A61K 47/38* (2013.01); *C07D 239/02* (2013.01); *C07D 239/24* (2013.01); *C07D 239/28* (2013.01); *C07D 403/14* (2013.01)

(58) Field of Classification Search
CPC ..... A61K 31/74; A61K 47/06; A61K 47/183; A61K 47/186; A61K 47/38; A61K 9/0046; A61K 9/0048; A61K 9/0051; A61K 31/506; C07D 239/02; C07D 239/24; C07D 239/28; C07D 403/14

See application file for complete search history.

(56) References Cited

U.S. PATENT DOCUMENTS

| | | | |
|---|---|---|---|
| 3,496,179 A | 2/1970 | Hans-Jurgen et al. | |
| 5,656,591 A | 8/1997 | Tomita | |
| 6,172,104 B1 | 1/2001 | Tidwell et al. | |
| 6,482,799 B1 | 11/2002 | Tuse et al. | |
| 6,835,808 B2 | 12/2004 | Quentin et al. | |
| 7,173,102 B2 | 2/2007 | DeGrado et al. | |
| 7,590,517 B2 | 9/2009 | Doerksen et al. | |
| 8,236,800 B2 * | 8/2012 | DeGrado et al. | 514/247 |
| 8,278,309 B2 * | 10/2012 | Degrado et al. | 514/256 |
| 2003/0109570 A1 | 6/2003 | Tsunoda et al. | |
| 2004/0102941 A1 | 5/2004 | Lopez et al. | |
| 2004/0185257 A1 | 9/2004 | DeGrado | |
| 2004/0202639 A1 | 10/2004 | DeGrado et al. | |
| 2004/0202687 A1 * | 10/2004 | Babu et al. | 424/401 |
| 2005/0065091 A1 | 3/2005 | Peyman | |
| 2005/0287108 A1 | 12/2005 | DeGrado et al. | |
| 2006/0024264 A1 | 2/2006 | Kuroda et al. | |
| 2006/0041023 A1 * | 2/2006 | DeGrado et al. | 514/616 |
| 2006/0041024 A1 | 2/2006 | Shaker | |
| 2006/0078626 A1 | 4/2006 | Smith | |
| 2008/0131731 A1 | 6/2008 | Igawa et al. | |
| 2008/0176807 A1 | 7/2008 | DeGrado et al. | |
| 2010/0081665 A1 | 4/2010 | Scott et al. | |
| 2010/0105703 A1 | 4/2010 | Degrado | |
| 2011/0178104 A1 | 7/2011 | Scott | |

FOREIGN PATENT DOCUMENTS

| | | |
|---|---|---|
| WO | 02/100295 | 12/2002 |
| WO | 2004/082634 A2 | 9/2004 |
| WO | 2004/082643 | 9/2004 |
| WO | 2005/072246 A2 | 8/2005 |
| WO | 2005/123660 | 12/2005 |
| WO | 2006/093813 | 9/2006 |
| WO | 2006/132647 A2 | 12/2006 |
| WO | 2008/083256 A2 | 7/2008 |
| WO | 2009/061697 | 5/2009 |

OTHER PUBLICATIONS

U.S. Appl. No. 13/563,928, filed Aug. 2012, DeGrado et al.*
U.S. Appl. No. 14/456,485, filed Aug. 2014, DeGrado et al.*
Notice of Allowance for related U.S. Appl. No. 12/605,854 dated May 1, 2012.
Non-final office action for related U.S. Appl. No. 12/605,584 dated Jan. 18, 2012.
Atherton E, "Solid Phase Peptide Synthesis: A Practical Approach," IRL Press, Oxford U.K., 1989.
Odian, G., "Principles of polymerization," John Wiley and Sons, Inc., New York, 1991.
Stevens, M. "Ploymer Chemistry," Oxford University Press, 1999.

(Continued)

*Primary Examiner* — Kara R McMillian
(74) *Attorney, Agent, or Firm* — Pepper Hamilton LLP

(57) ABSTRACT

The present invention discloses ophthalmic and otic compositions of facially amphiphilic antimicrobial polymers and oligomers and their uses, including their use in methods for treating and preventing ophthalmic infections and otic infections in humans and animals.

21 Claims, No Drawings

(56) References Cited

OTHER PUBLICATIONS

Metz et. al., "Protamine and newer heparin antagonists" in Stoetling, R. K. (ed): Pharmacology and Physiology in Anesthetic Practice. vol. 1. Philadelphia, PA, JB Lippincott, 1-15, 1994.
Wick, et al., J. Phys. Chem., 2000;104:3093-3104.
Solid-phase Synthesis: A Practical Guide, Kates, S. A., and Albericio, F., eds., Marcel Dekker, New York (2000).
T. W. Green and P.G.M. Wuts, Protective Groups in Organic Synthesis, 3rd Ed., 1999, Wiley & Sons, Inc., New York.
Maniatis, et al., Molecular Cloning—A Laboratory Manual, 2nd Ed., 1989, Cold Spring Harbor Press.
Jerry March, Advanced Organic Chemistry, 4th Ed., Wiley-Interscience.
A. R. Gennaro (editor), Remington's Pharmaceutical Sciences, Mack Publishing Co.
Yamaguchi, I., et al., Synthesis of polyurea rotaxanes using a cyclodextrin complex of a,ω-diamine, Polym. Bull., 2000;44:247-253.
Siepmann, J. I., et al., Configurational bias Monte Carlo: a new sampling scheme for flexible chains, Mol. Phys., 1992;75(1):59-70.
Ando et. al., in Kleinzeller, A. (ed): "Protamine: Molecular biology, biochemistry and biophysics" vol. 12. 1973. New York, Springer-Verlag, 1-109.
Barany G., et al. "Solid-phase peptide synthesis: a silver anniversary report," Int J Pept Protein Res. Dec. 1987;30 (6)705-39.
Brooks, B. R., et al., Charmm: A Program for Macromolecular Energy, Minimization, and Dynamics Calculations, J. Comp. Chem. 4, 187-217, 1983.
Martin, M. G., et al., Novel Configurational-Bias Monte Carlo Method for Branched Molecules. Transferable Potentials for Phase Equilibria. 2. United-Atom Description of Branched Alkanes, J. Phys. Chem. B 103, 4508-4517, 1999.
Car R., et al., "Unified approach for molecular dynamics and density-functional theory," Phys Rev Lett. Nov. 25, 1985;55(22):2471-2474.
Lee, M. K. and Lander, A. D., "Analysis of affinity and structural selectivity in the binding of proteins to glycosaminoglycans: development of a sensitive electrophoretic approach" Proc Natl Acad Sci U S A. Apr. 1, 1991;88 (7):2768-72.
Röthlisberger, U., et al., The torsional potential of perfluoro n-alkanes: A density functional study, J. Chem. Phys., 1996, 3692-3700.
Walenga et al, "Factor Xa inhibition in mediating anthrombotic actions: application of a synthetic haprin pentasaccharide," doctoral thesis. In. Paris: Universite Pierre et Marie Curie, Paris VI, Paris, France, Jun. 1987.
Hirsh J., et al., "Heparin and low-molecular-weight heparin: mechanisms of action, pharmacokinetics, dosing, monitoring, efficacy, and safety," Chest. Jan. 2001; 119 (1 Suppl): 64S-94S.
Bendetowicz AV, et al., "Pharmacokinetics and pharmacodynamics of a low molecular weight heparin (enoxaparin) after subcutaneous injection, comparison with unfractionated heparin—a three way cross over study in human volunteers," Thromb Haemost. Mar. 1994;71(3):305-13.
Morabia A., "Heparin doses and major bleeding," Lancet. May 31, 1986;1(8492):1278-9.
Mureebe L., et al., "Heparin-induced thrombocytopenia: pathophysiology and management," Vasc Endovascular Surg. May-Jun. 2002;36(3):163-70.
Lubenow N., et al., "Heparin-induced thrombocytopenia: temporal pattern of thrombocytopenia in relation to initial use or reexposure to heparin," Chest. Jul. 2002; 122(1): 37-42.
Hirsh J., et al., "Low Molecular Weight Heparin," Blood. Jan. 1, 1992; 79(1): 1-17.
Ofosu Fa., et al., "Mechanisms of Action of Low Molecular Weight Haparins and Heparinoids," Baillieres Clin Haematol. Jul. 1990; 3(3): 505-29.
Hirsh J., et al., "Heparin and low-molecular-weight heparin: the Seventh ACCP Conference on Antithrombotic and Thrombolytic Therapy," Chest. Sep. 2004; 126 (3 Suppl): 188S-203S.
Becker RC., "New thrombolytics, anticoagulants, and platelet antagonists: the future of clinical practice," J Thromb Thrombolysis. Apr. 1999; 7(2): 195-220.
Antman EM, et al., "Enoxaparin prevents death and cardiac ischemic events in unstable angina/non-Q-wave myocardial infarction. Results of the thrombolysis in myocardial infarction (TIMI) 11B trial, " Circulation. Oct. 12, 1999;100(15):1593-601.
Cohen M., et al., "A comparison of low-molecular-weight heparin with unfractionated heparin for unstable coronary artery disease. Efficacy and Safety of Subcutaneous Enoxaparin in Non-Q-Wave Coronary Events Study Group," N Engl J Med. Aug. 14, 1997;337(7):447-52.
Lee AY, et al., "Randomized comparison of low molecular weight heparin and coumarin derivatives on the survival of patients with cancer and venous thromboembolism," J Clin Oncol. Apr. 1, 2005;23(10):2123-9.
Walenga JM, et al., "Short- and long-acting synthetic pentasaccharides as antithrombotic agents," Expert Opin Investig Drugs. Jul. 2005; 14(7):847-58.
Mehta SR, et al, "Efficacy and safety of fondaparinux versus enoxaparin in patients with acute coronary syndromes undergoing percutaneous coronary intervention: results from the OASIS-5 trial," J Am Coll Cardiol. Oct. 30, 2007,50(18):1742-51. Epub Oct. 15, 2007.
Hubbard AR, et al., "Neutralisation of heparan sulphate and low molecular weight heparin by protamine," Thromb Haemost. Feb. 18, 1985;53(1):86-9.
Poon MC, et al., "Platelet factor four and protamine sulfate neutralization of heparin fractionated according to anionic charge density," Thromb Haemost. Apr. 30, 1982;47(2):162-5.
Massonnet-Castel S., et al. "Partial reversal of low molecular weight heparin (PK 10169) anti-Xa activity by protamine sulfate: in vitro and in vivo study during cardiac surgery with extracorporeal circulation," Haemostasis. 1986;16(2):139-46.
Doutremepuich C., et al. "In vivo neutralization of low-molecular weight heparin fraction CY 216 by protamine," Semin Thromb Hemost. Jul. 1985;11(3):318-22.
Weiler JM, et al. "Serious adverse reactions to protamine sulfate: are alternatives needed?" J Allergy Clin Immunol. Feb. 1985;75(2):297-303.
Horrow JC., "Protamine: a review of its toxicity," Anesth Analg. Mar. 1985;64(3):348-61.
Porsche R., et al. "Allergy to protamine sulfate," Heart Lung. Nov.-Dec. 1999; 28(6):418-28.
Vlugt, T. J. H., et al., Improving the efficiency of the configurational-bias Monte Carlo algorithm, Mol. Phys., 1998, 94, 727-733.
Guillemot, D. et al, Low Dosage and Long Treatment Duration of Beta-Lactam, JAMA, Feb. 4, 1998; 279 (5):365-370.
Arnt, L, et al., Rapid Communication: Nonhemolytic Abiogenic Polymers as Antimicrobial Peptide Mimics, Journal of Polymer Science, Part A: Polymer Chemistry, 2004; 42:3860-3864.
Tew, G. N., et al., De novo design of biomimetic antimicrobial polymers, PNAS, Apr. 16, 2002; 99(8):5110-5114.
Montecolvo, M. A., et al., Outbreak of Vancomycin-, Ampicillin-, and Aminoglycosid-Resistant Enterococcus faecium Bacteremia in an Adult Oncology Unit, Antimicrobial Agents and Chemotherapy, Jun. 1994; 38(6):1363-1367.
Lathers, C.M., Clinical pharmacology of antimicrobial use in humans and animals, The Journal of Clinical Pharmacology, 2002; 42:587-600.
Monroe, S., et al., Antimicrobial use and bacterial resistance, Curr Opin Microbiol, Oct. 2000; 3(5):496-501.
Liu, et al., Angew Chem Int Ed Engl, 2004;43:1158-1162.
Vippagunta et al., "Crystalline solids," Advanced Drug Delivery Reviews (2001) 48:3-26.
West "Solid State Chemistry and its Application," Wiley, New York, 1988, pp. 358 and 365.
Tang et al., Biomimetic facially amphilphilic antibacterial oligomers with conformationally stiff backbones, Chemistry & Biology 2006, 13:427-435.

* cited by examiner

ARYLAMIDE COMPOUNDS AND COMPOSITIONS AND USES THEREOF

FIELD OF THE INVENTION

The present invention relates to antimicrobial compositions of facially amphiphilic antimicrobial polymers and oligomers useful for the treatment or prevention of ophthalmic and otic infections. The present invention also relates to methods of using the compositions for treating and/or preventing ophthalmic and otic infections.

BACKGROUND OF THE INVENTION

Bacterial drug resistance is a significant current health problem throughout the world. Multiple drug resistance is being commonly seen in a number of human pathogens (see, e.g., Hiramatsu et al., J. Antimicrob. Chemother., 1998, 40, 311-313 and Montecalvo et al., Antimicro. Agents Chemother., 1994, 38, 1363-1367, and the incidence of drug-resistant hospital infections is growing at a rapid rate. For example, in some U.S. hospitals, nosocomial pathogens, such as E. faecium and Acinetobacter species, have acquired multiple resistance determinants and are virtually untreatable with current antimicrobial agents. Bacterial resistance has now reached epidemic proportions and has been attributed to a variety of abuses of antibiotic treatments, including overuse (Monroe et al., Curr. Opin. Microbiol., 2000, 3, 496-501), inappropriate dosing at sub-therapeutic levels (Guillemot et al., JAMA, 1998, 279, 365-370), and misuse as antimicrobial growth promoters in animal food (Lathers, J. Clin. Pharmacol., 2002, 42, 587-600). Moreover, the threat of bio-terrorism has provided a further impetus to develop novel classes of antibiotics, particularly ones against which it will be difficult to develop resistant bacterial strains.

The pharmaceutical scientific community is responding to this challenge by focusing on the development of new antibiotic drugs. Much of this work, however, is directed to synthesizing analogs of known drugs, such as cephalosporins and quinolones, that, while potentially useful for a short time, will inevitably also encounter bacterial drug resistance and become ineffective. Thus, therapeutically effective antimicrobial drugs that act by novel mechanisms would provide an economic as well as a human health benefit.

A series of nonpeptidic mimics of the natural antimicrobial peptides have been developed that are polymers, oligomers and small molecules comprised of non-natural building blocks. See, Tew et al., Proc. Natl. Acad. Sci. U.S.A., 2002, 99, 5110-5116; Arnt et al., J. Polym. Sci., Part A, 2004, 42, 3860-3864; and Liu et al., Angew Chem. Int. Ed. Engl., 2004, 43, 1158-1162. Many of these compounds are significantly smaller and easier to prepare than the natural antimicrobial peptides and peptidic mimetics, with the shortest of these oligomers having molecular weights typical of small molecule drugs. They have the same mechanism of action as magainin, are highly potent and have a broad spectrum of activity, killing gram-positive, gram-negative and antibiotic-resistant pathogens. Relative to the antimicrobial peptides, the non-peptidic mimetics are significantly less toxic towards human erythrocytes, much less expensive to prepare, and more stable.

See, for example, U.S. Published Patent Appl. Nos. US 2006-0041023 A1, US 2004-0202639 A1, US 2005-0287108 A1, and US 2006-0024264 A1, and U.S. Pat. No. 7,173,102.

There is a great need for improved compositions and methods of treatment based on the use of antimicrobials that are more effective than existing agents against key ophthalmic and otic pathogens, and less prone to the development of resistance by those pathogens. In particular, there is a great need for effective compositions and methods for the treatment of otic infections, especially bacterial infections. The use of oral antibacterials to treat otic infections in children has limited efficacy and creates a serious risk of pathogen resistance to the orally administered antibacterial agent.

Thus, a need remains for improved ophthalmic and otic antimicrobial compositions, in particular, for broad-spectrum antimicrobial agents useful for the treatment of ophthalmic and otic infections that are not prone to the development of resistance by ophthalmic and/or otic pathogens and that are effective in the treatment of ophthalmic and otic pathogens that have already developed resistance to existing antimicrobial agents.

SUMMARY OF THE INVENTION

The present invention provides compositions of antimicrobial, amphiphilic polymers and oligomers or Formulae I, II, IV, V, and VI,

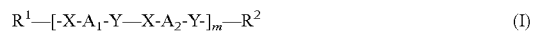
$$R^1\text{—}[\text{-}X\text{-}A_1\text{-}Y\text{—}X\text{-}A_2\text{-}Y\text{-}]_m\text{—}R^2 \quad (I)$$

$$R^1\text{—}[\text{-}X\text{-}A_1\text{-}X\text{—}Y\text{-}A_2\text{-}Y\text{-}]_m\text{—}R^2 \quad (II)$$

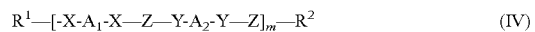
$$R^1\text{—}[\text{-}X\text{-}A_1\text{-}X\text{—}Z\text{—}Y\text{-}A_2\text{-}Y\text{—}Z]_m\text{—}R^2 \quad (IV)$$

$$R^1[\text{-}A_1\text{-}W\text{-}A_2\text{-}W\text{-}]_m\text{—}R^2 \quad (V)$$

$$A\text{-}(B)_{n1}\text{-}(D)_{m1}\text{-}H \quad (VI)$$

or acceptable salts or solvates thereof, wherein $R^1$, $R^2$, $A_1$, $A_2$, A, B, D, X, Y, Z, W, m, m1, and n1 are as defined below, including antimicrobial compositions that can be administered for the treatment or prevention of ophthalmic and otic infections in humans or animals.

The amphiphilic polymers and oligomers useful in the present invention include, but are not limited to, polyamide and polyester compounds of Formulae I and II wherein X is O, $NR^3$, or S, Y is C=O, C=S, or $SO_2$, and $A_1$ and $A_2$ are aromatic, heteroaromatic, or aliphatic moieties appropriately substituted with one or more polar and/or nonpolar groups; polyurea, polycarbamate, and polycarbonate compounds of Formula IV wherein X and Y are O, $NR^3$, or S, Z is C=O, C=S, or $SO_2$, and $A_1$ and $A_2$ are aromatic, heteroaromatic, or aliphatic moieties appropriately substituted with one or more polar and/or nonpolar groups. Also useful in the present invention are amphiphilic polyaryl and polyarylalkynyl polymers and oligomers of Formula V wherein W is —$CH_2$—, —$CH_2$—$CH_2$—, —CH=CH—, or —C≡C—, and $A_1$ and $A_2$ are aromatic or heteroaromatic moieties appropriately substituted with one or more polar and/or nonpolar groups; and random methacrylate copolymers of Formula VI wherein $R^1$ and $R^2$ are end groups appropriate for the specific polymer or oligomer and are as defined below.

Thus, the present invention is directed to an ophthalmic composition, comprising an effective amount of an antimicrobial polymer or oligomer of Formula I as disclosed herein, or an acceptable salt or solvate thereof, and an ophthalmically acceptable excipient.

The present invention is also directed to an ophthalmic composition, comprising an effective amount of an antimicrobial polymer or oligomer of Formula II as disclosed herein, or an acceptable salt or solvate thereof, and an ophthalmically acceptable excipient. In some embodiments, the antimicrobial oligomer of Formula II has Formula IIa as disclosed herein.

The present invention is further directed to an ophthalmic composition, comprising an effective amount of an antimicrobial polymer or oligomer of Formula IV as disclosed herein, or an acceptable salt or solvate thereof, and an ophthalmically acceptable excipient. In some embodiments, the antimicrobial oligomer of Formula IV has Formula IVa, Formula IVb, or Formula IVc as disclosed herein.

The present invention is also directed to an ophthalmic composition, comprising an effective amount of an antimicrobial polymer or oligomer of Formula V as disclosed herein, or an acceptable salt or solvate thereof, and an ophthalmically acceptable excipient. In some embodiments, the antimicrobial oligomer of Formula V has Formula Va as disclosed herein.

The present invention is further directed to an ophthalmic composition, comprising an effective amount of an antimicrobial random polymer or oligomer of Formula VI as disclosed herein, or an acceptable salt or solvate thereof, and an ophthalmically acceptable excipient.

The present invention is also directed to an antimicrobial ophthalmic composition, the composition comprising a) an antimicrobial oligomer of Formula I, Formula II, Formula IIa, Formula IV, Formula IVa, Formula IVb, Formula IVc, Formula V, Formula Va, or Formula VI as disclosed herein, or a pharmaceutically acceptable salt or solvate thereof, in an amount effective for treatment and/or prophylaxis of a microbial infection of an eye of an animal; and b) an ophthalmically acceptable excipient, wherein the composition is suitable for administration to one or more tissues of the eye.

The present invention is also directed to an ophthalmic composition for use in treatment or prevention of a microbial infection in an eye of an animal, wherein the improvement comprises employing an antimicrobial oligomer of Formula I, Formula II, Formula IIa, Formula IV, Formula IVa, Formula IVb, Formula IVc, Formula V, Formula Va, or Formula VI as disclosed herein, or an acceptable salt or solvate thereof, in the composition in an amount effective to treat or prevent the infection when the composition is administered to one or more tissues of the eye.

The present invention is also directed to any of the ophthalmic compositions disclosed herein, wherein the composition is suitable for topical administration to one or more tissues of an eye of an animal.

The present invention is also directed to any of the ophthalmic compositions disclosed herein, wherein the composition is in a form selected from the group consisting of a solution, a suspension, an emulsion, a gel, an ointment, and a solid article suitable for ocular implant.

The present invention is also directed to any of the ophthalmic compositions disclosed herein, wherein the oligomer is present in the composition at a concentration of from about 0.01% to about 20% by weight.

The present invention is also directed to any of the ophthalmic compositions disclosed herein, wherein the ophthalmically acceptable excipient is selected from a preservative, a stabilizer, an antioxidant, an anti-inflammatory agent, a viscosity-enhancing agent, and an agent to prolong residence time of the oligomer in ocular tissue, or any combination thereof.

The present invention is also directed to use of the compounds and compositions of the invention in the preparation of a medicament for treating or preventing ophthalmic and/or otic infections in a human or animal.

In some embodiments of the ophthalmic compositions of the present invention, the preservative is selected from a phenylmercuric salt, thimerosal, stabilized chlorine dioxide, a quaternary ammonium compound, imidazolidinyl urea, a paraben, phenoxyethanol, chlorophenoxyethanol, phenoxypropanol, chlorobutanol, chlorocresol, phenylethyl alcohol, and sorbic acid and its salts, or any combination thereof.

In some embodiments, the antioxidant is selected from ascorbic acid, sodium metabisulfite, sodium bisulfite, and acetylcysteine.

In some embodiments, the stabilizer is a chelating agent, such as, for example, disodium EDTA.

In some embodiments, the viscosity-enhancing agent is selected from methylcellulose, hydroxypropylmethyl cellulose, polyvinyl alcohol, and glycerol.

In some embodiments, the ophthalmic composition further comprises an additional ophthalmically acceptable excipient. The additional ophthalmically acceptable excipient is selected from a buffering agent, a solubilizing agent, a surfactant, a lubricating agent, and an ophthalmically acceptable salt, or any combination thereof.

In some embodiments, the ophthalmic composition further comprises an additional medicament. The additional medicament is selected from an anti-inflammatory agent, an antimicrobial agent, an anesthetic agent, and an anti-allergic agent.

The present invention is further directed to a method of treating or preventing a microbial infection in an eye of an animal, comprising administering to an eye of an animal in need of the treating or preventing an effective amount of an ophthalmic composition of the present invention.

The present invention is also directed to a method for treating or preventing a microbial infection in an eye of an animal by administering to one or more tissues of the eye an antimicrobial ophthalmic composition, wherein the composition comprises an antimicrobial oligomer of Formula I, Formula II, Formula IIa, Formula IV, Formula IVa, Formula IVb, Formula IVc, Formula V, Formula Va, or Formula VI, as disclosed herein, in an amount effective to treat or prevent the infection.

In some embodiments of the methods of the present invention, the antimicrobial ophthalmic composition is administered topically to one or more tissues of the eye of the animal.

In some embodiments of the methods present invention, the ophthalmic composition is in a form selected from a solution, a suspension, an emulsion, a gel, an ointment, and a solid article suitable for ocular implant. In other embodiments, the ophthalmic composition is administered 2 to 4 times daily. In yet other embodiments, the oligomer in the ophthalmic composition is present in the composition at a concentration of about 0.01% to about 20% by weight.

In some embodiments of the methods of the present invention, the microbial ophthalmic infection is a bacterial infection. For example, in some embodiments, the bacterial infection is caused by *Staphylococcus, Streptococcus, Enterococcus, Bacillus, Corynebacterium, Moraxella, Haemophilus, Serratia, Pseudomonas,* or *Neisseria* spp. In other embodiments, the microbial infection is a fungal infection. For example, in some embodiments, the fungal infection is caused by *Aspergillus* or *Fusarium* spp. In yet other embodiments, the microbial infection is a viral infection. For example, in some embodiments, the viral infection is caused by a herpes virus. In some embodiments of the methods of the present invention, the ophthalmic infection is selected from bacterial keratitis, bacterial conjunctivitis, and corneal ulcers.

The present invention is also directed to an otic composition, comprising an effective amount of an antimicrobial oligomer or polymer of Formula I, Formula II, Formula IV, Formula V, or Formula VI, or an acceptable salt or solvate thereof, and an otically acceptable excipient.

The present invention is also directed to an antimicrobial otic composition, the composition comprising a) an antimicrobial oligomer of Formula I, Formula II, Formula IIa, Formula IV, Formula IVa, Formula IVb, Formula IVc, Formula V, Formula Va, or Formula VI, or a pharmaceutically acceptable salt or solvate thereof, in an amount effective for treatment and/or prophylaxis of a microbial infection of an ear of an animal; and b) an otically acceptable excipient, wherein the composition is suitable for administration to one or more tissues of the ear.

The present invention is also directed to an otic composition for use in treatment or prevention of a microbial infection in an ear of an animal, wherein the composition comprises an antimicrobial oligomer of Formula I, Formula II, Formula IIa, Formula IV, Formula IVa, Formula IVb, Formula IVc, Formula V, Formula Va, or Formula VI as disclosed herein, or an acceptable salt or solvate thereof, in an amount effective to treat or prevent the infection when the composition is administered to one or more tissues of the ear.

The present invention is also directed to any of the otic compositions disclosed herein, wherein the composition is suitable for topical administration to one or more tissues of an ear of an animal.

The present invention is also directed to any of the otic compositions disclosed herein, wherein the composition is in a form selected from a solution, a suspension, an emulsion, a gel, an ointment, and a solid article suitable for otic implant.

The present invention is also directed to any of the otic compositions disclosed herein, wherein the polymer or oligomer is present in the otic composition at a concentration of about 0.01% to about 20% by weight.

The present invention is also directed to any of the otic compositions disclosed herein, wherein the otically acceptable excipient is selected from a preservative, a stabilizer, an antioxidant, and a viscosity-enhancing agent, or any combination thereof.

In some embodiments of the otic compositions, the preservative is selected from a phenylmercuric salt, thimerosal, stabilized chlorine dioxide, a quaternary ammonium compound, imidazolidinyl urea, paraben, phenoxyethanol, chlorophenoxyethanol, phenoxypropanol, chlorobutanol, chlorocresol, phenylethyl alcohol, and sorbic acid and its salts, or any combination thereof.

In some embodiments, the antioxidant is selected from ascorbic acid, sodium metabisulfite, sodium bisulfite, and acetylcysteine.

In some embodiments, the stabilizer is a chelating agent, such as, for example, disodium EDTA.

In some embodiments, the viscosity-enhancing agent is selected from methylcellulose, hydroxypropylmethyl cellulose, polyvinyl alcohol, and glycerol.

In some embodiments, the otic composition further comprises an additional otically acceptable excipient. The additional otically acceptable excipient is selected from a buffering agent, a solubilizing agent, a surfactant, a lubricating agent, and an ophthalmically acceptable salt, or any combination thereof.

In some embodiments, the otic composition further comprises an additional medicament. The additional medicament is selected from an anti-inflammatory agent, an antimicrobial agent, an anesthetic agent, and an anti-allergic agent.

The present invention is further directed to a method of treating or preventing a microbial infection in an ear of an animal, the method comprising administering to an ear of an animal in need of the treating or preventing an effective amount of an otic composition of the present invention.

The present invention is also directed to a method for treating or preventing a microbial infection in an ear of an animal by administering to one or more tissues of the ear an antimicrobial otic composition, wherein the composition comprises an antimicrobial oligomer of Formula I, Formula II, Formula IIa, Formula IV, Formula IVa, Formula IVb, Formula IVc, Formula V, Formula Va, or Formula VI, as disclosed herein, in an amount effective to treat or prevent the infection.

In some embodiments of the methods of the present invention, the antimicrobial otic composition is administered topically to one or more tissues of the ear of the animal.

In some embodiments of the methods of the present invention, the otic composition is in a form selected from a solution, a suspension, an emulsion, a gel, an ointment, and a solid article suitable for otic implant. In other embodiments, the otic composition is administered 2 to 4 times daily. In yet other embodiments, the polymer or oligomer is present in the otic composition at a concentration of about 0.01% to about 20% by weight.

In some embodiments of the methods of the present invention, the microbial otic infection is a bacterial infection. In other embodiments, the infection is a fungal infection. In yet other embodiments, the infection is a viral infection.

In some embodiments of the methods of the present invention, the otic infection is selected from otitis externa and otitis media.

In particular, the present embodiments include, for example:

1) An ophthalmic composition, comprising an effective amount of an antimicrobial oligomer of Formula I:

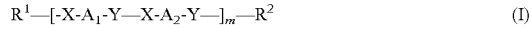

$$R^1\text{—}[-X-A_1-Y\text{—}X-A_2-Y\text{—}]_m\text{—}R^2 \quad\quad (I)$$

or an acceptable salt or solvate thereof,
wherein:
  X is $NR^8$, $-N(R^8)N(R^8)-$, O, or S;
  Y is $C=O$, $C=S$, $O=S=O$, or $-C(=O)C(=O)-$;
  $R^8$ is hydrogen or alkyl;
  $A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or
  $A_1$ is optionally substituted arylene or optionally substituted heteroarylene and $A_2$ is a $C_3$ to $C_8$ cycloalkyl or $-(CH_2)_q-$, wherein q is 1 to 7, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or
  $A_2$ is optionally substituted arylene or optionally substituted heteroarylene, and $A_1$ is a $C_3$ to $C_8$ cycloalkyl or $-(CH_2)_q-$, wherein q is 1 to 7, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);
  $R^1$ is
    (i) hydrogen, a polar (PL) group, or a non-polar (NPL) group, and $R^2$ is $-X-A_1-Y-R^{11}$, wherein $R^{11}$ is hydrogen, a polar (PL) group, or a non-polar (NPL) group; or
    (ii) $R^1$ and $R^2$ are, independently, hydrogen, a polar (PL) group, or a non-polar (NPL) group; or
    (iii) $R^1$ and $R^2$ together are a single bond;
  NPL is a nonpolar group independently selected from $-B(OR^4)_2$ and $-(NR^{3'})_{q1NPL}-U^{NPL}-(CH_2)_{pNPL}-(NR^{3''})_{q2NPL}-R^{4'}$, wherein:
    $R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are, independently, 0, 1, or 2; and m is 1 to about 20; and an ophthalmically acceptable excipient.

2) The composition of 1), wherein:

X is NR$^8$;

Y is C=O;

R$^8$ is hydrogen;

$A_1$ is optionally substituted o-, m-, or p-phenylene and $A_2$ is —(CH$_2$)$_q$—, wherein q is 1, and wherein one of $A_1$ and $A_2$ is substituted with one or two polar (PL) group(s), and the other of $A_1$ and $A_2$ is substituted with one or two non-polar (NPL) group(s); or $A_2$ is optionally substituted o-, m-, or p-phenylene and $A_1$ is —(CH$_2$)$_q$—, wherein q is 1, and wherein one of $A_1$ and $A_2$ is substituted with one or two polar (PL) group(s), and the other of $A_1$ and $A_2$ is substituted with one or two non-polar (NPL) group(s);

$R^1$ and $R^2$ are, independently, hydrogen, a polar (PL) group, or a non-polar (NPL) group;

NPL is —(NR$^3$)$_{q1NPL}$—U$^{NPL}$—(CH$_2$)$_{pNPL}$—(NR$^{3''}$)$_{q2NPL}$—R$^{4'}$, wherein:

$R^{4'}$ is selected from C$_1$-C$_{10}$ alkyl, C$_3$-C$_{18}$ branched alkyl, C$_2$-C$_{10}$ alkenyl, C$_2$-C$_{10}$ alkynyl, and C$_6$-C$_{10}$ aryl, any of which is optionally substituted with one or more alkyl or halo groups;

$U^{NPL}$ is absent or selected from NH, —C(=O)—, O, and S;

the —(CH$_2$)$_{pNPL}$— alkylene chain is optionally substituted with one or more amino groups;

pNPL is 0 to 8;

q1NPL and q2NPL are 0;

PL is —(NR$^{5'}$)$_{q1PL}$—U$^{PL}$—(CH$_2$)$_{pPL}$—(NR$^{5'}$)$_{q2PL}$—V, wherein:

$U^{PL}$ is absent or selected from O, S, NH, and —C(=O);

V is selected from amino, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidino;

the —(CH$_2$)$_{pPL}$— alkylene chain is optionally substituted with one or more amino groups;

pPL is 0 to 8;

q1PL and q2PL are 0; and m is 4 or 5.

3) An ophthalmic composition, comprising an effective amount of an antimicrobial oligomer of Formula II:

$$R^1—[-X-A_1-X—Y-A_2-Y-]_m—R^2 \qquad (II)$$

or an acceptable salt or solvate thereof, wherein:

X is NR$^8$, O, S, —N(R$^8$)N(R$^8$)—, —N(R$^8$)—(N=N)—, —(N=N)—N(R$^8$)—, —C(R$^7$R$^{7'}$)NR$^8$—, —C(R$^7$R$^{7'}$)O—, or —C(R$^7$R$^{7'}$)S—;

Y is C=O, C=S, O=S=O, —C(=O)C(=O)—, C(R$^6$R$^{6'}$)C=O, or C(R$^6$R$^{6'}$)C=S;

$R^8$ is hydrogen or alkyl;

$R^7$ and $R^{7'}$ are, independently, hydrogen or alkyl, or $R^7$ and $R^{7'}$ together are —(CH$_2$)$_p$—, wherein p is 4 to 8;

$R^6$ and $R^{6'}$ are, independently, hydrogen or alkyl, or $R^6$ and $R^{6'}$ together are (CH$_2$)$_2$NR$^{12}$(CH$_2$)$_2$, wherein R$^{12}$ is hydrogen, —C(=N)CH$_3$ or C(=NH)—NH$_2$;

$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);

$R^1$ is (i) hydrogen, a polar group (PL), or a non-polar group (NPL), and R$^2$ is —X-A$_1$-X—R$^1$, wherein A$_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and R$^2$ is —X-A'-X—R$^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s);

(iii) —Y-A$_2$-Y—R$^2$, and R$^2$ is hydrogen, a polar group (PL), or a non-polar group (NPL); or (iv) —Y-A' and R$^2$ is —X-A', wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (v) $R^1$ and $R^2$ are, independently, a polar group (PL) or a non-polar group (NPL); or (vi) $R^1$ and $R^2$ together form a single bond;

NPL is a nonpolar group independently selected from —B(OR$^4$)$_2$ and —(NR$^3$)$_{q1NPL}$—U$^{NPL}$—(CH$_2$)$_{pNPL}$—(NR$^{3''}$)$_{q2NPL}$—R$^{4'}$, wherein:

$R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more alkyl, amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5'}$)—V wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are, independently, 0, 1, or 2; and m is 1 to about 20, and an ophthalmically acceptable excipient.

4) The composition of 1) or 2), wherein the oligomer has Formula IIa:

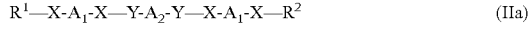

$$R^1\text{—}X\text{-}A_1\text{-}X\text{—}Y\text{-}A_2\text{-}Y\text{—}X\text{-}A_1\text{-}X\text{—}R^2 \quad \text{(IIa)}$$

or an acceptable salt or solvate thereof, wherein:

X is NR$^8$, O, S, or —N(R$^8$)N(R$^8$)—;

Y is C=O, C=S, or O=S=O;

$R^8$ is hydrogen or alkyl;

$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);

$R^1$ is a polar group (PL) or a non-polar group (NPL);

$R^2$ is $R^1$;

NPL is a nonpolar group —(NR$^{3'}$)$_{q1NPL}$—U$^{NPL}$—(CH$_2$)$_{pNPL}$—(NR$^{3''}$)$_{q2NPL}$—R$^{4'}$, wherein:

$R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more alkyl, amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5'}$)$_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are, independently, 0, 1, or 2.

5) The composition of any one of 1), 2), and 4), wherein:

X is NR$^8$;

Y is C=O;

$R^8$ is hydrogen or (C$_1$-C$_4$)alkyl;

$A_1$ and $A_2$ are, independently, optionally substituted phenylene or optionally substituted pyrimidinylene, wherein $A_1$ is substituted with one or more polar (PL) group(s) and one or more non-polar (NPL) group(s), and $A_2$ is substituted with one or more polar (PL) group(s) or is unsubstituted;

$R^1$ is a polar group (PL);

$R^2$ is $R^1$;

NPL is a nonpolar group —(NR$^{3'}$)$_{q1NPL}$—U$^{NPL}$—(CH$_2$)$_{pNPL}$—(NR$^{3''}$)$_{q2NPL}$—R$^{4'}$, wherein:

$R^4$ and $R^{4'}$ are, independently, selected from hydrogen and alkyl optionally substituted with one or more alkyl or halo groups;

$U^{NPL}$ is absent or selected from O, S, NR$^3$, and —C(=O)—;

pNPL is 0 to 6;

q1NPL and q2NPL are 0;

PL is a polar group —(NR$^{5'}$)$_{q1PL}$—U$^{PL}$—(CH$_2$)$_{pPL}$—(NR$^{5'}$)$_{q2PL}$—V, wherein:
U$^{PL}$ is absent or selected from O, S, NR$^5$, and —C(=O)—;
V is selected from amino, alkylamino, dialkylamino, —NH(CH$_2$)$_p$NH$_2$ wherein p is 1 to 4, —N(CH$_2$CH$_2$NH$_2$)$_2$, diazamino, amidino, and guanidino, any of which is optionally substituted with one or more of amino, halo, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, and lower acylamino;
pPL is 0 to 8; and
q1PL and q2PL are 0.
6) The composition of any one of 1), 2), 4), and 5), wherein:
A$_1$ is phenylene substituted with one (PL) group and one non-polar (NPL) group;
A$_2$ is unsubstituted pyrimidinylene or pyrimidinylene substituted with one or two polar (PL) group(s);
NPL is R$^{4'}$, wherein R$^{4'}$ is (C$_1$-C$_6$)alkyl optionally substituted with one or more halo groups;
PL is —U$^{PL}$—(CH$_2$)$_{pPL}$—V, wherein:
U$^{PL}$ is O or S;
V is selected from amino, amidino, and guanidino; and
pPL is 0 to 6.
7) The composition of any one of 1), 2), 4), and 5), wherein:
A$_1$ is phenylene substituted with one (PL) group and one non-polar (NPL) group;
A$_2$ is unsubstituted phenylene or phenylene substituted with one or two polar (PL) group(s);
NPL is R$^{4'}$, wherein R$^{4'}$ is (C$_1$-C$_6$)alkyl optionally substituted with one or more halo groups;
PL is —U$^{PL}$—(CH$_2$)$_{pPL}$—V, wherein:
U$^{PL}$ is O or S;
V is selected from amino, amidino, and guanidino; and
pPL is 0 to 6.
8) The composition of any one of 1), 2), 4), 5), and 6), wherein the oligomer is

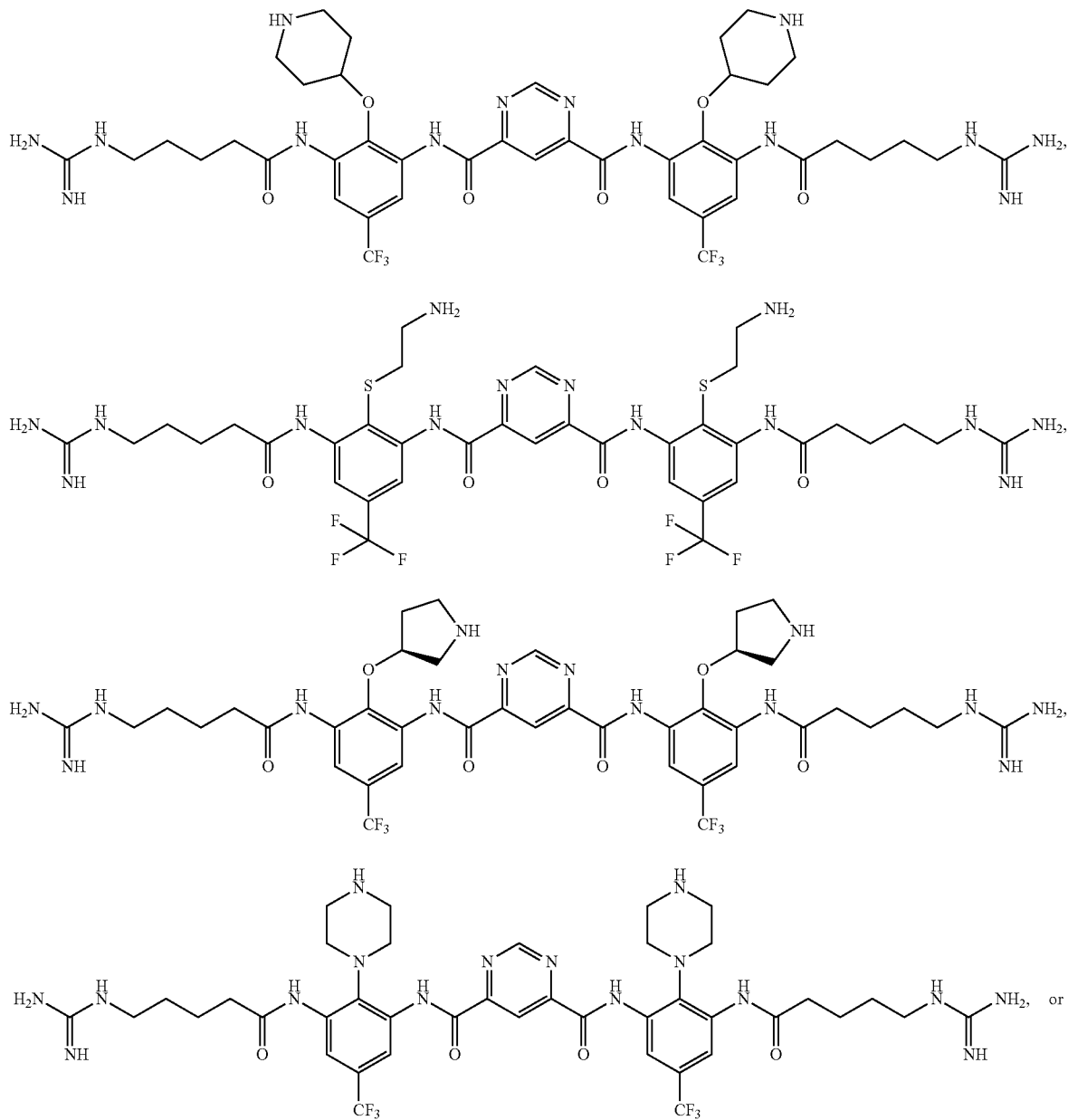

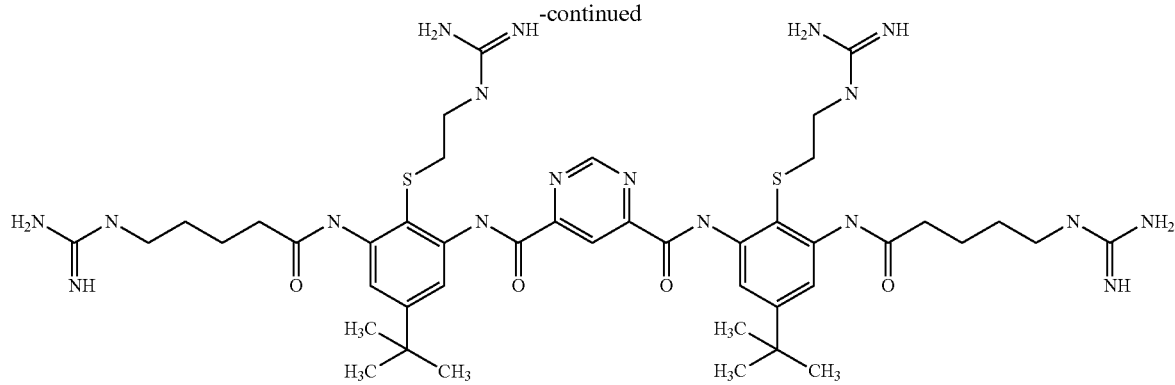
or a salt or solvate thereof
9) The composition of any one of 1), 2), and 4), wherein the oligomer is
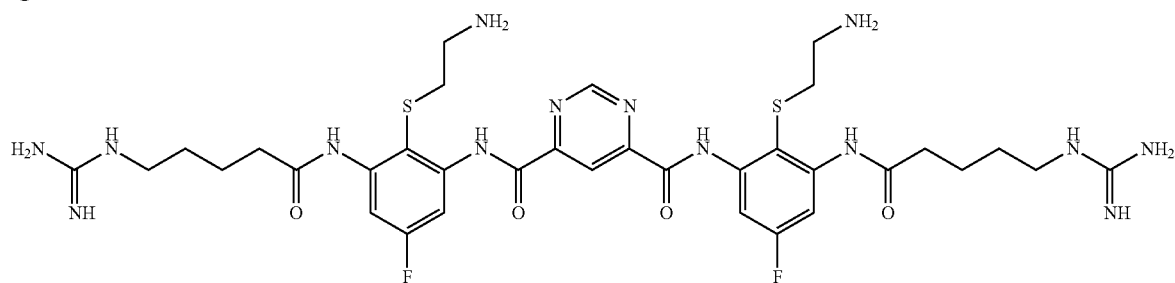
or a salt or solvate thereof
10) The composition of any one of 1), 2), 4), 5), 6), and 8), wherein the oligomer is
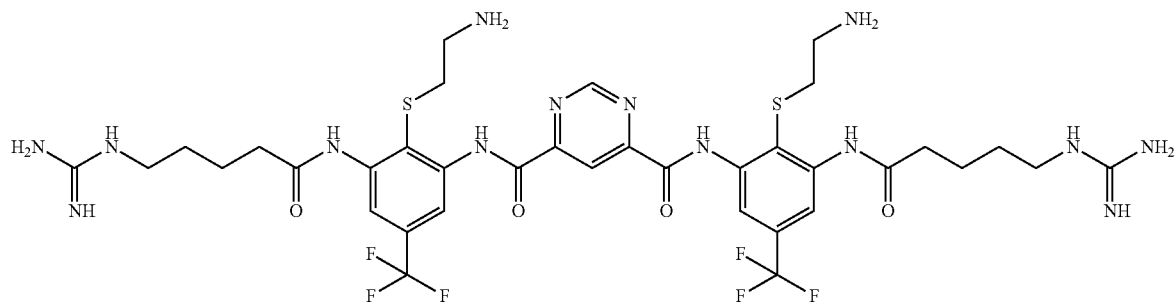 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN]
or a salt or solvate thereof
11) The composition of any one of 1), 2), 4), 5), 6), and 8), wherein the oligomer is
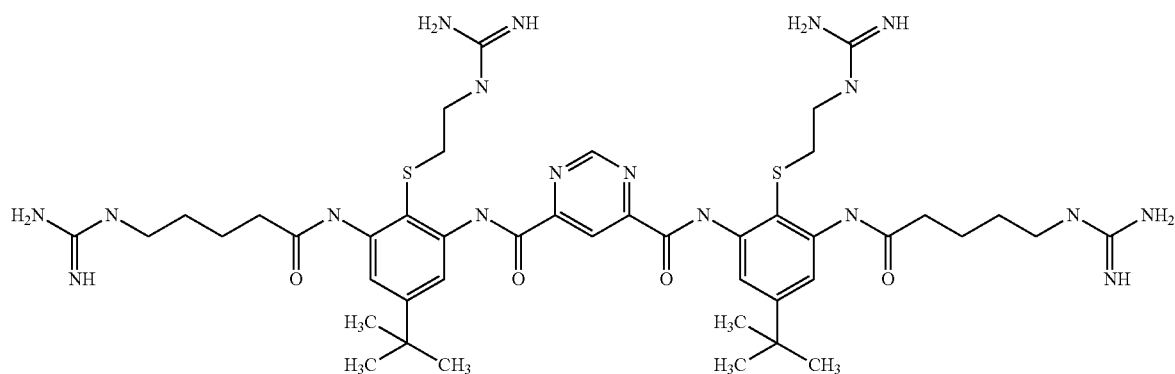 [SMILES: CC(C)(C)c1cc(NC(=O)CCCCNC(=N)N)c(SCCNC(=N)N)c(NC(=O)c2cc(C(=O)Nc3cc(C(C)(C)C)cc(NC(=O)CCCCNC(=N)N)c3SCCNC(=N)N)ncn2)c1]
or a salt or solvate thereof 12) The composition of any one of 1), 2), 4), 5), 6), and 8), wherein the oligomer is
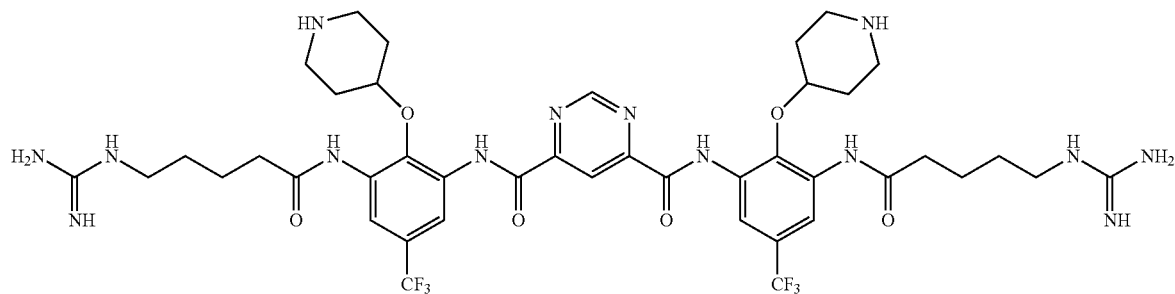 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNCC3)ncn2)c1OC1CCNCC1]
or a salt or solvate thereof
13) The composition of any one of 1), 2), 4), 5), 6), and 8), wherein the oligomer is
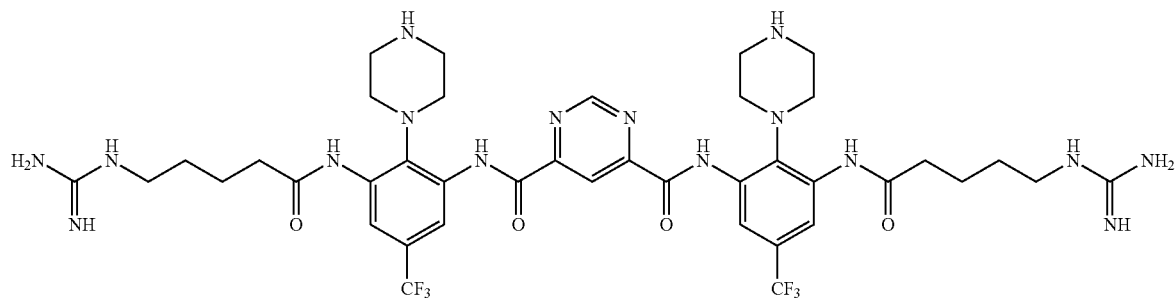 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3N3CCNCC3)ncn2)c1N1CCNCC1]
or a salt or solvate thereof
14) The composition of any one of 1), 2), 4), 5), 6), and 8), wherein the oligomer is
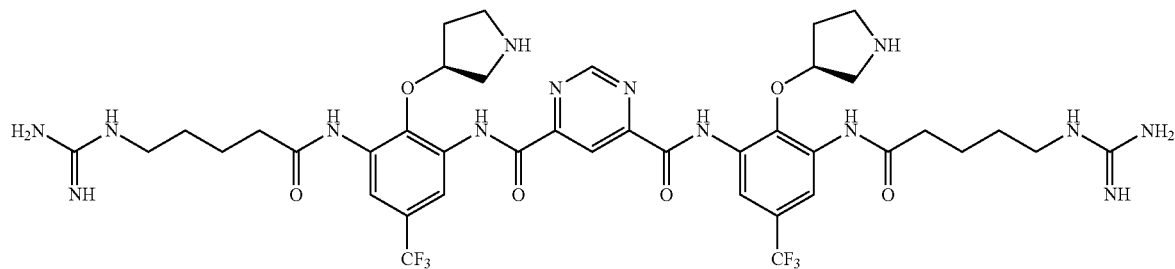 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3O[C@H]3CCNC3)ncn2)c1O[C@H]1CCNC1]
or a salt or solvate thereof
15) The composition of any one of 1), 2), 4), and 5), wherein the oligomer is
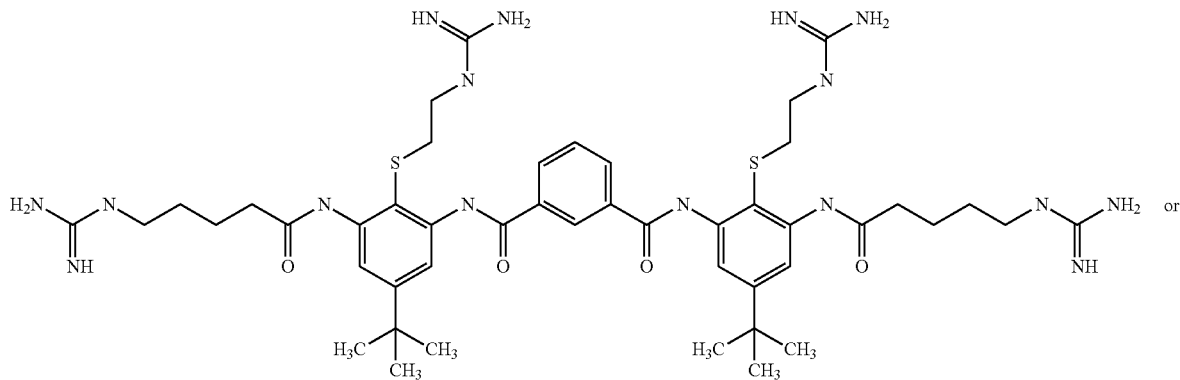

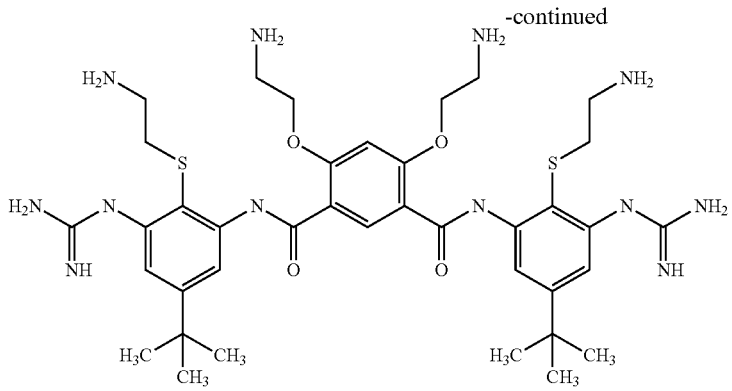

or a salt or solvate thereof

16) The composition of any one of 1), 2), 4), 5), and 15), wherein the oligomer is

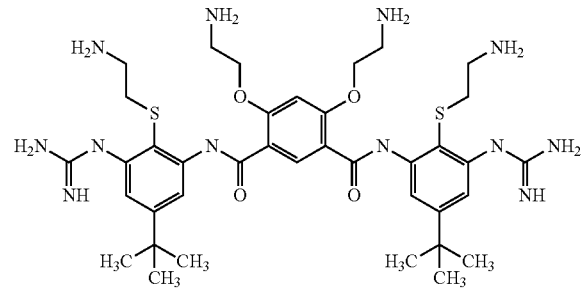 [SMILES: CC(C)(C)c1cc(NC(=N)N)c(SCCN)c(NC(=O)c2cc(C(=O)Nc3cc(C(C)(C)C)cc(NC(=N)N)c3SCCN)c(OCCN)cc2OCCN)c1]

or a salt or solvate thereof

17) An ophthalmic composition, comprising an effective amount of an antimicrobial oligomer of Formula IV:

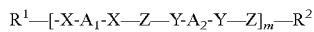 (IV)

or an acceptable salt or solvate thereof,
wherein:
X is $NR^8$, —$NR^8NR^8$—, C=O, or O;
Y is $NR^8$, —$NR^8NR^8$—, C=O, S, or O;
$R^8$ is hydrogen or alkyl;
Z is C=O, C=S, O=S=O, —$NR^8NR^8$—, or —C(=O)C(=O)—;
$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);
$R^1$ is
(i) hydrogen, a polar group (PL), or a non-polar group (NPL), and $R^2$ is —X-$A_1$-X—$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or
(ii) hydrogen, a polar group (PL), or a non-polar group (NPL), and $R^2$ is —X-$A_1$-X—Z—Y-$A_2$-Y—$R^1$, wherein $A_1$ and $A_2$ are as defined above, and each of which is optionally substituted with one or more polar (PL) group(s), one or more non-polar (NPL) group(s), or a combination of one or more polar (PL) group(s) and one or more non-polar (NPL) group(s); or
(iii) hydrogen, a polar group (PL), or a non-polar group (NPL), and $R^2$ is —X-A'-X—$R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or
(iv) hydrogen, a polar group (PL), or a non-polar group (NPL), and $R^2$ is —X-$A_1$-X—Z—Y-A'-Y—$R^1$, wherein $A_1$ is as defined above, A' is aryl or heteroaryl, and each of $A_1$ and A' is optionally substituted with one or more polar (PL) group(s), one or more non-polar (NPL) group(s), or a combination of one or more polar (PL) group(s) and one or more non-polar (NPL) group(s); or
(v) —Z—Y-A' and $R^2$ is hydrogen, a polar group (PL), or a non-polar group (NPL), wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or
(vi) —Z—Y-A', and $R^2$ is —X-A", wherein A' and A" are, independently, aryl or heteroaryl, and each of A and A" is optionally substituted with one or more polar (PL) group(s), one or more non-polar (NPL) group(s), or a combination of one or more polar (PL) group(s) and one or more non-polar (NPL) group(s); or
(vii) $R^1$ and $R^2$ are, independently, a polar group (PL) or a non-polar group (NPL); or
(viii) $R^1$ and $R^2$ together form a single bond;
NPL is a nonpolar group independently selected from —$B(OR^4)_2$ and —$(NR^{3'})_{q1NPL}$—$U^{NPL}$—$(CH_2)_{pNPL}$—$(NR^{3''})_{q2NPL}$—$R^4$, wherein:
$R^3$, $R^{3'}$, and $R^{3''}$ are, independently, selected from hydrogen, alkyl, and alkoxy;
$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;
$U^{NPL}$ is absent or selected from O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N—, and —C(=O)—$NR^3$—O—, wherein groups with two chemically nonequivalent termini can adopt both possible orientations;
the —$(CH_2)_{pNPL}$— alkylene chain is optionally substituted with one or more amino or hydroxy groups, or is unsaturated;
pNPL is 0 to 8;
q1NPL and q2NPL are, independently, 0, 1, or 2;

PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5''})_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, $NR^5$, —C(=O)—, —C(=O)—N=N—$NR^5$—, —C(=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N—, and —C(=O)—$NR^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are, independently, 0, 1, or 2; and m is 1 to about 20;

and an ophthalmically acceptable excipient.

18) The composition of 17), wherein the oligomer has Formula IVa, Formula IVb, or Formula IVc:

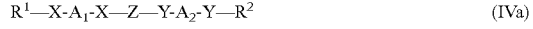

$R^1$—X-A$_1$-X—Z—Y-A$_2$-Y—$R^2$ (IVa)

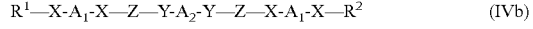

$R^1$—X-A$_1$-X—Z—Y-A$_2$-Y—Z—X-A$_1$-X—$R^2$ (IVb)

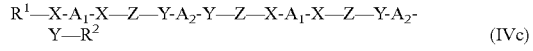

$R^1$—X-A$_1$-X—Z—Y-A$_2$-Y—Z—X-A$_1$-X—Z—Y-A$_2$-Y—$R^2$ (IVc)

or an acceptable salt or solvate thereof, wherein:

X is $NR^8$, —$NR^8NR^8$—, C=O, or O;

Y is $NR^8$, —$NR^8NR^8$—, C=O, S, or O;

$R^8$ is hydrogen or alkyl;

Z is C=O, C=S, O=S=O, —$NR^8NR^8$—, or —C(=O)C(=O)—;

A$_1$ and A$_2$ are, independently, optionally substituted arylene or optionally substituted heteroarylene, wherein A$_1$ and A$_2$ are, independently, optionally substituted with one or more polar (PL) group(s), one or more non-polar (NPL) group(s), or a combination of one or more polar (PL) group(s) and one or more non-polar (NPL) group(s);

$R^1$ is hydrogen, a polar group (PL), or a non-polar group (NPL);

$R^2$ is $R^1$;

NPL is a nonpolar group —$(NR^{3'})_{q1NPL}$—$U^{NPL}$—$(CH_2)_{pNPL}$—$(NR^{3''})_{q2NPL}$—$R^{4'}$, wherein:

$R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N—, and —C(=O)—$NR^3$—O—, wherein groups with two chemically nonequivalent termini can adopt both possible orientations;

the —(CH$_2$)$_{pNPL}$— alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5''})_{q2PL}$—V wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, $NR^5$, —C(=O)—, —C(=O)—N=N—$NR^5$—, —C(=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N—, and —C(=O)—$NR^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are, independently, 0, 1, or 2.

19) An ophthalmic composition, comprising an effective amount of an antimicrobial oligomer of Formula V:

$R^1$—[-A$_1$-W-A$_2$-W-]$_m$—$R^2$ (V)

or an acceptable salt or solvate thereof, wherein:

A$_1$ and A$_2$ are, independently, optionally substituted arylene or optionally substituted heteroarylene, wherein:

(i) A$_1$ and A$_2$ are, independently, optionally substituted with one or more polar (PL) group(s), one or more non-polar (NPL) group(s), or a combination of one or more polar (PL) group(s) and one or more non-polar (NPL) group(s); or (ii) one of A$_1$ or A$_2$ is as defined above and is optionally substituted with one or more polar (PL) group(s), one or more non-polar (NPL) group(s), or a combination of one or more polar (PL) group(s) and one or more non-polar (NPL) group(s); and the other of A$_1$ or A$_2$ is the group —C≡C(CH$_2$)$_p$C≡C—, wherein p is 0 to 8, and the —(CH$_2$)$_p$— alkylene chain is optionally substituted with one or more amino or hydroxyl groups;

W is absent, or represents —CH$_2$—, —CH$_2$—CH$_2$—, —CH=CH—, or —C≡C—;

$R^1$ is (i) hydrogen, a polar group (PL), or a non-polar group (NPL), and $R^2$ is -A$_1$-$R^1$, wherein A$_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is -A$_1$-W-A$_2$-$R^1$, wherein each of A$_1$ and A$_2$ is as defined above and is optionally substituted with one or more polar (PL) group(s), one or more non-polar (NPL) group(s), or a combination of one or more polar (PL) group(s) and one or more non-polar (NPL) group(s); or (iii) A'-W— and $R^2$ is -$A_1$-W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or (iv) A'-W— and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or (iv) $R^1$ and $R^2$ together form a single bond;

NPL is a nonpolar group independently selected from —$B(OR^4)_2$ or —$(NR^{3'})_{q1NPL}$—$U^{NPL}$—$(CH_2)_{pNPL}$—$(NR^{3''})_{q2NPL}$—$R^4$, wherein:

$R^3$, $R^{3'}$, and $R^{3''}$ are, independently, selected from hydrogen, alkyl, and alkoxy;

$R^4$ is selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, $NR^3$, —(C=O)—, —(C=O)—N=N—$NR^3$—, —(C=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N— and —(C=O)—$NR^3$—O—, wherein groups with two chemically nonequivalent termini can adopt both possible orientations;

the —$(CH_2)_{pNPL}$— alkylene chain is optionally substituted with one or more alkyl, amino or hydroxyl groups, or the alkylene chain is unsaturated;

pNPL is 0 to 8;

q1NPL and q2NPL are, independently, 0 to 2;

PL is a polar group selected from halo, hydroxyethoxymethyl, methoxyethoxymethyl, polyoxyethylene, and —$(NR^{5'})_{q1PL}$—$U^{PL}$—$(CH_2)$—$(NR^{5''})_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, $NR^5$, —(C=O)—, —(C=O)—N=N—$NR^5$—, —(C=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N—, and —(C=O)—$NR^5$—O—, wherein groups with two chemically nonequivalent termini can adopt both possible orientations;

V is selected from nitro, cyano, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the —$(CH_2)_{pPL}$— alkylene chain is optionally substituted with one or more amino or hydroxyl groups, or the alkylene chain is unsaturated;

pPL is 0 to 8;

q1PL and q2PL are, independently, 0 to 2; and m is 1 to about 25;

and an ophthalmically acceptable excipient.

20) The composition of 19), wherein the oligomer has Formula Va:

$$R^1\text{-}A_1\text{-}W\text{-}A_2\text{-}W\text{-}A_1\text{-}R^2 \quad (Va)$$

or an acceptable salt or solvate thereof, wherein:

$A_1$ and $A_2$ are, independently, optionally substituted arylene or optionally substituted heteroarylene, wherein:

(i) $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C=C(CH$_2$)$_p$C=C—, wherein p is 0 to 8, and the —(CH$_2$)$_p$— alkylene chain is optionally substituted with one or more amino or hydroxyl groups;

W is —C=C—;

$R^1$ is hydrogen, a polar group (PL), a non-polar group (NPL), or —W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

$R^2$ is $R^1$;

NPL is a nonpolar group —$(NR^{3'})_{q1NPL}$—$U^{NPL}$—$(CH_2)_{pNPL}$—$(NR^{3''})_{q2NPL}$—$R^4$;

$R^3$, $R^{3'}$, and $R^{3''}$ are, independently, selected from hydrogen, alkyl, and alkoxy;

$R^4$ is selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, $NR^3$, —(C=O)—, —(C=O)—N=N—$NR^3$—, —(C=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N—, and —(C=O)—$NR^3$—O—, wherein groups with two chemically nonequivalent termini can adopt both possible orientations;

the alkylene chain —$(CH_2)_{pNPL}$— is optionally substituted with one or more alkyl, amino or hydroxyl groups, or the alkylene chain is unsaturated;

pNPL is 0 to 8;

q1NPL and q2NPL are, independently, 0 to 2;

PL is a polar group selected from halo, hydroxyethoxymethyl, methoxyethoxymethyl, polyoxyethylene, and —$(NR^{5'})_{q1PL}$—$U^{PL}$—$(CH_2)$—$(NR^{5''})$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, $NR^5$, —(C=O)—, —(C=O)—N=N—$NR^5$—, —(C=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N—, and —(C=O)—$NR^5$—O—, wherein groups with two chemically nonequivalent termini can adopt both possible orientations;

V is selected from nitro, cyano, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the alkylene chain —(CH$_2$)$_{pPL}$— is optionally substituted with one or more amino or hydroxyl groups, or the alkylene chain is unsaturated;

pPL is 0 to 8; and q1PL and q2PL are, independently, 0 to 2.

21) The composition of 19) or 20), wherein

A$_1$ and A$_2$ are, independently, optionally substituted m-phenylene, wherein A$_1$ is optionally substituted with two polar (PL) groups, and A$_2$ is unsubstituted;

R$^1$ is a polar group;

PL is independently halo or —(NR$^{5'}$)$_{q1PL}$—U$^{PL}$—(CH$_2$)$_{pPL}$—(NR$^5$)$_{q2PL}$—V, wherein:

U$^{PL}$ is absent or selected from O, S, NR$^5$, and —C(=O)—;

V is selected from amino, amidino, and guanidino, any of which is optionally substituted with one or more of amino, halo, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylhio, and lower acylamino;

pPL is 0 to 8; and q1PL and q2PL are 0.

22) The composition of any one of 19) to 21), wherein:

R$^1$ is halo;

PL is or —U$^{PL}$—(CH$_2$)$_{pPL}$—V, wherein:

U$^{PL}$ is absent;

V is selected from amino, amidino, and guanidino, any of which is optionally substituted with one or more of amino and halo; and pPL is 0 to 6.

23) The composition of any one of 19) to 21), wherein the oligomer is one of

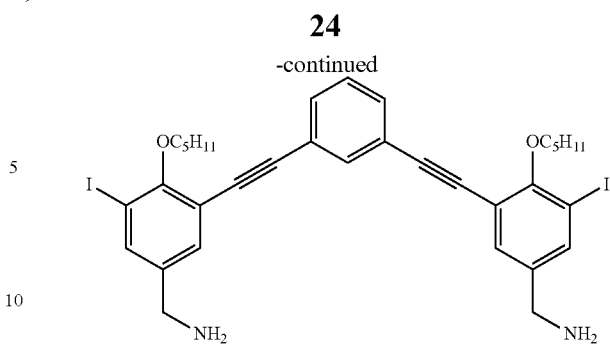

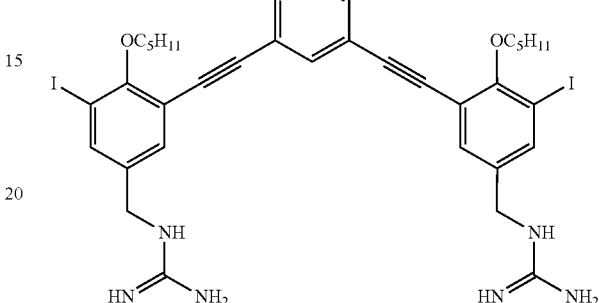

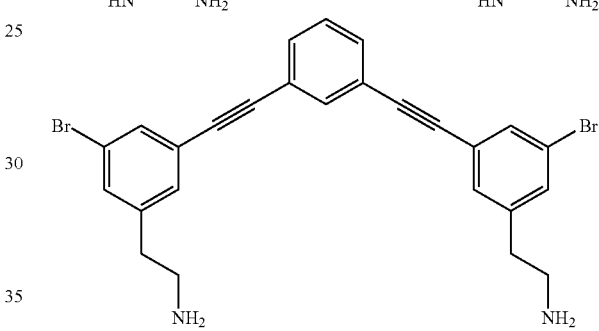

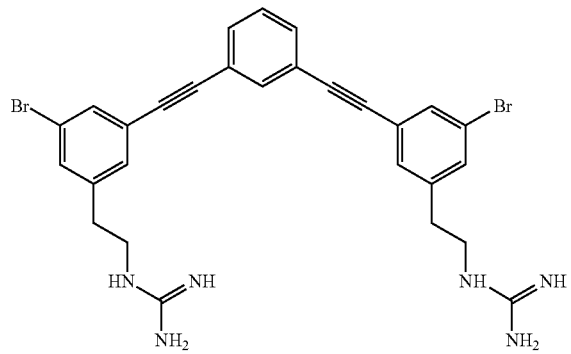

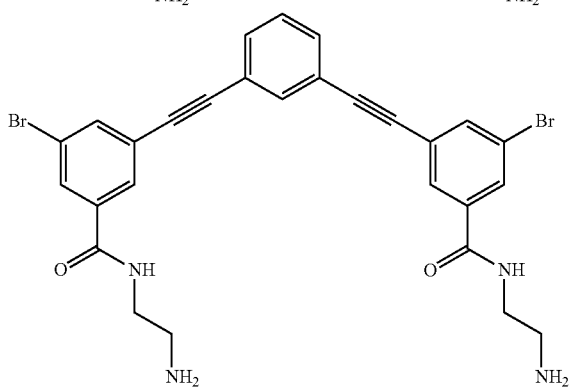

or a salt or solvate thereof

24) The composition of any one of 19) to 21), wherein the oligomer is

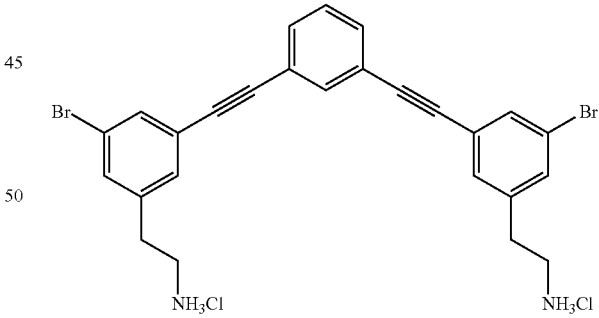

25) An ophthalmic composition, comprising an effective amount of an antimicrobial random copolymer of Formula VI:

$$A\text{-}(B)_{n1}\text{-}(D)_{m1}\text{-}H \quad (VI)$$

or an acceptable salt or solvate thereof,
wherein:

A is the residue of a chain transfer agent;

B is —[CH$_2$—C(R$^{11}$)(B$_{11}$)]—, wherein B$_{11}$ is —X$_{11}$—Y$_{11}$—Z$_{11}$, wherein X$_{11}$ is carbonyl (—C(=O)—) or optionally substituted C$_{1-6}$ alkylene; or X$_{11}$ is absent;

Y$_{11}$ is O, NH, or optionally substituted C$_{1-6}$ alkylene; or Y$_{11}$ is absent;

Z$_{11}$ is —Z$_{11A}$-Z$_{11B}$, wherein Z$_{11A}$ is alkylene, arylene, or heteroarylene, any of which is optionally substituted; or Z$_{11A}$ is absent; and Z$_{11B}$ is -guanidino, -amidino, —N(R$^3$)(R$^4$), or —N$^+$(R$^3$)(R$^4$)(R$^5$), wherein R$^3$, R$^4$, and R$^5$ are, independently, hydrogen, alkyl, aminoalkyl, aryl, heteroaryl, heterocyclic, or aralkyl; or Z$_{11}$ is pyridinium

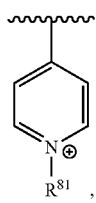

or phosphonium

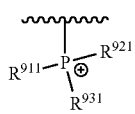

wherein R$^{81}$, R$^{911}$, R$^{921}$, and R$^{931}$ are, independently, hydrogen or alkyl;

R$^{11}$ is hydrogen or C$_{1-4}$ alkyl;

D is —[CH$_2$—C(R$^{21}$)(D$_{21}$)]—, wherein D$_{21}$ is —X$_{21}$—Y$_{21}$—Z$_{21}$, wherein X$_{21}$ is carbonyl (—C(=O)—) or optionally substituted C$_{1-6}$ alkylene; or X$_{21}$ is absent;

Y$_{21}$ is O, NH, or optionally substituted C$_{1-6}$ alkylene, or Y$_{21}$ is absent;

Z$_{21}$ is alkyl, cycloalkyl, alkoxy, aryl, or aralkyl, any of which is optionally substituted;

R$^{21}$ is hydrogen or C$_{1-4}$ alkyl;

m$_1$, the mole fraction of D monomer, is about 0.1 to about 0.9; and n$_1$, the mole fraction of B monomer, is 1-m$_1$;

wherein the copolymer is a random copolymer of B and D monomers, and wherein the copolymer has a degree of polymerization of about 5 to about 50; and an ophthalmically acceptable excipient.

26) The composition of 25), wherein:

A is C$_{1-4}$ alkoxycarbonyl(C$_{1-4}$alkylthio;

X$_{11}$ and X$_{21}$ are carbonyl;

Y$_{11}$ and Y$_{21}$ are O;

Z$_{11}$ is —Z$_{11A}$-Z$_{11B}$, wherein Z$_{11A}$ is C$_{1-6}$ alkylene optionally substituted with C$_{1-4}$ alkyl) or aryl; and Z$_{11B}$ is —N(R$^{31}$)(R$^{41}$) or —N$^+$(R$^{31}$)(R$^{41}$)(R$^{51}$), wherein R$^{31}$, R$^{41}$, and R$^{51}$ are independently hydrogen C$_{1-4}$ alkyl;

Z$_{21}$ is C$_{1-6}$ alkyl, C$_{1-6}$ aryl, or C$_{1-6}$ ar(C$_{1-4}$alkyl; and R$^{11}$ and R$^{21}$ are, independently, hydrogen or methyl;

m$_1$ is about 0.35 to about 0.60; and wherein the copolymer has a degree of polymerization of about 5 to about 10.

27) An antimicrobial ophthalmic composition, the composition comprising:

(a) an antimicrobial oligomer of Formula IIa:

R$^1$—X-A$_1$-X—Y-A$_2$-Y—X-A$_1$-X—R$^2$ (IIa)

or an acceptable salt or solvate thereof, wherein:

X is NR$^8$, O, S, or —N(R$^8$)N(R$^8$)—;

Y is C=O, C=S, or O=S=O;

R$^8$ is hydrogen or alkyl;

A$_1$ and A$_2$ are, independently, optionally substituted arylene or optionally substituted heteroarylene, wherein A$_1$ and A$_2$ are, independently, optionally substituted with one or more polar (PL) group(s), one or more non-polar (NPL) group(s), or a combination of one or more polar (PL) group(s) and one or more non-polar (NPL) group(s);

R$^1$ is a polar group (PL) or a non-polar group (NPL);

R$^2$ is R$^1$;

NPL is a nonpolar group independently selected from —B(OR$^4$)$_2$ and —(NR$^{3'}$)$_{q1NPL}$—U$^{NPL}$—(CH$_2$)$_{pNPL}$—(NR$^{3''}$)$_{q2NPL}$—R$^{4'}$, wherein:

R$^3$, R$^{3'}$, and R$^{3''}$ are, independently, selected from hydrogen, alkyl, and alkoxy;

R$^4$ and R$^{4'}$ are, independently, selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

R$^5$, R$^{5'}$, and R$^{5''}$ are, independently, selected from hydrogen, alkyl, and alkoxy;

U$^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are, independently, 0, 1, or 2;

or a pharmaceutically acceptable salt or solvate thereof, in an amount effective for treatment and/or prophylaxis of a microbial infection of an eye of an animal; and (b) an ophthalmically acceptable excipient, wherein the composition is suitable for administration to one or more tissues of the eye.

28) The composition of 27), wherein:

$A_1$ is m-phenylene substituted with one (PL) group and one non-polar (NPL) group;

$A_2$ is unsubstituted m-pyrimidinylene or m-pyrimidinylene substituted with one or two polar (PL) group(s);

NPL is $R^{4'}$, wherein $R^{4'}$ is $(C_1-C_6)$alkyl optionally substituted with one or more halo groups;

PL is —$U^{PL}$—$(CH_2)_{pPL}$—V, wherein:

$U^{PL}$ is O or S;

V is selected from amino, amidino, and guanidino; and pPL is 0 to 6.

29) The composition of 27), wherein:

$A_1$ is m-phenylene substituted with one (PL) group and one non-polar (NPL) group;

$A_2$ is unsubstituted m-phenylene or m-phenylene substituted with one or two polar (PL) group(s);

NPL is $R^{4'}$, wherein $R^{4'}$ is $(C_1-C_6)$alkyl optionally substituted with one or more halo groups;

PL is —$U^{PL}$—$(CH_2)_{pPL}$—V, wherein:

$U^{PL}$ is O or S;

V is selected from amino, amidino, and guanidino; and pPL is 0 to 6.

30) The composition of 27) or 28), wherein the oligomer is one of

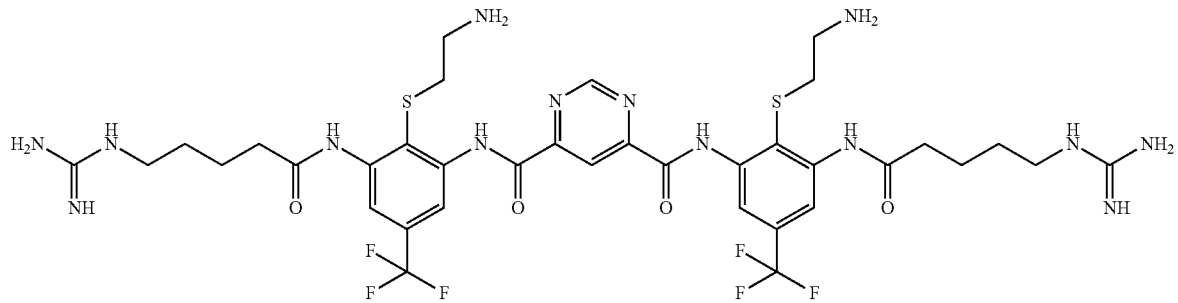

or

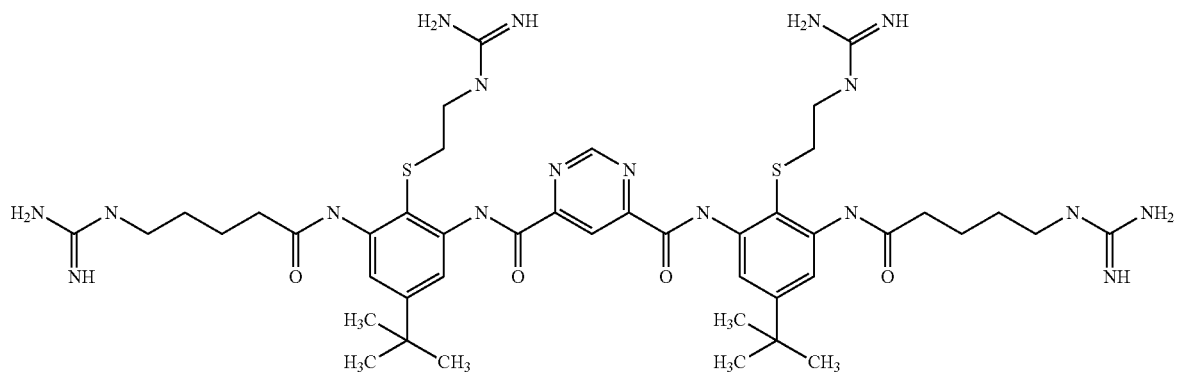 [SMILES: CC(C)(C)c1cc(NC(=O)CCCCNC(=N)N)c(SCCNC(=N)N)c(NC(=O)c2cc(C(=O)Nc3cc(C(C)(C)C)cc(NC(=O)CCCCNC(=N)N)c3SCCNC(=N)N)ncn2)c1]

or a salt or solvate thereof

31) The composition of 27) or 29), wherein the oligomer is one of

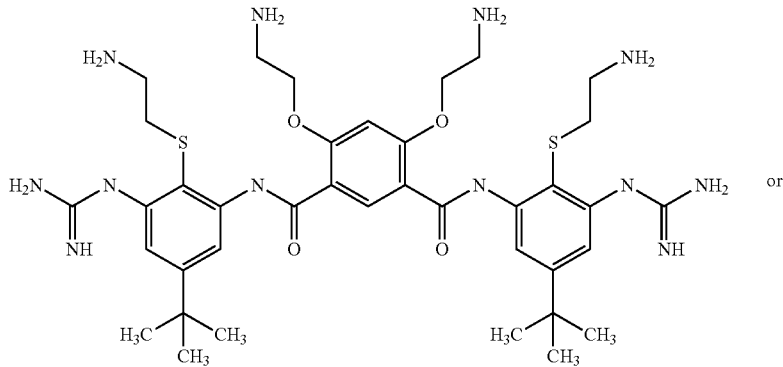

or

-continued

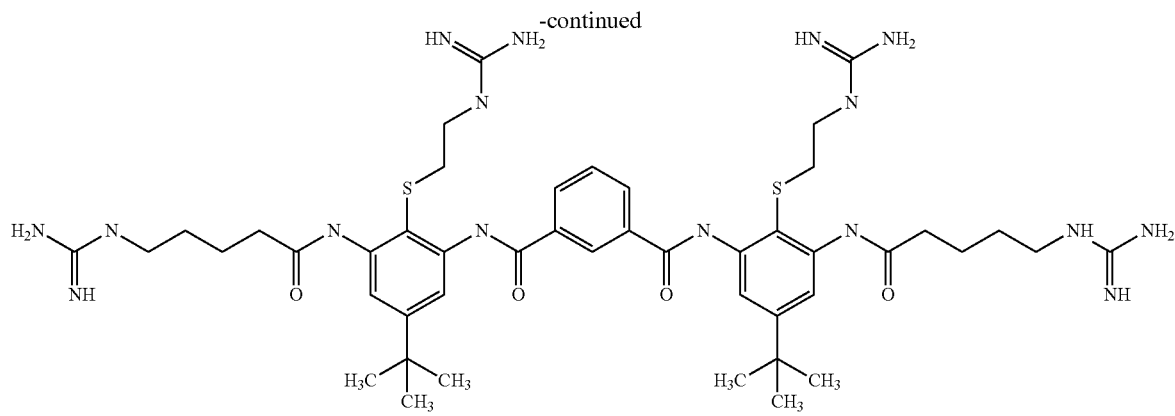

or a salt or solvate thereof.

32) An ophthalmic composition for use in treatment or prevention of a microbial infection in an eye of an animal, wherein composition comprises the antimicrobial oligomer of Formula I of 1) in an amount effective to treat or prevent the infection when the composition is administered to one or more tissues of the eye.

33) An ophthalmic composition for use in treatment or prevention of a microbial infection in an eye of an animal, wherein the composition comprises the antimicrobial oligomer of Formula II of 3) in an amount effective to treat or prevent the infection when the composition is administered to one or more tissues of the eye.

34) An ophthalmic composition for use in treatment or prevention of a microbial infection in an eye of an animal, wherein the composition comprises the antimicrobial oligomer of Formula IV of 17) in an amount effective to treat or prevent the infection when the composition is administered to one or more tissues of the eye.

35) An ophthalmic composition for use in treatment or prevention of a microbial infection in an eye of an animal, wherein the composition comprises the antimicrobial oligomer of Formula V of 19) in an amount effective to treat or prevent the infection when the composition is administered to one or more tissues of the eye.

36) An ophthalmic composition for use in treatment or prevention of a microbial infection in an eye of an animal, wherein the composition comprises the antimicrobial oligomer of Formula VI of 25) in an amount effective to treat or prevent the infection when the composition is administered to one or more tissues of the eye.

37) The composition of any one of 1) to 36), wherein the composition is suitable for topical administration to one or more tissues of an eye of an animal.

38) The composition of any one of 1) to 36), wherein the composition is in a form selected from a solution, a suspension, an emulsion, a gel, an ointment, and a solid article suitable for ocular implant.

39) The composition of 38), wherein the oligomer is present in the composition at a concentration of about 0.01% to about 20% by weight.

40) The composition of any one of 1) to 31), wherein the ophthalmically acceptable excipient is selected from a preservative, a stabilizer, an antioxidant, and a viscosity-enhancing agent, or any combination thereof.

41) The composition of 40), wherein the preservative is selected from a phenylmercuric salt, thimerosal, stabilized chlorine dioxide, quaternary ammonium compound, imidazolidinyl urea, paraben, phenoxyethanol, chlorophenoxyethanol, phenoxypropanol, chlorobutanol, chlorocresol, phenylethyl alcohol, and sorbic acid or a salt thereof, or any combination thereof 42) The composition of 40), wherein the antioxidant is selected from ascorbic acid, sodium metabisulfite, sodium bisulfite, and acetylcysteine.

43) The composition of 40), wherein the stabilizer is a chelating agent.

44) The composition of 43), wherein the chelating agent is disodium EDTA (disodium edetate).

45) The composition of 40), wherein the viscosity-enhancing agent is selected from methylcellulose, hydroxypropylmethyl cellulose, polyvinyl alcohol, and glycerol.

46) The composition of 37), wherein the composition further comprises an additional ophthalmically acceptable excipient.

47) The composition of 46), wherein the additional ophthalmically acceptable excipient is selected from a buffering agent, a solubilizing agent, a surfactant, a lubricating agent, and an ophthalmically acceptable salt, or any combination thereof 48) The composition of 37), wherein the composition further comprises an additional medicament.

49) The composition of 48), wherein the additional medicament is selected from an anti-inflammatory agent, an antimicrobial agent, an anesthetic agent, and an anti-allergic agent.

50) The composition of 49), wherein the additional medicament is a steroidal anti-inflammatory agent.

51) The composition of 50), wherein the steroidal anti-inflammatory agent is a glucocorticoid.

52) The composition of 50), wherein the steroidal anti-inflammatory agent is selected from dexamethasone, rimexolone, prednisolone, fluorometholone, and hydrocortisone.

53) The composition of 49), wherein the additional medicament is an antimicrobial agent.

54) The composition of 53), wherein the antimicrobial agent is selected from an anti-bacterial agent, an anti-fungal agent, and an anti-viral agent.

55) A method of treating or preventing a microbial infection in an eye of an animal, said method comprising administering to an eye of an animal in need of said treating or preventing an effective amount of an ophthalmic composition of any one of 1) to 36).

56) The method of 55), wherein the ophthalmic composition is in a form selected from a solution, a suspension, an emulsion, a gel, an ointment, and a solid article suitable for ocular implant.

57) The method of 55), wherein the composition is administered 2 to 4 times daily.

58) The method of 55), wherein the oligomer is present in the composition at a concentration of about 0.01% to about 20% by weight
59) The method of 55), wherein the microbial infection is a bacterial infection.
60) The method of 59), wherein the bacterial infection is caused by *Staphylococcus, Streptococcus, Enterococcus, Bacillus, Corynebacterium, Moraxella, Haemophilus, Serratia, Pseudomonas* or *Neisseria* spp.
61) The method of 55), wherein the microbial infection is a fungal infection.
62) The method of 61), wherein the fungal infection is caused by *Aspergillus* or *Fusarium* spp.
63) The method of 55), wherein the microbial infection is a viral infection.
64) The method of 63), wherein the viral infection is caused by a herpes virus.
65) The method of 55), wherein the infection is selected from bacterial keratitis, bacterial conjunctivitis, and corneal ulcer.
66) A method for treating or preventing a microbial infection in an eye of an animal by administering to one or more tissues of the eye an antimicrobial ophthalmic composition, the composition comprising an antimicrobial oligomer of Formula I of 1) in an amount effective to treat or prevent the infection.
67) A method for treating or preventing a microbial infection in an eye of an animal by administering to one or more tissues of the eye an antimicrobial ophthalmic composition, the composition comprising an antimicrobial oligomer of Formula II of 3) in an amount effective to treat or prevent the infection.
68) A method for treating or preventing a microbial infection in an eye of an animal by administering to one or more tissues of the eye an antimicrobial ophthalmic composition, the composition comprising an antimicrobial oligomer of Formula IV of 17) in an amount effective to treat or prevent the infection.
69) A method for treating or preventing a microbial infection in an eye of an animal by administering to one or more tissues of the eye an antimicrobial ophthalmic composition, the composition comprising an antimicrobial oligomer of Formula V of 19) in an amount effective to treat or prevent the infection.
70) A method for treating or preventing a microbial infection in an eye of an animal by administering to one or more tissues of the eye an antimicrobial ophthalmic composition, the composition comprising employing an antimicrobial oligomer of Formula VI of 25) in an amount effective to treat or prevent the infection.
71) The method of any one of 66) to 70), wherein the antimicrobial ophthalmic composition is administered topically to one or more tissues of the eye of the animal.
72) The method of 71), wherein the ophthalmic composition is in a form selected from a solution, a suspension, an emulsion, a gel, an ointment, and a solid article suitable for ocular implant.
73) The method of 71), wherein the composition is administered 2 to 4 times daily.
74) The method of 71), wherein the oliogmer is present in the composition at a concentration of about 0.01% to about 20% by weight.
75) The method of 71), wherein the microbial infection is a bacterial infection.
76) The method of 75), wherein the bacterial infection is caused by *Staphylococcus, Streptococcus, Enterococcus, Bacillus, Corynebacterium, Moraxella, Haemophilus, Serratia, Pseudomonas* or *Neisseria* spp.
77) The method of 71), wherein the microbial infection is a fungal infection.
78) The method of 77), wherein the fungal infection is caused by *Aspergillus* or *Fusarium* spp.
79) The method of 71), wherein the microbial infection is a viral infection.
80) The method of 79), wherein the viral infection is caused by a herpes virus.
81) The method of 71), wherein the infection is selected from bacterial keratitis, bacterial conjunctivitis, and corneal ulcer.
82) Use of a compound of 1) in the preparation of a medicament for treating or preventing an ophthalmic and/or otic infection in an animal.

DESCRIPTION OF EMBODIMENTS

The present invention provides compositions of amphiphilic, antimicrobial polymers, and/or oligomers that can be used in the treatment or prevention of ophthalmic and otic infections in humans and animals. The present invention also provides methods of using the compositions to treat or prevent ophthalmic and otic infections in humans and animals.

The antimicrobial polymers and oligomers useful in the present invention are polymers and oligomers of Formulae I, II, IV, V and VI:

$$R^1\text{—}[\text{-X-A}_1\text{-Y—X-A}_2\text{-Y-}]_m\text{—}R^2 \quad (I)$$

$$R^1\text{—}[\text{-X-A}_1\text{-X—Y-A}_2\text{-Y-}]_m\text{—}R^2 \quad (II)$$

$$R^1\text{—}[\text{-X-A}_1\text{-X—Z—Y-A}_2\text{-Y—Z}]_m\text{—}R^2 \quad (IV)$$

$$R^1\text{—}[\text{-A}_1\text{-W-A}_2\text{-W-}]_m\text{—}R^2 \quad (V)$$

$$A\text{-}(B)_{n1}\text{-}(D)_{m1}\text{-H} \quad (VI)$$

or acceptable salts or solvates thereof, wherein $R^1$, $R^2$, $A_1$, $A_2$, A, B, D, X, Y, Z, W, m, m1, and n1 are as defined below.

The polymers and oligomers useful in the present invention are capable of adopting amphiphilic conformations that allow for the segregation of polar and nonpolar regions of the molecule into different spatial regions. This separation of charge, or facial amphiphilicity, forms the basis for the anti-microbial activity observed for these polymers and oligomers, making them useful as anti-microbial agents. Use of the polymers and oligomers of Formulae I, II, and IV generally as anti-microbial agents is described in US Published Patent Appl. No. US 2006-0041023 A1 and U.S. Pat. No. 7,173,102. Use of the polymers and oligomers of Formula V generally as anti-microbial agents is described in US Published Patent Appl. Nos. US 2004-0202639 A1 and US 2005-0287108 A1. Use of the random copolymers of Formula VI generally as anti-microbial agents is described in US Published Patent Appl. No. US 2006-0024264 A1.

The polymers and oligomers employed in the present invention were originally designed to mimic the antimicrobial activities of host defense peptides, which were potentially exciting therapeutic agents because of their broad spectrum of activity, rapid bacteriocidal activity, and very low incidence of development of bacterial resistance, but which presented a number of significant pharmaceutical issues, including systemic toxicity and difficulty and expense of manufacturing, that severely hampered clinical progress in their use as therapeutics.

Many of the oligomers of Formulae I, II, and IV are significantly smaller and easier to prepare than their naturally occurring counterparts. They have the same mechanism of action as magainin (a naturally occurring host defense peptide) and are approximately equipotent and as broad in their spectrum of action as magainin. However, the non-peptidic polymers and oligomers of the present invention are significantly less toxic towards human erythrocytes, much less expensive to prepare, and are expected to be much more stable in vivo.

The present invention discloses ophthalmic and otic compositions comprising anti-microbial, facially amphiphilic polymers and oligomers. Polymers are generally defined as synthetic compounds assembled from monomer subunits that are polydisperse in molecular weight, and are most commonly prepared by one-pot synthetic procedures. The term "polymer" as used herein refers to a macromolecule comprising a plurality of repeating units or monomers. The term includes homopolymers, which are formed from a single type of monomer, and copolymers, which are formed from two or more different monomers. In copolymers, the monomers may be distributed randomly (random copolymer), in alternating fashion (alternating copolymers), or in blocks (block copolymer). The polymers of the present invention are either homopolymers or alternating copolymers having about 2 monomer units to about 500 monomer units, with average molecular weights that range from about 300 Daltons to about 1,000,000 Daltons, or from about 400 Daltons to about 120,000 Daltons. Preferred polymers are those having about 5 to about 100 monomer units, with average molecular weights that range from about 1,000 Daltons to about 25,000 Daltons.

The term "oligomer" as used herein refers to a homogenous polymer with a defined sequence and molecular weight. Modern methods of solid phase organic chemistry have allowed the synthesis of homodisperse, sequence-specific oligomers with molecular weights approaching 5,000 Daltons. An oligomer, in contrast to a polymer, has a defined sequence and molecular weight and is usually synthesized either by solid phase techniques or by step-wise solution chemistry and purified to homogeneity. Oligomers of the present invention are those having about 2 monomer units to about 25 monomer units, with molecular weights that range from about 300 Daltons to about 6,000 Daltons. Preferred oligomers are those having about 2 monomer units to about 10 monomer units, with molecular weights that range from about 300 Daltons to about 2,500 Daltons.

For the ophthalmic and otic compositions described herein, oligomers are the preferred species because of their defined size and structure.

The term "polymer backbone," "oligomer backbone," or "backbone" as used herein refers to that portion of the polymer or oligomer which is a continuous chain comprising the bonds formed between monomers upon polymerization. The composition of the polymer or oligomer backbone can be described in terms of the identity of the monomers from which it is formed without regard to the composition of branches, or side chains, of the polymer or oligomer backbone.

The term "polymer side chain," "oligomer side chain," or "side chain" refers to portions of the monomer which, following polymerization, forms an extension of the polymer or oligomer backbone. In homopolymers and homooligomers, all the side chains are derived from the same monomer.

The term "amphiphilic" as used herein describes a three-dimensional structure having discrete hydrophobic and hydrophilic regions. An amphiphilic polymer requires the presence of both hydrophobic and hydrophilic elements along the polymer backbone. The presence of hydrophobic and hydrophilic groups is a necessary, but not sufficient, condition to produce an amphiphilic molecule, polymer, or oligomer.

The term "facially amphiphilic" or "facial amphiphilicity" as used herein describes polymers or oligomers with polar (hydrophilic) and nonpolar (hydrophobic) side chains that adopt conformation(s) leading to segregation of polar and nonpolar side chains to opposite faces or separate regions of the structure or molecule.

The phrase "groups with chemically nonequivalent termini" refers to functional groups such as esters amides, sulfonamides, and N-hydroxyoximes where reversing the orientation of the substituents, for example, $R^1C(=O)OR^2$ versus $R^1O(O=)CR^2$, produces unique chemical entities.

The present invention is directed to antimicrobial ophthalmic and otic compositions comprising one or more of the polymers or oligomers disclosed herein, as defined below, and an ophthalmically acceptable excipient.

Thus, in some aspects of the present invention, the ophthalmic or otic composition comprises a polymer or oligomer of Formula I:

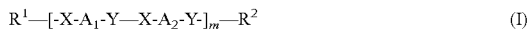

$$R^1-[-X-A_1-Y-X-A_2-Y-]_m-R^2 \qquad (I)$$

or an acceptable salt or solvate thereof,
wherein:
X is $NR^8$, $-N(R^8)N(R^8)-$, O, or S;
Y is C=O, C=S, O=S=O, or $-C(=O)C(=O)-$;
$R^8$ is hydrogen or alkyl;
$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or
$A_1$ is optionally substituted arylene or optionally substituted heteroarylene and $A_2$ is a $C_3$ to $C_8$ cycloalkyl or $-(CH_2)_q-$, wherein q is 1 to 7, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or
$A_2$ is optionally substituted arylene or optionally substituted heteroarylene, and $A_1$ is a $C_3$ to $C_8$ cycloalkyl or $-(CH_2)_q-$, wherein q is 1 to 7, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);
$R^1$ is
(i) hydrogen, a polar (PL) group, or a non-polar (NPL) group, and $R^2$ is $-X-A_1-Y-R^{11}$, wherein $R^{11}$ is hydrogen, a polar (PL) group, or a non-polar (NPL) group; or
(ii) $R^1$ and $R^2$ are, independently, hydrogen, a polar (PL) group, or a non-polar (NPL) group; or
(iii) $R^1$ and $R^2$ together are a single bond;
NPL is a nonpolar group independently selected from $-B(OR^4)_2$ and $-(NR^{3'})_{q1NPL}-U^{NPL}-(CH_2)_{pNPL}-(NR^{3''})_{q2NPL}-R^{4'}$, wherein:
$R^3$, $R^{3'}$, and $R^{3''}$ are, independently, selected from the group consisting of hydrogen, alkyl, and alkoxy;
$R^4$ and $R^{4'}$ are, independently, selected from the group consisting of hydrogen, alkyl, alkenyl, alkynyl, cycloalkyl, aryl, and heteroaryl, any of which is optionally substituted with one or more alkyl or halo groups;
$U^{NPL}$ is absent or selected from O, S, S(=O), S(=O)$_2$, $NR^3$, $-C(=O)-$, $-C(=O)-N=N-NR^3-$, $-C(=O)-NR^3-N=N-$, $-N=N-NR^3-$, $-C(=N-N(R^3)_2)-$, $-C(=NR^3)-$, $-C(=O)O-$, $-C(=O)S-$, $-C(=S)-$, $-O-P(=O)_2O-$, $-R^3O-$, $-R^3S-$, $-S-C=N-$, and $-C(=O)-NR^3-O-$, wherein groups with two chemically nonequivalent termini can adopt both possible orientations;

the —$(CH_2)_{pNPL}$— alkylene chain is optionally substituted with one or more alkyl, amino or hydroxy groups, or is unsaturated; pNPL is 0 to 8;

q1NPL and q2NPL are, independently, 0, 1, or 2;

PL is a polar group selected from halo, hydroxyethoxymethyl, methoxyethoxymethyl, polyoxyethylene, and —$(NR^5)_{q1PL}$—$U^{PL}$—$(CH_2)_{pPL}$—$(NR^{5"})_{q2PL}$—V, wherein:

$R^5$, $R^{5'}$, and $R^{5"}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, N(CH$_2$CH$_2$NH$_2$)$_2$, amidino, guanidino, guanyl, aminosulfonyl, aminoalkoxy, aminoalkylhio, lower acylamino, or benzyloxycarbonyl, wherein p is 1 to 4;

the —$(CH_2)_{pPL}$— alkylene chain is optionally substituted with one or more amino or hydroxy groups, or is unsaturated;

pPL is 0 to 8;

q1PL and q2PL are independently 0, 1 or 2; and m is 1 to about 500;

and an ophthalmically or optically acceptable excipient.

US Patent Application Publ. No. US 2006-0041023 A1 discloses antimicrobial polymers and oligomers of Formula I that can be used in the compositions of the present invention.

For example, oligomers of Formula I preferred for use in the ophthalmic and otic compositions of the present invention are those wherein m is 1 to about 25, 1 to about 20, 1 to 10, 2 to 8, 2 to 6, 2 to 5, or 4 or 5.

Preferred oligomers of Formula I are also those wherein X is NR$^8$, O, or —N(R$^8$)N(R$^8$)—, and R$^8$ is hydrogen or C$_1$-C$_6$ alkyl. Especially preferred are those polymers and oligomers wherein X is NR$^8$ and Y is C=O. For example, oligomers of Formula I wherein X is NH and Y is C=O are especially preferred.

Also preferred are those oligomers of Formula I wherein A$_1$ or A$_2$ are, independently, optionally substituted o-, m-, or p-phenylene. Those oligomers wherein A$_1$ or A$_2$ are optionally substituted m-phenylene are especially preferred.

Preferred oligomers of Formula I are also those wherein one of A$_1$ and A$_2$ is substituted arylene and the other of A$_1$ and A$_2$ is —(CH$_2$)$_q$—, wherein q is 1 or 2, wherein one of A$_1$ and A$_2$ is substituted with one or two polar (PL) group(s), and the other of A$_1$ and A$_2$ is substituted with one or two non-polar (NPL) group(s).

Preferred are oligomers of Formula I wherein (i) R$^1$ is hydrogen, a polar (PL) group, or a non-polar (NPL) group, and R$^2$ is —X-A$_1$-Y—R$^{11}$, wherein R$^{11}$ is hydrogen, a polar (PL) group, or a non-polar (NPL) group. Especially preferred are oligomers of Formula I wherein R$^1$ is hydrogen, R$^2$ is —X-A$_1$-Y—R$^{11}$, and R$^{11}$ is a polar (PL) group, for example, amino.

In some embodiments, preferred oligomers of Formula I are those wherein R$^1$ and R$^2$ are, independently, hydrogen, a polar (PL) group, or a non-polar (NPL) group. Especially preferred are oligomers of Formula I wherein R$^1$ is hydrogen, and R$^2$ is a polar group, for example, amino.

In other aspects of the invention, preferred oligomers of Formula I are those wherein NPL is —$(NR^{3'})_{q1NPL}$—$U^{NPL}$—$(CH_2)_{pNPL}$—$(NR^{3"})_{q2NPL}$—R$^{4'}$, and R$^3$, R$^{3'}$, R$^{3"}$, R$^{4'}$, U$^{NPL}$, pNPL, q1NPL, and q2NPL are as defined above. Especially preferred are those oligomers of Formula I wherein q1NPL and q2NPL are 0, so that NPL is —$U^{NPL}$—$(CH_2)_{pNPL}$—R$^{4'}$.

Preferred values for each of R$^3$, R$^{3'}$, and R$^{3"}$ are hydrogen, C$_1$-C$_6$ alkyl, and C$_1$-C$_6$ alkoxy. Hydrogen is an especially preferred value for R$^3$, R$^{3'}$, and R$^{3"}$.

Preferred values of R$^{4'}$ are hydrogen, C$_1$-C$_{10}$ alkyl, C$_3$-C$_{18}$ branched alkyl, C$_2$-C$_{10}$ alkenyl, C$_2$-C$_{10}$ alkynyl, C$_3$-C$_8$ cycloalkyl, C$_6$-C$_{10}$ aryl, especially phenyl, and heteroaryl, any of which is optionally substituted with one or more C$_1$-C$_6$ alkyl or halo groups. Especially preferred values of R$^{4'}$ are C$_1$-C$_{10}$ alkyl and C$_3$-C$_{18}$ branched alkyl. Suitable C$_1$-C$_{10}$ alkyl and C$_3$-C$_{18}$ branched alkyl groups are methyl, ethyl, n-propyl, isopropyl, n-butyl, tert-butyl, n-pentyl, and isopentyl.

Preferred values of U$^{NPL}$ are NH, —C(=O)—, —C(=O)O—, O, and S. Especially preferred values are NH, —C(=O)—, O, and S, or NH, O, and S. Especially preferred oligomers of Formula I also are those wherein U$^{NPL}$ is absent.

Preferred values of pNPL are 0 to 6; values of pNPL of 0 to 4 are especially preferred, with values of pNPL of 0 to 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred ophthalmic and otic compositions, oligomers of Formula I wherein the —$(CH_2)_{pNPL}$— alkylene chain in NPL is unsubstituted or substituted with one or more alkyl groups are preferred. More preferred are those oligomers of Formula I wherein the —$(CH_2)_{pNPL}$— alkylene chain in NPL is unsubstituted.

An especially preferred value of NPL for the polymers and oligomers of Formula I is C$_1$-C$_6$ alkyl or aryl C$_1$-C$_6$ alkyl. Examples of preferred values for NPL are n-propyl, isopropyl, n-butyl, tert-butyl, and benzyl.

In some embodiments of the invention, preferred oligomers of Formula I are those wherein PL is —$(NR^{5'})_{q1PL}$—$U^{PL}$$(CH_2)_{pPL}$—$(NR^{5"})_{q2PL}$—V, and R$^5$, R$^{5'}$, R$^{5"}$, V, U$^{PL}$, pPL, q1PL, and q2PL are as defined above. Especially preferred are those oligomers of Formula I wherein q1PL and q2PL are 0, so that PL is —$U^{PL}$—$(CH_2)_{pPL}$—V.

Preferred values for R$^5$, R$^{5'}$, and R$^{5"}$ are hydrogen, C$_1$-C$_6$ alkyl, and C$_1$-C$_6$ alkoxy. Hydrogen is an especially preferred value for each of R$^5$, R$^{5'}$, and R$^{5"}$.

Preferred values of U$^{PL}$ are O, S, NH, —C(=O)O—, and —C(=O). Especially preferred values are NH, —C(=O)—, O, and S, or NH, O, and S. Preferred oligomers of Formula I are also those wherein U$^{PL}$ is absent.

Preferred values of V are amino, C$_1$-C$_6$ alkylamino, C$_1$-C$_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, and semicarbazone, preferably any of which is optionally substituted with one or more of amino, halo, cyano, nitro, hydroxy, —NH(CH$_2$)$_p$NH$_2$, —N(CH$_2$CH$_2$NH$_2$)$_2$, amidino, guanidino, guanyl, aminosulfonyl, aminoalkoxy, lower acylamino, or benzyloxycarbonyl.

Especially preferred values of V are amino, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidino. Values of V that are most preferred are amino and guanidino.

Preferred values of pPL are 0 to 6, with values of pPL of 2 to 5 especially preferred.

Preferred values of q1PL and q2PL are 0 or 1. Values of q1PL and q2PL of 0 or 1 are especially preferred, with a value of 0 being especially preferred for each of q1PL and q2PL.

In preferred ophthalmic compositions, oligomers of Formula I wherein the —(CH$_2$)$_{pPL}$— alkylene chain in PL is optionally substituted with one or more amino groups are preferred.

Thus, preferred ophthalmic or otic compositions comprise an oligomer of Formula I, or an acceptable salt or solvate thereof, wherein:

X is NR$^8$, Y is C=O, and R$^8$ is hydrogen;

A$_1$ is optionally substituted o-, m-, or p-phenylene and A$_2$ is —(CH$_2$)$_q$—, wherein q is 1, and wherein one of A$_1$ and A$_2$ is substituted with one or two polar (PL) group(s), and the other of A$_1$ and A$_2$ is substituted with one or two non-polar (NPL) group(s); or A$_2$ is optionally substituted o-, m-, or p-phenylene and A$_1$ is —(CH$_2$)$_q$—, wherein q is 1, and wherein one of A$_1$ and A$_2$ is substituted with one or two polar (PL) group(s), and the other of A$_1$ and A$_2$ is substituted with one or two non-polar (NPL) group(s);

R$^1$ and R$^2$ are, independently, hydrogen, a polar (PL) group, or a non-polar (NPL) group;

NPL is —(NR$^{3'}$)$_{q1NPL}$—U$^{NPL}$—(CH$_2$)$_{pNPL}$—(NR$^{3''}$)$_{q2NPL}$—R$^{4'}$, wherein:

R$^{4'}$ is selected from C$_1$-C$_{10}$ alkyl, C$_3$-C$_{18}$ branched alkyl, C$_2$-C$_{10}$ alkenyl, C$_2$-C$_{10}$ alkynyl, and C$_6$-C$_{10}$ aryl, any of which is optionally substituted with one or more alkyl or halo groups;

U$^{NPL}$ is absent or selected from NH, —C(=O)—, O, and S;

the —(CH$_2$)$_{pNPL}$— alkylene chain is optionally substituted with one or more amino groups;

pNPL is 0 to 8;

q1NPL and q2NPL are 0;

PL is —(NR$^{5'}$)$_{q1PL}$—U$^{PL}$—(CH$_2$)$_{pPL}$—(NR$^{5'}$)$_{q2PL}$—V, wherein:

U$^{PL}$ is absent or selected from O, S, NH, and —C(=O);

V is selected from amino, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidino;

the —(CH$_2$)$_{pPL}$— alkylene chain is optionally substituted with one or more amino groups;

pPL is 0 to 8;

q1PL and q2PL are 0; and m is 4 or 5;

and an ophthalmically or otically acceptable excipient.

Preferred ophthalmic or otic compositions also comprise an oligomer of Formula I, or an acceptable salt or solvate thereof, wherein:

X is NR$^8$, Y is C=O, and R$^8$ is hydrogen;

A$_1$ is optionally substituted o-, m-, or p-phenylene and A$_2$ is —(CH$_2$)$_q$—, wherein q is 1 or 2, and wherein one of A$_1$ and A$_2$ is substituted with one polar (PL) group, and the other of A$_1$ and A$_2$ is substituted with one non-polar (NPL) group; or A$_2$ is optionally substituted o-, m-, or p-phenylene and A$_1$ is —(CH$_2$)$_q$—, wherein q is 1 or 2, and wherein one of A$_1$ and A$_2$ is substituted with one polar (PL) group, and the other of A$_1$ and A$_2$ is substituted with one non-polar (NPL) group;

R$^1$ and R$^2$ are, independently, hydrogen or amino;

NPL is —U$^{NPL}$—(CH$_2$)$_{pNPL}$—R$^{4'}$, wherein:

R$^{4'}$ is selected from C$_1$-C$_{10}$ alkyl and C$_3$-C$_{18}$ branched alkyl, any of which is optionally substituted with one or more alkyl or halo groups;

U$^{NPL}$ is absent or selected from NH, —C(=O)—, O, and S;

the —(CH$_2$)$_{pNPL}$— alkylene chain is unsubstituted;

pNPL is 0 to 8;

q1NPL and q2NPL are 0;

PL is —U$^{PL}$—(CH$_2$)$_{pPL}$—V, wherein:

U$^{PL}$ is absent or selected from O, S, NH, and —C(=O);

V is selected from amino, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidino;

the —(CH$_2$)$_{pPL}$— alkylene chain is optionally substituted with one or more amino groups;

pPL is 0 to 8;

q1PL and q2PL are 0; and m is 4 or 5;

and an ophthalmically or otically acceptable excipient.

In other aspects of the present invention, the ophthalmic or otic composition comprises a polymer or oligomer of Formula II:

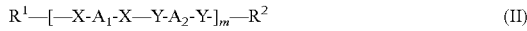

$$R^1\text{—}[\text{—}X\text{-}A_1\text{-}X\text{—}Y\text{-}A_2\text{-}Y\text{-}]_m\text{—}R^2 \quad (II)$$

or an acceptable salt or solvate thereof, wherein:

X is NR$^8$, O, S, —N(R$^8$)N(R$^8$)—, —N(R$^8$)—(N=N)—, —(N=N)—N(R$^8$)—, —C(R$^7$R$^{7'}$)NR$^8$—, —C(R$^7$R$^{7'}$)O—, or —C(R$^7$R$^{7'}$)S—; and Y is C=O, C=S, O=S=O, —C(=O)C(=O)—, C(R$^6$R$^{6'}$)C=O or C(R$^6$R$^{6'}$)C=S; or X and Y are taken together to be pyromellitic diimide;

wherein

R$^8$ is hydrogen or alkyl;

R$^7$ and R$^{7'}$ are, independently, hydrogen or alkyl, or

R$^7$ and R$^{7'}$ together are —(CH$_2$)$_p$—, wherein p is 4 to 8; and

R$^6$ and R$^{6'}$ are, independently, hydrogen or alkyl, or

R$^6$ and R$^{6'}$ together are (CH$_2$)$_2$NR$^{12}$(CH$_2$)$_2$, wherein R$^{12}$ is hydrogen, —C(=N)CH$_3$ or C(=NH)—NH$_2$;

A$_1$ and A$_2$ are, independently, optionally substituted arylene or optionally substituted heteroarylene, wherein A$_1$ and A$_2$ are, independently, optionally substituted with one or more polar (PL) group(s), one or more non-polar (NPL) group(s), or a combination of one or more polar (PL) group(s) and one or more non-polar (NPL) group(s);

R$^1$ is (i) hydrogen, a polar group (PL), or a non-polar group (NPL), and R$^2$ is —X-A$_1$-X—R$^1$, wherein A$_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and R$^2$ is —X-A'-X—R$^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s);

(iii) —Y-A$_2$-Y—R$^2$, and R$^2$ is hydrogen, a polar group (PL), or a non-polar group (NPL); or (iv) —Y-A' and R$^2$ is —X-A', wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (v) R$^1$ and R$^2$ are, independently, a polar group (PL) or a non-polar group (NPL); or (vi) R$^1$ and R$^2$ together form a single bond;

NPL is a nonpolar group independently selected from —B(OR$^4$)$_2$ and —(NR$^{3'}$)$_{q1NPL}$—U$^{NPL}$—(CH$_2$)$_{pNPL}$—(NR$^{3''}$)$_{qNPL}$—R$^{4'}$, wherein:

R$^3$, R$^{3'}$, and R$^{3''}$ are independently selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more alkyl, amino, or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^5$)$_{q1PL}$—U$^{PL}$—(CH$_2$)$_{pPL}$—(NR$^{5'}$)$_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are, independently, 0, 1, or 2; and m is 1 to about 500; and an ophthalmically or otically acceptable excipient.

US Patent Publ. No. US 2006-0041023 A1 discloses antimicrobial polymers and oligomers of Formula II that can be used in the compositions of the present invention. For example, oligomers of Formula II that are preferred for use in the ophthalmic or otic compositions of the present invention are those wherein m is 1 to about 25, 1 to about 20, 1 to about 10, 1 to about 5, or 1, 2, or 3.

Thus, preferred ophthalmic or otic compositions of the present invention also comprise an oligomer of Formula IIa:

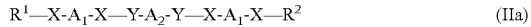

$$R^1\text{—}X\text{-}A_1\text{—}X\text{—}Y\text{-}A_2\text{-}Y\text{—}X\text{-}A_1\text{-}X\text{—}R^2 \quad \text{(IIa)}$$

or an acceptable salt or solvate thereof, wherein:

X is NR$^8$, O, S, or —N(R$^8$)N(R$^8$)—; and Y is C=O, C=S, or O=S=O; wherein R$^8$ is hydrogen or alkyl;

$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);

$R^1$ is a polar group (PL) or a non-polar group (NPL); and $R^2$ is $R^1$;

NPL is a nonpolar group —(NR$^3$)$_{q1NPL}$—U$^{NPL}$—(CH$_2$)$_{pNPL}$—(NR$^{3''}$)$_{q2NPL}$—R$^{4'}$, wherein:

$R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$— alkylene chain is optionally substituted with one or more alkyl, amino, or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^5$)$_{q1n}$—U$^{PL}$—(CH$_2$)$_{pPL}$—(NR$^{5'}$)$_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are, independently, 0, 1, or 2;

and an ophthalmically or otically acceptable excipient.

Preferred oligomers of Formula IIa for use in the ophthalmic or otic compositions of the present invention are those wherein X is NR$^8$ and Y is C=O. For example, oligomers of Formula IIa wherein X is NH and Y is C=O are especially preferred.

Preferred also are those oligomers of Formula IIa wherein $A_1$ and $A_2$ are independently optionally substituted o-, m-, or p-phenylene. Those oligomers wherein $A_1$ and $A_2$ are optionally substituted m-phenylene are especially preferred.

Also preferred are those oligomers of Formula IIa wherein one of $A_1$ and $A_2$ is o-, m-, or p-phenylene, and the other of $A_1$ and $A_2$ is o-, m-, or p-heteroarylene. Preferred heteroarylene groups include, but are not limited to, pyridinylene, pyrimidinylene, and pyrazinylene. An especially preferred heteroarylene group is pyrimidinylene, in particular, m-pyrimidinylene.

Also preferred are oligomers of Formula IIa wherein $A_1$ and $A_2$ are, independently, optionally substituted arylene or optionally substituted heteroarylene, and (i) one of $A_1$ and $A_2$ is substituted with one or more polar (PL) group(s) and one or more nonpolar (NPL) group(s) and the other of $A_1$ and $A_2$ is unsubstituted; or (ii) one of $A_1$ and $A_2$ is substituted with one or more polar (PL) group(s) and one or more nonpolar (NPL) group(s) and the other of $A_1$ and $A_2$ is substituted with one or more polar (PL) group(s). Especially preferred are oligomers in which either (i) one of $A_1$ and $A_2$ is substituted with one polar (PL) group and one nonpolar (NPL) group, and the other of $A_1$ and $A_2$ is unsubstituted, or (ii) one of $A_1$ and $A_2$ is substituted with one polar (PL) group and one nonpolar (NPL) group and the other of $A_1$ and $A_2$ is substituted with one or two polar (PL) group(s), as defined above.

Preferred oligomers of Formula IIa are also those wherein $R^1$ is hydrogen or a polar group (PL). Especially preferred oligomers are those wherein $R^1$ is —$(NR^5)_{q1PL}$—$U^{PL}$—$(CH_2)_{pPL}$—$(NR^{5''})_{q2PL}$—V, wherein $R^5$, $R^{5'}$, $R^{5''}$, V, $U^{PL}$, and pPL are as defined above, and q1PL and q2PL are each 0, so that especially preferred oligomers of Formula IIa are those wherein $R^1$ is —$U^{PL}$—$(CH_2)_{pPL}$—V. Preferred $R^1$ polar groups are those wherein $U^{PL}$ is absent or is O, S, NH, —C(=O)O—, or —C(=O); pPL is 0 to 6, especially 1 to 4; and V is amino, aminoalkyl, amidino, guanidino, aryl, or heteroaryl optionally substituted with one or more amino, guanidino, amidino, or halo groups.

Preferred values for each of $R^3$, $R^{3'}$, and $R^{3''}$ are hydrogen, $C_1$-$C_6$ alkyl, and $C_1$-$C_6$ alkoxy. Hydrogen is an especially preferred value for $R^3$, $R^{3'}$, and $R^{3''}$.

Preferred values of $R^{4'}$ are hydrogen and alkyl optionally substituted with one or more alkyl or halo groups. More preferred values of $R^{4'}$ are hydrogen, $C_1$-$C_{10}$ alkyl, $C_3$-$C_{18}$ branched alkyl, $C_2$-$C_{10}$ alkenyl, $C_2$-$C_{10}$ alkynyl, and $C_6$-$C_{10}$ aryl, especially phenyl. Especially preferred values of $R^{4'}$ are $C_1$-$C_{10}$ alkyl and $C_3$-$C_{18}$ branched alkyl. Suitable $C_1$-$C_{10}$ alkyl and $C_3$-$C_{18}$ branched alkyl groups are methyl, ethyl, n-propyl, isopropyl, n-butyl, tert-butyl, and n-pentyl.

Preferred oligomers of Formula IIa are those wherein $U^{NPL}$ is absent. In other embodiments, preferred oligomers of Formula IIa are those wherein $U^{NPL}$ is O, S, NH, —C(=O)—, —C(=O)O—, —$R^3$S—, or —$R^3$O—. Especially preferred values of $U^{NPL}$ are O, —C(=O)—, and —C(=O)O—.

Preferred values of pNPL are 0 to 6; values of pNPL of 0 to 4 are especially preferred, with values of pNPL of 0, 1 or 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred oligomers of Formula IIa, the —$(CH_2)_{pNPL}$— alkylene chain in NPL is unsubstituted or substituted with one or more alkyl groups.

An especially preferred value of NPL for oligomers of Formula II is $C_1$-$C_6$ alkyl optionally substituted with one or more halo groups. Examples of preferred values for NPL are n-propyl, isopropyl, n-butyl, tert-butyl, and trifluoromethyl.

Preferred oligomers of Formula IIa are those wherein PL is —$(NR^{5'})_{q1PL}$—$U^{PL}$—$(CH_2)_{pPL}$—$(NR^{5''})_{q2PL}$—V, and $R^5$, $R^{5'}$, $R^{5''}$, V, $U^{PL}$, pPL, q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, $NR^5$, —C(=O)—, —C(=O)—N=N—NH—, —C(=O)—NH—N=N—, —N=N—NH—, —C(=N—N($R^5$)$_2$)—, —C(=$NR^5$)—, —C(=O)O—, —$R^5$S—, and —$R^5$O—, wherein $R^5$ is hydrogen. Especially preferred values of $U^{PL}$ are O, S, NH, —C(=O)O—, and —C(=O). Preferred oligomers of Formula IIa are also those wherein $U^{PL}$ is absent.

Preferred values of V are nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, $C_6$-$C_{10}$ aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Values of V that are more preferred are amino, $C_1$-$C_6$ alkylamino, —NH(CH$_2$)$_p$NH$_2$ wherein p is 1 to 4, —N(CH$_2$CH$_2$NH$_2$)$_2$, diazamino, amidino, and guanidino, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanyl, guanidino, or aminoalkoxy. Values of V that are most preferred are amino and guanidino.

Preferred values of pPL are 0 to 6; values of pPL of 0 to 4 are especially preferred, with values of pPL of 2 to 4 especially preferred.

Preferred values of q1PL and q2PL are 0 or 1. Values of q1PL and q2PL of 0 or 1 are especially preferred, with a value of 0 being especially preferred for each of q1PL and q2PL.

In preferred polymers and oligomers of Formula IIa, the —$(CH_2)_{pPL}$— alkylene chain in PL is optionally substituted with one or more amino or hydroxy groups.

Thus, preferred ophthalmic or otic compositions comprise an oligomer of Formula IIa, or an acceptable salt or solvate thereof, wherein:

X is $NR^8$, and Y is C=O; wherein $R^8$ is hydrogen or ($C_1$-$C_4$)alkyl;

$A_1$ and $A_2$ are, independently, optionally substituted phenylene or optionally substituted pyrimidinylene, wherein $A_1$ is substituted with one or more polar (PL) group(s) and one or more non-polar (NPL) group(s), and $A_2$ is substituted with one or more polar (PL) group(s) or is unsubstituted;

$R^1$ is a polar group (PL); and $R^2$ is $R^1$;

NPL is a nonpolar group —$(NR^3)_{q1NPL}$—$U^{NPL}$—$(CH_2)_{pNPL}$—$(NR^{3''})_{q2NPL}$—$R^{4'}$, wherein:

$R^4$ and $R^{4'}$ are, independently, selected from hydrogen and alkyl optionally substituted with one or more alkyl or halo groups;

$U^{NPL}$ is absent or selected from O, S, $NR^3$, and —C(=O)—; pNPL is 0 to 6;

q1NPL and q2NPL are, independently, 0;

PL is a polar group —$(NR^5)_{q1PL}$—$U^{PL}$—$(CH_2)_{pPL}$—$(NR^{5'})_{q2PL}$—V, wherein:

$U^{PL}$ is absent or selected from O, S, $NR^5$, and —C(=O)—;

V is selected from amino, alkylamino, dialkylamino, —NH(CH$_2$)$_p$NH$_2$ wherein p is 1 to 4, —N(CH$_2$CH$_2$NH$_2$)$_2$, diazamino, amidino, and guanidino, any of which is optionally substituted with one or more of amino, halo, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylhio, and lower acylamino;

pPL is 0 to 8; and q1PL and q2PL are, independently, 0;

and an ophthalmically or otically acceptable excipient.

In some embodiments, preferred ophthalmic or otic compositions of the present invention comprise an oligomer of Formula IIa, or an acceptable salt or solvate thereof, wherein:

$A_1$ is phenylene substituted with one (PL) group and one non-polar (NPL) group, and $A_2$ is unsubstituted pyrimidinylene or pyrimidinylene substituted with one or two polar (PL) group(s);

NPL is $R^{4'}$, wherein $R^{4'}$ is $(C_1-C_6)$alkyl optionally substituted with one or more halo groups;

PL is $-U^{PL}-(CH_2)_{pPL}-V$, wherein:

$U^{PL}$ is O or S;

V is selected from amino, amidino, and guanidino; and pPL is 0 to 6;

and an ophthalmically or otically acceptable excipient.

Examples of oligomers of Formula IIa for use in the ophthalmic or otic compositions of the present invention include

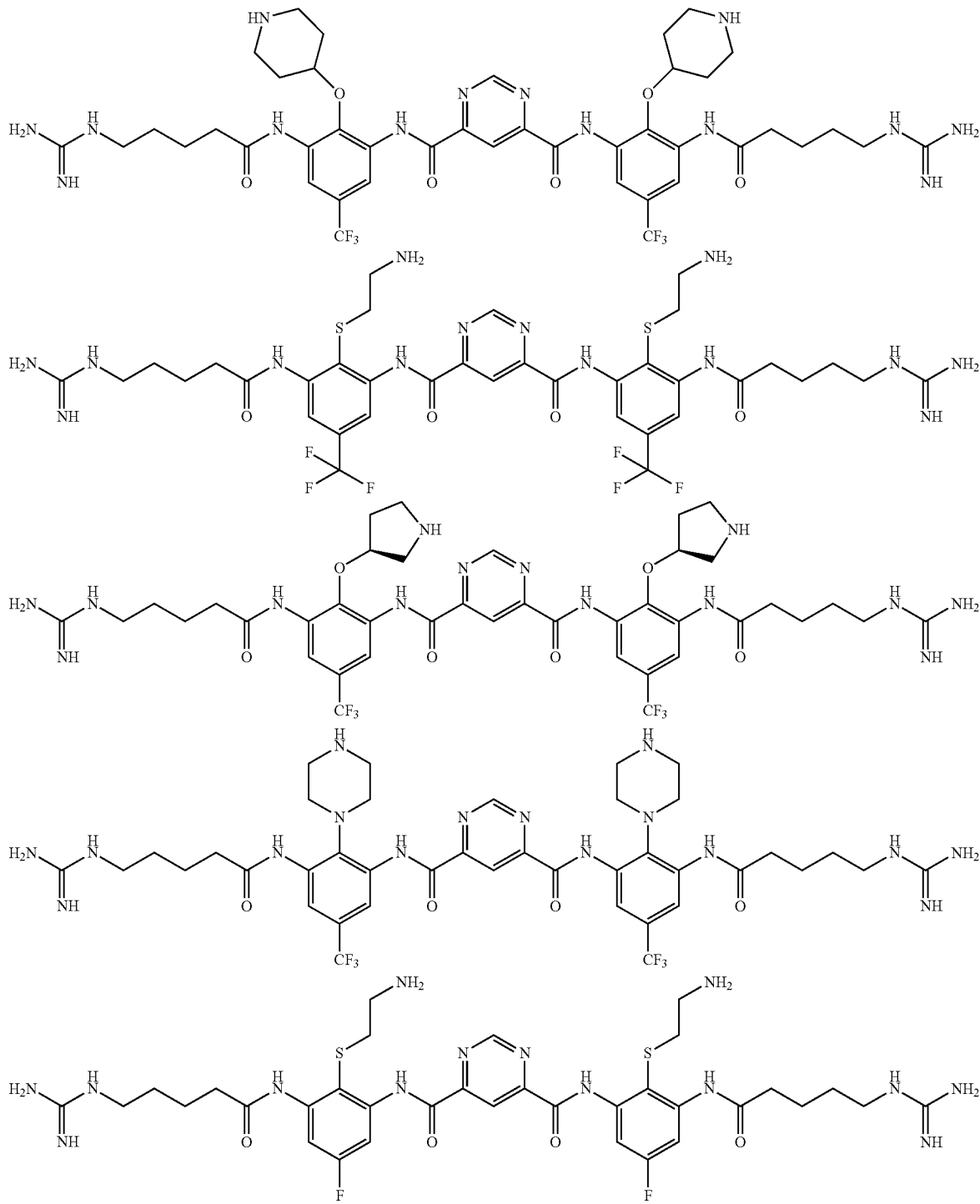

and

-continued

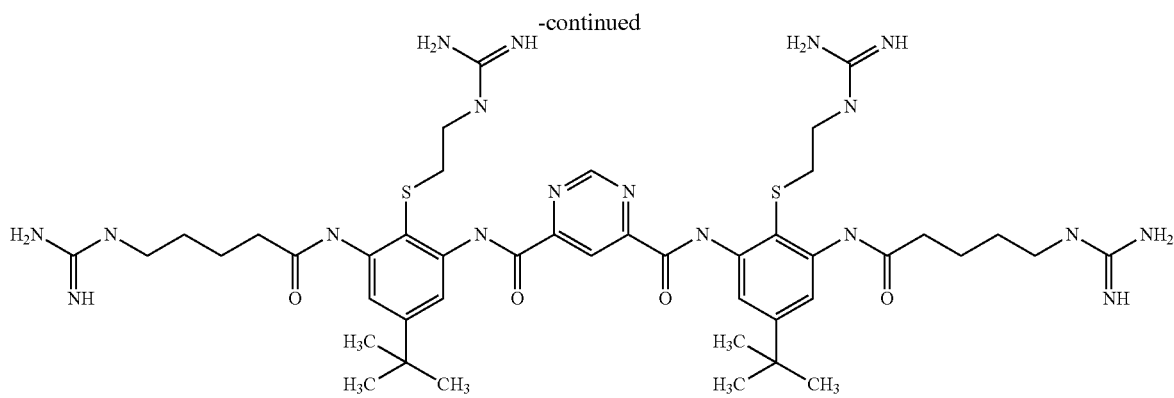

and ophthalmically or otically acceptable salts thereof.

In other embodiments, preferred ophthalmic or otic compositions comprise an oligomer of Formula IIa, or an acceptable salt or solvate thereof, wherein:

$A_1$ is phenylene substituted with one (PL) group and one non-polar (NPL) group, and $A_2$ is unsubstituted phenylene or phenylene substituted with one or two polar (PL) group(s);

NPL is $R^{4'}$, wherein $R^{4'}$ is $(C_1-C_6)$alkyl optionally substituted with one or more halo groups;

PL is —$U^{PL}$—$(CH_2)_{pPL}$—V, wherein:

$U^{PL}$ is O or S;

V is selected from amino, amidino, and guanidino; and pPL is 0 to 6; and an ophthalmically or otically acceptable excipient.

In some of these embodiments, preferred ophthalmic or otic compositions comprise oligomers of Formula IIa wherein $A_1$ is phenylene substituted with one (PL) group and one non-polar (NPL) group, and $A_2$ is phenylene substituted with one or two polar (PL) group(s). Oligomers of Formula IIa falling within the scope of these embodiments include to following:

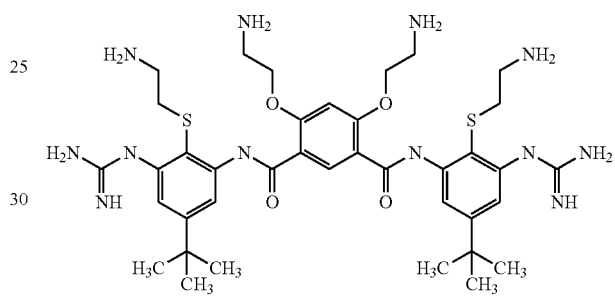

and ophthalmically or otically acceptable salts thereof.

In other embodiments, preferred ophthalmic or otic compositions comprise oligomers wherein $A_1$ is phenylene substituted with one (PL) group and one non-polar (NPL) group, and $A_2$ is unsubstituted phenylene. Oligomers falling within the scope of these embodiments include the following:

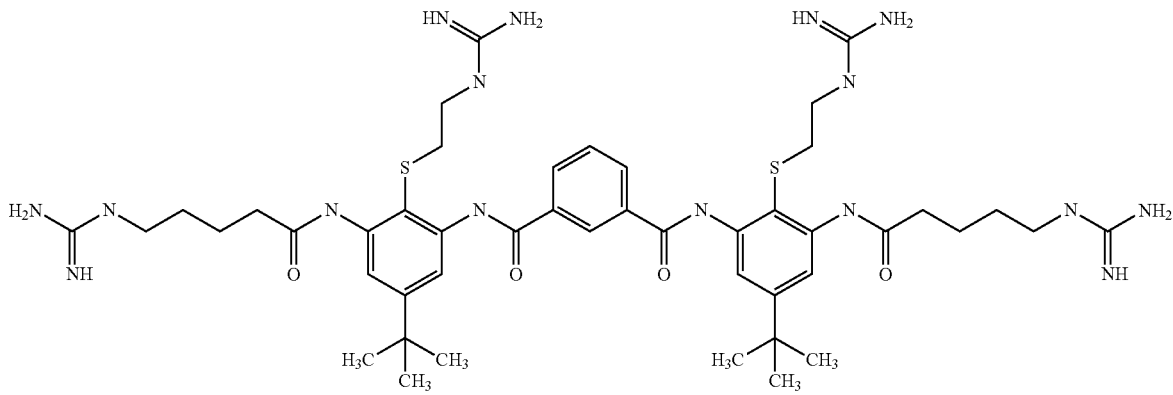 [SMILES: CC(C)(C)c1cc(NC(=O)CCCCNC(=N)N)c(SCCNC(=N)N)c(NC(=O)c2cccc(C(=O)Nc3cc(C(C)(C)C)cc(NC(=O)CCCCNC(=N)N)c3SCCNC(=N)N)c2)c1]

and ophthalmically or otically acceptable salts thereof.

In other aspects, the ophthalmic or otic compositions of the present invention comprise a polymer or oligomer of Formula IV:

$$R^1—[-X-A_1-X—Z—Y-A_2-Y—Z]_m—R^2 \quad \text{(IV)}$$

or an acceptable salt or solvate thereof, wherein:

X is NR$^8$, —NR$^8$NR$^8$—, C=O, or O; Y is NR$^8$, —NR$^8$NR$^8$—, C=O, S, or O; and R$^8$ is hydrogen or alkyl;

Z is C=O, C=S, O=S=O, —NR$^8$NR$^8$—, or —C(=O)C(=O)—;

A$_1$ and A$_2$ are, independently, optionally substituted arylene or optionally substituted heteroarylene, wherein A$_1$ and A$_2$ are, independently, optionally substituted with one or more polar (PL) group(s), one or more non-polar (NPL) group(s), or a combination of one or more polar (PL) group(s) and one or more non-polar (NPL) group(s);

R$^1$ is
(i) hydrogen, a polar group (PL), or a non-polar group (NPL), and R$^2$ is —X-A$_1$-X—R$^1$, wherein A$_1$ is as defined above and is optionally substituted with one or more polar (PL) group(s), one or more non-polar (NPL) group(s), or a combination of one or more polar (PL) group(s) and one or more non-polar (NPL) group(s); or
(ii) hydrogen, a polar group (PL), or a non-polar group (NPL), and R$^2$ is —X-A$_1$-X—Z—Y-A$_2$-Y—R$^1$, wherein A$_1$ and A$_2$ are as defined above, and each of which is optionally substituted with one or more polar (PL) group(s), one or more non-polar (NPL) group(s), or a combination of one or more polar (PL) group(s) and one or more non-polar (NPL) group(s); or
(iii) hydrogen, a polar group (PL), or a non-polar group (NPL), and R$^2$ is —X-A'-X—R$^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or
(iv) hydrogen, a polar group (PL), or a non-polar group (NPL), and R$^2$ is —X-A$_1$-X—Z—Y— A'-Y—R$^1$, wherein A$_1$ is as defined above, A' is aryl or heteroaryl, and each of A$_1$ and A' is optionally substituted with one or more polar (PL) group(s), one or more non-polar (NPL) group(s), or a combination of one or more polar (PL) group(s) and one or more non-polar (NPL) group(s); or
(v) —Z—Y-A' and R$^2$ is hydrogen, a polar group (PL), or a non-polar group (NPL), wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or
(vi) —Z—Y-A', and R$^2$ is —X-A", wherein A' and A" are, independently, aryl or heteroaryl, and each of A' and A" is optionally substituted with one or more polar (PL) group(s), one or more non-polar (NPL) group(s), or a combination of one or more polar (PL) group(s) and one or more non-polar (NPL) group(s); or
(vii) R$^1$ and R$^2$ are, independently, a polar group (PL) or a non-polar group (NPL); or
(viii) R$^1$ and R$^2$ together form a single bond;

NPL is a nonpolar group independently selected from —B(OR$^4$)$_2$ and —(NR$^{3'}$)$_{q1NPL}$—U$^{NPL}$—(CH$_2$)$_{pNPL}$—(NR$^{3''}$)$_{q2NPL}$—R$^{4'}$, wherein:

R$^3$, R$^{3'}$, and R$^{3''}$ are, independently, selected from hydrogen, alkyl, and alkoxy;

R$^4$ and R$^{4'}$ are, independently, selected from hydrogen, alkyl, alkenyl, alkynyl, cycloalkyl, aryl, and heteroaryl, any of which is optionally substituted with one or more alkyl or halo groups;

U$^{NPL}$ is absent or selected from O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —C(=O)—NR$^3$—O—, wherein groups with two chemically nonequivalent termini can adopt both possible orientations;

the —(CH$_2$)$_{pNPL}$—alkylene chain is optionally substituted with one or more alkyl, amino, or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

R$^5$, R$^{5'}$, and R$^{5''}$ are, independently, selected from the group consisting of hydrogen, alkyl, and alkoxy;

U$^{PL}$ is absent or selected from O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —C(=O)—NR$^5$—O—, wherein groups with two chemically nonequivalent termini can adopt both possible orientations;

V is selected from nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are, independently, 0, 1, or 2; and m is 1 to about 500;

and an ophthalmically or otically acceptable excipient.

US Application Publ. No. US 2006-0041023 A1 discloses antimicrobial polymers and oligomers of Formula IV that can be used in the compositions of the present invention.

For example, oligomers that are preferred for use in the ophthalmic or otic compositions of the present invention are those oligomers of Formula IV wherein m is 1 to about 25, 1 to about 20, 1 to about 10, 1 to about 5, or 1, 2, or 3.

Thus, preferred ophthalmic or otic compositions also comprise an oligomer of Formula IV having Formula IVa, Formula IVb, or Formula IVc:

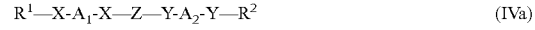

R$^1$—X-A$_1$-X—Z—Y-A$_2$-Y—R$^2$ (IVa)

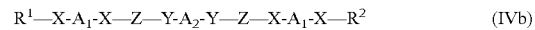

R$^1$—X-A$_1$-X—Z—Y-A$_2$-Y—Z—X-A$_1$-X—R$^2$ (IVb)

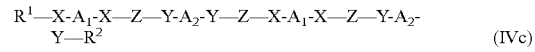

R$^1$—X-A$_1$-X—Z—Y-A$_2$-Y—Z—X-A$_1$-X—Z—Y-A$_2$-Y—R$^2$ (IVc)

or an acceptable salt or solvate thereof,
wherein:

X is NR$^8$, —NR$^8$NR$^8$—, C=O, or O; Y is NR$^8$, —NR$^8$NR$^8$—, C=O, S, or O; and R$^8$ is hydrogen or alkyl;

Z is C=O, C=S, O=S=O, —NR$^8$NR$^8$—, or —C(=O)C(=O)—;

A$_1$ and A$_2$ are, independently, optionally substituted arylene or optionally substituted heteroarylene, wherein A$_1$ and A$_2$ are, independently, optionally substituted with one or more polar (PL) group(s), one or more non-polar (NPL) group(s), or a combination of one or more polar (PL) group(s) and one or more non-polar (NPL) group(s);

$R^1$ is hydrogen, a polar group (PL), or a non-polar group (NPL), and $R^2$ is $R^1$;

NPL is a nonpolar group $-(NR^{3'})_{q1NPL}-U^{NPL}-(CH_2)_{pNPL}-(NR^{3''})_{q2NPL}-R^{4'}$, wherein:

$R^3$, $R^{3'}$, and $R^{3''}$ are, independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), S(=O)$_2$, $NR^3$, $-C(=O)-$, $-C(=O)-N=N-NR^3-$, $-C(=O)-NR^3-N=N-$, $-N=N-NR^3-$, $-C(=N-N(R^3)_2)-$, $-C(=NR^3)-$, $-C(=O)O-$, $-C(=O)S-$, $-C(=S)-$, $-O-P(=O)_2O-$, $-R^3O-$, $-R^3S-$, $-S-C=N-$, and $-C(=O)-NR^3-O-$, wherein groups with two chemically nonequivalent termini can adopt both possible orientations;

the $-(CH_2)_{pNPL}-$ alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and $-(NR^{5'})_{q1PL}-U^{PL}-(CH_2)_{pPL}-(NR^{5''})-V$, wherein:

$R^5$, $R^{5'}$, and $R^{5''}$ are, independently, selected from hydrogen, alkyl, and alkoxy;

$U^{PL}$ is absent or selected from O, S, S(=O), S(=O)$_2$, $NR^5$, $-C(=O)-$, $-C(=O)-N=N-NR^5-$, $-C(=O)-NR^5-N=N-$, $-N=N-NR^5-$, $-C(=N-N(R^5)_2)-$, $-C(=NR^5)-$, $-C(=O)O-$, $-C(=O)S-$, $-C(=S)-$, $-O-P(=O)_2O-$, $-R^5O-$, $-R^5S-$, $-S-C=N-$, and $-C(=O)-NR^5-O-$, wherein groups with two chemically nonequivalent termini can adopt both possible orientations;

V is selected from nitro, cyano, amino, hydroxy, alkoxy, alkylthio, alkylamino, dialkylamino, $-NH(CH_2)_pNH_2$ wherein p is 1 to 4, $-N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxy, $-NH(CH_2)_pNH_2$ wherein p is 1 to 4, $-N(CH_2CH_2NH_2)_2$, amidino, guanidino, guanyl, aminosulfonyl, aminoalkoxy, aminoalkylthio, lower acylamino, or benzyloxycarbonyl;

the $-(CH_2)_{pPL}-$ alkylene chain is optionally substituted with one or more amino or hydroxy groups, or is unsaturated;

pPL is 0 to 8; and q1PL and q2PL are, independently, 0, 1, or 2;

and an ophthalmically or otically acceptable excipient.

US Application Publ. No. US 2006-0041023 A1 discloses antimicrobial polymers and oligomers of Formulae IVa, IVb, and IVc that can be used in the compositions of the present invention.

Preferred ophthalmic or otic compositions comprise oligomers of Formulae IVa, IVb and IVc wherein X and Y are, independently, $NR^8$, C=O, or O; Z is C=O or $-NR^8NR^8$; and $R^8$ is hydrogen or $C_1$-$C_6$ alkyl. Especially preferred for use in the ophthalmic or otic compositions are those oligomers wherein X and Y are each $NR^8$, Z is C=O, and $R^8$ is hydrogen. Also preferred are oligomers wherein X and Y are each C=O, and Z is $-N(R^8)N(R^8)-$, especially wherein $R^8$ is hydrogen.

Also preferred for use in the ophthalmic or otic compositions are those oligomers of Formulae IVa, IVb and IVc wherein $A_1$ and $A_2$ are independently optionally substituted o-, m-, or p-phenylene. Those oligomers wherein $A_1$ and $A_2$ are optionally substituted m-phenylene are especially preferred. Also preferred are polymers and oligomers of Formula IV wherein one of $A_1$ and $A_2$ is o-, m-, or p-phenylene, and the other of $A_1$ and $A_2$ is heteroarylene. Preferred heteroarylene groups include, but are not limited to, pyridinylene, pyrimidinylene, and pyrazinylene.

Also preferred are oligomers of Formulae IVa, IVb and IVc wherein $A_1$ and $A_2$ are, independently, optionally substituted arylene or optionally substituted heteroarylene, and (i) each of $A_1$ and $A_2$ is substituted with one or two polar (PL) group(s) and one or two nonpolar (NPL) group(s); or (ii) one of $A_1$ and $A_2$ is substituted with one or two polar (PL) group(s) and the other of $A_1$ and $A_2$ is substituted with one or two nonpolar (NPL) group(s).

Preferred ophthalmic or otic compositions also comprise oligomers of Formulae IVa, IVb and IVc are those wherein $R^1$ is hydrogen or a polar group (PL). Especially preferred oligomers are those wherein $R^1$ is $-(NR^{5'})_{q1PL}-U^{PL}-(CH_2)_{pPL}-(NR^{5''})_{q2PL}-V$, wherein $R^5$, $R^{5'}$, $R^{5''}$, V, $U^{PL}$, and pPL are as defined above, and q1PL and q2PL are each 0, so that especially preferred oligomers of Formulae IVa, IVb and IVc are those wherein $R^1$ is $-U^{PL}-(CH_2)_{pPL}-V$. Preferred $R^1$ polar groups are those wherein $U^{PL}$ is absent or is O, S, NH, $-C(=O)O-$, or $-C(=O)$; pPL is 0 to 6, especially 1 to 4; and V is amino, aminoalkyl, amidino, guanidino, aryl, or heteroaryl optionally substituted with one or more amino, guanidino, amidino, or halo groups.

Preferred values for each of $R^3$, $R^{3'}$, and $R^{3''}$ are hydrogen, $C_1$-$C_6$ alkyl, and $C_1$-$C_6$ alkoxy. Hydrogen is an especially preferred value for $R^3$, $R^{3'}$, and $R^{3''}$.

Preferred values of $R^{4'}$ are hydrogen, $C_1$-$C_{10}$ alkyl, $C_3$-$C_{18}$ branched alkyl, $C_2$-$C_{10}$ alkenyl, $C_2$-$C_{10}$ alkynyl, and $C_6$-$C_{10}$ aryl, especially phenyl. Especially preferred values of $R^{4'}$ are $C_1$-$C_{10}$ alkyl and $C_3$-$C_{18}$ branched alkyl. Suitable $C_1$-$C_{10}$ alkyl and $C_3$-$C_{18}$ branched alkyl groups are methyl, ethyl, n-propyl, isopropyl, n-butyl, tert-butyl, and n-pentyl.

Preferred values of $U^{NPL}$ are O, S, NH, $-C(=O)-$, $-C(=O)O-$, $-R^3S-$ and $-R^3O-$. Preferred oligomers of Formulae IVa, IVb and IVc are also those wherein $U^{NPL}$ is absent.

Preferred values of pNPL are 0 to 6; values of pNPL of 0 to 4 are especially preferred, with values of pNPL of 0, 1, or 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred ophthalmic or otic compositions, in the oligomers of Formulae IVa, IVb and IVc, the $-(CH_2)_{pNPL}-$ alkylene chain in NPL is unsubstituted or substituted with one or more alkyl groups. More preferred are those oligomers wherein the $-(CH_2)_{pNPL}-$ alkylene chain in NPL is unsubstituted.

An especially preferred value of NPL for polymers and oligomers of Formulae IVa, IVb and IVc is $C_1$-$C_6$ alkyl. Examples of preferred values for NPL are n-propyl, isopropyl, n-butyl, and tert-butyl.

Preferred oligomers of Formulae IVa, IVb and IVc for use in the ophthalmic or otic compositions are also those wherein PL is $-(NR^{5'})_{q1PL}-U^{PL}-(CH_2)_{pPL}-(NR^{5''})_{q2PL}-V$, and $R^5$, $R^{5'}$, $R^{5''}$, V, $U^{PL}$, pPL, q1PL, and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, NH, —C(=O)—, —C(=O)O—, —$R^5$S—, and —$R^5$O—, wherein $R^5$ is hydrogen or $C_1$-$C_6$ alkyl. Especially preferred values of $U^{PL}$ are O, S, and —C(=O).

Preferred values of V are nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH$(CH_2)_p$NH$_2$ wherein p is 1 to 4, —N(CH$_2$CH$_2$NH$_2$)$_2$, diazamino, amidino, guanidino, guanyl, semicarbazone, $C_6$-$C_{10}$ aryl, heterocycle, and heteroaryl, preferably any of which is optionally substituted with one or more of amino, halo, cyano, nitro, hydroxy, —NH$(CH_2)_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Especially preferred values of V are amino, $C_1$-$C_6$ alkylamino, —NH$(CH_2)_p$NH$_2$ wherein p is 1 to 4, —N(CH$_2$CH$_2$NH$_2$)$_2$, diazamino, amidino, and guanidino, preferably any of which is optionally substituted with one or more of amino, halo, cyano, nitro, hydroxy, —NH$(CH_2)_p$NH$_2$ wherein p is 1 to 4, —N(CH$_2$CH$_2$NH$_2$)$_2$, amidino, guanyl, guanidino, or aminoalkoxy. Values of V that are most preferred are amino and guanidino.

Preferred values of pPL are 0 to 6; values of pPL of 0 to 4 are especially preferred, with values of pPL of 2 to 4 especially preferred.

Preferred values of q1PL and q2PL are 0 or 1. Values of q1PL and q2PL of 0 or 1 are especially preferred, with a value of 0 being especially preferred for each of q1PL and q2PL.

In the preferred ophthalmic or otic compositions of the invention, in the oligomers of Formulae IVa, IVb, and IVc, the —$(CH_2)_{pPL}$— alkylene chain in PL is optionally substituted with one or more amino or hydroxy groups.

Examples of oligomers of Formulae I, II, IIa, IV, IVa, IVb, and IVc that can be used in the ophthalmic or otic compositions of the present invention include, but are not limited to, the individual oligomers disclosed in US Application Publ. No. 2006-0041023 A1 and U.S. Pat. No. 7,173,102.

In some aspects, the ophthalmic or otic compositions of the present invention comprise a polymer or oligomer of Formula V:

$R^1$—[-$A_1$-W-$A_2$-W-]$_m$—$R^2$ (V)

or an acceptable salt or solvate thereof,
wherein:
$A_1$ and $A_2$ are, independently, optionally substituted arylene or optionally substituted heteroarylene, wherein:
(i) $A_1$ and $A_2$ are independently optionally substituted with one or more polar (PL) group(s), one or more non-polar (NPL) group(s), or a combination of one or more polar (PL) group(s) and one or more non-polar (NPL) group(s); or
(ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C$(CH_2)_p$C≡C—, wherein p is 0 to 8, and the —$(CH_2)_p$— alkylene chain is optionally substituted with one or more amino or hydroxyl groups;
W is absent, or represents —$CH_2$—, —$CH_2$—$CH_2$—, —CH=CH—, or —C≡C—;

$R^1$ is
(i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or
(ii) hydrogen, a polar group (PL), or a non-polar group (NPL), and $R^2$ is -$A_1$-W-$A_2$-$R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or
(iii) A'-W— and $R^2$ is -$A_1$-W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or
(iv) A'-W— and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or
(v) $R^1$ and $R^2$ together form a single bond;
NPL is a nonpolar group independently selected from —B(OR$^4$)$_2$ and —(NR$^3$)$_{q1NPL}$—U$^{NPL}$—$(CH_2)_{pNPL}$—(NR$^{3"}$)$_{q2NPL}$—R$^4$, wherein:
$R^3$, $R^{3'}$, and $R^{3"}$ are, independently, selected from hydrogen, alkyl, and alkoxy;
$R^4$ is selected from hydrogen, alkyl, alkenyl, alkynyl, cycloalkyl, aryl, and heteroaryl, any of which is optionally substituted with one or more alkyl or halo groups;
$U^{NPL}$ is absent or selected from O, S, S(=O), S(=O)$_2$, NR$^3$, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N—, and —(C=O)—NR$^3$—O—, wherein groups with two chemically nonequivalent termini can adopt both possible orientations;
the —$(CH_2)_{pNPL}$—alkylene chain is optionally substituted with one or more alkyl, amino or hydroxyl groups, or the alkylene chain is unsaturated;
pNPL is 0 to 8;
q1NPL and q2NPL are, independently, 0 to 2;
PL is a polar group selected from halo, hydroxyethoxymethyl, methoxyethoxymethyl, polyoxyethylene, and —(NR$^{5'}$)$_{con}$—U$^{PL}$—$(CH_2)_{pPL}$—(NR$^{5"}$)$_{q2PL}$—V, wherein:
$R^5$, $R^{5'}$, and $R^{5"}$ are, independently, selected from hydrogen, alkyl, and alkoxy;
$U^{PL}$ is absent or selected from O, S, S(=O), S(=O)$_2$, NR$^5$, —(C=O)—, —(C=O)—N=N—NR$^5$—, —(C=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —(C=O)—NR$^5$—O—, wherein groups with two chemically nonequivalent termini can adopt both possible orientations;
V is selected from nitro, cyano, amino, hydroxyl, alkoxy, alkylthio, alkylamino, dialkylamino, —NH$(CH_2)_p$NH$_2$, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxyl, —NH$(CH_2)_p$NH$_2$, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the —(CH$_2$)$_{pPL}$— alkylene chain is optionally substituted with one or more amino or hydroxyl groups, or the alkylene chain is unsaturated;

pPL is 0 to 8;

q1PL and q2PL are, independently, 0 to 2; and m is 1 to at least about 500;

with the proviso that if A$_1$ and A$_2$ are thiophene, the polar groups cannot be 3-(propionic acid) or methoxy(diethoxy)ethyl and the nonpolar group cannot be n-dodecyl; and an ophthalmically or otically acceptable excipient.

US Appl. Publ. No. US 2005-0287108 A1 discloses antimicrobial polymers and oligomers of Formula V that can be used in the compositions of the present invention.

For example, oligomers that are preferred for use in the ophthalmic or otic compositions of the present invention are those oligomers of Formula V wherein m is 1 to about 25, 1 to about 20, 1 to about 10, 1 to about 7, 1 to about 5, or 1, 2, or 3.

Thus, preferred ophthalmic or otic compositions of the invention also comprise oligomers of Formula Va:

$$R^1\text{-}A_1\text{-}W\text{-}A_2\text{-}W\text{-}A_1\text{-}R^2 \quad \text{(Va)}$$

or an acceptable salt or solvate thereof, wherein:

A$_1$ and A$_2$ are, independently, optionally substituted arylene or optionally substituted heteroarylene, wherein:

(i) A$_1$ and A$_2$ are independently optionally substituted with one or more polar (PL) group(s), one or more non-polar (NPL) group(s), or a combination of one or more polar (PL) group(s) and one or more non-polar (NPL) group(s); or (ii) one of A$_1$ or A$_2$ is as defined above and is optionally substituted with one or more polar (PL) group(s), one or more non-polar (NPL) group(s), or a combination of one or more polar (PL) group(s) and one or more non-polar (NPL) group(s); and the other of A$_1$ or A$_2$ is the group —C≡C(CH$_2$)$_p$C≡C—, wherein p is 0 to 8, and the —(CH$_2$)$_p$— alkylene chain is optionally substituted with one or more amino or hydroxyl groups;

W is —C≡C—;

R$^1$ is hydrogen, a polar group (PL), a non-polar group (NPL), or —W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

R$^2$ is R$^1$;

NPL is a nonpolar group —(NR$^{3'}$)$_{q1NPL}$—U$^{NPL}$—(CH$_2$)$_{pNPL}$—(NR$^{3''}$)$_{q2NPL}$—R$^4$, wherein R$^3$, R$^{3'}$, and R$^{3''}$ are, independently, selected from hydrogen, alkyl, and alkoxy;

R$^4$ is selected from hydrogen, alkyl, alkenyl, alkynyl, cycloalkyl, aryl, and heteroaryl, any of which is optionally substituted with one or more alkyl or halo groups;

U$^{NPL}$ is absent or selected from O, S, S(=O), S(=O)$_2$, NR$^3$, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N— and —(C=O)—NR$^3$—O—, wherein groups with two chemically nonequivalent termini can adopt both possible orientations;

the alkylene chain —(CH$_2$)$_{pNPL}$— is optionally substituted with one or more alkyl, amino, or hydroxyl groups, or the alkylene chain is unsaturated;

pNPL is 0 to 8;

q1NPL and q2NPL are, independently, 0 to 2;

PL is a polar group selected from halo, hydroxyethoxymethyl, methoxyethoxymethyl, polyoxyethylene, and —(NR$^{5'}$)$_{q1PL}$—U$^{PL}$—(CH$_2$)—(NR$^{5'}$)$_{q2PL}$—V, wherein:

R$^5$, R$^{5'}$, and R$^{5''}$ are, independently, selected from hydrogen, alkyl, and alkoxy;

U$^{PL}$ is absent or selected from O, S, S(=O), S(=O)$_2$, NR$^5$, —(C=O)—, —(C=O)—N=N—NR$^5$—, —(C=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, and —(C=O)—NR$^5$—O—, wherein groups with two chemically nonequivalent termini can adopt both possible orientations;

V is selected from nitro, cyano, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, aryl, heterocycle, and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, aminoalkylhio, lower acylamino, or benzyloxycarbonyl;

the alkylene chain —(CH$_2$)$_{pPL}$— is optionally substituted with one or more amino or hydroxyl groups, or the alkylene chain is unsaturated;

pPL is 0 to 8; and q1PL and q2PL are, independently, 0 to 2;

and an ophthalmically or otically acceptable excipient.

Preferred oligomers of Formula Va for use in the ophthalmic or otic compositions are those oligomers of Formula Va wherein A$_1$ and A$_2$ are, independently, optionally substituted o-, m-, or p-phenylene, with m-phenylene being especially preferred. Also preferred are oligomers of Formula Va wherein one of A$_1$ or A$_2$ is o-, m-, or p-phenylene, and the other of A$_1$ or A$_2$ is heteroarylene. Preferred heteroarylene groups include, but are not limited to, pyridinyl, pyrimidinyl, and pyrazinyl.

Preferred oligomers of Formula Va are also those wherein A$_1$ is substituted with one or two polar (PL) group(s) and A$_2$ is unsubstituted. Especially preferred are those oligomers wherein A$_1$ is substituted with one polar (PL) group and A$_2$ is unsubstituted.

Preferred ophthalmic or otic compositions also comprise oligomers of Formula Va wherein R$^1$ is hydrogen, a polar group (PL), or a non-polar group (NPL); and R$^2$ is R$^1$. More preferred are oligomers of Formula Va wherein R$^1$ is selected from hydrogen, halo, nitro, cyano, C$_1$-C$_6$ alkoxy, C$_1$-C$_6$ alkoxycarbonyl, and benzyloxycarbonyl. Oligomers of Formula Va wherein R$^1$ and R$^2$ are halo are especially preferred.

Preferred R$^3$, R$^{3'}$, and R$^{3''}$ groups include hydrogen and C$_1$-C$_4$ alkyl. Especially preferred are those oligomers of Formula Va wherein R$^3$, R$^{3'}$, and R$^{3''}$ are each hydrogen.

Preferred R$^4$ groups include hydrogen, C$_1$-C$_{10}$ alkyl, C$_3$-C$_{18}$ branched alkyl, C$_2$-C$_{10}$ alkenyl, C$_2$-C$_{10}$ alkynyl, or C$_6$-C$_{10}$ aryl, especially phenyl. Oligomers wherein R$^4$ is hydrogen, C$_1$-C$_{10}$ alkyl, and C$_3$-C$_{18}$ branched alkyl, any of which is optionally substituted with one or more C$_1$-C$_4$ alkyl or halo groups, are especially preferred.

Preferred oligomers of Formula Va are also those wherein U$^{NPL}$ is O, S, NH, —(C=O)—, —C(=O)O—, —R$^3$O—, or —R$^3$S—. Oligomers of Formula Va wherein U$^{NPL}$ is O, S, or —(C=O)— are especially preferred. Oligomers of Formula Va wherein $U^{NPL}$ is absent are also preferred.

Preferred oligomers of Formula Va also include those oligomers wherein the alkylene chain —$(CH_2)_{pNPL}$— is optionally substituted with one or more alkyl groups. Especially preferred are those oligomers in which the alkylene chain is unsubstituted. Also preferred are those oligomers of Formula Va wherein pNPL is 0 to 8, or 1 to 6, or, more preferably, 2 to 4.

Preferred oligomers of Formula Va are those wherein q1NPL and q2NPL are independently 0 or 1.

In some embodiments, preferred ophthalmic or otic compositions comprise oligomers wherein NPL is n-pentoxy, n-butoxy, sec-butoxy, tert-butoxy, propyloxy, ethyloxy, methoxy, or phenoxy.

Preferred ophthalmic or otic compositions also comprise oligomers of Formula Va wherein one or more PL are halo, especially bromo or iodo.

Preferred oligomers of Formula Va for use in the ophthalmic or otic compositions include those wherein PL is —$(NR^{5'})_{q1PL}$—$U^{PL}$—$(CH_2)_{pPL}$—$(NR^{5''})_{q2PL}$—V, and $R^5$, $R^{5'}$, $R^{5''}$, V, $U^{PL}$, and pPL, and q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, NH, —(C=O)—, —C(=O)O—, —$R^5$O—, and —$R^5$S—. Also preferred are oligomers of Formula Va wherein $U^{PL}$ is absent.

Preferred oligomers of Formula Va also are those wherein q1PL and q2PL are, independently, 0 or 1.

Preferred ophthalmic or otic compositions also comprise oligomers of Formula Va wherein V is nitro, cyano, amino, hydroxyl, $C_1$-$C_6$ alkoxy, $C_1$-$C_6$ alkylthio, $C_1$-$C_6$ alkylamino, $C_1$-$C_6$ dialkylamino, —$NH(CH_2)_pNH_2$, —$N(CH_2CH_2NH_2)_2$, diazamino, amidino, guanidino, guanyl, semicarbazone, heterocycle, or heteroaryl, any of which is optionally substituted with one or more of amino, halo, cyano, nitro, hydroxyl, —$NH(CH_2)_pNH_2$, —$N(CH_2CH_2NH_2)_2$, amidino, guanyl, guanidine, or aminoalkoxy. Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Especially preferred values of V include amino, $C_1$-$C_6$ alkylamino, $C_1$-$C_6$ dialkylamino, —$NH(CH_2)_pNH_2$, —$N(CH_2CH_2NH_2)_2$, diazamino, amidino, guanidino, and guanyl, any of which is optionally substituted with one or more of amino, halo, —$NH(CH_2)_pNH_2$, —$N(CH_2CH_2NH_2)_2$, amidino, guanyl, guanidine, or aminoalkoxy.

Especially preferred oligomers of Formula Va for use in the preferred ophthalmic compositions are those wherein PL is halo, guanidinomethyl, guanidinoethyl, guanidinopropyl, aminomethyl, aminoethyl, aminopropyl, aminoethylaminocarbonyl, or aminomethylaminocarbonyl.

Preferred oligomers of Formula Va are also those wherein pPL is 0 to 4. Especially preferred are those oligomers wherein pPL is 0 to 2.

Thus, in some embodiments, especially preferred ophthalmic or otic compositions of the present invention comprise an oligomer of Formula Va wherein:

$A_1$ and $A_2$ are, independently, optionally substituted m-phenylene, wherein $A_1$ is optionally substituted with two polar (PL) groups, and $A_2$ is unsubstituted;

$R^1$ is a polar group;

PL is —$(NR^{5'})_{q1PL}$—$U^{PL}$—$(CH_2)_{pPL}$—$(NR^{5'})_{q2PL}$—V, wherein:

$U^{PL}$ is absent or selected from O, S, $NR^5$, and —C(=O)—;

V is selected from amino, amidino, and guanidino, any of which is optionally substituted with one or more of amino, halo, —$NH(CH_2)_pNH_2$ wherein p is 1 to 4, —$N(CH_2CH_2NH_2)_2$, amidino, guanidino, guanyl, aminosulfonyl, aminoalkoxy, aminoalkylhio, and lower acylamino;

pPL is 0 to 8; and q1PL and q2PL are, independently, 0;

and an ophthalmically acceptable excipient.

Especially preferred are oligomers of Formula Va wherein $R^1$ is halo, and PL is —$U^{PL}$—$(CH_2)_{pPL}$—V, wherein $U^{PL}$ is absent; V is selected from amino, amidino, and guanidino, any of which is optionally substituted with one or more of amino or halo; and pPL is 0 to 6.

Exemplary structures of oligomers of Formula Va within the scope of the invention include the following, as well as those individual oligomers disclosed in U.S. Application Publication No. 2005-0287108, the contents of which is fully incorporated herein by reference.

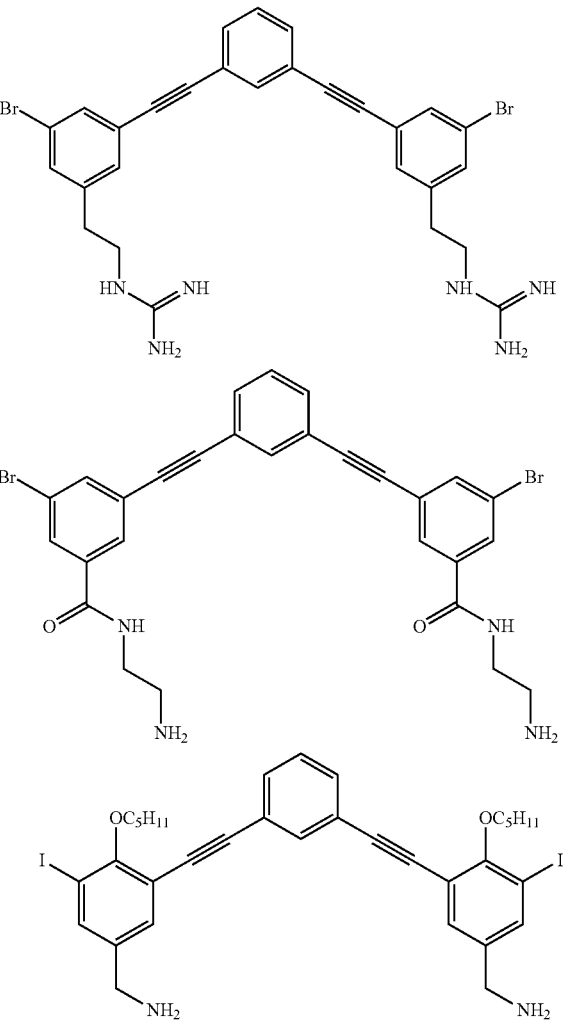

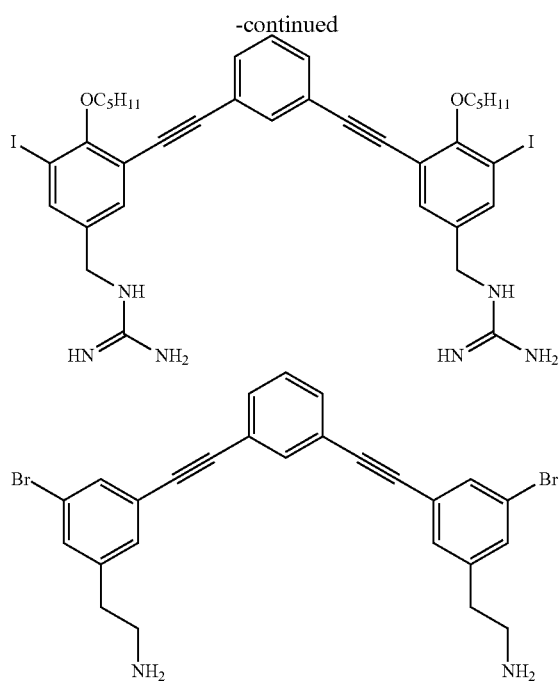

and ophthalmically or otically acceptable salts thereof.

In some aspects, the ophthalmic or otic compositions of the present invention comprise a random copolymer of Formula VI:

$$A\text{-}(B)_{n1}\text{-}(D)_{m1}\text{-}H \qquad (VI)$$

or an acceptable salt or solvate thereof,
wherein:

A is the residue of a chain transfer agent;

B is —[CH$_2$—C(R$^{11}$)(B$_{11}$)]— wherein B$_{11}$ is —X$_{11}$—Y$_{11}$—Z$_{11}$, wherein X$_{11}$ is carbonyl (—C(=O)—) or optionally substituted C$_{1-6}$ alkylene; or X$_{11}$ is absent;

Y$_{11}$ is O, NH, or optionally substituted C$_{1-6}$ alkylene; or Y$_{11}$ is absent;

Z$_{11}$ is —Z$_{11A}$-Z$_{11B}$, wherein Z$_{11A}$ is alkylene, arylene, or heteroarylene, any of which is optionally substituted; or Z$_{11A}$ is absent; and Z$_{11B}$ is -guanidino, -amidino, —N(R$^3$)(R$^4$), or —N$^+$(R$^3$)(R$^4$)(R$^5$), wherein R$^3$, R$^4$, and R$^5$ are, independently, hydrogen, alkyl, aminoalkyl, aryl, heteroaryl, heterocyclic, or aralkyl; or Z$_{11}$ is pyridinium

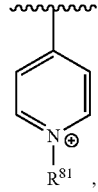

or phosphonium

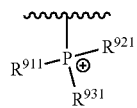

wherein

R$^{81}$, R$^{911}$, R$^{921}$, and R$^{931}$ are independently, hydrogen or alkyl;

R$^{11}$ is hydrogen or C$_{1-4}$ alkyl;

D is —[CH$_2$—C(R$^{21}$)(D$_{21}$)]—, wherein D$_{21}$ is —X$_{21}$—Y$_{21}$—Z$_{21}$, wherein X$_{21}$ is carbonyl (—C(=O)—) or optionally substituted C$_{1-6}$ alkylene; or X$_{21}$ is absent;

Y$_{21}$ is O, NH, or optionally substituted C$_{1-6}$ alkylene, or Y$_{21}$ is absent;

Z$_{21}$ is alkyl, cycloalkyl, alkoxy, aryl, or aralkyl, any of which is optionally substituted;

R$^{21}$ is hydrogen or C$_{1-4}$ alkyl;

m$_1$, the mole fraction of D monomer, is about 0.1 to about 0.9; and n$_1$, the mole fraction of B monomer, is 1-m$_1$;

wherein the copolymer is a random copolymer of B and D monomers, and wherein the copolymer has a degree of polymerization of about 5 to about 50;

and an ophthalmically or otically acceptable excipient.

US Application Publ. No. US 2006/0024264 A1 discloses random antimicrobial copolymers of Formula VI that can be used in the compositions of the present invention. Preferred ophthalmic or otic compositions comprise a random copolymer of Formula VI wherein:

A is C$_{1-4}$ alkoxycarbonyl(C$_{1-4}$alkylthio;

X$_{11}$ and X$_{21}$ are carbonyl;

Y$_{11}$ and Y$_{21}$ are O;

Z$_{11}$ is —Z$_{11A}$-Z$_{11B}$, wherein Z$_{11A}$ is C$_{1-6}$ alkylene optionally substituted with C$_{1-4}$ alkyl or aryl; and Z$_{11B}$ is —N(R$^{31}$)(R$^{41}$) or —N$^+$(R$^{31}$)(R$^{41}$)(R$^{51}$), wherein R$^{31}$, R$^{41}$, and R$^{51}$ are, independently, hydrogen C$_{1-4}$ alkyl;

Z$_{21}$ is C$_{1-6}$ alkyl, C$_{1-6}$ aryl, or C$_{1-6}$ ar(C$_{1-4}$)alkyl;

R$^{11}$ and R$^{21}$ are independently hydrogen or methyl;

m$_1$ is about 0.35 to about 0.60; and wherein the copolymer has a degree of polymerization of about 5 to about 10; and an ophthalmically or otically acceptable excipient.

When any variable occurs more than one time in any constituent or in any of the polymers or oligomers recited for any of the general Formulae above (for example, in Formula I, Formula II, Formula IIa, Formula IV, Formula IVa, Formula IVb, Formula IVc, Formula V, Formula Va, or Formula VI), its definition on each occurrence is independent of its definition at every other occurrence. Also, combinations of substituents and/or variables are permissible only if such combinations result in stable compounds.

It is understood that the present invention encompasses the use of stereoisomers, diastereomers and optical isomers of the polymers and oligomers disclosed herein, as well as mixtures thereof, for use in the ophthalmic or otic compositions and methods of the present invention. Additionally, it is understood that stereoisomers, diastereomers and optical isomers of the disclosed polymers and oligomers, and mixtures thereof, are within the scope of the present invention. By way of non-limiting example, the mixture can be a racemate or the mixture may comprise unequal proportions of one particular stereoisomer over the other. Thus, in some aspects of the invention, the disclosed polymers and oligomers are provided as mixtures that are racemates. Additionally, the polymers and oligomers can be provided as a substantially pure stereoisomers, diastereomers and optical isomers. Thus, in some aspects of the invention, the polymers and oligomers in the compositions of the invention are provided as substantially pure stereoisomers, diastereomers, or optical isomers.

In other aspects of the present invention, the polymers and oligomers in the ophthalmic or otic compositions are provided in the form of an acceptable salt (for example, a pharmaceutically acceptable salt) for treating microbial infections. Polymer or oligomer salts can be provided for pharmaceutical use, or as an intermediate in preparing the pharmaceutically desired form of the polymer or oligomer. One polymer or oligomer salt that is considered to be acceptable is the hydrochloride acid addition salt. Since one or more of the disclosed polymers and oligomers may be polyionic, such as a polyamine, the acceptable polymer or oligomer salt can be provided in the form of a poly(amine hydrochloride). Examples of other acceptable salts include, but are not limited to, those having sodium, potassium, or ammonium cations, and/or those having chloride, citrate, ascorbate, borate, phosphate, bicarbonate, sulfate, thiosulfate, bisulfite, mesylate, esylate, napsydisylate, tosylate, besylate, orthophoshate, acetate, gluconate, glutamate, lactate, malonate, fumarate, tartrate, maleate, or trifluoroacetate anions. In some embodiments, acceptable salts are those having mesylate, chloride, sulfate, esylate, napsydisylate, tosylate, besylate, phosphate, orthophoshate, acetate, gluconate, glutamate, lactate, malonate, citrate, fumarate, tartrate, maleate, or trifluoroacetate anions. In other embodiments, acceptable salts include sodium chloride, potassium chloride, sodium thiosulfate, sodium bisulfite, and ammonium sulfate.

In some aspects of the invention, the disclosed polymers and oligomers (such as the polymers and/or oligomers of Formulae I, II, IIa, IV, IVa, IVb, IVc, V, Va, and VI) are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process.

Unless otherwise defined, the terms below have the following meanings.

The term "alkyl" as used herein by itself or as part of another group refers to both straight and branched chain radicals from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "alkenyl" as used herein refers to a straight or branched chain radical of 2 to 20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" as used herein refers to a straight or branched chain radical of 2 to 20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

The term "alkylene" as used herein refers to an alkyl linking group, for example, an alkyl group that links one group to another group in a molecule.

The term "alkoxy" as used herein refers to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length, and even more preferred 1 to 6 carbon atoms in length.

The term "aryl" as used herein by itself or as part of another group refers to monocyclic or bicyclic aromatic groups containing from 6 to 12 carbons in the ring portion, preferably 6 to 10 carbons in the ring portion, such as the carbocyclic groups phenyl, naphthyl or tetrahydronaphthyl. The term "aryl" can represent carbocyclic aryl groups, such as phenyl, naphthyl or tetrahydronaphthyl, as well as heterocyclic aryl ("heteroaryl") groups, such as pyridyl, pyrimidinyl, pyridazinyl, furyl, and pyranyl.

The term "arylene" as used herein by itself or as part of another group refers to an aryl linking group, for example, an aryl group that links one group to another group in a molecule.

The term "cycloalkyl" as used herein by itself or as part of another group refers to cycloalkyl groups containing 3 to 9 carbon atoms, more preferably, 3 to 8 carbon atoms. Typical examples are cyclopropyl, cyclobutyl, cyclopentyl, cyclohexyl, cycloheptyl, cyclooctyl, and cyclononyl.

The term "halogen" or "halo" as used herein by itself or as part of another group refers to chlorine, bromine, fluorine, or iodine.

The term "hydroxy" or "hydroxyl" as used herein by itself or as part of another group refers to an —OH group.

The term "heteroaryl" as used herein refers to groups having 5 to 14 ring atoms; 6, 10, or 14 π-electrons shared in a cyclic array; and containing carbon atoms and 1, 2, or 3 oxygen, nitrogen or sulfur heteroatoms. Examples of heteroaryl groups include, but are not limited to, thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

The term "heteroarylene" as used herein by itself or as part of another group refers to a heteroaryl linking group, such as, a heteroaryl group that links one group to another group in a molecule.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from N, O, and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "alkylamino" as used herein by itself or as part of another group refers to an amino group which is substituted with one alkyl group having from 1 to 6 carbon atoms. The term "dialkylamino" as used herein by itself or as part of an other group refers to an amino group which is substituted with two alkyl groups, each having from 1 to 6 carbon atoms.

The term "alkylthio" as used herein by itself or as part of an other group refers to a thio group which is substituted with one alkyl group having from 1 to 6 carbon atoms.

The term "lower acylamino" as used herein by itself or as part of an other group refers to an amino group substituted with a $C_1$-$C_6$ alkylcarbonyl group.

The term "chemically nonequivalent termini" as used herein refers to a functional group such as an ester, amide, sulfonamide, or N-hydroxyoxime that, when reversing the orientation of the functional group (for example, —C(=O)O—) produces different chemical entities (for example, —$R^1$C(=O)O$R^2$— versus —$R^1$OC(=O)$R^2$—).

The polymers and oligomers employed in the ophthalmic compositions of the present invention (e.g., the polymers and/or oligomers of Formulae I, II, IIa, IV, IVa, IVb, IVc, V, Va, and VI) can be prepared as described in the following patents and patent publications: US Published Patent Appl. Nos. US 2006-0041023 A1, US 2004-0202639 A1, US 2005-0287108 A1, and US 2006-0024264 A1, as well as U.S. Pat. No. 7,173,102. For example, US Pat. Appl. Publ. No. US 2006-0041023 A1 discloses methods for the design, synthesis, and testing of polymers and oligomers of Formulae I, II, IIa, IV, IVa, IVb, and IVc. US Pat. Appl. Publ. No. US 2005/0287108 A1 discloses methods for the design, synthesis, and testing of polymers and oligomers of Formula V and Formula Va.

Examples of the design, synthesis, and testing of arylamide oligomers, a subgroup of oligomers of Formula II and Formula IIa, are also presented in Tew et al., Proc. Natl. Acad. Sci. USA, 2002, 99, 5110-5114 and in WIPO Publication No. WO 2004/082634.

The oligomers can be synthesized by solid-phase synthetic procedures well know to those of skill in the art. See, for example, Tew et al., Proc. Natl. Acad. Sci. USA, 2002, 99, 5110-5114; Barany et al., Int. J. Pept. Prot. Res., 1987, 30, 705-739; Solid-phase Synthesis: A Practical Guide, Kates, S. A., and Albericio, F., eds., Marcel Dekker, New York (2000); and Dörwald, F. Z., Organic Synthesis on Solid Phase: Supports, Linkers, Reactions, 2nd Ed., Wiley-VCH, Weinheim (2002).

The ophthalmic or otic compositions can be tested for anti-microbial activity by methods known to those of skill in the art. For example, anti-microbial assays suitable for testing the antimicrobial activity of the ophthalmic or otic compositions of the invention are described, for example, US Pat. Appl. Publ. No. US 2006-0041023 A1; Tew et al., Proc. Natl. Acad. Sci. USA, 2002, 99, 5110-5114; and Liu et al., J. Amer. Chem. Soc., 2001, 123, 7553-7559.

Compositions

The ophthalmic and otic compositions of the present invention can take the form of a liquid or solid, including, e.g., but not limited to, a solution, a suspension, an emulsion, a gel, an ointment, or a solid article that can be inserted in a suitable location in the eye.

In some embodiments, a composition of the present invention is in the form of a liquid wherein the active agent (i.e., one of the facially amphiphilic polymers or oligomers disclosed herein) is present in solution, in suspension, as an emulsion, or as a "solution/suspension." The term "solution/suspension" as used herein refers to a liquid composition wherein a first portion of the active agent is present in solution and a second portion of the active agent is present in particulate form, in suspension in a liquid matrix. In some embodiments, the liquid composition is in the form of a gel. In other embodiments, the liquid composition is aqueous. In other embodiments, the composition is in the form of an ointment.

In yet other embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and U.S. Pat. No. 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The present invention provides anti-microbial ophthalmic or otic compositions comprising a polymer of an oligomer of Formula I, Formula II, Formula IIa, Formula IV, Formula IVa, Formula IVb, Formula IVc, Formula V, Formula Va, or Formula VI and an ophthalmically or otically acceptable excipient.

The polymer or oligomer is typically present in the ophthalmic or otic composition in an "effective amount" or "effective concentration." The terms "effective amount," "effective concentration," or "amount effective," as used herein in reference to a polymer or oligomer in a composition of the present invention, refers to the amount of the polymer or oligomer sufficient to treat or prevent an ophthalmic infection in an eye of an animal, or to treat or prevent an otic infection in an ear of an animal.

The "effective amount" or concentration of the polymer or oligomer in the composition will vary and depends, among other factors, on the particular facially amphiphilic polymer or oligomer (active agent) being administered (e.g., on the relative antimicrobial activity of the specific polymer or oligomer); the mode of administration; the residence time provided by the particular formulation of the polymer or oligomer; the species, age and body weight of the subject; the intended use of the composition (e.g., treatment of existing infections or prevention of post-surgical infections); the particular condition for which treatment or prophylaxis is sought; and the severity of the condition.

The activity of antimicrobials is generally expressed as the minimum concentration of a compound (active agent) required to inhibit the growth of a specified pathogen. This concentration is also referred to as the "minimum inhibitory concentration" or "MIC." The term "$MIC_{90}$" refers to the minimum concentration of an antimicrobial active agent required to inhibit the growth of ninety percent (90%) of the tested isolates for one particular organism. The concentration of a compound required to totally kill a specified bacterial species is referred to as the "minimum bactericidal concentration" or "MCB."

The "effective amount" or concentration of the polymer or oligomer in the compositions of the invention will generally be an amount sufficient to provide a concentration on or in the affected eye or ear tissue equal to or greater than the $MIC_{90}$ level for the selected polymer or oligomer, relative to the microbes commonly associated with the infection. Thus, the "effective amount" or concentration of the polymer or oligomer in the ophthalmic or otic composition will generally be the amount of the polymer or oligomer sufficient to provide a concentration on or in the eye or ear tissue(s) equal to or greater than the $MIC_{90}$ level for the polymer or oligomer, relative to microbes commonly associated with the ophthalmic or otic infection.

Thus, for example, in the ophthalmic and otic compositions of the present invention, an effective concentration of the antimicrobial polymer or oligomer in the composition will generally be from about 0.01% to about 20% by weight (i.e., wt %) of the composition. More typically, it will be about 0.05% to about 10% by weight, about 0.1% to about 8.0% by weight, about 0.5% to about 5.0% by weight, about 1.0% to about 5.0% by weight, or about 2.0% to about 4.0% of the composition. For example, in ophthalmic compositions in the form of solid suspensions, such as ointments, an effective concentration of the antimicrobial polymer or oligomer will generally be from about 1% to about 5% by weight (wt %) of the composition.

The ophthalmic and otic compositions of the invention are preferably sterile and have physical properties (e.g., osmolality and pH) that are specially suited for application to ophthalmic or otic tissues, including tissues that have been compromised as the result of preexisting disease, trauma, surgery or other physical conditions. For example, aqueous compositions of the invention typically have a pH in the range of 4.5 to 8.0, more preferably, 6.0 to 8.0, or 6.5 to 8.0, or 7.0 to 8.0.

In addition to one or more of the polymers or oligomers disclosed herein, the ophthalmic or otic compositions of the invention can also comprise one or more ophthalmically or otically acceptable excipients.

The term "ophthalmically acceptable" as used herein means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined. However, preferred ophthalmically acceptable compositions, formulations, and excipients are those that cause no substantial detrimental effect, even of a transient nature.

Similarly, the term "otically acceptable," as used herein, means having no persistent detrimental effect on the treated ear or the functioning thereof, or on the general health of the subject being treated. Preferred otically acceptable compositions, formulations, and excipients are those that cause no substantial detrimental effect, even of a transient nature.

Ophthalmically and otically acceptable excipients include, but are not limited to, viscosity-enhancing agents, preservatives, stabilizers, antioxidants, suspending agents, solubilizing agents, buffering agents, lubricating agents, ophthalmically or otically acceptable salts, and combinations thereof.

For example, aqueous ophthalmic compositions of the present invention, when in suspension or solution form, are preferably viscous or mucoadhesive, or both viscous or mucoadhesive, and thus comprise a viscosity-enhancing agent. Examples of suitable viscosity-enhancing agents include, but are not limited to, glycerin, polyvinyl alcohol, polyvinyl pyrrolidone, methylcellulose, hydroxypropylmethylcellulose, hydroxyethyl-cellulose, carboxymethylcellulose, hydroxypropylcellulose, and/or various gelling agents. For example, in some embodiments, the viscosity-enhancing agent is selected from methylcellulose, hydroxypropyl-methylcellulose, polyvinyl alcohol, and glycerol. Such agents are generally employed in the compositions of the invention at a concentration of about 0.01% to about 3% by weight.

Thus, for ophthalmic compositions of the present invention, in some embodiments, the ophthalmically acceptable excipient is a viscosity-enhancing agent or a promoter of mucoadhesion, such as carboxymethylcellulose. In such embodiments, the concentration of carboxymethylcellulose in the aqueous suspension or solution is 0.1% to 5% by weight or about 0.1% to about 2.5% by weight. The carboxymethylcellulose is preferably in the form of sodium carboxymethylcellulose substituted to a degree that the sodium content of the sodium carboxymethylcellulose is about 1% to about 20%.

In other embodiments, the ophthalmic composition is an in situ gellable aqueous composition, more preferably, an in situ gellable aqueous solution. Such a composition comprises a gelling agent in a concentration effective to promote gelling upon contact with the eye or with lacrimal fluid in the exterior of the eye, enabling the composition to remain in the eye for a prolonged period without loss by lacrimal drainage. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums.

The phrase "in situ gellable" as used herein is to be understood as embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

For example, in some embodiments of the present invention, the ophthalmic composition is an in situ gellable aqueous solution, suspension or solution/suspension, comprising about 0.1% to about 6.5%, preferably about 0.5% to about 4.5%, by weight, based on the total weight of the composition, of one or more lightly cross-linked carboxyl-containing polymers as gelling agents. A preferred gelling agent in this embodiment is polycarbophil. In other embodiments, the composition is an in situ gellable aqueous solution, suspension or solution/suspension, preferably a solution, comprising about 0.1% to about 2% by weight of a polysaccharide that gels when it contacts an aqueous medium having the ionic strength of lacrimal fluid. A preferred polysaccharide is gellan gum, more preferably a low acetyl clarified grade of gellan gum such as that sold under the trademark Gelrite®. Suitable partially deacylated gellan gums are disclosed in U.S. Pat. No. 5,190,927.

In yet other embodiments, the composition is an in situ gellable aqueous solution, suspension or solution/suspension, comprising about 0.2% to about 3%, preferably about 0.5% to about 1%, by weight of a gelling polysaccharide, preferably selected from gellan gum, alginate gum and chitosan, and about 1% to about 50% of a water-soluble film-forming polymer, preferably selected from alkylcelluloses (e.g., methylcellulose, ethylcellulose), hydroxyalkylcelluloses (e.g., hydroxyethylcellulose, hydroxypropyl methylcellulose), hyaluronic acid and salts thereof, chondroitin sulfate and salts thereof, polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carrageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin.

In yet other embodiments, the composition is an in situ gellable aqueous solution, suspension or solution/suspension comprising about 0.1% to about 5% of a carrageenan gum, e.g., a carrageenan gum having no more than 2 sulfate groups per repeating disaccharide unit, such as e.g., kappa-carrageenan, having 18-25% ester sulfate by weight, iota-carrageenan, having 25-34% ester sulfate by weight, and mixtures thereof.

In still other embodiments, the composition comprises a bioerodible polymer substantially as disclosed in U.S. Pat. No. 3,914,402.

In some embodiments, the composition comprises an ophthalmically acceptable mucoadhesive polymer, selected, for example, from hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate, and dextran.

Ophthalmic compositions of the invention preferably incorporate means to inhibit microbial growth, for example through preparation and packaging under sterile conditions and/or through inclusion of an antimicrobially effective amount of an ophthalmically acceptable preservative.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Several preservatives may precipitate in the presence of other excipients in the composition and/or in the presence of the polymers and oligomers in the ophthalmic compositions of the present invention. For example, benzalkonium chloride can precipitate in a composition using iota-carrageenan as a gelling agent. Thus, in those embodiments of the invention in which a preservative is present, the preservative is one that does not precipitate but remains in solution in the composition.

Optionally one or more stabilizers can be included in the compositions of the invention to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the ophthalmic compositions of the invention. Suitable antioxidants include ascorbic acid, sodium metabisulfite, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments of the present invention, the facially amphiphilic polymer(s) or oligomer(s) of the compositions are solubilized at least in part by an ophthalmically acceptable solubilizing agent. The term "solubilizing agent" herein includes agents that result in formation of a micellar solution or a true solution of the drug. Certain ophthalmically acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Particularly preferred solubilizing agents for solution and solution/suspension compositions of the invention are cyclodextrins. Suitable cyclodextrins can be selected from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

An ophthalmically acceptable cyclodextrin can optionally be present in an ophthalmic composition of the invention at a concentration of about 1 to about 200 mg/ml, preferably about 5 to about 100 mg/ml and more preferably about 10 to about 50 mg/ml.

In some embodiments, the ophthalmic composition optionally contains a suspending agent. For example, in those embodiments in which the ophthalmic composition is an aqueous suspension or solution/suspension, the composition can contain one or more polymers as suspending agents. Useful polymers include water-soluble polymers such as cellulosic polymers, for example, hydroxypropyl methylcellulose, and water-insoluble polymers such as cross-linked carboxyl-containing polymers. However, preferred ophthalmic compositions of the invention do not contain substantial amounts of solid particulate matter, whether of the anti-microbial polymer or oligomer active agent, an excipient, or both, as solid particulate matter, if present, can cause discomfort and/or irritation of a treated eye.

One or more ophthalmically acceptable pH adjusting agents and/or buffering agents can be included in the ophthalmic compositions of the invention, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

One or more ophthalmically acceptable salts can be included in the compositions of the invention in an amount required to bring osmolality of the composition into an ophthalmically acceptable range. Such salts include, but are not limited to, those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate, with sodium chloride being especially preferred.

Optionally an ophthalmically acceptable xanthine derivative such as caffeine, theobromine or theophylline can be included in the compositions of the invention, e.g., as disclosed in U.S. Pat. No. 4,559,343. Inclusion of the xanthine derivative can reduce ocular discomfort associated with administration of the composition.

Optionally one or more ophthalmically acceptable surfactants, preferably nonionic surfactants, or co-solvents can be included in the compositions of the invention to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

One or more ophthalmic lubricating agents can also be included optionally in the compositions of the invention to promote lacrimation or as a "dry eye" medication. Such agents include, but are not limited to, polyvinyl alcohol, methylcellulose, hydroxypropyl methylcellulose, polyvinylpyrrolidone, and the like. It will be understood that promotion of lacrimation is beneficial in the present invention only where lacrimation is naturally deficient, to restore a normal degree of secretion of lacrimal fluid. Where excessive lacrimation occurs, residence time of the composition in the eye can be reduced.

Ophthalmic compositions of the present invention typically include a combination of one or more of the optional excipients listed above. For example, in some embodiments of the invention, the ophthalmic composition can optionally further comprise glycerin in an amount of about 0.5% to about 5%, more preferably about 1% to about 2.5%, for example about 1.5% to about 2%, by weight. Glycerin can be useful to increase viscosity of the composition and for adjustment of osmolality. Independently of the presence of glycerin, the composition can also further comprise a cyclodextrin, preferably hydroxypropyl-β-cyclodextrin, in an amount of about 0.5% to about 25% by weight, as a solubilizing agent, and an antimicrobially effective amount of a preservative, e.g., imidazolidinyl urea in an amount of about 0.03% to about 0.5%; methylparaben in an amount of about 0.015% to about 0.25%; propylparaben in an amount of about 0.005% to about 0.01%; phenoxyethanol in an amount of about 0.25% to about 1%; disodium EDTA in an amount of about 0.05% to about 0.2%; thimerosal in an amount of 0.001% to about 0.15%; chlorobutanol in an amount of about 0.1% to about 0.5%; and/or sorbic acid in an amount of about 0.05% to about 0.2%; all by weight.

The otic compositions of the present invention also optionally comprise one or more otically acceptable excipients. Otically acceptable excipients include, but are not limited to, one or more of the preservatives, stabilizers, antioxidants, viscosity-enhancing agents, buffering agents, solubilizing agents, surfactants, lubricating agents, or acceptable salts described above, or combinations thereof, as described above for the ophthalmic compositions of the invention.

Thus, for example, in some embodiments, an otic composition of the present invention optionally comprises one or more buffering agents, solubilizing agents, and antioxidants, typically in an aqueous solution. In some embodiments, the otic composition further comprises glycerin (e.g., anhydrous glycerin) or propylene glycol as a viscosity-enhancing agent. The otic composition may also comprise a surfactant in combination with the glycerin or propylene glycol to aid in the removal of cerum (ear wax). Sodium bicarbonate may also be used if wax is to be removed from the ear.

Thus, e.g., in some embodiments, the otic composition of the present invention is a sterile aqueous solution comprising one or more of the disclosed polymers or oligomers, glycerin, sodium bicarbonate, and, optionally, a preservative, in purified water.

The ophthalmic and otic compositions of the present invention can be prepared by methods known in the art and described in patents and publications cited herein and incorporated herein by reference.

Methods of Treatment and Administration

The ophthalmic or otic compositions of the present invention possess anti-microbial activity and can be used in methods of treating or preventing ophthalmic infections in an eye of an animal, or otic infections in the ear of an animal.

The term "animal" as used herein includes, but is not limited to, humans and non-human vertebrates such as wild, domestic and farm animals. Preferably, the animal is a warm-blooded, mammalian subject, including, but not limited to, domestic, farm and exotic mammals, and humans. The methods of the present invention can be useful, for example, in the treatment of eye infections in dogs, cats, horses, cattle, sheep and/or pigs, but is more particularly useful where the subject is human.

The phrases "treating an ophthalmic infection" and "treatment of an ophthalmic infection" refer to both the prevention and the therapeutic treatment, e.g., the alleviation or amelioration, of an ophthalmic infection, wherein the object is to prevent or slow down (lessen) the progress of an ophthalmic infection, or obtain beneficial or desired clinical results. For example, "beneficial or desired clinical results" include, but are not limited to, alleviation of the symptoms of an ophthalmic infection; diminishment of the extent of an ophthalmic infection; stabilization (for example, not worsening) of the state of an ophthalmic infection; delay in the onset or the slowing of an ophthalmic infection or its progression; amelioration of an ophthalmic infection or remission (whether partial or total), whether detectable or undetectable, or enhancement or improvement of an ophthalmic infection. Treatment includes eliciting a clinically significant response without excessive levels of side effects.

Similarly, the phrases "treating an otic infection" and "treatment of an otic infection" refer to both the prevention and the therapeutic treatment, e.g., the alleviation or amelioration, of an otic infection, wherein the object is to prevent or slow down (lessen) the progress of an otic infection, or obtain beneficial or desired clinical results. For example, "beneficial or desired clinical results" include, but are not limited to, alleviation of the symptoms of an otic infection; diminishment of the extent of an otic infection; stabilization (for example, not worsening) of the state of an otic infection; delay in the onset or the slowing of an otic infection or its progression; amelioration of an otic infection or remission (whether partial or total), whether detectable or undetectable, or enhancement or improvement of an otic infection. Treatment includes eliciting a clinically significant response without excessive levels of side effects.

Ophthalmic infections for which the compositions and methods of the present invention are useful include, but are not limited to, infections of one or more tissues of the eye, including, for example, conjunctivitis, keratitis (including ulcerative keratitis with bacterial infection), keratoconjunctivitis (including, e.g., keratoconjunctivitis sicca (KCS) commonly found in dogs), blepharitis, blepharoconjunctivitis, dacryocystitis, hordeolum, corneal ulcers, orbital and preseptal cellulitis, and endophthalmitis In preferred methods of the invention, the infected tissue is one that is directly bathed by the lacrimal fluid, as in conjunctivitis, keratitis, keratoconjunctivitis, blepharitis, and blepharoconjunctivitis.

The ophthalmic compositions of the present invention may also be used prophylactically in connection with various ophthalmic surgical procedures that create a risk of infection.

Otic infections for which the compositions and methods of the present invention are useful include, but are not limited to, otitis externa and otitis media. With respect to the treatment of otitis media, the compositions of the present invention are primarily useful in cases where the tympanic membrane has ruptured or tympanostomy tubes have been implanted. The otic compositions may also be used to treat infections associated with otic surgical procedures, such as tympanostomy, or to prevent such infections.

The ophthalmic and otic compositions of the invention are effective in killing or inhibiting the growth of a broad spectrum of pathogens or microbes often associated with ophthalmic and/or otic infections, including a range of bacteria (both gram-postive and gram-negative), fungi and viruses.

For example, the ophthalmic and otic compositions are useful in killing or inhibiting the growth of any of the following clinically relevant ocular or otic pathogens, and can be administered topically to treat and/or prevent ophthalmic or otic infections caused by the following pathogens or mixtures of the following pathogens: *Staphylococcus* spp. (e.g., *Staphylococcus aureus, Staphylococcus epidermidis*), *Streptococcus* spp. (e.g., *Streptococcus viridans, Streptococcus pneumoniae*), *Enterococcus* spp., *Bacillus* spp., *Corynebacterium* spp., *Propionibacterium* spp., *Chlamydia* spp., *Moraxella* spp. (e.g., *Moraxella lacunata* and *Moraxella catarrhalis*), *Haemophilus* spp. (e.g., *Haemophilus influenza* and *Haemophilus aegyptius*), *Pseudomonas* spp. (e.g., *Pseudomonas aeruginosa*, and, for otic infections, *Pseudomonas otitidis*), *Serratia* spp. (e.g., *Serratia marcescens*), *Neisseria* spp., and *Mycoplasma* spp., as well as *Enterobacter* spp. (e.g., *Enterobacter aerogenes*), *Eschericia* spp. (e.g., *Eschericia coli*), *Klebsiella* spp. (e.g., *Klebsiella pneumoniae*), *Proteus* spp. (e.g., *Proteus mirabillis* and *Proteus vulgaris*), *Acinetobacter* spp. (e.g., *Acinetobacter calcoaceticus*), *Prevotella* spp., *Fusobacterium* spp., *Porphyromonas* spp., and *Bacteroides* spp. (e.g., *Bacteroides fragilis*). This list of microbes is purely illustrative and is in no way to be interpreted as restrictive.

Thus, for example, the ophthalmic compositions of the present invention can be administered to treat or prevent a bacterial infection of the eye caused by one or more of the following species: *Staphylococcus aureus, Staphylococcus epidermidis, Streptococcus pneumoniae, Streptococcus pyogenes, Streptococcus viridans, Enterococcus faecalis, Corynebacterium* spp., *Propionibacterium* spp., *Moraxella catarrhalis* and *Haemophilus influenzae*.

For example, treatment of bacterial conjunctivitis by administering an ophthalmic composition of the present invention is appropriate where infection with one or more of the following species is present: *Staphylococcus aureus, Staphylococcus epidermidis, Streptococcus pneumoniae, Streptococcus pyogenes, Streptococcus viridans, Enterococcus faecalis, Corynebacterium* spp., *Propionibacterium* spp., *Moraxella catarrhalis* and *Haemophilus influenzae*.

Similarly, treatment of bacterial blepharitis by administering an ophthalmic composition of the present invention is appropriate where infection with one or more of the following species is present: *Staphylococcus aureus, Staphylococcus epidermidis* and *Streptococcus pneumoniae*. Treatment of bacterial keratitis by administering an ophthalmic composition of the present invention is also appropriate where infection with one or more of the following species is present: *Staphylococcus aureus, Staphylococcus epidermidis, Streptococcus pneumoniae* and *Streptococcus viridans*.

The otic compositions of the present invention, for example, can also be administered to treat or prevent a bacterial infection of the ear caused by one or more of the following species: *Pseudomonas aeruginosa, Staphylococcus aureus, Staphylococcus epidermidis, Streptococcus pneumoniae, Moraxella catarrhalis, Pseudomonas otitidis,* and *Proteus* spp. (e.g., *Proteus mirabillis* and *Proteus vulgaris*), as well as one or more of the following anaerobes: *Prevotella* spp., *Fusobacterium* spp., *Porphyromonas* spp., and *Bacteroides* spp. (e.g., *Bacteroides fragilis*). Thus, for example, treatment of chronic suppurative otitis media by administering an otic composition of the present invention is appropriate where infection with one or more of the following species is present: *Staphylococcus aureus, Pseudomonas aeruginosa, Eschericia coli, Klebsiella* spp. (e.g., *Klebsiella pneumoniae*), *Proteus* spp. (e.g., *Proteus mirabillis* and *Proteus vulgaris*), *Prevotella* spp., *Fusobacterium* spp., *Porphyromonas* spp., and *Bacteroides* spp. (e.g., *Bacteroides fragilis*).

The ophthalmic or otic compositions are also useful in killing or inhibiting the growth of clinically relevant ocular or otic fungi, and can be administered topically to treat and/or prevent ophthalmic or otic infections caused by one or more species of fungi, or a mixture of species of fungi, including, but not limited to, *Aspergillus* spp. (e.g., *Aspergillus fumigatus, Aspergillus favus, Aspergillus niger* and *Aspergillus terreus*), *Fusarium* spp. (e.g., *Fusarium solani, Fusarium moniliforme* and *Fusarium proliferartum*), *Malessezia* spp. (e.g., *Malessezia pachydermatis*), and/or *Candida* spp. (e.g., *Candida albicans*), as well as *Chrysosporium parvum, Metarhizium anisopliae, Phaeoisaria clematidis,* and *Sarcopodium oculorum*. This list of microbes is purely illustrative and is in no way to be interpreted as restrictive.

Thus, the ophthalmic compositions of the present invention can be administered to treat or prevent a fungal infection of the eye caused by one or more of the following species: *Aspergillus* spp., *Fusarium* spp., *Chrysosporium parvum, Metarhizium anisopliae, Phaeoisaria clematidis,* and *Sarcopodium oculorum*. For example, the ophthalmic composition can be administered to treat fungal keratitis caused by one or more *Aspergillus* spp. and/or *Fusarium* spp.

The otic compositions of the present invention, for example, can also be administered to treat or prevent a fungal infection of the ear caused by one or more of the following species: *Candida* spp., *Aspergillus* spp., and/or *Malessezia* spp. (e.g., *Malessezia pachydermatis*).

The ophthalmic or otic compositions are also useful in killing or inhibiting the growth of clinically relevant ocular or otic viruses and can be administered topically to treat and/or prevent ophthalmic or otic infections caused by one or more viruses, including, but not limited to, adenoviruses and herpes viruses (including, e.g., Herpes simplex 1 virus and/or varicella-zoster virus), Eneroviruses and Cytomegaloviruses.

Thus, for example, the ophthalmic compositions of the present invention can be administered to treat or prevent a viral infection of the eye, e.g., Herpes keratitis, caused by Herpes simplex 1 virus.

In some embodiments, the ophthalmic or otic compositions of the invention are useful and effective in killing and/or preventing the growth of microbes that have developed significant levels of resistance to anti-microbial agents other than the disclosed polymers and oligomers. For example, in some embodiments, the ophthalmic compositions and otic compositions are especially effective in methods of treating ophthalmic infections or otic infections cased by bacterial strains that have developed resistance to ciprofloxacin, e.g., Ciprofloxacin Resistant (CR)S. aureus and CR S. epidermidis, or to fluoroquinolone, or bacterial strains that have developed resistance to penicillin.

In some embodiments, the compositions of the invention are administered topically to one or more tissues of the eye or ear to treat an existing microbial infection, or as a prophylactic measure to prevent a microbial infection.

Thus, for example, in some embodiments, an ophthalmic composition of the present invention is administered topically to one or more tissues of the eye to treat an existing microbial infection, e.g., conjunctivitis, keratitis, blepharitis, or blepharoconjunctivitis.

In other embodiments, an ophthalmic composition of the present invention is administered topically to one or more tissues of the eye as a prophylactic measure. That is, the compositions are administered for prophylactic uses, e.g., in connection with various ophthalmic surgical procedures that create a risk of infection. Thus, for example, a composition of the invention can be administered in a method of post-traumatic prophylaxis, especially post-surgical prophylaxis, to prevent infection after ocular surgery, or in a method of prophylaxis prior to ocular surgery, for example, administered prior to surgery to prevent infection as a consequence of surgery.

The ophthalmic and otic compositions of the present invention possess broad-spectrum anti-microbial activity due to the facially amphiphilic and cationic properties of the facially amphiphilic polymers and oligomers in the compositions. As a consequence, an ophthalmic infection or an otic infection can be treated or prevented by administering only one of the compositions of the present invention, rather than by administering two or more separate antimicrobial compositions or one antimicrobial composition containing a combination of antimicrobial agents.

For example, because the ophthalmic compositions of the invention can be used to treat or prevent both viral and bacterial ophthalmic infections in an eye, only one of the present compositions needs to be administered to the eye to treat a viral ophthalmic infection where there is a risk of a secondary bacterial infection. Similarly, for an eye infection caused by multiple strains of bacteria (e.g., by both gram-positive bacteria and gram-negative bacteria), only one composition containing one of the disclosed amphiphilic oligomers needs to be administered, rather than a composition containing multiple anti-microbial agents, or a combination of separate treatments administered concurrently.

In some embodiments, the ophthalmic or otic compositions of the present invention are administered with an additional anti-microbial agent, such as, e.g., an anti-bacterial, anti-fungal, or anti-viral agent. For example, the additional anti-microbial agent can be a second facially amphiphilic polymer or oligomer disclosed herein, or the additional anti-microbial agent can be another anti-microbial agent such as, for example, an antibiotic selected from the group consisting of aminoglycosides, cephalosporins, diaminopyridines, fluoroquinolones, sulfonamides and tetracyclines. Examples of useful antibiotics which can serve as additional anti-microbials include, but are not limited to, amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin, and trimethoprim.

In those embodiments in which the ophthalmic or otic composition is administered with another anti-microbial agent, the present invention provides a method of treating or preventing multiple bacterial infections in an eye or an ear, the method comprising application to the eye or ear in co-therapy (including co-formulation) one or more facially amphiphilic polymers or oligomers disclosed herein and one or more additional anti-microbial agents. "Co-therapy" herein means administration to the eye or ear, at the same time or sequentially, of an ophthalmically or otically acceptable composition comprising one or more of the facially amphiphilic polymers or oligomers disclosed herein and a separate ophthalmically or otically acceptable composition of the additional anti-microbial agent, in a treatment regimen intended to provide a beneficial effect from co-action of the two types of antimicrobial agents. "Co-formulation" herein means that the facially amphiphilic polymer or oligomer active agent and the additional anti-microbial agent are administered to the eye or ear as components of a single ophthalmically or otically acceptable composition.

The ophthalmic or otic compositions of the present invention also can be used in co-therapy with one or more drugs, or medicaments, other than anti-microbial agents. Such medicaments other than anti-microbial agents can be co-administered to the eye or ear together with a composition of the invention. Thus, e.g., an ophthalmic composition of the present invention can further comprise, in co-formulation with the facially amphiphilic polymer or oligomer active agent, a therapeutically and/or prophylactically effective amount of one or more medicaments that are other than anti-microbial agents.

These additional medicaments other than anti-microbial agents can cooperate with the anti-microbial facially amphiphilic polymer or oligomer active agent(s) in treating and/or preventing an infective disease of the eye or ear, or can be used to treat a related or unrelated condition simultaneously affecting the eye or ear.

Any medicament having utility in an ophthalmic or otic application can be used in co-therapy, co-administration or co-formulation with an ophthalmic or otic composition of the present invention as described above. Such additional medicaments include, but are not limited to, anti-inflammatory agents (e.g., steroidal anti-inflammatory agents, non-steroidal anti-inflammatory agents (NSAIDs), and selective cyclooxygenase-2 inhibitors); topical and/or regional anesthetic agents; anti-allergic agents (e.g., anti-histamines); demulcents; acetylcholine blocking agents; adrenergic agonists, beta-adrenergic blocking agents and other anti-glaucoma agents; anti-hypertensives; and anti-cataract agents.

For example, ophthalmic and otic infections are frequently accompanied by inflammation of the infected ophthalmic and/or otic tissues and surrounding tissues. In addition, ophthalmic and otic surgical procedures that create a risk of microbial infections frequently also causes inflammation of the affected tissues. Thus, the ophthalmic and otic compositions of the present invention can be co-formulated with an anti-inflammatory agent to combine the anti-infective activity of one or more antibiotics with the anti-inflammatory activity of one or more steroid or non-steroid agents in a single composition.

The anti-inflammatory agents can be steroidal or non-steroidal. Examples of suitable steroidal anti-inflammatory agents include, but are not limited to, dexamethasone; dexamethasone derivatives such as those disclosed in U.S. Pat. No. 5,223,492; rimexolone; prednisolone; fluorometholone; and hydrocortisone.

Examples of suitable non-steroidal anti-inflammatory agents include, but are not limited to, prostaglandin H synthetase inhibitors (Cos I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, tenoxicam and carprofen; cyclooxygenase type II selective inhibitors, such as vioxx, celecoxib, etodolac; PAF antagonists, such as apafant, bepafant, minopafant, nupafant and modipafant; PDE IV inhibitors, such as ariflo, torbafylline, rolipram, filaminast, piclamilast, cipamfylline, and roflumilast; inhibitors of cytokine production, such as inhibitors of the NFkB transcription factor; or other anti-inflammatory agents know to those skilled in the art.

Examples of suitable topical or regional anesthetic agents include, but are not limited to, benzocaine.

Examples of suitable anti-allergic agents include, but are not limited to, pemirolast, olopatadine, and the corticosteroids (prednisolone, fluorometholone, loteprenol and dexamthasone).

The additional medicament can be administered in co-therapy (including co-formulation) with the one or more facially amphiphilic polymers of the ophthalmic or otic composition. For example, in some embodiments, an ophthalmic composition of the present invention comprising one of the anti-microbial oligomer disclosed herein is administered in co-therapy with an anti-inflammatory agent, e.g., a glucocorticoid. The glucocorticoid can be co-formulated with the oligomer in a single ophthalmically acceptable composition, which is administered to one or more tissues of an eye, to not only treat or prevent an ophthalmic infection but also to treat and/or prevent inflammation.

The ophthalmic or otic compositions can be administered by any appropriate route of administration. In some aspects of the invention, the ophthalmic and otic compositions are administered topically, for example, the composition is topically administered in an antimicrobially effective amount to one or more tissues of the eye of the animal, or to one or more tissues of the ear of an animal.

An appropriate dosage, frequency and duration of administration, for example, treatment regimen, to be used in any particular situation will be readily determined by one of skill in the art without undue experimentation, and will depend, among other factors, on the particular polymer(s) or oligomer(s) present in the composition, on the particular ophthalmic infection being treated, on the age, weight and general physical condition of the subject, and on other medication being administered to the subject. It is preferred that response of the ophthalmic or otic infection to treatment according to the present methods be monitored and the treatment regimen be adjusted if necessary in light of such monitoring.

Frequency of administration is typically such that the dosing interval, for example, the period of time between one dose and the next, during waking hours is about 2 to about 12 hours, more typically about 3 to about 8 hours, for example about 4 to about 6 hours. It will be understood by those of skill in the art that an appropriate dosing interval is dependent to some degree on the length of time for which the selected composition is capable of maintaining a concentration of the anti-microbial polymer(s) or oligomer(s) in the lacrimal fluid and/or in the target tissue (e.g., the conjunctiva) above the $MIC_{90}$ (the minimum concentration of the oligomer or polymer which inhibits microbial growth by 90%). Ideally the concentration remains above the $MIC_{90}$ for at least 100% of the dosing interval. Where this is not achievable it is desired that the concentration should remain above the $MIC_{90}$ for at least about 60% of the dosing interval, in a worst case at least about 40% of the dosing interval.

For example, in some embodiments of the ophthalmic compositions of the invention, the ophthalmic composition is formulated as an in situ gellable aqueous liquid and is administered as eye drops. Typically each drop, generated by a conventional dispensing means, has a volume of about 10 to about 40 µL. From 1 to about 6 such drops typically provides a suitable dose of the oligomer active agent in about 25-1500_, of the composition. For example, preferably no more than 3 drops, more preferably no more than 2 drops, and most preferably no more than 1 drop, should contain the desired dose of the active agent for administration to an eye. Where the composition is administered in a form other than eye drops, for example, as an ophthalmic ointment or as a solid implant, an equivalent dose is provided. Such a dose can be administered as needed, but typically administration to the eye 1 to about 6 times per day, in most cases 2 to 4 times a day, provides adequate continuing relief or prevention of the infective disease indicated.

The ophthalmic compositions of the invention, e.g., the aqueous suspension compositions, can be packaged in single-dose non-reclosable containers. Such containers can maintain the composition in a sterile condition and thereby eliminate need for preservatives such as mercury-containing preservatives, which can sometimes cause irritation and sensitization of the eye. Alternatively, multiple-dose reclosable containers can be used, in which case it is preferred to include a preservative in the composition.

For example, in some embodiments, the ophthalmic composition is an aqueous solution, suspension or solution/suspension which is administered in the form of eye drops. In these embodiments, a desired dosage of the active agent can be administered by means of a suitable dispenser as a known number of drops into the eye. Examples of suitable dispensers are disclosed in International Patent Publication No. WO 96/06581.

The following examples will serve to further typify the nature of this invention but should not be construed as a limitation in the scope thereof, which scope is defined solely by the appended claims. In order that the invention disclosed herein may be more efficiently understood, examples are provided below. It should be understood that these examples are for illustrative purposes only and are not to be construed as limiting the invention in any manner.

EXAMPLES

Example 1

Antimicrobial Activity—Minimum Inhibitory Concentrations

The following three oligomers of the invention were screened for antimicrobial activity against a number of clinically relevant ocular pathogens.

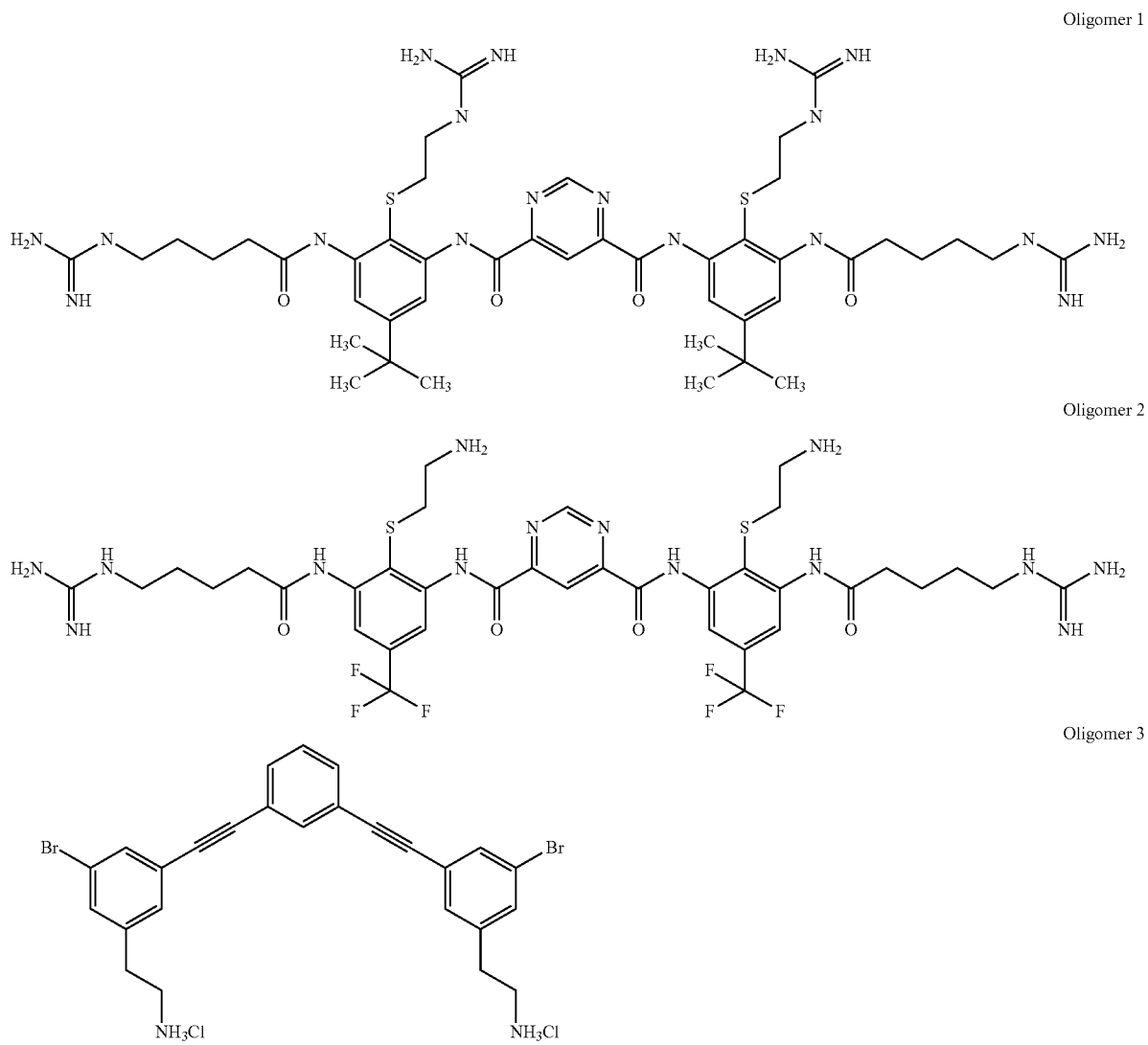

Minimum Inhibitory Concentrations (MIC) of each of the 3 oligomers were determined using standard procedures for clinical ocular isolates of Ciprofloxacin Susceptible (CS) *S. aureus* (CSSA) (n=27), Ciprofloxacin Resistant (CR)*S. aureus* (CRSA) (n=28), CS *S. epidermidis* (CSSE) (n=26), CR *S. epidermidis* (CRSE) (n=26), *St. pneumoniae* (SP) (n=27), *St. viridans* group (SV), *Moraxella* Species (MS) (n=25), *H. influenzae* (HI) (n=26), *P. aeruginosa* (PA) (n=26), and *Serratia marcescens* (SM) (n=27).

The results are presented in Table 1. Data is expressed as $MIC_{50}$, $MIC_{90}$, in µg/ml for Oligomer 1, Oligomer 2, and Oligomer 3, respectively.

TABLE 1

| Microbial Strain | Oligomer 1 | | Oligomer 2 | | Oligomer 3 | |
|---|---|---|---|---|---|---|
| | $MIC_{50}$ (µg/ml) | $MIC_{90}$ (µg/ml) | $MIC_{50}$ (µg/ml) | $MIC_{90}$ (µg/ml) | $MIC_{50}$ (µg/ml) | $MIC_{90}$ (µg/ml) |
| CSSA | 0.125 | 0.25 | 0.125 | 0.25 | 0.5 | 0.5 |
| CRSA | 0.25 | 0.25 | 0.25 | 0.25 | 0.5 | 0.5 |
| CSSE | 0.03 | 0.125 | 0.03 | 0.03 | 0.25 | 0.25 |

TABLE 1-continued

| Microbial Strain | Oligomer 1 | | Oligomer 2 | | Oligomer 3 | |
|---|---|---|---|---|---|---|
| | $MIC_{50}$ (µg/ml) | $MIC_{90}$ (µg/ml) | $MIC_{50}$ (µg/ml) | $MIC_{90}$ (µg/ml) | $MIC_{50}$ (µg/ml) | $MIC_{90}$ (µg/ml) |
| CRSE | 0.03 | 0.03 | 0.03 | 0.03 | 0.25 | 0.25 |
| SP | 0.5 | 1 | 1 | 2 | 2 | 2 |
| SV | 4 | 16 | 4 | 32 | 4 | 8 |
| MS | 0.5 | 0.5 | 0.25 | 0.5 | 1 | 2 |
| HI | 16 | 32 | 8 | 16 | 4 | 8 |
| PA | 4 | 8 | 4 | 8 | 4 | 4 |
| SM | 16 | 64 | 16 | 32 | 64 | 256 |

Oligomers 1, 2, and 3 demonstrated broad spectrum in vitro activity against a number of clinically relevant ocular pathogens.

Example 2

Ophthalmic Ointment Formulation

The following represents an example of a typical ophthalmic ointment formulation comprising an antimicrobial oligomer of the invention (oligomer 1 in Example 1 above).

Ophthalmic Ointment

| Ingredient | Amount (weight %) |
| --- | --- |
| Oligomer 1 | 0.35 |
| Mineral Oil, USP | 2.0 |
| White petrolatum, USP | q.s. 100 |

Example 3

Ophthalmic Ointment Formulation

The following represents an example of a typical ophthalmic ointment formulation comprising an antimicrobial oligomer of the invention (oliogmer 2 in Example 1 above) and an anti-inflammatory agent.

Ophthalmic Ointment

| Ingredient | Amount (weight %) |
| --- | --- |
| Oligomer 2 | 0.3 |
| Dexamethasone | 0.1 |
| Chlorobutanol, Anhydrous, NF | 0.5 |
| Mineral Oil, USP | 5.0 |
| White petrolatum, USP | q.s. 100 |

Example 4

Ophthalmic/Otic Solution Formulation

The following represents an example of a typical ophthalmic/otic solution formulation comprising an antimicrobial oligomer of the invention (oliogmer 3 in Example 1 above).

Ophthalmic/Otic Solution

| Ingredient | Amount (weight %) |
| --- | --- |
| Oligomer 3 | 0.35 |
| Sodium Acetate | 0.3 |
| Acetic Acid | 0.04 |
| Mannitol | 4.60 |
| EDTA | 0.05 |
| Benzalkonium chloride | 0.006 |
| Water | q.s. 100 |

Example 5

Ophthalmic/Otic Suspension Formulation

The following represents an example of a typical ophthalmic/otic suspension formulation comprising an antimicrobial oligomer of the invention (oliogmer 3 in Example 1 above) and an anti-inflammatory agent (dexamethasone).

Ophthalmic/Otic Suspension

| Ingredient | Amount (weight %) |
| --- | --- |
| Oligomer 3 | 0.3 |
| Dexamethasone, micronized USP | 0.10 |
| Benzalkonium chloride | 0.01 |
| Edetate Disodium USP | 0.01 |
| Sodium chloride USP | 0.3 |
| Sodium sulfate USP | 1.2 |
| Tyloxapol USP | 0.05 |
| Hydroxyethylcellulose | 0.25 |
| Sulfuric Acid and/or Sodium hydroxide, NF | q.s. for pH adjustment to 7.0-8.0 |
| Purified sterilized water | q.s. to 100 |

Example 6

Toxicity

The ocular toxicity of several concentrations of Oligomer 2, using the Draize ocular toxicity scoring system, in the NZW rabbit ocular toxicity model was carried out.

Nine rabbits were received from Myrtles' Rabbitry, Thompson Station, Tenn. and were subsequently divided into 5 groups:

| Group | Oligomer 2 Concentration | N Rabbits | N Eyes | Rabbit Numbers |
| --- | --- | --- | --- | --- |
| I | 1% Oligomer 2 | 2 | 4 | 1-2 |
| II | 0.25% Oligomer 2 | 2 | 4 | 3-4 |
| III | 0.1% Oligomer 2 | 2 | 4 | 5-6 |
| IV | 0.01% Oligomer 2 | 2 | 4 | 7-8 |
| V | Tris-Buffered Saline | 1 | 2 | 9 |

Rabbits were treated in both eyes with (37 µl) topical drops every 30 minutes for 3 hours (7 total doses). One rabbit was treated with Tris-Buffered Saline and served as a negative control. Rabbits were evaluated in a masked fashion for ocular toxicity by an ophthalmologist with specialty training in corneal and external disease. Ocular toxicity was evaluated using the Draize scoring system after treatment on Day 0 and on Day 3 post treatment for any delayed toxicity. (Draize et al., J. Pharmacol. Exp. Ther., 1944, 82, 377-390).

IACUC Protocol #0701145 "The In Vivo Evaluation of Biomimetics as Topical Ocular Antibiotics". Formulations: 1) 1% Oligomer 2: 31.36 mg of Oligomer 2 in powder form was stored at −20° C. until use. The vial containing Oligomer 2 was removed from the freezer and 3.126 ml of Tris-Buffered Saline (TBS) was added to the vial to yield 3.126 ml of 1% (10 mg/ml) Oligomer 2; 2) 0.25% Oligomer 2: 0.5 ml of 1% Oligomer 2 was added to 1.5 ml of TBS to yield 2 ml of 0.25% Oligomer 2; 3) 0.1% Oligomer 2: 0.2 ml of 1% Oligomer 2 was added to 1.8 ml of TBS to yield 2 ml of 0.1% Oligomer 2; 4) 0.01% Oligomer 2: 0.2 ml of 0.1% Oligomer 2 was added to 1.8 ml of TBS to yield 2 ml of 0.01% Oligomer 2; and 5) Tris-Buffered Saline: 25 ml of Tris-Buffered Saline (10 mM TRIS, 150 mM NaCl, pH=7.4) was filter sterilized prior to use in preparation of the above samples and use in rabbits. The following schedule was adhered to.

Ocular Toxicity Evaluation
Drop Schedule

| Drop | Elapsed Time | Time of Day | Group I 1% Oligomer 2 | Group II 0.25% Oligomer 2 | Group III 0.1% Oligomer 2 | Group IV 0.01% Oligomer 2 | Group V TBS |
|---|---|---|---|---|---|---|---|
| 1 | 0 | 11:40 am | X | X | X | X | X |
| 2 | :30 | 12:10 pm | X | X | X | X | X |
| 3 | 1:00 | 12:40 pm | X | X | X | X | X |
| 4 | 1:30 | 1:10 pm | X | X | X | X | X |
| 5 | 2:00 | 1:40 pm | X | X | X | X | X |
| 6 | 2:30 | 2:10 pm | X | X | X | X | X |
| 7 | 3:00 | 2:40 pm | X | X | X | X | X |
| Examine | 3:20 | 3:00 pm | X | X | X | X | X |

A brief summary of the Draize scoring system for ocular lesions is provided below 1. Cornea

| A. Opacity-degree of density (area most dense taken for reading) | |
|---|---|
| No Opacity | 0 |
| Scattered or diffuse area, details of iris clearly visible | 1 |
| Easily discernible translucent areas, details of iris slightly obscured | 2 |
| Opalescent areas, no details of iris visible, size of pupil barely discernible | 3 |
| Opaque, iris invisible | 4 |
| B. Area of cornea involved | |
| One quarter (or less) but not zero | 1 |
| Greater than one quarter, but less than half | 2 |
| Greater than half, but less than three quarters | 3 |
| Greater than three quarters, up to whole area | 4 |

A × B × 5 Total Maximum = 80

2. Iris

| A Values | |
|---|---|
| Normal | 0 |
| Folds above normal, congestion, swelling, circumcorneal injection (any or all of these or combination of any thereof) iris still reacting to light (sluggish reaction is positive) | 1 |
| No reaction to light, hemorrhage, gross destruction (any or all of these) | 2 |

A × 5 Total Maximum = 10

3. Conjunctivae

| A. Redness (refers to palpebral and bulbar conjunctivas excluding cornea and iris) | |
|---|---|
| Vessels normal | 0 |
| Vessels definitely injected above normal | 1 |
| More diffuse, deeper crimson red, individual vessels not easily discernible | 2 |
| Diffuse beefy red | 3 |
| B. Chemosis | |
| No swelling | 0 |
| Any swelling above normal (includes nictitating membrane) | 1 |
| Obvious swelling with partial eversion of lids | 2 |
| Swelling with lids about half-closed | 3 |
| Swelling with lids about half-closed to completely closed | 4 |
| C. Discharge | |
| No discharge | 0 |
| Any amount different from normal (does not include small amounts observed in inner canthus of normal animals) | 1 |
| Discharge with moistening of the lids and hairs just adjacent to lids | 2 |
| Discharge with moistening of the lids and hairs, and considerable area around the eye | 3 |

Score (A + B + C) × 2 Total Maximum = 20

Total Maximum Score: 110 represents the sum of all scores obtained for the cornea, iris and conjunctivae.

Classification of Eye Irritation Scores:

| MMTS | Classification | Symbol |
|---|---|---|
| 0.0-0.5 | Non-Irritating | N |
| 0.6-2.5 | Practically Non-Irritating | PN |
| 2.6-15.0 | Minimally Irritating | M1 |
| 15.1-25.0 | Mildly Irritating | M2 |
| 25.1-50.0 | Moderately Irritating | M3 |
| 50.1-80.0 | Severely Irritating | S |
| 80.1-100.0 | Extremely Irritating | E |
| 100.1-110.0 | Maximally Irritating | Mx |

MMTS = Maximum Mean Total Score (The mean total score per group)
Kay et al., J. Soc. Cos. Chem., 1962, 13, 281-289.

Acute Ocular Toxicity Evaluation
Observations of Rabbit Behavior After Instillation of Test Drugs on Day 0:

| Group | Oligomer 2 Concentration |
|---|---|
| I | 1% Oligomer 2 |
| II | 0.25% Oligomer 2 |
| III | 0.1% Oligomer 2 |
| IV | 0.01% Oligomer 2 |
| V | Tris-Buffered Saline |

Drop 1 (11:40 am)
No adverse behavior observed after instillation of ALL test drugs.
Drop 2 (12:10 pm)
No adverse behavior observed after instillation of ALL test drugs.
Drop 3 (12:40 pm)
No adverse behavior observed after instillation of ALL test drugs.
Group I-1% Oligomer 2—Eyes have developed noticeable conjunctivitis.
Drop 4 (1:10 pm)
No adverse behavior observed after instillation of ALL test drugs.

Group I-1% Oligomer 2—Eyes have developed noticeable discharge.

Drop 5 (1:40 pm)

No adverse behavior observed after instillation of ALL test drugs.

Drop 6 (2:10 pm)

No adverse behavior observed after instillation of ALL test drugs.

Drop 7 (2:40 pm)

No adverse behavior observed after instillation of ALL test drugs.

Group: I
1% Oligomer 2

| Test/Eye | Day 0 | | | | Day 3 | | | |
|---|---|---|---|---|---|---|---|---|
| | 1L | 1R | 2L | 2R | 1L | 1R | 2L | 2R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 1 | 1 | 1 | 1 | 0 | 0 | 0 | 0 |
| II. Tot | 5 | 5 | 5 | 5 | 0 | 0 | 0 | 0 |
| III. A. | 2 | 2 | 1 | 1 | 0 | 0 | 0 | 0 |
| III. B. | 2 | 2 | 1 | 2 | 0 | 0 | 0 | 0 |
| III. C. | 3 | 2 | 3 | 2 | 0 | 0 | 0 | 0 |
| III. Tot | 14 | 12 | 10 | 10 | 0 | 0 | 0 | 0 |
| Score | 19 | 17 | 15 | 15 | 0 | 0 | 0 | 0 |
| MMTS | 16.5 - $M_2$ | | | | 0.0 - N | | | |

Group: II
0.25% Oligomer 2

| Test/Eye | Day 0 | | | | Day 3 | | | |
|---|---|---|---|---|---|---|---|---|
| | 3L | 3R | 4L | 4R | 3L | 3R | 4L | 4R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 1 | 2 | 1 | 0 | 0 | 0 | 0 | 0 |
| III. B. | 1 | 1 | 0 | 0 | 0 | 0 | 0 | 0 |
| III. C. | 2 | 1 | 1 | 0 | 0 | 0 | 0 | 0 |
| III. Tot | 8 | 8 | 4 | 0 | 0 | 0 | 0 | 0 |
| Score | 8 | 8 | 4 | 0 | 0 | 0 | 0 | 0 |
| MMTS | 5.0 - $M_1$ | | | | 0.0 - N | | | |

Group: III
0.1% Oligomer 2

| Test/Eye | Day 0 | | | | Day 3 | | | |
|---|---|---|---|---|---|---|---|---|
| | 5L | 5R | 6L | 6R | 5L | 5R | 6L | 6R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 0 | 0 | 0 | 0 | 0 | 0 |
| III. B. | 0 | 0 | 0 | 0 | 0 | 0 | 0 | 0 |
| III. C. | 0 | 0 | 0 | 0 | 0 | 0 | 0 | 0 |
| III. Tot | 0 | 0 | 0 | 0 | 0 | 0 | 0 | 0 |
| Score | 0 | 0 | 0 | 0 | 0 | 0 | 0 | 0 |
| MMTS | 0.0 - N | | | | 0.0 - N | | | |

Group: IV
0.01% Oligomer 2

| Test/Eye | Day 0 | | | | Day 3 | | | |
|---|---|---|---|---|---|---|---|---|
| | 7L | 7R | 8L | 8R | 7L | 7R | 8L | 8R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 1 | 0 | 0 | 0 | 1 | 0 |
| III. B. | 0 | 0 | 0 | 0 | 0 | 0 | 0 | 0 |
| III. C. | 0 | 0 | 0 | 0 | 0 | 0 | 0 | 0 |
| III. Tot | 0 | 0 | 2 | 0 | 0 | 0 | 2 | 0 |
| Score | 0 | 0 | 2 | 0 | 0 | 0 | 2 | 0 |
| MMTS | 0.5 - N | | | | 0.5 - N | | | |

Group: V TBS Control

| Test/Eye | Day 0 | | Day 3 | |
|---|---|---|---|---|
| | 9L | 9R | 9L | 9R |
| I. A. | 0 | 0 | 0 | 0 |
| I. B. | 0 | 0 | 0 | 0 |
| I. Tot | 0 | 0 | 0 | 0 |
| II. A. | 0 | 0 | 0 | 0 |
| II. Tot | 0 | 0 | 0 | 0 |
| III. A. | 0 | 0 | 0 | 0 |
| III. B. | 0 | 0 | 0 | 0 |
| III. C. | 0 | 0 | 0 | 0 |
| III. Tot | 0 | 0 | 0 | 0 |
| Score | 0 | 0 | 0 | 0 |
| MMTS | 0.0 - N | | 0.0 - N | |

Summary of MMTS Results

| Group | Day 0 | Day 3 |
|---|---|---|
| 1% Oligomer 2 | 16.5 - $M_2$ | 0.0 - N |
| | Mildly Irritating | Non-Irritating |
| 0.25% Oligomer 2 | 5.0 - $M_1$ | 0.0 - N |
| | Minimally Irritating | Non-Irritating |
| 0.1% Oligomer 2 | 0.0 - N | 0.0 - N |
| | Non-Irritating | Non-Irritating |
| 0.01% Oligomer 2 | 0.5 - N | 0.5 - N |
| | Non-Irritating | Non-Irritating |
| Tris-Buffered Saline | 0.0 - N | 0.0 - N |
| | Non-Irritating | Non-Irritating |

Oligomer 2 demonstrated dose dependent ocular toxicity after 7 topical installations (every 30 minutes for 3 hours) in the NZW rabbit ocular toxicity model. 1% Oligomer 2 was determined to be Mildly Irritating, 0.25% Oligomer 2 was determined to be Minimally Irritating, while 0.1% and 0.01% Oligomer 2 were determined to be Non-Irritating.

There were no acute reactions by the rabbits (flinching, immediate wiping of eyes, vocalization, hopping to rear of cage) upon instillation of any of the Oligomer 2 concentrations suggesting that Oligomer 2 does not sting upon instillation.

There was no prolonged toxicity (3 days after drops) demonstrated in any treatment group.

1% Oligomer 2, though Mildly Irritating, is suitable for use to determine whether Oligomer 2 demonstrates efficacy in the *Staphylococcus aureus* keratitis model.

Example 7

Toxicity

The ocular toxicity of several formulations of Oligomer 4 with and without farnesol, using the Draize ocular toxicity scoring system, in the NZW rabbit ocular toxicity model was carried out.

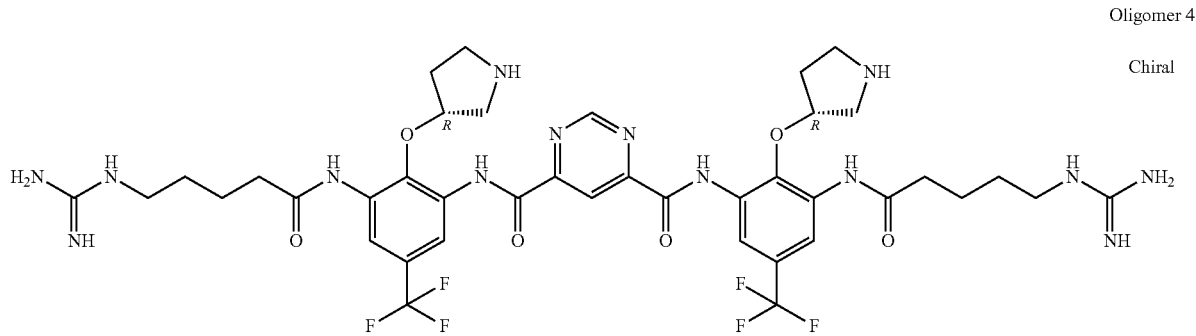

Oligomer 4

Fifteen rabbits were received from Myrtles' Rabbitry, Thompson Station, Tenn. and were divided into 8 groups:

| Group | Formulation | N Rabbits | N Eyes | Rabbit Numbers |
|---|---|---|---|---|
| I | 0.25% Oligomer 4 in Tris Buffered Saline (TBS) | 2 | 4 | 1-2 |
| II | 0.5% Oligomer 4 Tris Buffered Saline (TBS) | 2 | 4 | 3-4 |
| III | 100 µM Farnesol in 1% Propylene Glycol (PG) and TBS | 2 | 4 | 5-6 |
| IV | 200 µM Farnesol in 1% Propylene Glycol (PG) and TBS | 2 | 4 | 7-8 |
| V | 0.25% Oligomer 4 + 100 µM Farnesol in 1% PG and TBS | 2 | 4 | 9-10 |
| VI | 0.5% Oligomer 4 + 100 µM Farnesol in 1% PG and TBS | 2 | 4 | 11-12 |
| VII | 1% Propylene Glycol in TBS | 2 | 4 | 13-14 |
| VIII | Tris-Buffered Saline | 1 | 2 | 15 |

Rabbits were treated in both eyes with (37 µl) topical drops every 30 minutes for 3 hours (7 total doses). One rabbit was treated with Tris-Buffered Saline and served as a negative control. Rabbits were evaluated in a masked fashion for ocular toxicity by an ophthalmologist with specialty training in corneal and external disease 30 minutes after the final dose. Ocular toxicity was evaluated using the Draize scoring system (see above) after treatment on Day 0 and on Day 2 post treatment for any delayed toxicity.

Formulations: 1) 0.25% Oligomer 4: Vial 1 of Oligomer 4 in powder form was stored at 4° C. until use. The vial was removed from the refrigerator and 1.04 ml of sterile water for injection was added and vortexed until solid was completely dissolved. Then, 1.04 ml of Solution A (2×TBS) was added and vortexed for 10 seconds; 2) 0.5% Oligomer 4: Vial 2 of Oligomer 4 in powder form was stored at 4° C. until use. The vial was removed from the refrigerator and 1.04 ml of sterile water for injection was added and vortexed until solid was completely dissolved. Then, 1.04 ml of Solution A (2×TBS) was added and vortexed for 10 seconds; 3) 100 µM Farnesol in 1% Propylene Glycol (PG) and TBS: Vial 3 containing about 2 ml of 100 µM Farnesol in 1% Propylene Glycol (PG) and TBS was stored at 4° C. until use; 4) 200 µM Farnesol in 1% Propylene Glycol (PG) and TBS: Vial 4 containing about 2 ml of 200 µM Farnesol in 1% Propylene Glycol (PG) and TBS was stored at 4° C. until use; 5) 0.25% Oligomer 4+100 µM Farnesol in 1% PG and TBS: Vial 5 of Oligomer 4 in powder form was stored at 4° C. until use; at the time of use, the vial was removed from the refrigerator and 1.016 ml of sterile water for injection was added and vortexed until solid was completely dissolved; then 1.016 ml of Solution B (2% PG, 2×TBS, 200 µM Farnesol) was added and vortexed for 10 seconds; 6) 0.5% Oligomer 4+100 µM Farnesol in 1% PG and TBS: Vial 6 of Oligomer 4 in powder form was stored at 4° C. until use; at the time of use, the vial was removed from the refrigerator and 1.02 ml of sterile water for injection was added and vortexed until solid was completely dissolved; then 1.02 ml of Solution B (2% PG, 2×TBS, 200 µM Farnesol) was added and vortexed for 10 seconds; 7) 1% Propylene Glycol in TBS: Vial 7 containing about 2 ml of 1% Propylene Glycol was stored at 4° C. until use; and 8) Tris-Buffered Saline: Vial 8 containing about 2 ml of Tris-Buffered Saline (10 mM TRIS, 150 mM NaCl, pH=7.4) was stored at 4° C. until use.

IACUC Protocol #0701145-1 "The In Vivo Evaluation of Biomimetics as Topical Ocular Antibiotics".

| | | | Ocular Toxicity Evaluation Drop Schedule - Groups | | | | | | | |
|---|---|---|---|---|---|---|---|---|---|---|
| Drop | Elapsed Time | Time of Day | I | II | III | IV | V | VI | VII | VIII |
| 1 | 0 | 10:45 | X | X | X | X | X | X | X | X |
| 2 | :30 | 11:15 | X | X | X | X | X | X | X | X |
| 3 | 1:00 | 11:45 | X | X | X | X | X | X | X | X |
| 4 | 1:30 | 12:15 | X | X | X | X | X | X | X | X |
| 5 | 2:00 | 12:45 | X | X | X | X | X | X | X | X |
| 6 | 2:30 | 1:15 | X | X | X | X | X | X | X | X |
| 7 | 3:00 | 1:45 | X | X | X | X | X | X | X | X |
| Exam | 3:30 | 2:15 | X | X | X | X | X | X | X | X |

Acute Ocular Toxicity Evaluation

Observations of Rabbit Behavior After Instillation of Test Drugs on Day 0

| Group | Formulation |
|---|---|
| I | 0.25% Oligomer 4 in Tris Buffered Saline (TBS) |
| II | 0.5% Oligomer 4 Tris Buffered Saline (TBS) |
| III | 100 µM Farnesol in 1% Propylene Glycol (PG) and TBS |

| Group | Formulation |
|---|---|
| IV | 200 μM Farnesol in 1% Propylene Glycol (PG) and TBS |
| V | 0.25% Oligomer 4 + 100 μM Farnesol in 1% PG and TBS |
| VI | 0.5% Oligomer 4 + 100 μM Farnesol in 1% PG and TBS |
| VII | 1% Propylene Glycol in TBS |
| VIII | Tris-Buffered Saline |

Drop 1 (10:45 am)
No adverse behavior observed after instillation of ALL test drugs.
Drop 2 (11:15 am)
No adverse behavior observed after instillation of ALL test drugs.
Drop 3 (11:45 am)
No adverse behavior observed after instillation of ALL test drugs.
Drop 4 (12:15 am)
No adverse behavior observed after instillation of ALL test drugs.
Drop 5 (12:45 pm)
No adverse behavior observed after instillation of ALL test drugs.
Drop 6 (1:15 pm)
No adverse behavior observed after instillation of ALL test drugs.
Drop 7 (1:45 pm)
No adverse behavior observed after instillation of ALL test drugs.

| Group: I 0.25% Oligomer 4 | | | | | | | | |
|---|---|---|---|---|---|---|---|---|
| | Day 0 | | | | Day 2 | | | |
| Test/Eye | 1L | 1R | 2L | 2R | 1L | 1R | 2L | 2R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 0 | 0 | 0 | 0 | 0 | 0 |
| III. B. | 0 | 0 | 0 | 0 | 0 | 0 | 0 | 0 |
| III. C. | 0 | 1 | 1 | 1 | 0 | 1 | 0 | 0 |
| III. Tot | 0 | 2 | 2 | 2 | 0 | 2 | 0 | 0 |
| Score | 0 | 2 | 2 | 2 | 0 | 2 | 0 | 0 |
| MMTS | 1.5 - PN Practically Non-Irritating | | | | 0.5 - N Non-Irritating | | | |

| Group: II 0.5% Oligomer 4 | | | | | | | | |
|---|---|---|---|---|---|---|---|---|
| | Day 0 | | | | Day 2 | | | |
| Test/Eye | 3L | 3R | 4L | 4R | 3L | 3R | 4L | 4R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 1 | 1 | 1 | 0 | 0 | 0 | 0 | 0 |
| III. B. | 1 | 1 | 1 | 0 | 0 | 0 | 0 | 0 |
| III. C. | 2 | 2 | 2 | 1 | 0 | 0 | 1 | 1 |
| III. Tot | 8 | 8 | 8 | 2 | 0 | 0 | 2 | 2 |
| Score | 8 | 8 | 8 | 2 | 0 | 0 | 2 | 2 |
| MMTS | 6.5 - $M_1$ Minimally Irritating | | | | 1.0 - N Practically Non-Irritating | | | |

| Group: III 100 μM Farnesol in 1% Propylene Glycol (PG) and TBS | | | | | | | | |
|---|---|---|---|---|---|---|---|---|
| | Day 0 | | | | Day 2 | | | |
| Test/Eye | 5L | 5R | 6L | 6R | 5L | 5R | 6L | 6R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 0 | 0 | 0 | 0 | 0 | 0 |
| III. B. | 0 | 0 | 0 | 0 | 0 | 0 | 0 | 0 |
| III. C. | 0 | 0 | 0 | 0 | 1 | 0 | 1 | 1 |
| III. Tot | 0 | 0 | 0 | 0 | 2 | 0 | 2 | 2 |
| Score | 0 | 0 | 0 | 0 | 2 | 0 | 2 | 2 |
| MMTS | 0.0 - N Non-Irritating | | | | 1.5 - PN Practically Non-Irritating | | | |

| Group: IV 200 μM Farnesol in 1% Propylene Glycol (PG) and TBS | | | | | | | | |
|---|---|---|---|---|---|---|---|---|
| | Day 0 | | | | Day 2 | | | |
| Test/Eye | 7L | 7R | 8L | 8R | 7L | 7R | 8L | 8R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 0 | 0 | 0 | 0 | 0 | 0 |
| III. B. | 0 | 0 | 0 | 0 | 0 | 0 | 0 | 0 |
| III. C. | 0 | 0 | 0 | 1 | 0 | 0 | 0 | 1 |
| III. Tot | 0 | 0 | 0 | 2 | 0 | 0 | 0 | 2 |
| Score | 0 | 0 | 0 | 2 | 0 | 0 | 0 | 2 |
| MMTS | 0.5 - N Non-Irritating | | | | 0.5 - N Non-Irritating | | | |

| Group: V 0.25% Oligomer 4 + 100 μM Farnesol in 1% PG and TBS | | | | | | | | |
|---|---|---|---|---|---|---|---|---|
| | Day 0 | | | | Day 2 | | | |
| Test/Eye | 9L | 9R | 10L | 10R | 9L | 9R | 10L | 10R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 1 | 0 | 0 | 0 | 0 | 0 | 0 |
| III. B. | 0 | 1 | 0 | 0 | 0 | 0 | 0 | 0 |
| III. C. | 0 | 2 | 1 | 1 | 0 | 1 | 1 | 1 |
| III. Tot | 0 | 8 | 2 | 2 | 0 | 2 | 2 | 2 |
| Score | 0 | 8 | 2 | 2 | 0 | 2 | 2 | 2 |

Group: V 0.25% Oligomer 4 + 100 µM Farnesol in 1% PG and TBS

| | Day 0 | | | | Day 2 | | | |
|---|---|---|---|---|---|---|---|---|
| Test/Eye | 9L | 9R | 10L | 10R | 9L | 9R | 10L | 10R |
| MMTS | 3.0 - $M_1$ Minimally Irritating | | | | 1.5 - PN Practically Non-Irritating | | | |

Group: VI 0.5% Oligomer 4 + 100 µM Farnesol in 1% PG and TBS

| | Day 0 | | | | Day 2 | | | |
|---|---|---|---|---|---|---|---|---|
| Test/Eye | 11L | 11R | 12L | 12R | 11L | 11R | 12L | 12R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 2 | 2 | 2 | 2 | 0 | 0 | 0 | 0 |
| III. B. | 1 | 2 | 1 | 1 | 0 | 0 | 0 | 0 |
| III. C. | 2 | 2 | 2 | 2 | 1 | 0 | 1 | 0 |
| III. Tot | 10 | 12 | 10 | 10 | 2 | 0 | 2 | 0 |
| Score | 10 | 12 | 10 | 10 | 2 | 0 | 2 | 0 |
| MMTS | 10.5 - $M_1$ Minimally Irritating | | | | 1.0 - PN Practically Non-Irritating | | | |

Group: VII 1% Propylene Glycol in TBS

| | Day 0 | | | | Day 2 | | | |
|---|---|---|---|---|---|---|---|---|
| Test/Eye | 13L | 13R | 14L | 14R | 13L | 13R | 14L | 14R |
| I. A. | 0 | 0 | 0 | 0 | 0 | 0 | 0 | 0 |
| I. B. | 0 | 0 | 0 | 0 | 0 | 0 | 0 | 0 |
| I. Tot | 0 | 0 | 0 | 0 | 0 | 0 | 0 | 0 |
| II. A. | 0 | 0 | 0 | 0 | 0 | 0 | 0 | 0 |
| II. Tot | 0 | 0 | 0 | 0 | 0 | 0 | 0 | 0 |
| III. A. | 0 | 0 | 0 | 0 | 0 | 0 | 0 | 0 |
| III. B. | 0 | 0 | 0 | 0 | 0 | 0 | 0 | 0 |
| III. C. | 0 | 1 | 0 | 0 | 1 | 1 | 0 | 1 |
| III. Tot | 0 | 2 | 0 | 0 | 2 | 2 | 0 | 2 |
| Score | 0 | 2 | 0 | 0 | 2 | 2 | 0 | 1 |
| MMTS | 0.5 - N Non-Irritating | | | | 1.5 - PN Practically Non-Irritating | | | |

Group: VIII TBS Treated Control

| | Day 0 | | Day 2 | |
|---|---|---|---|---|
| Test/Eye | 15L | 15R | 15L | 15R |
| I. A. | 0 | 0 | 0 | 0 |
| I. B. | 0 | 0 | 0 | 0 |
| I. Tot | 0 | 0 | 0 | 0 |
| II. A. | 0 | 0 | 0 | 0 |
| II. Tot | 0 | 0 | 0 | 0 |
| III. A. | 0 | 0 | 0 | 0 |
| III. B. | 0 | 0 | 0 | 0 |
| III. C. | 1 | 1 | 1 | 1 |
| III. Tot | 2 | 2 | 2 | 2 |
| Score | 2 | 2 | 2 | 2 |
| MMTS | 2.0 - PN Practically Non-Irritating | | 2.0 - PN Practically Non-Irritating | |

Summary of MMTS Results

| Group | Day 0 | Day 2 |
|---|---|---|
| 0.25% Oligomer 4 in Tris Buffered Saline (TBS) | 1.5 - PN Practically Non-Irritating | 0.5 - N Non-Irritating |
| 0.5% Oligomer 4 Tris Buffered Saline (TBS) | 6.5 - $M_1$ Minimally Irritating | 1.0 - N Practically Non-Irritating |
| 100 µM Farnesol in 1% Propylene Glycol (PG) and TBS | 0.0 - N Non-Irritating | 1.5 - PN Practically Non-Irritating |
| 200 µM Farnesol in 1% Propylene Glycol (PG) and TBS | 0.5 - N Non-Irritating | 0.5 - N Non-Irritating |
| 0.25% Oligomer 4 + 100 µM Farnesol in 1% PG and TBS | 3.0 - $M_1$ Minimally Irritating | 1.5 - PN Practically Non-Irritating |
| 0.5% Oligomer 4 + 100 µM Farnesol in 1% PG and TBS | 10.5 - $M_1$ Minimally Irritating | 1.0 - PN Practically Non-Irritating |
| 1% Propylene Glycol in TBS | 0.5 - N Non-Irritating | 1.5 - PN Practically Non-Irritating |
| Tris-Buffered Saline | 2.0 - PN Practically Non-Irritating | 2.0 - PN Practically Non-Irritating |

Oligomer 4 demonstrated dose dependent ocular toxicity after 7 topical instillations (every 30 minutes for 3 hours) in the NZW rabbit ocular toxicity model. 0.5% Oligomer 4 was determined to be Mildly Irritating, while 0.25% was determined to be Practically Non-Irritating. The addition of 100 µM Farnesol in 1% Propylene Glycol to the Oligomer 4 concentrations increased the toxicity of both 0.5% and 0.25% Oligomer 4. Both formulations were determined to be Mildly Irritating. This was the same category as 0.5% Oligomer 4 alone, but the scores were higher. This classification was an increase for 0.25% Oligomer 4. 100 µM Farnesol, 200 µM Farnesol, and 1% Propylene Glycol individually were determined to be Non-Irritating. Tris-buffered Saline was determined to be Practically Non-Irritating. Rabbits demonstrated no adverse behavior upon instillation of any the test drugs. This indicates all of the test drugs did not sting upon instillation. There was really no prolonged or delayed toxicity (2 days after drops) demonstrated in any treatment group. The only finding on Day 2 was a slight discharge in some of the eyes which accounted for all of the scores. Although the complete formulations of 0.5% Oligomer 4 and 0.25% Oligomer 4 (including 100 µM Farnesol and 1% Propylene Glycol) were both classified as Mildly Irritating, the MMTS score for the 0.5% Oligomer 4 formulation was at the higher end of the classification whereas 0.25% Oligomer 4 formulation was at the lower end of the classification. It appears that the complete 0.5% Oligomer 4 formulation (including 100 µM Farnesol and 1% Propylene Glycol), though Mildly Irritating in uninfected eyes is probably not as suitable as other formulations for use in the efficacy studies in the *Staphylococcus aureus* keratitis model. The complete formulation of 0.25% Oligomer 4 (including 100 µM Farnesol and 1% Propylene Glycol) may be acceptable from a toxicity point of view. Experience with other formulations have generally shown that ocular toxicity can increase when instilled more frequently (21 drops vs. 7 drops) in infected eyes in the *Staphylococcus aureus* keratitis efficacy model.

Example 8

MIC

One purpose of the following experiments was to determine the MICs of two biomimetic compounds vs. 25 ocular isolates of *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Serratia marcescens*, *Streptococcus pneumoniae*, *Streptococcus viridans* group, *Moraxella* species (including *Moraxella catarrhalis*) and *Pseudomonas aeruginosa* and *Haemophilus influenzae*.

General Procedures:

Mueller-Hinton Broth in tubes was inoculated with 25 ocular isolates of *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Pseudomonas aeruginosa* and *Serratia marcescens*, plus two controls (*Staphylococcus aureus* and *E. coli*) and incubated at 37° C. overnight on a shaker set at 250 rpm.

Mueller-Hinton Broth supplemented with 2% lysed horse blood in tubes was inoculated with 25 ocular isolates of *Streptococcus pneumoniae*, *Streptococcus viridans* group, and *Moraxella* species (including *Moraxella catarrhalis*) plus two controls (*Staphylococcus aureus* and *E. coli*) and incubated at 37° C. overnight. Additionally, Mueller-Hinton Broth in tubes was inoculated with two controls (*Staphylococcus aureus* and *E. coli*) and incubated at 37° C. overnight on a shaker set at 250 rpm.

HTM (Haemophilus Test Medium) in tubes was inoculated with 25 ocular isolates of *Haemophilus influenzae* plus two controls (*Staphylococcus aureus* and *E. coli*) and incubated at 37° C. overnight. Additionally, Mueller-Hinton Broth in tubes was inoculated with two controls (*Staphylococcus aureus* and *E. coli*) and incubated at 37° C. overnight on a shaker set at 250 rpm.

On the day of testing, a 640 µg/ml (1280 µg/ml for *Serratia marcescens* and *Pseudomonas aeruginosa*) concentration was prepared from a 1% stock solution in 0.01% acetic acid, 0.2% BSA in polypropylene tubes.

Serial doubling dilutions in 0.01% acetic acid, 0.2% BSA in 96 well polypropylene plates, which are used as reservoirs for the inoculation of the test plates, were carried out to obtain serial dilutions of test agents at 10 times the required test concentrations: 640, 320, 160, 80, 40, 20, 10, 5, 2.5, 1.25, and 0.625 µg/ml (1280, 640, 320, 160, 80, 40, 20, 10, 5, 2.5, and 1.25 µg/ml for *Serratia marcescens* and *Pseudomonas aeruginosa*).

Ten µl of diluted 10× test agents was added to each well of one row of the 96 well polypropylene plates from column 2 to column 12 (column 1 is a control for bacteria alone, with no peptide). Test agent concentrations in columns 2-12 were as follows: 64, 32, 16, 8, 4, 2, 1, 0.5, 0.25, 0.125, and 0.0625 µg/ml (128, 64, 32, 16, 8, 4, 2, 1, 0.5, 0.25, and 0.125 µg/ml for *Serratia marcescens* and *Pseudomonas aeruginosa*). The same peptide was in each of the 8 rows. One plate contained dilutions of one test agent and 8 bacterial isolates.

On the day of testing, the overnight bacterial broth cultures of *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Serratia marcescens*, and *Pseudomonas aeruginosa*, plus two controls (*Staphylococcus aureus* and *E. coli*) were diluted in 5 ml of trypticase soy broth to yield turbidity equal to a 0.5 McFarland standard. The final inoculum for MIC testing for *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Serratia marcescens*, and *Pseudomonas aeruginosa* was achieved by placing 0.05 ml of the turbidity adjusted sample to 5 ml of Mueller-Hinton broth.

Control Bacteria—The two control bacteria (*Staphylococcus aureus* and *E. coli*) were treated as above.

On the day of testing, the overnight bacterial broth cultures of *Streptococcus pneumoniae*, *Streptococcus viridans* and *Moraxella* species (including *Moraxella catarrhalis*) plus two controls (*Staphylococcus aureus* and *E. coli*) were diluted in 5 ml of trypticase soy broth to yield turbidity equal to a 0.5 McFarland standard. The final inoculum for MIC testing for *Streptococcus pneumoniae*, *Streptococcus viridans* and *Moraxella* species (including *Moraxella catarrhalis*) was achieved by placing 0.1 ml of the turbidity adjusted sample to 5 ml of Mueller-Hinton broth containing 2% lysed horse red blood cells.

Control Bacteria Set #1—this set of control bacteria were treated as the *Streptococcus pneumoniae*, *Streptococcus viridans* and *Moraxella* species (including *Moraxella catarrhalis*) test isolates above; the control bacteria underwent the same conditions as the test *Streptococcus pneumoniae*, *Streptococcus viridans* and *Moraxella* species (including *Moraxella catarrhalis*) isolates. This set of control bacteria was to determine whether there was a difference in the MICs by performing the MIC determinations in 2% lysed horse red blood cells with the standard method performed in Mueller-Hinton broth.

Control Bacteria Set #2—the control bacteria were added to 5 ml of Mueller-Hinton Broth without the 2% lysed horse red blood cells to achieve the standard inoculum concentration. This set of control bacteria is the normal control to determine whether the compounds are at the target MICs.

On the day of testing, the overnight bacterial broth cultures of *Haemophilus* species was diluted in 5 ml of trypticase soy broth to yield turbidity equal to a 0.5 McFarland standard. The final inoculum for MIC testing for *Haemophilus* species was achieved by placing 0.1 ml of the turbidity adjusted sample to 5 ml of HTM medium.

Control Bacteria Set #1—this set of control bacteria were treated as the *Haemophilus influenzae* test isolates above; the control bacteria underwent the same conditions as the test *Haemophilus influenzae* isolates. This set of control bacteria is to determine whether there was a difference in the MICs by performing the MIC determinations in HTM broth with the standard method performed in Mueller-Hinton broth.

Control Bacteria Set #2—the control bacteria were added to 5 ml of Mueller-Hinton Broth to achieve the standard inoculum concentration. This set of control bacteria is the normal control to determine whether the compounds are at the target MICs.

Ninety μl of the bacterial suspensions was dispensed in each well from column 1 to column 12. Each bacterial isolate was placed in one row of a 96 well polypropylene plate containing the test agents. The plates were placed on shaker at 15 minutes at room temperature, and then incubated at 37° C. overnight. MICs were determined visually as the lowest concentration of drug that inhibits visible bacterial growth.

The MICs of the 2 compounds Oligomer 4 and Oligomer 5 were compared statistically with the Kruskal-Wallis ANOVA with Duncan's Multiple Comparisons Test using True Epistat statistical software (True Epistat, Richardson, Tex.).

Isolate numbers with a "K" before the number indicates they have been isolated from cases of Keratitis. Isolate numbers with an "E" before the number indicates they have been isolated from cases of Endophthalmitis. Isolate numbers with a "B" before the number indicates they have been isolated from cases of Blepharitis and or Conjunctivitis. Most *Streptococcus pneumoniae* isolates are from cases of conjunctivitis. "Fluoroquinolone-resistant" indicates the bacteria are resistant to the second generation fluoroquinolones ciprofloxacin and ofloxacin but, not necessarily resistant to the fourth generation fluoroquinolones gatifloxacin and moxifloxacin by CLSI serum standards.

| | *S. aureus* fluoroquinolone-susceptible MICs μg/ml | |
|---|---|---|
| Isolate | Oligomer 4 | Oligomer 5 |
| 1 - E402 | 0.25 | 0.5 |
| 2 - E1512 | 0.25 | 0.25 |
| 3 - E253 | 0.25 | 0.25 |
| 4 - K1518 | 0.25 | 0.125 |
| 5 - K1525 | 0.125 | 0.125 |
| 6 - K1663 | 0.5 | 0.125 |
| 7 - K1648 | 0.25 | 0.125 |
| 8 - K1646 | 0.25 | 0.25 |
| 9 - K1642 | 0.5 | 0.25 |
| 10 - K1638 | 0.5 | 0.25 |

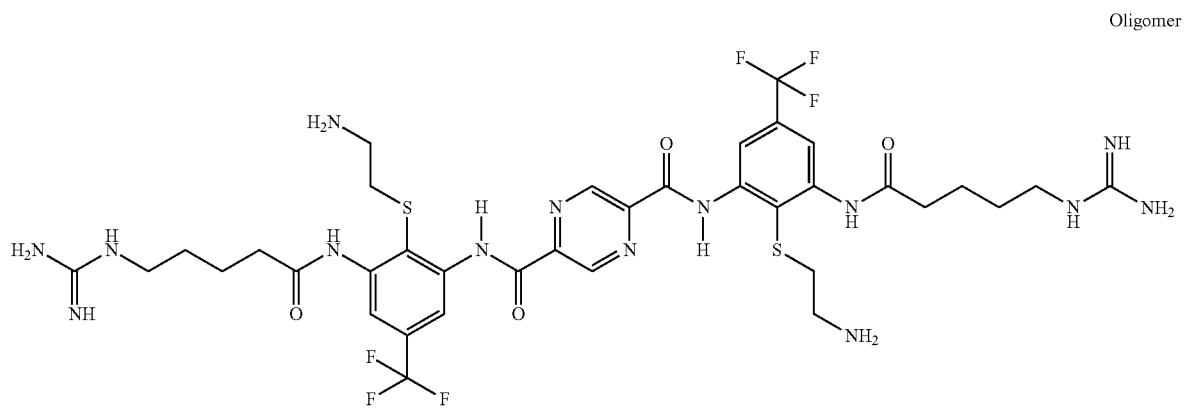 [SMILES: N=C(N)NCCCCC(=O)Nc1cc(C(F)(F)F)cc(NC(=O)c2cnc(C(=O)Nc3cc(C(F)(F)F)cc(NC(=O)CCCCNC(=N)N)c3SCCN)cn2)c1SCCN]

Oligomer 5

| | MIC (ug/mL) | |
|---|---|---|
| Oligomer | *E. coli* D31 | *S. aureus* ATCC27660 |
| Oligomer 4 | 0.78 | 0.098 |
| Oligomer 5 | 1.56 | 0.78 |

| | MIC | | | | |
|---|---|---|---|---|---|
| Compound | *E. coli* Lab Strain D31 | *S. aureus* ATCC 27660 | *E. faecalis* ATCC 29212 | *P. aeruginosa* ATCC 10145 | *K. pneumoniae* Lab Strain KP10 |
| Oligomer 4 | 0.78 | 0.098 | 0.78 | 12.5 | 0.78 |
| Oligomer 5 | 1.56 | 0.78 | 1.56 | >100 | 1.56 |

-continued

S. aureus fluoroquinolone-susceptible MICs µg/ml

| Isolate | Oligomer 4 | Oligomer 5 |
|---|---|---|
| 11 - K1628 | 0.25 | 0.25 |
| 12 - K1618 | 0.5 | 0.125 |
| 13 - K1617 | 0.25 | 0.25 |
| 14 - K1611 | 0.25 | 0.25 |
| 15 - K1607 | 0.25 | 0.25 |
| 16 - K1600 | 0.25 | 0.125 |
| 17 - K1591 | 0.25 | 0.5 |
| 18 - K1585 | 0.25 | 0.25 |
| 19 - K1583 | 0.25 | 0.25 |
| 20 - K1574 | 0.25 | 0.25 |
| 21 - K1566 | 0.25 | 0.25 |
| 22 - K1551 | 0.25 | 0.125 |
| 23 - K1545 | 0.25 | 0.25 |
| 24 - K1540 | 0.25 | 0.25 |
| 25 - K1530 | 0.25 | 0.5 |
| E. coli D31 | 1 (0.78) | 16 (1.56) |
| S. aureus ATCC 27660 | 2 (0.098) | 16 (0.78) |

MICs for Control Bacteria (E. coli, S. aureus) are within the parentheses.

S. aureus fluoroquinolone-susceptible MIC$_{50}$ and MIC$_{90}$ Determinations and Statistics

| Row | Oligomer 4 QSSA-A | Oligomer 5 QSSA-A | |
|---|---|---|---|
| 1 | 0.125 | 0.125 | |
| 2 | 0.250 | 0.125 | |
| 3 | 0.250 | 0.125 | |
| 4 | 0.250 | 0.125 | |
| 5 | 0.250 | 0.125 | |
| 6 | 0.250 | 0.125 | |
| 7 | 0.250 | 0.125 | |
| 8 | 0.250 | 0.250 | |
| 9 | 0.250 | 0.250 | |
| 10 | 0.250 | 0.250 | |
| 11 | 0.250 | 0.250 | |
| 12 | 0.250 | 0.250 | |
| 13 | 0.250 | 0.250 | MIC$_{50}$ |
| 14 | 0.250 | 0.250 | |
| 15 | 0.250 | 0.250 | |
| 16 | 0.250 | 0.250 | |
| 17 | 0.250 | 0.250 | |
| 18 | 0.250 | 0.250 | |
| 19 | 0.250 | 0.250 | |
| 20 | 0.250 | 0.250 | |
| 21 | 0.250 | 0.250 | |
| 22 | 0.500 | 0.250 | MIC$_{90}$ |
| 23 | 0.500 | 0.500 | |
| 24 | 0.500 | 0.500 | |
| 25 | 0.500 | 0.500 | |

Descriptive Statistics

| Variable | N | N* | Mean | SE Mean | StDev | Minimum | Median | Maximum |
|---|---|---|---|---|---|---|---|---|
| Olig 4 QSSA | 25 | 0 | 0.2850 | 0.0198 | 0.0990 | 0.1250 | 0.2500 | 0.5000 |
| Olig 5 QSSA | 25 | 0 | 0.2450 | 0.0222 | 0.1111 | 0.1250 | 0.2500 | 0.5000 |

Summary of Results

| | MIC$_{50}$ | MIC$_{90}$ | Median MIC | Range of MICs |
|---|---|---|---|---|
| Oligomer 4 | 0.25 µg/ml | 0.25 µg/ml | 0.25 µg/ml | 0.125-0.5 µg/ml |
| Oligomer 5 | 0.25 µg/ml | 0.5 µg/ml | 0.25 µg/ml | 0.125-0.5 µg/ml |

Mann-Whitney Test and CI: Oligomer 4 QSSA, Oligomer 5 QSSA

| | N | Median |
|---|---|---|
| Olig 4 QSSA | 25 | 0.2500 |
| Olig 5 QSSA | 25 | 0.2500 |

Point estimate for ETA1-ETA2 is 0.0000

95.2 Percent CI for ETA1-ETA2 is (−0.0000, 0.1250)

W=712.5

Test of ETA1=ETA2 vs ETA1 not=ETA2 is significant at 0.1483

The test is significant at 0.0731 NS (adjusted for ties)

S. aureus fluoroquinolone-resistant MICs µg/ml

| Isolate | Oligomer 4 | Oligomer 5 |
|---|---|---|
| 1 - E504 | 0.25 | 0.5 |
| 2 - E475 | 0.25 | 0.25 |
| 3 - E442 | 0.25 | 0.25 |
| 4 - E427 | 0.5 | 0.5 |
| 5 - E425 | 0.25 | 0.25 |
| 6 - E424 | 0.25 | 0.25 |
| 7 - E417 | 1 | 0.25 |
| 8 - E407 | 0.25 | 0.125 |
| 9 - E401 | 0.25 | 0.25 |
| 10 - K1659 | 0.25 | 0.25 |
| 11 - E96 | 0.125 | 0.25 |
| 12 - E379 | 0.5 | 0.5 |
| 13 - E369 | 0.125 | 0.5 |
| 14 - E361 | 0.25 | 0.25 |
| 15 - E339 | 0.25 | 0.25 |
| 16 - E333 | 0.25 | 0.125 |
| 17 - E332 | 0.25 | 0.25 |
| 18 - E327 | 0.5 | 0.25 |
| 19 - E325 | 0.5 | 0.25 |
| 20 - K950 | 0.5 | 0.25 |
| 21 - K839 | 0.25 | 0.25 |
| 22 - K1679 | 0.25 | 0.25 |
| 23 - K1677 | 0.25 | 0.5 |
| 24 - K1672 | 0.25 | 0.25 |
| 25 - K1670 | 0.25 | 0.25 |
| E. coli D31 | 1 (0.78) | 4 (1.56) |
| S. aureus ATCC 27660 | 1 (0.098) | 8 (0.78) |

MICs for Control Bacteria (*E. coli, S. aureus*) are within the parentheses.

S. aureus fluoroquinolone-resistant MIC$_{50}$ and MIC$_{90}$ Determinations and Statistics

| Row | Oligomer 4 QRSA-A | Oligomer 5 QRSA-A | |
|---|---|---|---|
| 1 | 0.125 | 0.125 | |
| 2 | 0.125 | 0.125 | |
| 3 | 0.250 | 0.250 | |
| 4 | 0.250 | 0.250 | |
| 5 | 0.250 | 0.250 | |
| 6 | 0.250 | 0.250 | |
| 7 | 0.250 | 0.250 | |
| 8 | 0.250 | 0.250 | |
| 9 | 0.250 | 0.250 | |
| 10 | 0.250 | 0.250 | |
| 11 | 0.250 | 0.250 | |
| 12 | 0.250 | 0.250 | |
| 13 | 0.250 | 0.250 | MIC$_{50}$ |
| 14 | 0.250 | 0.250 | |
| 15 | 0.250 | 0.250 | |
| 16 | 0.250 | 0.250 | |
| 17 | 0.250 | 0.250 | |
| 18 | 0.250 | 0.250 | |
| 19 | 0.250 | 0.250 | |
| 20 | 0.500 | 0.250 | |
| 21 | 0.500 | 0.500 | |
| 22 | 0.500 | 0.500 | MIC$_{90}$ |
| 23 | 0.500 | 0.500 | |
| 24 | 0.500 | 0.500 | |
| 25 | 1.000 | 0.500 | |

Descriptive Statistics

| Variable | N | N* | Mean | SE Mean | StDev | Minimum | Median | Maximum |
|---|---|---|---|---|---|---|---|---|
| Olig 4 QRSA | 25 | 0 | 0.3200 | 0.0361 | 0.1807 | 0.1250 | 0.2500 | 1.0000 |
| Olig 5 QRSA | 25 | 0 | 0.2900 | 0.0225 | 0.1125 | 0.1250 | 0.2500 | 0.5000 |

Summary of Results

| | MIC50 | MIC90 | Median MIC | Range of MICs |
|---|---|---|---|---|
| Oligomer 4 | 0.25 µg/ml | 0.5 µg/ml | 0.25 µg/ml | 0.125-1.0 µg/ml |
| Oligomer 5 | 0.25 µg/ml | 0.5 µg/ml | 0.25 µg/ml | 0.125-0.5 µg/ml |

Mann-Whitney Test and CI: Oligomer 4 QRSA, Oligomer 5 QRSA

| | N | Median |
|---|---|---|
| Olig 4 QRSA | 25 | 0.2500 |
| Olig 5 QRSA | 25 | 0.2500 |

Point estimate for ETA1-ETA2 is −0.0000
95.2 Percent CI for ETA1-ETA2 is (−0.0000, 0.0000)
W=651.5
Test of ETA1=ETA2 vs ETA1 not=ETA2 is significant at 0.7934
The test is significant at 0.7450 NS (adjusted for ties)

Control Bacteria

During the first sets of MICs performed with the *S. aureus* fluoroquinolone-susceptible and *S. aureus* fluoroquinolone-resistant, the MICs for the control bacteria (*E. coli* D31, and *S. aureus* ATC═C 27660) for both Oligomer 4 and Oligomer 5 were much higher than those shown below.

| Control Isolate | Control for MIC Test | Oligomer 4 | Oligomer 5 |
|---|---|---|---|
| *E. coli* D31 | SA-FQS | 1 (0.78) | 16 (1.56) |
| *S. aureus* ATCC 27660 | SA-FQS | 2 (0.098) | 16 (0.78) |
| *E. coli* D31 | SA-FQR | 1 (0.78) | 4 (1.56) |
| *S. aureus* ATCC 27660 | SA-FQR | 1 (0.098) | 8 (0.78) |

MICs for Control Bacteria (*E. coli, S. aureus*) are within the parentheses.

A new set of MICs were performed with new batches of both Oligomer 4 and Oligomer 5, and control bacteria, in quadruplicate. The results from the experiment is as follows:

| Control Isolate | Control for MIC Test | Oligomer 4 | Oligomer 5 |
|---|---|---|---|
| *E. coli* D31 | Control Only 1 | 1 (0.78) | 8 (1.56) |
| *S. aureus* ATCC 27660 | Control Only 1 | 0.25 (0.098) | 0.25 (0.78) |
| *E. coli* D31 | Control Only 2 | 1 (0.78) | 8 (1.56) |
| *S. aureus* ATCC 27660 | Control Only 2 | 0.25 (0.098) | 0.25 (0.78) |
| *E. coli* D31 | Control Only 3 | 1 (0.78) | 8 (1.56) |
| *S. aureus* ATCC 27660 | Control Only 3 | 0.25 (0.098) | 0.5 (0.78) |
| *E. coli* D31 | Control Only 4 | 1 (0.78) | 16 (1.56) |

-continued

| Control Isolate | Control for MIC Test | Oligomer 4 | Oligomer 5 |
|---|---|---|---|
| *S. aureus* ATCC 27660 | Control Only 4 | 0.5 (0.098) | 0.5 (0.78) |

MICs for Control Bacteria (*E. coli, S. aureus*) are within the parentheses.

Although the MICs for Oligomer 5 for *E. coli* D31 remained high, the MICs for *S. aureus* ATC═C 27660 were for both Oligomer 4 and Oligomer 5 and Oligomer 4 for *E. coli* D31 were within the acceptable range (1-2 doubling dilutions) of the MICs previously obtained. It was decided to continue with the MIC determinations using the new batches of Oligomer 4 and Oligomer 5 for all subsequent MIC determinations.

Since the MICs for both Oligomer 4 and Oligomer 5 with the *S. aureus* fluoroquinolone-susceptible and *S. aureus* fluoroquinolone-resistant were similar to that of the control *S. aureus* ATC═C 27660 MIC performed previously, these MICs performed with the first batch of drugs would not be repeated using the new batches of compounds.

| *Staphylococcus epidermidis* (Coagulase-negative *Staphylococcus*) fluoroquinolone-susceptible MICs µg/ml | | |
|---|---|---|
| Isolate | Oligomer 4 | Oligomer 5 |
| 1 - E511 | 0.25 | 0.25 |
| 2 - E489 | 0.125 | 0.125 |
| 3 - E491 | 0.125 | 0.125 |
| 4 - E476 | 0.25 | 0.25 |
| 5 - E473 | 0.25 | 0.125 |
| 6 - E462 | 0.125 | 0.125 |
| 7 - E460 | 0.125 | 0.125 |
| 8 - E453 | 0.125 | 0.125 |
| 9 - E448 | 0.125 | 0.125 |
| 10 - E443 | <0.0625 | <0.0625 |
| 11 - E441 | <0.0625 | 0.125 |
| 12 - E438 | 0.125 | 0.125 |
| 13 - E437 | 0.125 | 0.125 |
| 14 - E434 | 0.125 | 0.125 |
| 15 - E433 | 0.125 | 0.125 |
| 16 - E430 | <0.0625 | 0.125 |
| 17 - E420 | 0.125 | 0.125 |
| 18 - E419 | 0.125 | 0.125 |
| 19 - E403 | 0.125 | 0.125 |
| 20 - E394 | 0.125 | 0.125 |
| 21 - E393 | 0.125 | 0.125 |
| 22 - E328 | 0.25 | 0.25 |
| 23 - E382 | 0.125 | 0.125 |
| 24 - E381 | 0.125 | 0.25 |
| 25 - E372 | 0.25 | <0.0625 |
| *E. coli* D31 | 1 (0.78) | 4 (1.56) |
| *S. aureus* ATCC 27660 | 0.25 (0.098) | 0.25 (0.78) |

MICs for Control Bacteria (*E. coli*, *S. aureus*) are within the parentheses.

| *Staphylococcus epidermidis* (Coagulase-negative *Staphylococcus*) fluoroquinolone-susceptible $MIC_{50}$ and $MIC_{90}$ Determinations and Statistics For Statistical Calculation Purposes, <0.0625 was Replaced with 0.03125. | | | |
|---|---|---|---|
| Row | Oligomer 4 QSSE-A | Oligomer 5 QSSE-A | |
| 1 | 0.03125 | 0.03125 | |
| 2 | 0.03125 | 0.03125 | |
| 3 | 0.03125 | 0.12500 | |
| 4 | 0.12500 | 0.12500 | |
| 5 | 0.12500 | 0.12500 | |
| 6 | 0.12500 | 0.12500 | |
| 7 | 0.12500 | 0.12500 | |
| 8 | 0.12500 | 0.12500 | |
| 9 | 0.12500 | 0.12500 | |
| 10 | 0.12500 | 0.12500 | |
| 11 | 0.12500 | 0.12500 | |
| 12 | 0.12500 | 0.12500 | |
| 13 | 0.12500 | 0.12500 | $MIC_{50}$ |
| 14 | 0.12500 | 0.12500 | |
| 15 | 0.12500 | 0.12500 | |
| 16 | 0.12500 | 0.12500 | |
| 17 | 0.12500 | 0.12500 | |
| 18 | 0.12500 | 0.12500 | |
| 19 | 0.12500 | 0.12500 | |
| 20 | 0.12500 | 0.12500 | |
| 21 | 0.25000 | 0.12500 | |
| 22 | 0.25000 | 0.25000 | $MIC_{90}$ |
| 23 | 0.25000 | 0.25000 | |
| 24 | 0.25000 | 0.25000 | |
| 25 | 0.25000 | 0.25000 | |

Descriptive Statistics

| Variable | N | N* | Mean | SE Mean | StDev | Minimum | Median | Maximum |
|---|---|---|---|---|---|---|---|---|
| Olig 4 QSSE | 25 | 0 | 0.1388 | 0.0129 | 0.0645 | 0.0313 | 0.1250 | 0.2500 |
| Olig 5 QSSE | 25 | 0 | 0.1375 | 0.0113 | 0.0563 | 0.0313 | 0.1250 | 0.2500 |

Summary of Results

| | $MIC_{50}$ | $MIC_{90}$ | Median MIC | Range of MICs |
|---|---|---|---|---|
| Oligomer 4 | 0.125 µg/ml | 0.25 µg/ml | 0.125 µg/ml | 0.03125-0.25 µg/ml |
| Oligomer 5 | 0.125 µg/ml | 0.25 µg/ml | 0.125 µg/ml | 0.03125-0.25 µg/ml |

Mann-Whitney Test and CI: Oligomer 4 QSSE, Oligomer 5 QSSE

| | N | Median |
|---|---|---|
| Olig 4 QSSE | 25 | 0.12500 |
| Olig 5 QSSE | 25 | 0.12500 |

Point estimate for ETA1-ETA2 is 0.00000

95.2 Percent CI for ETA1-ETA2 is (−0.00002, 0.00000)

W=638.5

Test of ETA1=ETA2 vs ETA1 not=ETA2 is significant at 0.9923

The test is significant at 0.9902 NS (adjusted for ties)

| Staphylococcus epidermidis (Coagulase-negative Staphylococcus) fluoroquinolone-resistant MICs µg/ml | | |
|---|---|---|
| Isolate | Oligomer 4 | Oligomer 5 |
| 1 - E515 | 0.125 | 0.125 |
| 2 - E514 | <0.0625 | 0.125 |
| 3 - E513 | 0.125 | 0.125 |
| 4 - E510 | <0.0625 | 0.125 |
| 5 - E509 | 0.125 | 0.125 |
| 6 - E508 | 0.125 | 0.125 |
| 7 - E505 | 0.125 | 0.125 |
| 8 - E503 | 0.125 | 0.125 |
| 9 - E502 | 0.125 | 0.25 |
| 10 - E499 | 0.125 | 0.25 |
| 11 - E498 | 0.125 | 0.125 |
| 12 - E494 | <0.0625 | 0.125 |
| 13 - E493 | 0.125 | 0.125 |
| 14 - E485 | 0.125 | 0.125 |
| 15 - E487 | 0.125 | <0.0625 |
| 16 - E486 | <0.0625 | 0.125 |
| 17 - E480 | 0.125 | 0.125 |
| 18 - E475 | 0.25 | 0.125 |
| 19 - E471 | 0.125 | 0.125 |
| 20 - E458 | 0.125 | 0.125 |
| 21 - E452 | 0.25 | 0.5 |
| 22 - E450 | 0.125 | 0.125 |
| 23 - E440 | 0.25 | 0.125 |
| 24 - E446 | 0.125 | <0.0625 |
| 25 - E444 | 0.25 | 0.25 |
| E. coli D31 | 1 (0.78) | 4 (1.56) |
| S. aureus ATCC 27660 | 0.25 (0.098) | 0.25 (0.78) |

MICs for Control Bacteria (*E. coli*, *S. aureus*) are within the parentheses.

*Staphylococcus epidermidis* (Coagulase-negative *Staphylococcus*) fluoroquinolone-resistant $MIC_{50}$ and $MIC_{90}$ Determinations and Statistics For Statistical Calculation Purposes, <0.0625 was Replaced with 0.03125.

| Row | Oligomer 4 QRSE-A | Oligomer 5 QRSE-A | |
|---|---|---|---|
| 1 | 0.03125 | 0.03125 | |
| 2 | 0.03125 | 0.03125 | |
| 3 | 0.03125 | 0.12500 | |
| 4 | 0.03125 | 0.12500 | |
| 5 | 0.12500 | 0.12500 | |
| 6 | 0.12500 | 0.12500 | |
| 7 | 0.12500 | 0.12500 | |
| 8 | 0.12500 | 0.12500 | |
| 9 | 0.12500 | 0.12500 | |
| 10 | 0.12500 | 0.12500 | |
| 11 | 0.12500 | 0.12500 | |
| 12 | 0.12500 | 0.12500 | |
| 13 | 0.12500 | 0.12500 | $MIC_{50}$ |
| 14 | 0.12500 | 0.12500 | |
| 15 | 0.12500 | 0.12500 | |
| 16 | 0.12500 | 0.12500 | |
| 17 | 0.12500 | 0.12500 | |
| 18 | 0.12500 | 0.12500 | |
| 19 | 0.12500 | 0.12500 | |
| 20 | 0.12500 | 0.12500 | |
| 21 | 0.12500 | 0.12500 | |
| 22 | 0.25000 | 0.25000 | $MIC_{90}$ |
| 23 | 0.25000 | 0.25000 | |
| 24 | 0.25000 | 0.25000 | |
| 25 | 0.25000 | 0.50000 | |

Descriptive Statistics

| Variable | N | N* | Mean | SE Mean | StDev | Minimum | Median | Maximum |
|---|---|---|---|---|---|---|---|---|
| Olig 4 QRSE | 25 | 0 | 0.1300 | 0.0127 | 0.0636 | 0.0313 | 0.1250 | 0.2500 |
| Olig 5 QRSE | 25 | 0 | 0.1475 | 0.0179 | 0.0895 | 0.0313 | 0.1250 | 0.5000 |

Summary of Results

| | $MIC_{50}$ | $MIC_{90}$ | Median MIC | Range of MICs |
|---|---|---|---|---|
| Oligomer 4 | 0.125 µg/ml | 0.25 µg/ml | 0.125 µg/ml | 0.03125-0.25 µg/ml |
| Oligomer 5 | 0.125 µg/ml | 0.25 µg/ml | 0.125 µg/ml | 0.03125-0.5 µg/ml |

Mann-Whitney Test and CI: Oligomer 4 QRSE, Oligomer 5 QRSE

| | N | Median |
|---|---|---|
| Olig 4 QRSE | 25 | 0.12500 |
| Olig 5 QRSE | 25 | 0.12500 |

Point estimate for ETA1-ETA2 is −0.00000

95.2 Percent CI for ETA1-ETA2 is (0.00001,−0.00002)

W=614.5

Test of ETA1=ETA2 vs ETA1 not=ETA2 is significant at 0.6624

The test is significant at 0.5800 NS (adjusted for ties)

Serratia marcescens MICs μg/ml

| Isolate | Oligomer 4 | Oligomer 5 |
|---|---|---|
| 1 - K1681 | 32 | >128 |
| 2 - K1674 | 32 | >128 |
| 3 - K1558 | 4 | >128 |
| 4 - K1538 | 16 | >128 |
| 5 - K1503 | 32 | >128 |
| 6 - K1216 | 4 | >128 |
| 7 - K1496 | 8 | >128 |
| 8 - K1481 | 2 | >128 |
| 9 - K1470 | 32 | >128 |
| 10 - K1468 | 2 | >128 |
| 11 - K1467 | 32 | >128 |
| 12 - K1462 | 16 | >128 |
| 13 - K1461 | 8 | 128 |
| 14 - K1413 | 16 | >128 |
| 15 - K1402 | 0.25 | 8 |
| 16 - K1357 | 1 | >128 |
| 17 - K1351 | 0.5 | 64 |
| 18 - K1327 | 8 | >128 |
| 19 - K1321 | 8 | >128 |
| 20 - K1315 | 16 | >128 |
| 21 - K1306 | 8 | >128 |
| 22 - K1290 | 8 | >128 |
| 23 - K1265 | 8 | >128 |
| 24 - K1263 | 8 | >128 |
| 25 - K1239 | 8 | >128 |
| E. coli D31 | 0.5 (0.78) | 4 (1.56) |
| S. aureus ATCC 27660 | 0.25 (0.098) | 0.5 (0.78) |

MICs for Control Bacteria (E. coli, S. aureus) are within the parentheses.

Serratia marcescens $MIC_{50}$ and $MIC_{90}$ Determinations and Statistics For Statistical Calculation Purposes, >128 was Replaced with 256.

| Row | Oligomer 4 SM-A | Oligomer 5 SM-A | |
|---|---|---|---|
| 1 | 0.25 | 8 | |
| 2 | 0.50 | 64 | |
| 3 | 1.00 | 128 | |
| 4 | 2.00 | 256 | |
| 5 | 2.00 | 256 | |
| 6 | 4.00 | 256 | |
| 7 | 4.00 | 256 | |
| 8 | 8.00 | 256 | |
| 9 | 8.00 | 256 | |
| 10 | 8.00 | 256 | |
| 11 | 8.00 | 256 | |
| 12 | 8.00 | 256 | |
| 13 | 8.00 | 256 | $MIC_{50}$ |
| 14 | 8.00 | 256 | |
| 15 | 8.00 | 256 | |
| 16 | 8.00 | 256 | |
| 17 | 16.00 | 256 | |
| 18 | 16.00 | 256 | |
| 19 | 16.00 | 256 | |
| 20 | 16.00 | 256 | |
| 21 | 32.00 | 256 | |
| 22 | 32.00 | 256 | $MIC_{90}$ |
| 23 | 32.00 | 256 | |
| 24 | 32.00 | 256 | |
| 25 | 32.00 | 256 | |

Descriptive Statistics

| Variable | N | N* | Mean | SE Mean | StDev | Minimum | Median | Maximum |
|---|---|---|---|---|---|---|---|---|
| Olig 4 SM | 25 | 0 | 12.39 | 2.21 | 11.04 | 0.25 | 8.00 | 32.00 |
| Olig 5 SM | 25 | 0 | 233.3 | 13.0 | 65.1 | 8.0 | 256.0 | 256.0 |

Summary of Results

| | $MIC_{50}$ | $MIC_{90}$ | Median MIC | Range of MICs |
|---|---|---|---|---|
| Oligomer 4 | 8 μg/ml | 32 μg/ml | 8 μg/ml | 0.25-32 μg/ml |
| Oligomer 5 | 256 μg/ml | 256 μg/ml | 256 μg/ml | 8-256 μg/ml |

Mann-Whitney Test and CI: Oligomer 4 SM, Oligomer 5 SM

| | N | Median |
|---|---|---|
| Olig 4 SM | 25 | 8.00 |
| Olig 5 SM | 25 | 256.00 |

Point estimate for ETA1-ETA2 is −248.00

95.2 Percent CI for ETA1-ETA2 is (−247.98,−239.99)

W=338.5

Test of ETA1=ETA2 vs ETA1 not=ETA2 is significant at 0.0000

The test is significant at 0.0000 (adjusted for ties)

Oligomer 4>Oligomer 5 (More Potent>Less Potent)

Pseudomonas aeruginosa MICs μg/ml

| Isolate | Oligomer 4 | Oligomer 5 |
|---|---|---|
| 1—K1673 | 2 | 32 |
| 2—K1668 | 2 | 64 |
| 3—K1662 | 2 | 64 |
| 4—K1657 | 2 | 64 |
| 5—K1651 | 4 | 128 |
| 6—K1649 | 4 | 64 |
| 7—K1564 | 8 | >128 |
| 8—K1636 | 0.5 | 4.0 |
| 9—K1634 | 2 | 128 |
| 10—K1633 | 4 | 64 |
| 11—K1632 | 4 | 64 |
| 12—K1631 | 8 | 64 |
| 13—K1629 | 4 | 64 |
| 14—K1627 | 2 | 64 |
| 15—K1626 | 8 | 128 |
| 16—K1625 | 4 | 64 |
| 17—K1562 | 4 | 128 |
| 18—K1613 | 4 | 32 |
| 19—K1553 | 2 | 128 |
| 20—K1594 | 2 | 64 |
| 21—K1588 | 4 | 128 |
| 22—K1554 | 4 | 128 |
| 23—K1580 | 2 | 32 |
| 24—K1577 | 2 | 64 |
| 25—K1576 | 4 | 128 |
| E. coli D31 | 0.5 (0.78) | 8 (1.56) |
| S. aureus ATCC 27660 | 0.5 (0.098) | 0.25 (0.78) |

MICs for Control Bacteria (*E. coli, S. aureus*) are within the parentheses.

*Pseudomonas aeruginosa*
$MIC_{50}$ and $MIC_{90}$ Determinations and Statistics
For Statistical Calculation Purposes, >128 was Replaced with 256.

| Row | Oligomer 4 PA-A | Oligomer 5 PA-A | |
|---|---|---|---|
| 1 | 0.5 | 4 | |
| 2 | 2.0 | 32 | |
| 3 | 2.0 | 32 | |
| 4 | 2.0 | 32 | |
| 5 | 2.0 | 64 | |
| 6 | 2.0 | 64 | |
| 7 | 2.0 | 64 | |
| 8 | 2.0 | 64 | |
| 9 | 2.0 | 64 | |
| 10 | 2.0 | 64 | |
| 11 | 2.0 | 64 | |
| 12 | 4.0 | 64 | |
| 13 | 4.0 | 64 | $MIC_{50}$ |
| 14 | 4.0 | 64 | |
| 15 | 4.0 | 64 | |
| 16 | 4.0 | 64 | |
| 17 | 4.0 | 128 | |
| 18 | 4.0 | 128 | |
| 19 | 4.0 | 128 | |
| 20 | 4.0 | 128 | |
| 21 | 4.0 | 128 | |
| 22 | 4.0 | 128 | $MIC_0$ |
| 23 | 8.0 | 128 | |
| 24 | 8.0 | 128 | |
| 25 | 8.0 | 256 | |

Descriptive Statistics

| Variable | N | N* | Mean | SE Mean | StDev | Minimum | Median | Maximum |
|---|---|---|---|---|---|---|---|---|
| Olig 4 PA | 25 | 0 | 3.540 | 0.398 | 1.989 | 0.500 | 4.000 | 8.000 |
| Olig 5 PA | 25 | 0 | 85.9 | 10.4 | 51.8 | 4.0 | 64.0 | 256.0 |

Summary of Results

| | $MIC_{50}$ | $MIC_{90}$ | Median MIC | Range of MICs |
|---|---|---|---|---|
| Oligomer 4 | 4 µg/ml | 4 µg/ml | 4 µg/ml | 0.5-8 µg/ml |
| Oligomer 5 | 64 µg/ml | 128 µg/ml | 64 µg/ml | 4-256 µg/ml |

Mann-Whitney Test and CI: Oligomer 4 PA, Oligomer 5 PA

| | N | Median |
|---|---|---|
| Olig 4 PA | 25 | 4.00 |
| Olig 5 PA | 25 | 64.00 |

Point estimate for ETA1-ETA2 is −62.00

95.2 Percent CI for ETA1-ETA2 is (−120.00,−60.00)

W=333.5

Test of ETA1=ETA2 vs ETA1 not=ETA2 is significant at 0.0000

The test is significant at 0.0000 (adjusted for ties)

Oligomer 4>Oligomer 5 (More Potent>Less Potent)

*Streptococcus pneumoniae*

| Isolate | Oligomer 4 MICs µg/ml | Oligomer 5 |
|---|---|---|
| 1—B1386 | >64 | >64 |
| 2—B1380 | 1 | 4 |
| 3—B1378 | 1 | 0.5 |
| 4—B1377 | 2 | 8 |
| 5—B1373 | 1 | 8 |
| 6—B1367 | 1 | 16 |
| 7—B1355 | 2 | 8 |
| 8—B1353 | 1 | 4 |
| 9—B1351 | 1 | 1 |
| 10—B1339 | 1 | 2 |
| 11—B1337 | 0.5 | 1 |
| 12—B1335 | 2 | 1 |
| 13—B1334 | 1 | 1 |
| 14—B1333 | 1 | 1 |
| 15—B1255 | 0.5 | 1 |
| 16—B1288 | 1 | 8 |
| 17—B1287 | 1 | 16 |
| 18—B1272 | 0.5 | 1 |
| 19—B1264 | 0.5 | 1 |
| 20—B1252 | 1 | 16 |
| 21—B1245 | 0.5 | 2 |
| 22—B1211 | 1 | 8 |
| 23—B1213 | 1 | 16 |
| 24—B1208 | 0.5 | 8 |
| 25—B1214 | 1 | 4 |
| *E. coli* D31* | 2 | 2 |
| *S. aureus* ATCC 27660* | 1 | 1 |
| *E. coli* D31** | 0.5 (0.78) | 16 (1.56) |
| *S. aureus* ATCC 27660** | 0.25 (0.098) | 2 (0.78) |

*Control Bacteria Set #1;
**Control Bacteria Set #2; (MICs for Control Bacteria (*E. coli, S. aureus*) are within the parentheses.)

*Streptococcus pneumoniae*
$MIC_{50}$ and $MIC_{90}$ Determinations and Statistics
For Statistical Calculation Purposes, >64 was Replaced with 128.

| Row | Oligomer 4 SP-A | Oligomer 5 SP-A | |
|---|---|---|---|
| 1 | 0.5 | 0.5 | |
| 2 | 0.5 | 1.0 | |
| 3 | 0.5 | 1.0 | |
| 4 | 0.5 | 1.0 | |
| 5 | 0.5 | 1.0 | |
| 6 | 0.5 | 1.0 | |
| 7 | 1.0 | 1.0 | |
| 8 | 1.0 | 1.0 | |
| 9 | 1.0 | 1.0 | |
| 10 | 1.0 | 2.0 | |
| 11 | 1.0 | 2.0 | |
| 12 | 1.0 | 4.0 | |
| 13 | 1.0 | 4.0 | $MIC_{50}$ |
| 14 | 1.0 | 4.0 | |
| 15 | 1.0 | 8.0 | |
| 16 | 1.0 | 8.0 | |
| 17 | 1.0 | 8.0 | |
| 18 | 1.0 | 8.0 | |
| 19 | 1.0 | 8.0 | |
| 20 | 1.0 | 8.0 | |
| 21 | 1.0 | 16.0 | |
| 22 | 2.0 | 16.0 | $MIC_{90}$ |
| 23 | 2.0 | 16.0 | |
| 24 | 2.0 | 16.0 | |
| 25 | 128.0 | 128.0 | |

Descriptive Statistics

| Variable | N | N* | Mean | SE Mean | StDev | Minimum | Median | Maximum |
|---|---|---|---|---|---|---|---|---|
| Olig 4 SP | 25 | 0 | 6.08 | 5.08 | 25.40 | 0.50 | 1.00 | 128.00 |
| Olig 5 SP | 25 | 0 | 10.58 | 5.01 | 25.05 | 0.50 | 4.00 | 128.00 |

Summary of Results

| | $MIC_{50}$ | $MIC_{90}$ | Median MIC | Range of MICs |
|---|---|---|---|---|
| Oligomer 4 | 1 µg/ml | 2 µg/ml | 1 µg/ml | 0.5-128 µg/ml |
| Oligomer 5 | 4 µg/ml | 16 µg/ml | 4 µg/ml | 4-128 µg/ml |

Mann-Whitney Test and CI: Oligomer 4 SP, Oligomer 5 SP

| | N | Median |
|---|---|---|
| Olig 4 SP | 25 | 1.000 |
| Olig 5 SP | 25 | 4.000 |

Point estimate for ETA1-ETA2 is −3.000
95.2 Percent CI for ETA1-ETA2 is (−6.999,−0.499)
W=457.5
Test of ETA1=ETA2 vs ETA1 not=ETA2 is significant at 0.0005
 The test is significant at 0.0002 (adjusted for ties)
Oligomer 4>Oligomer 5 (More Potent>Less Potent)

*Streptococcus viridans* group

| Isolate | Oligomer 4 | Oligomer 5 |
|---|---|---|
| | | MICs µg/ml |
| 1—K1684 | 2 | 8 |
| 2—K1680 | 4 | 64 |
| 3—E546 | 1 | 8 |
| 4—E272 | 2 | 16 |
| 5—E506 | 16 | >64 |
| 6—E496 | 1 | 0.5 |
| 7—E456 | 4 | 16 |
| 8—E432 | 4 | 8 |
| 9—E423 | 4 | >64 |
| 10—E418 | 8 | >64 |
| 11—E412 | 2 | 8 |
| 12—E409 | 8 | 32 |
| 13—E405 | 4 | >64 |
| 14—E404 | 32 | >64 |
| 15—E396 | 16 | 32 |
| 16—E262 | 1 | 4 |
| 17—E362 | 4 | 16 |
| 18—E359 | 4 | 32 |
| 19—E348 | 8 | 16 |
| 20—E344 | 4 | 4 |
| 21—E308 | 4 | 4 |
| 22—E294 | 4 | 2 |
| 23—E292 | 4 | 0.5 |
| 24—E285 | 4 | 0.5 |
| 25—E265 | 1 | 8 |
| *E. coli* D31* | 2 | 2 |
| *S. aureus* ATCC 27660* | 2 | 1 |
| *E. coli* D31** | 0.5 (0.78) | 16 (1.56) |
| *S. aureus* ATCC 27660** | 1 (0.098) | 1 (0.78) |

*Control Bacteria Set #1;
**Control Bacteria Set #2; (MICs for Control Bacteria (*E. coli*, *S. aureus*) are within the parentheses.)

*Streptococcus viridans* group $MIC_{50}$ and $MIC_{90}$ Determinations and Statistics
For Statistical Calculation Purposes, >64 was Replaced with 128.

| Row | Oligomer 4 SV-A | Oligomer 5 SV-A | |
|---|---|---|---|
| 1 | 1 | 0.5 | |
| 2 | 1 | 0.5 | |
| 3 | 1 | 0.5 | |
| 4 | 1 | 2.0 | |
| 5 | 2 | 4.0 | |
| 6 | 2 | 4.0 | |
| 7 | 2 | 4.0 | |
| 8 | 4 | 8.0 | |
| 9 | 4 | 8.0 | |
| 10 | 4 | 8.0 | |
| 11 | 4 | 8.0 | |
| 12 | 4 | 8.0 | |
| 13 | 4 | 16.0 | $MIC_{50}$ |
| 14 | 4 | 16.0 | |
| 15 | 4 | 16.0 | |
| 16 | 4 | 16.0 | |
| 17 | 4 | 32.0 | |
| 18 | 4 | 32.0 | |
| 19 | 4 | 32.0 | |
| 20 | 8 | 64.0 | |
| 21 | 8 | 128.0 | |
| 22 | 8 | 128.0 | $MIC_{90}$ |
| 23 | 16 | 128.0 | |
| 24 | 16 | 128.0 | |
| 25 | 32 | 128.0 | |

Descriptive Statistics

| Variable | N | N* | Mean | SE Mean | StDev | Minimum | Median | Maximum |
|---|---|---|---|---|---|---|---|---|
| Olig 4 SV | 25 | 0 | 5.84 | 1.34 | 6.72 | 1.00 | 4.00 | 32.00 |
| Olig 5 SV | 25 | 0 | 36.78 | 9.72 | 48.59 | 0.50 | 16.00 | 128.00 |

Summary of Results

| | $MIC_{50}$ | $MIC_{90}$ | Median MIC | Range of MICs |
|---|---|---|---|---|
| Oligomer 4 | 4 µg/ml | 8 µg/ml | 4 µg/ml | 1-32 µg/ml |
| Oligomer 5 | 16 µg/ml | 128 µg/ml | 16 µg/ml | 0.5-128 µg/ml |

Mann-Whitney Test and CI: Oligomer 4 SV, Oligomer 5 SV

| | N | Median |
|---|---|---|
| Olig 4 SV | 25 | 4.00 |
| Olig 5 SV | 25 | 16.00 |

Point estimate for ETA1-ETA2 is −7.00
95.2 Percent CI for ETA1-ETA2 is (−23.99,−3.01)
W=487.5
Test of ETA1=ETA2 vs ETA1 not=ETA2 is significant at 0.0037
The test is significant at 0.0031 (adjusted for ties)
Oligomer 4>Oligomer 5 (More Potent>Less Potent)

*Moraxella* species & *Moraxella catarrhalis* Combined
MS = *Moraxella* species; MC = *Moraxella* (*Branhamella*) *catarrhalis*

| Isolate | Oligomer 4 | Oligomer 5 |
|---|---|---|
| 1—K1614 - MS | 16 | 64 |
| 2—K1661 - MS | 32 | 16 |

-continued

| Moraxella species & Moraxella catarrhalis Combined MS = Moraxella species; MC = Moraxella (Branhamella) catarrhalis | | |
|---|---|---|
| Isolate | Oligomer 4 | Oligomer 5 |
| 3—K1643 - MS | 64 | 0.125 |
| 4—K1640 - MS | 8.0 | 8.0 |
| 5—B1431 - MS | 32 | 0.5 |
| 6—B1429 - MS | 1 | 1 |
| 7—B1418 - MS | 32 | 0.25 |
| 8—K1784 - MS | 64 | 0.25 |
| 9—K1773 - MS | 64 | 0.25 |
| 10—K1369 - MS | 2.0 | 2.0 |
| 11—B1275 - MS | 2.0 | 0.125 |
| 12—B1221 - MS | 2.0 | 0.125 |
| 13—B1172 - MS | >64 | >64 |
| 14—E542 - MS | 2.0 | 2.0 |
| 15—K678 - MS | 2.0 | 0.5 |
| 16—K660 - MS | 2.0 | 0.25 |
| 17—K599 - MC | 0.5 | 0.25 |
| 18—K1650 - MC | 64 | 0.25 |
| 19—K1373 - MC | 1.0 | 0.125 |
| 20—K1553 - MC | 4.0 | 2.0 |
| 21—K1453 - MC | 4.0 | 64 |
| 22—K1227 - MC | 2.0 | 1.0 |
| 23—B1102 - MC | 1.0 | 0.5 |
| 24—K1819 - MC | 4.0 | 32 |
| 25—K1855 - MC | 2.0 | 8.0 |
| E. coli D31* | 4 | 2 |
| S. aureus ATCC 27660* | 1 | 1 |
| E. coli D31** | 1 (0.78) | 16 (1.56) |
| S. aureus ATCC 27660** | 0.5 (0.098) | 0.5 (0.78) |

*Control Bacteria Set #1;
**Control Bacteria Set #2; (MICs for Control Bacteria (E. coli, S. aureus) are within the parentheses.)

| Moraxella species & Moraxella catarrhalis Combined $MIC_{50}$ and $MIC_{90}$ Determinations and Statistics For Statistical Calculation Purposes, >64 was Replaced with 128. | | | |
|---|---|---|---|
| Row | Oligomer 4 MS-A | Oligomer 5 MS-A | |
| 1 | 0.5 | 0.125 | |
| 2 | 1.0 | 0.125 | |
| 3 | 1.0 | 0.125 | |
| 4 | 1.0 | 0.125 | |
| 5 | 2.0 | 0.250 | |
| 6 | 2.0 | 0.250 | |
| 7 | 2.0 | 0.250 | |
| 8 | 2.0 | 0.250 | |
| 9 | 2.0 | 0.250 | |
| 10 | 2.0 | 0.250 | |
| 11 | 2.0 | 0.500 | |
| 12 | 2.0 | 0.500 | |
| 13 | 4.0 | 0.500 | $MIC_{50}$ |
| 14 | 4.0 | 1.000 | |
| 15 | 4.0 | 1.000 | |
| 16 | 8.0 | 2.000 | |
| 17 | 16.0 | 2.000 | |
| 18 | 32.0 | 2.000 | |
| 19 | 32.0 | 8.000 | |
| 20 | 32.0 | 8.000 | |
| 21 | 64.0 | 16.000 | |
| 22 | 64.0 | 32.000 | $MIC_{90}$ |
| 23 | 64.0 | 64.000 | |
| 24 | 64.0 | 64.000 | |
| 25 | 128.0 | 128.000 | |

Descriptive Statistics

| Variable | N | N* | Mean | SE Mean | StDev | Minimum | Median | Maximum |
|---|---|---|---|---|---|---|---|---|
| Olig 4 MS | 25 | 0 | 21.42 | 6.43 | 32.13 | 0.50 | 4.00 | 128.00 |
| Olig 5 MS | 25 | 0 | 13.26 | 6.00 | 30.00 | 0.13 | 0.50 | 128.00 |

Summary of Results

| | $MIC_{50}$ | $MIC_{90}$ | Median MIC | Range of MICs |
|---|---|---|---|---|
| Oligomer 4 | 4 µg/ml | 64 µg/ml | 4 µg/ml | 0.5-128 µg/ml |
| Oligomer 5 | 0.5 µg/ml | 32 µg/ml | 0.5 µg/ml | 0.125-128 µg/ml |

Mann-Whitney Test and CI: Oligomer 4 MS, Oligomer 5 MS

| | N | Median |
|---|---|---|
| Olig 4 MS | 25 | 4.00 |
| Olig 5 MS | 25 | 0.50 |

Point estimate for ETA1-ETA2 is 1.75

95.2 Percent CI for ETA1-ETA2 is (0.75, 6.00)

W=785.0

Test of ETA1=ETA2 vs ETA1 not=ETA2 is significant at 0.0043

The test is significant at 0.0040 (adjusted for ties)

Oligomer 4>Oligomer 5 (More Potent>Less Potent)

| Haemophilus influenzae | | |
|---|---|---|
| Isolate | Oligomer 4 | MICs µg/ml Oligomer 5 |
| 1—B1359 | 8 | >64 |
| 2—B1346 | 8 | >64 |
| 3—B1345 | 8 | >64 |
| 4—B1343 | 8 | >64 |
| 5—B1338 | 4 | 16 |
| 6—B1332 | 8 | 64 |
| 7—B1331 | 8 | >64 |
| 8—B1330 | 8 | >64 |
| 9—B1379 | 16 | 8 |
| 10—B1378 | 8 | 4 |
| 11—B1313 | 4 | 2 |
| 12—B1477 | 8 | 4 |
| 13—B1286 | 8 | 2 |
| 14—B1282 | 32 | 8 |
| 15—B1291 | 8 | 16 |
| 16—B1280 | 8 | 16 |
| 17—B1279 | 16 | 64 |
| 18—B1260 | 8 | 16 |
| 19—B1238 | 2 | 8 |
| 20—B1209 | 4 | 8 |
| 21—B1249 | 4 | 16 |
| 22—B1248 | 8 | 4 |
| 23—B1244 | 8 | 32 |
| 24—B1419 | 4 | 32 |
| 25—B1222 | 8 | >64 |
| E. coli D31 | 8 | 16 |
| S. aureus ATCC 27660 | 4 | 4 |
| E. coli D31 | 1 (0.78) | 16 (1.56) |
| S. aureus ATCC 27660 | 0.5 (0.098) | 0.5 (0.78) |

* Control Bacteria Set #1;
** Control Bacteria Set #2; (MICs for Control Bacteria (E. coli, S. aureus) are within the parentheses.)

Haemophilus influenzae
$MIC_{50}$ and $MIC_{90}$ Determinations and Statistics
For Statistical Calculation Purposes, >64 was Replaced with 128.

| Row | Oligomer 4 HI-A | Oligomer 5 HI-A | |
|---|---|---|---|
| 1 | 2 | 2 | |
| 2 | 4 | 2 | |
| 3 | 4 | 4 | |
| 4 | 4 | 4 | |
| 5 | 4 | 4 | |
| 6 | 4 | 8 | |
| 7 | 8 | 8 | |
| 8 | 8 | 8 | |
| 9 | 8 | 8 | |
| 10 | 8 | 16 | |
| 11 | 8 | 16 | |
| 12 | 8 | 16 | |
| 13 | 8 | 16 | $MIC_{50}$ |
| 14 | 8 | 16 | |
| 15 | 8 | 32 | |
| 16 | 8 | 32 | |
| 17 | 8 | 64 | |
| 18 | 8 | 64 | |
| 19 | 8 | 128 | |
| 20 | 8 | 128 | |
| 21 | 8 | 128 | |
| 22 | 8 | 128 | $MIC_{50}$ |
| 23 | 16 | 128 | |
| 24 | 16 | 128 | |
| 25 | 32 | 128 | |

Descriptive Statistics

| Variable | N | N* | Mean | SE Mean | StDev | Minimum | Median | Maximum |
|---|---|---|---|---|---|---|---|---|
| Olig 4 HI | 25 | 0 | 8.56 | 1.16 | 5.82 | 2.00 | 8.00 | 32.00 |
| Olig 5 HI | 25 | 0 | 48.6 | 10.6 | 53.0 | 2.0 | 16.0 | 128.0 |

Summary of Results

| | $MIC_{50}$ | $MIC_{90}$ | Median MIC | Range of MICs |
|---|---|---|---|---|
| Oligomer 4 | 8 µg/ml | 8 µg/ml | 8 µg/ml | 2-32 µg/ml |
| Oligomer 5 | 16 µg/ml | 128 µg/ml | 16 µg/ml | 2-128 µg/ml |

Mann-Whitney Test and CI: Oligomer 4 HI, Oligomer 5 HI

| | N | Median |
|---|---|---|
| Olig 4 HI | 25 | 8.00 |
| Olig 5 HI | 25 | 16.00 |

Point estimate for ETA1-ETA2 is −8.00
95.2 Percent CI for ETA1-ETA2 is (−56.00, 0.00)
W=493.5
Test of ETA1=ETA2 vs ETA1 not=ETA2 is significant at 0.0054
The test is significant at 0.0038 (adjusted for ties)
Oligomer 4>Oligomer 5 (More Potent>Less Potent)

Summary of Results

MIC Determinations of Control Bacteria from Each Day of MIC Testing MICs

[µg/ml]

| Control Isolate | Control for MIC Test | Oligomer 4 | Oligomer 5 |
|---|---|---|---|
| E. coli D31 | SA-FQS | 1 (0.78) | 16 (1.56) |
| S. aureus ATCC 27660 | SA-FQS | 2 (0.098) | 16 (0.78) |
| E. coli D31 | SA-FQR | 1 (0.78) | 4 (1.56) |
| S. aureus ATCC 27660 | SA-FQR | 1 (0.098) | 8 (0.78) |
| E. coli D31 | Control Only 1 | 1 (0.78) | 8 (1.56) |
| S. aureus ATCC 27660 | Control Only 1 | 0.25 (0.098) | 0.25 (0.78) |
| E. coli D31 | Control Only 2 | 1 (0.78) | 8 (1.56) |
| S. aureus ATCC 27660 | Control Only 2 | 0.25 (0.098) | 0.25 (0.78) |
| E. coli D31 | Control Only 3 | 1 (0.78) | 8 (1.56) |
| S. aureus ATCC 27660 | Control Only 3 | 0.25 (0.098) | 0.5 (0.78) |
| E. coli D31 | Control Only 4 | 1 (0.78) | 16 (1.56) |
| S. aureus ATCC 27660 | Control Only 4 | 0.5 (0.098) | 0.5 (0.78) |
| E. coli D31 | SE-FQS | 1 (0.78) | 4 (1.56) |
| S. aureus ATCC 27660 | SE-FQS | 0.25 (0.098) | 0.25 (0.78) |
| E. coli D31 | SE-FQR | 1 (0.78) | 4 (1.56) |
| S. aureus ATCC 27660 | SE-FQR | 0.25 (0.098) | 0.25 (0.78) |
| E. coli D31 | SM | 0.5 (0.78) | 4 (1.56) |
| S. aureus ATCC 27660 | SM | 0.25 (0.098) | 0.5 (0.78) |
| E. coli D31 | PA | 0.5 (0.78) | 8 (1.56) |
| S. aureus ATCC 27660 | PA | 0.5 (0.098) | 0.25 (0.78) |
| E. coli D31 | SP | 0.5 (0.78) | 16 (1.56) |
| S. aureus ATCC 27660 | SP | 0.25 (0.098) | 2 (0.78) |
| E. coli D31 | SV | 0.5 (0.78) | 16 (1.56) |
| S. aureus ATCC 27660 | SV | 1 (0.098) | 1 (0.78) |
| E. coli D31 | MS | 1 (0.78) | 16 (1.56) |
| S. aureus ATCC 27660 | MS | 0.5 (0.098) | 0.5 (0.78) |
| E. coli D31 | HI | 1 (0.78) | 16 (1.56) |
| S. aureus ATCC 27660 | HI | 0.5 (0.098) | 0.5 (0.78) |

MICs for Control Bacteria (E. coli, S. aureus) are within the parentheses.
Summary of MIC Results (n=25 per group)

S. aureus fluoroquinolone-susceptible

| | $MIC_{50}$ | $MIC_{90}$ | Median MIC | Range of MICs |
|---|---|---|---|---|
| Oligomer 4 | 0.25 µg/ml | 0.25 µg/ml | 0.25 µg/ml | 0.125-0.5 µg/ml |
| Oligomer 5 | 0.25 µg/ml | 0.5 µg/ml | 0.25 µg/ml | 0.125-0.5 µg/ml |

S. aureus fluoroquinolone-resistant

| | $MIC_{50}$ | $MIC_{90}$ | Median MIC | Range of MICs |
|---|---|---|---|---|
| Oligomer 4 | 0.25 µg/ml | 0.5 µg/ml | 0.25 µg/ml | 0.125-1.0 µg/ml |
| Oligomer 5 | 0.25 µg/ml | 0.5 µg/ml | 0.25 µg/ml | 0.125-0.5 µg/ml |

Staphylococcus epidermidis (Coagulase-negative Staphylococcus) FQ-susceptible

| | $MIC_{50}$ | $MIC_{90}$ | Median MIC | Range of MICs |
|---|---|---|---|---|
| Oligomer 4 | 0.125 µg/ml | 0.25 µg/ml | 0.125 µg/ml | 0.03125-0.25 µg/ml |
| Oligomer 5 | 0.125 µg/ml | 0.25 µg/ml | 0.125 µg/ml | 0.03125-0.25 µg/ml |

*Staphylococcus epidermidis* (Coagulase-negative *Staphylococcus*) FQ-resistant

|  | MIC$_{50}$ | MIC$_{90}$ | Median MIC | Range of MICs |
|---|---|---|---|---|
| Oligomer 4 | 0.125 μg/ml | 0.25 μg/ml | 0.125 μg/ml | 0.03125-0.25 μg/ml |
| Oligomer 5 | 0.125 μg/ml | 0.25 μg/ml | 0.125 μg/ml | 0.03125-0.5 μg/ml |

*Serratia marcescens*

|  | MIC$_{50}$ | MIC$_{90}$ | Median MIC | Range of MICs |
|---|---|---|---|---|
| Oligomer 4 | 8 μg/ml | 32 μg/ml | 8 μg/ml | 0.25-32 μg/ml |
| Oligomer 5 | 256 μg/ml | 256 μg/ml | 256 μg/ml | 8-256 μg/ml |

*Pseudomonas aeruginosa*

|  | MIC$_{50}$ | MIC$_{90}$ | Median MIC | Range of MICs |
|---|---|---|---|---|
| Oligomer 4 | 4 μg/ml | 4 μg/ml | 4 μg/ml | 0.5-8 μg/ml |
| Oligomer 5 | 64 μg/ml | 128 μg/ml | 64 μg/ml | 4-256 μg/ml |

*Streptococcus pneumoniae*

|  | MIC$_{50}$ | MIC$_{90}$ | Median MIC | Range of MICs |
|---|---|---|---|---|
| Oligomer 4 | 1 μg/ml | 2 μg/ml | 1 μg/ml | 0.5-128 μg/ml |
| Oligomer 5 | 4 μg/ml | 16 μg/ml | 4 μg/ml | 4-128 μg/ml |

*Streptococcus viridans* group

|  | MIC$_{50}$ | MIC$_{90}$ | Median MIC | Range of MICs |
|---|---|---|---|---|
| Oligomer 4 | 4 μg/ml | 8 μg/ml | 4 μg/ml | 1-32 μg/ml |
| Oligomer 5 | 16 μg/ml | 128 μg/ml | 16 μg/ml | 0.5-128 μg/ml |

*Moraxella* species (Including *Moraxella catarrhalis*)

|  | MIC$_{50}$ | MIC$_{90}$ | Median MIC | Range of MICs |
|---|---|---|---|---|
| Oligomer 4 | 4 μg/ml | 64 μg/ml | 4 μg/ml | 0.5-128 μg/ml |
| Oligomer 5 | 0.5 μg/ml | 32 μg/ml | 0.5 μg/ml | 0.125-128 μg/ml |

*Haemophilus influenzae*

|  | MIC$_{50}$ | MIC$_{90}$ | Median MIC | Range of MICs |
|---|---|---|---|---|
| Oligomer 4 | 8 μg/ml | 8 μg/ml | 8 μg/ml | 2-32 μg/ml |
| Oligomer 5 | 16 μg/ml | 128 μg/ml | 16 μg/ml | 2-128 μg/ml |

Oligomer 4 and Oligomer 5 demonstrated the lowest MICs for *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant. Median MIC determinations were less than or equal to 0.25 μg/ml for the compounds against the ocular isolates of these species. The median MICs for Oligomer 4 and Oligomer 5 against *Streptococcus pneumoniae* and *Moraxella* species (including *Moraxella catarrhalis*) were less than or equal to 4 μg/ml. The median MIC for Oligomer 4 against *Streptococcus viridans* group was 4 μg/ml whereas the median MIC for Oligomer 5 was 16 μg/ml. Oligomer 4 and Oligomer 5 demonstrated the highest MICs against the Gram-negative pathogens *Serratia marcescens*, *Pseudomonas aeruginosa*, and *Haemophilus influenzae*. The median MIC of Oligomer 4 to *Pseudomonas aeruginosa*, *Serratia marcescens* and *Haemophilus influenzae* were 4, 8, and 8 μg/ml respectively The median MICs of Oligomer 5 to *Pseudomonas aeruginosa*, *Serratia marcescens* and *Haemophilus influenzae* were 64, 128, and 16 μg/ml respectively. Overall, MICs for the Control Bacteria (*E. coli* D31 and *S. aureus* ATC═C 27660) for each date on which MICs were performed were within the acceptable standard of a 1-2 dilution range in MICs from the MICs previously obtained for those compounds and between different preparation days. The addition of 2% lysed horse red blood cells to the Mueller-Hinton broth for MIC testing with *Streptococcus pneumoniae*, *Moraxella* species (including *Moraxella catarrhalis*), and *Streptococcus viridans* group appeared to decrease the activity of the Oligomer 4 against the Control Bacteria (*E. coli* D31 and *S. aureus* ATC═C 27660) approximately 4 fold. It is unknown whether the 2% lysed horse red blood cells had the same effect on the test isolates. The addition of 2% lysed horse red blood cells to the Mueller-Hinton broth for MIC testing with *Streptococcus pneumoniae*, *Moraxella* species (including *Moraxella catarrhalis*), and *Streptococcus viridans* group generally appeared to increase or have no effect on the activity of the Oligomer 5 against the Control Bacteria (*E. coli* D31 and *S. aureus* ATC═C 27660). It is unknown whether the 2% lysed horse red blood cells had the same effect on the test isolates. The use of HTM broth for the MIC testing of *Haemophilus influenzae* appeared to decrease the activity of the Oligomer 4 and Oligomer 5 against the Control Bacteria *S. aureus* ATC═C 27660 approximately 8 fold. The use of HTM broth for the MIC testing of *Haemophilus influenzae* appeared to decrease the activity of the Oligomer 4 against the Control Bacteria *E. coli* D31 approximately 8 fold but appeared to have no effect on the activity of Oligomer 5 against the Control Bacteria *E. coli* D31.

Oligomer 4 and Oligomer 5 demonstrated the lowest MICs against a variety of Gram-positive ocular bacterial isolates and at least one Gram-negative ocular bacterial species (*Moraxella*). Oligomer 4 and Oligomer 5 demonstrated varying in vitro antibacterial activity against the three species that are the leading causes of conjunctivitis (*Staphylococcus aureus*, *Streptococcus pneumoniae*, and *Haemophilus influenzae*). The order of the lower MICs for Oligomer 4 and Oligomer 5 against the species was: *Staphylococcus aureus*<*Streptococcus pneumoniae*<*Haemophilus influenzae*. (<=lower MICs). Oligomer 4 demonstrated lower MICs than Oligomer 5 for all bacterial species tested except for the Staphylococcal species (equipotent) and for *Moraxella* species (less potent).

Example 9

Ker-1

One purpose of the following experiments was to compare the efficacy of 1% Oligomer 2, 0.5% Oligomer 2, and 5% vancomycin in the treatment of a fluoroquinolone-resistant, methicillin-resistant *Staphylococcus aureus* infection in the NZW rabbit keratitis model with or without intact corneal epithelia.

Fifteen rabbits were received from Myrtles' Rabbitry, Thompson Station, Tenn. The clinical isolate of fluoroquinolone-resistant, methicillin-resistant (MRSA) *Staphylococcus aureus* ($K_{950}$) was subcultured on 5% sheep blood agar and incubated at 37° C. in 6% $CO_2$ overnight. The next morning, the MRSA strain was suspended in sterile trypticase soy broth to a 0.5 McFarland Standard, containing approximately $5 \times 10^8$ cfu/ml of bacteria. The absorbance of the suspension was measured at 650 nm using a Beckman DU-70 spectrophotometer. OD readings of 0.07 corresponded to $5 \times 10^8$ cfu/ml of bacteria. This concentration was appropriately diluted in sterile trypticase soy broth to provide the inoculum of approximately 1,000 ($1.0 \times 10^3$) cfu/eye in 25 µl. Colony counts were performed on the inoculum to determine the actual cfu inoculated. Following general anesthesia with ketamine and xylazine and topical anesthesia with proparacaine and prior to bacterial inoculation in the left eyes, 6 mm areas of the corneal epithelia was removed centrally with an Amoils epithelial scrubber. Nothing was done to the right eyes. The 15 rabbits were then inoculated intrastromally in both eyes with 25 µl of the bacterial dilution of approximately $10^3$ cfu/eye of the bacteria. The bacterial inoculation of the left eyes was directly under the epithelial defect created by the Amoils epithelial scrubber. The epithelia were removed in the left corneas in order to determine whether this layer of the cornea is a barrier for Oligomer 2 penetration when compared to the right cornea with an intact epithelium. A colony count was done on the inoculum to determine the actual cfu inoculated. The rabbits were immediately treated with analgesia in the form of and intramuscular injection of ketoprofen, 1.5 mg/kg. After 4 hours, the 15 rabbits were divided into 4 treatment groups and one untreated control group sacrificed at the onset of therapy. Both eyes of each rabbit of the treatment groups were treated with one 37 µl drop of the coded solutions or control Saline or 1 drop of vancomycin from its dropper bottle. The Oligomer 2 concentrations were masked and labeled as 1 and 2. The masked concentrations were 1% Oligomer 2 and 0.5% Oligomer 2 but the specific concentrations of solutions were not known to the lab workers who carried out the experiment. The vancomycin and control (Tris-Buffered Saline) were not masked.

Groups:

| Group | Left Eye | Right Eye | Rx - Both Eyes | Treatment Regimen | Rabbit # |
|---|---|---|---|---|---|
| I | Abraded Epithelium | Intact Epithelium | Oligomer 2 (PMX-1) | Every 15 minutes for 5 hours (21 total doses) | 1-3 |
| II | Abraded Epithelium | Intact Epithelium | Oligomer 2 (PMX-2) | Every 15 minutes for 5 hours (21 total doses) | 4-6 |
| III | Abraded Epithelium | Intact Epithelium | Vancomycin (50 mg/ml) (Van) | Every 15 minutes for 5 hours (21 total doses) | 7-9 |
| IV | Abraded Epithelium | Intact Epithelium | Tris-Buffered Saline (Con) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment was scheduled for every 15 minutes for 5 hours (21 total doses). However, PMX-1 and PMX-2 were exhausted after the $19^{th}$ dose. Therefore, the actual treatment was 15 minutes for 4.5 hours (19 total doses). The 3 rabbits in group V were sacrificed 4 hours PI and large 9.5 mm buttons were removed from the corneas. These were placed in 1 ml of PBS and kept on ice. The corneal buttons were homogenized for 25 seconds on ice using the motorized homogenizer. After homogenization, colony counts were done on the homogenates using 5% sheep blood agar plates to determine the amount of bacteria contained in the corneas at the onset of therapy. Following the completion of therapy, the eyes were examined for clinical signs of infection. One hour after the final treatment, the treated rabbits (Groups I-IV) were sacrificed and large 9.5 mm buttons were removed from the corneas. These were placed in 1 ml of PBS and kept on ice. The corneal buttons were homogenized for 25 seconds on ice using the motorized homogenizer. After homogenization, colony counts were performed on the homogenates using 5% sheep blood agar plates to determine the amount of bacteria contained in the corneas after treatment. The next morning, the plates were counted and the number of cfu/eye of *Staphylococcus aureus* was determined for each cornea.

Formulations: 1) Oligomer 2 (PMX-1): Oligomer 2 powder, on the day of treatment, was dissolved in 5 ml of Tris-Buffered Saline (TBS) before use. The solution was stored at room temperature during the 5 hours of use. 37 µl drops were instilled using a Rainin EDP electronic pipet set in the multi-dispense mode. This solution was designated PMX-1. 2) Oligomer 2 (PMX-2): Oligomer 2 powder, on the day of treatment, was dissolved in 5 ml of Tris-Buffered Saline (TBS) before use. The solution was stored at room temperature during the 5 hours of use. 37 µl drops were instilled using a Rainin EDP electronic pipet set in the multi-dispense mode. This solution was designated PMX-2. 3) 5% Vancomycin (50 mg/ml): Vancomycin (50 mg/ml) eye drops was purchased from the UPMC pharmacy as the fortified preparation used in patients. Vancomycin was administered using is supplied dropper bottle. 4) Control (Tris-Buffered Saline): 37 µl drops were instilled using a Rainin EDP electronic pipet set in the multi-dispense mode.

IACUC Protocol #0701145 "The In Vivo Evaluation of Biomimetics as Topical Ocular Antibiotics".

MIC Characterization of Fluoroquinolone-Resistant Methicillin-Resistant *Staphylococcus aureus* Strain K950

| Antibiotic | MIC [μg/ml] (Minimum Inhibitory Concentration) |
|---|---|
| Oligomer 2 | 0.25 μg/ml |
| Vancomycin | 2 μg/ml |

Drop Schedule

| Drop # | Time | Time of Day |
|---|---|---|
| 1 | 0 | 9:30 |
| 2 | :15 | 9:45 |
| 3 | :30 | 10:00 |

-continued

MIC Characterization of Fluoroquinolone-Resistant Methicillin-Resistant *Staphylococcus aureus* Strain K950

| Drop # | Time | Time of Day |
|---|---|---|
| 4 | :45 | 10:15 |
| 5 | 1:00 | 10:30 |
| 6 | 1:15 | 10:45 |
| 7 | 1:30 | 11:00 |
| 8 | 1:45 | 11:15 |
| 9 | 2:00 | 11:30 |
| 10 | 2:15 | 11:45 |
| 11 | 2:30 | 12:00 |
| 12 | 2:45 | 12:15 |
| 13 | 3:00 | 12:30 |
| 14 | 3:15 | 12:45 |
| 15 | 3:30 | 1:00 |
| 16 | 3:45 | 1:15 |
| 17 | 4:00 | 1:30 |
| 18 | 4:15 | 1:45 |
| 19 | 4:30 | 2:00** |

**Drops were stopped after Drop 19 because all of the PMX-1 and PMX-2 solutions were used at that time. Sacrifice rabbits 1 hour after final drop (3:00).

DEFINITIONS OF ABBREVIATIONS

PMX-1-IE Oligomer 2 with Intact Epithelium
PMX-1-AE Oligomer 2 with Abraded Epithelium
PMX-2-IE Oligomer 2 with Intact Epithelium
PMX-2-AE Oligomer 2 with Abraded Epithelium
VAN-IE 5% Vancomycin with Intact Epithelium
VAN-AE 5% Vancomycin with Abraded Epithelium
CON-AE Tris-Buffered Saline Control with Abraded Epithelium
CON-IE Tris-Buffered Saline Control with Intact Epithelium Clinical Evaluation—Results

| Eye | Group | Conj. | Chemosis | Discharge | Iritis | Corneal Edema | Corneal Infiltrate | Total Score |
|---|---|---|---|---|---|---|---|---|
| 1R | PMX-1-IE | 2.5 | 2.5 | 3.0 | 1.5 | 2.0 | 2.5 | 14.0 |
| 2R | PMX-1-IE | 3.0 | 3.0 | 2.5 | 0.5 | 1.0 | 2.5 | 12.5 |
| 3R | PMX-1-IE | 3.0 | 3.0 | 3.0 | 0.5 | 1.5 | 2.5 | 14.5 |
| 1L | PMX-1-AE | 2.5 | 2.5 | 3.0 | 1.5 | 2.5 | 1.0 | 13.0 |
| 2L | PMX-1-AE | 3.0 | 3.0 | 3.0 | 0.5 | 1.0 | 0 | 10.5 |
| 3L | PMX-1-AE | 2.0 | 2.0 | 3.0 | 0.5 | 1 | 0.5 | 9.0 |
| 4R | PMX-2-IE | 3.0 | 3.0 | 3.0 | 2.0 | 2.5 | 2.0 | 15.5 |
| 5R | PMX-2-IE | 3.0 | 3.0 | 3.0 | 2.0 | 2.0 | 2.5 | 15.5 |
| 6R | PMX-2-IE | 3.0 | 3.0 | 3.0 | 0.5 | 2.0 | 2.0 | 13.5 |
| 4L | PMX-2-AE | 3.0 | 3.0 | 3.0 | 2.0 | 1.0 | 0 | 12.0 |
| 5L | PMX-2-AE | 3.0 | 3.0 | 2.5 | 1.0 | 2.0 | 0 | 11.5 |
| 6L | PMX-2-AE | 3.0 | 3.0 | 2.5 | 1.0 | 1.0 | 0 | 10.5 |
| 7R | VAN-IE | 2.5 | 3.0 | 3.0 | 2.0 | 1.0 | 0 | 11.5 |
| 8R | VAN-IE | 3.0 | 3.0 | 3.0 | 2.0 | 1.0 | 0 | 12.0 |
| 9R | VAN-IE | 3.0 | 3.0 | 2.5 | 1.0 | 1.0 | 0.5 | 11.0 |
| 7L | VAN-AE | 3.0 | 3.0 | 3.0 | 1.0 | 0.5 | 0.5 | 11.0 |
| 8L | VAN-AE | 2.5 | 2.5 | 2.0 | 1.5 | 1.0 | 0 | 9.5 |
| 9L | VAN-AE | 2.5 | 2.5 | 2.5 | 1.5 | 1.0 | 0 | 10.0 |
| 10R | CON-IE | 1.5 | 2.0 | 0.5 | 1.0 | 1.0 | 2.5 | 8.5 |
| 11R | CON-IE | 1.0 | 0 | 0 | 0.5 | 2.0 | 2.5 | 6.0 |
| 12R | CON-IE | 0 | 0 | 0 | 1.5 | 1.0 | 2.5 | 5.0 |
| 10L | CON-AE | 1.5 | 2.0 | 1.0 | 1.5 | 1.0 | 0.5 | 7.5 |
| 11L | CON-AE | 1.5 | 2.0 | 0.5 | 0.5 | 0 | 0.5 | 5.0 |
| 12L | CON-AE | 0.5 | 0.5 | 1.0 | 1.0 | 1.5 | 2.0 | 6.5 |

Scale
0 = Normal;
0.5 = Trace;
1.0 = Mild;
1.5 = Mild/Moderate;
2.0 = Moderate;
2.5 = Moderate/Severe;
3.0 = Severe Clinical Evaluation—Statistics Descriptive Statistics

| Variable | N | Total Ocular Score | | | | |
|---|---|---|---|---|---|---|
| | | Mean | Median | TrMean | StDev | SE Mean |
| PMX-1-IE Score | 3 | 13.667 | 14.000 | 13.667 | 1.041 | 0.601 |
| PMX-1-AE Score | 3 | 10.83 | 10.50 | 10.83 | 2.02 | 1.17 |
| PMX-2-IE Score | 3 | 14.833 | 15.500 | 14.833 | 1.155 | 0.667 |
| PMX-2-AE Score | 3 | 11.333 | 11.500 | 11.333 | 0.764 | 0.441 |
| VAN-IE Score | 3 | 11.500 | 11.500 | 11.500 | 0.500 | 0.289 |
| VAN-AE Score | 3 | 10.167 | 10.000 | 10.167 | 0.764 | 0.441 |
| CON-IE Score | 3 | 6.50 | 6.00 | 6.50 | 1.80 | 1.04 |
| CON-AE Score | 3 | 6.333 | 6.500 | 6.333 | 1.258 | 0.726 |

-continued

Duncan Multiple Comparisons Test

| Row # | Group/Level | Mean Rank | Total Score C.I. Overlaps | |
|---|---|---|---|---|
| 1 | CON-IE Sco | 3.5000 | 2, | |
| 2 | CON-AE Sco | 3.5000 | 1, | |
| 3 | VAN-AE Sco | 9.8333 | 4, 5, 6, | |
| 4 | PMX-1-AE S | 12.1667 | 3, 5, 6, | $P = 0.05$ |
| 5 | PMX-2-AE S | 13.8333 | 3, 4, 6, | |
| 6 | VAN-IE Sco | 14.5000 | 3, 4, 5, | |
| 7 | PMX-1-IE S | 20.3333 | 8, | |
| 8 | PMX-2-IE S | 22.3333 | 7, | |

CON IE = CON AE < VAN AE = PMX-1AE = PMX-2AE = VAN IE < PMX-1 IE = PMX-2 IE

Microbiological Results

Inoculum = 1048 cfu/cornea
Data Display

CFU/ml

| Row | PMX-1-IE | PMX-1-AE | PMX-2-IE | PMX-2-AE |
|---|---|---|---|---|
| 1 | 1700000 | 35 | 130000 | 5 |
| 2 | 16400 | 2380 | 1550000 | 100 |
| 3 | 10300000 | 750 | 15600000 | 0 |

| Row | VAN-IE | VAN-AE | CON-IE | CON-AE | Onset-IE | Onset-AE |
|---|---|---|---|---|---|---|
| 1 | 550 | 200 | 16000000 | 12000000 | 90000000 | 79500 |
| 2 | 450 | 700 | 3550000 | 85000 | 140000 | 32000 |
| 3 | 600 | 750 | 8700000 | 7500000 | 98000 | 110000 |

$\text{Log}_{10}$ CFU/ml

| Row | PMX-1-IE Log | PMX-1-AE Log | PMX-2-IE Log | PMX-2-AE Log |
|---|---|---|---|---|
| 1 | 6.23045 | 1.54407 | 5.11394 | 0.69897 |
| 2 | 4.21484 | 3.37658 | 6.19033 | 2.00000 |
| 3 | 7.01284 | 2.87506 | 7.19312 | 0.00000 |

| Row | VAN-IE Log | VAN-AE Log | CON-IE Log | CON-AE Log |
|---|---|---|---|---|
| 1 | 2.74036 | 2.30103 | 7.20412 | 6.07918 |
| 2 | 2.65321 | 2.84510 | 6.55023 | 4.92942 |
| 3 | 2.77815 | 2.87506 | 6.93952 | 6.87506 |

| Row | Onset-IE Log | Onset-AE Log |
|---|---|---|
| 1 | 7.95424 | 4.90037 |
| 2 | 5.14613 | 4.50515 |
| 3 | 4.99123 | 5.04139 |

Descriptive Statistics

$\text{Log}_{10}$ CFU/ml

| Variable | N | Mean | Median | TrMean | StDev | SE Mean |
|---|---|---|---|---|---|---|
| PMX-1-IE | 3 | 5.819 | 6.230 | 5.819 | 1.444 | 0.833 |
| PMX-1-AE | 3 | 2.599 | 2.875 | 2.599 | 0.947 | 0.547 |
| PMX-2-IE | 3 | 6.166 | 6.190 | 6.166 | 1.040 | 0.600 |
| PMX-2-AE | 3 | 0.900 | 0.699 | 0.900 | 1.015 | 0.586 |
| VAN-IE Log | 3 | 2.7239 | 2.7404 | 2.7239 | 0.0641 | 0.0370 |
| VAN-AE Log | 3 | 2.674 | 2.845 | 2.674 | 0.323 | 0.187 |
| CON-IE Log | 3 | 6.898 | 6.940 | 6.898 | 0.329 | 0.190 |
| CON-AE Log | 3 | 5.961 | 6.079 | 5.961 | 0.978 | 0.565 |
| Onset-IE Log | 3 | 6.031 | 5.146 | 6.031 | 1.668 | 0.963 |
| Onset-AE Log | 3 | 4.816 | 4.900 | 4.816 | 0.278 | 0.160 |

Microbiological Results—Intact Epithelium

One-way Analysis of Variance
Analysis of Variance for Counts I   $\text{Log}_{10}$ CFU/ml

| Source | DF | SS | MS | F | P |
|---|---|---|---|---|---|
| Rx Corn | 4 | 31.45 | 7.86 | 6.49 | 0.008 |
| Error | 10 | 12.12 | 1.21 | | |
| Total | 14 | 43.57 | | | |

Individual 95% CIs For Mean Based on Pooled StDev

| Level | N | Mean | StDev | ----+---------+---------+---------+-- |
|---|---|---|---|---|
| CON | 3 | 6.898 | 0.329 | (------*------) |
| Onset | 3 | 6.031 | 1.668 | (------*------) |
| PMX-1 | 3 | 5.819 | 1.444 | (------*------) |
| PMX-2 | 3 | 6.166 | 1.040 | (------*------) |
| VAN | 3 | 2.724 | 0.064 | (------*------) |

Pooled StDev = 1.101   2.0   4.0   6.0   8.0

Fisher's pairwise comparisons
Family error rate = 0.245
Individual error rate = 0.0500
Critical value = 2.228

Intervals for (column level mean) − (row level mean)

| | CON | Onset | PMX-1 | PMX-2 |
|---|---|---|---|---|
| Onset | −1.135 | | | |
| | 2.870 | | | |
| PMX-1 | −0.924 | −1.791 | | |
| | 3.081 | 2.214 | | |
| PMX-2 | −1.270 | −2.138 | −2.349 | |
| | 2.735 | 1.867 | 1.656 | |
| VAN | 2.172 | 1.304 | 1.093 | 1.439 |
| | 6.177 | 5.309 | 5.098 | 5.444 |

VAN < PMX-1 = ONSET = PMX-2 = CON

Microbiological Results—Intact Epithelium

Power and Sample Size
One-way ANOVA

Sigma = 1.101   Alpha = 0.05   Number of Levels = 5

Corrected Sum of Squares of Means = 10.4840

Means = 6.898, 6.031, 5.819, 6.166, 2.724

| Sample Size | Power |
|---|---|
| 3 | 0.9137 |

Duncan Multiple Comparisons Test $\text{Log}_{10}$ CFU/ml

| Row # | Group/Level | Mean Rank | C.I. Overlaps | |
|---|---|---|---|---|
| 1 | VAN-IE Log | 2.0000 | | |
| 2 | PMX-1-IE L | 8.3333 | 3, 4, 5, | |
| 3 | PMX-2-IE L | 9.0000 | 2, 4, 5, | $P = 0.05$ |
| 4 | Onset-IE L | 9.0000 | 2, 3, 5, | |
| 5 | CON-IE Log | 11.6667 | 2, 3, 4, | |

VAN < PMX-1 = PMX-2 = ONSET = CON

Microbiological Results—Abraded Epithelium

One-way Analysis of Variance
Analysis of Variance for Counts A  Log$_{10}$ CFU/ml

| Source | DF | SS | MS | F | P |
|---|---|---|---|---|---|
| Rx Corn | 4 | 47.954 | 11.989 | 19.55 | 0.000 |
| Error | 10 | 6.131 | 0.613 | | |
| Total | 14 | 54.086 | | | |

Individual 95% CIs For Mean
Based on Pooled StDev

| Level | N | Mean | StDev | |
|---|---|---|---|---|
| CON | 3 | 5.9612 | 0.9782 | (----*----) |
| Onset | 3 | 4.8156 | 0.2780 | (----*----) |
| PMX-1 | 3 | 2.5986 | 0.9470 | (----*----) |
| PMX-2 | 3 | 0.8997 | 1.0150 | (----*-----) |
| VAN | 3 | 2.6737 | 0.3231 | (----*----) |

Pooled StDev = 0.7830    0.0    2.0    4.0    6.0

Fisher's pairwise comparisons
Family error rate = 0.245
Individual error rate = 0.0500
Critical value = 2.228

Intervals for (column level mean) − (row level mean)

| | CON | Onset | PMX-1 | PMX-2 |
|---|---|---|---|---|
| Onset | −0.2788 2.5700 | | | |
| PMX-1 | 1.9382 4.7871 | 0.7926 3.6415 | | |
| PMX-2 | 3.6371 6.4860 | 2.4916 5.3404 | 0.2745 3.1233 | |
| VAN | 1.8631 4.7119 | 0.7175 3.5663 | −1.4996 1.3493 | −3.1985 −0.3496 |

PMX-2 < PMX-1 = VAN < ONSET = CON

Power and Sample Size
One-way ANOVA
Sigma = 0.783 Alpha = 0.05 Number of Levels = 5
Corrected Sum of Squares of Means = 16.0707
Means = 5.9612, 4.8456, 2.5986, 0.8997, 2.6737

| Sample Size | Power |
|---|---|
| 3 | 1.0000 |

Duncan Multiple Comparisons Test Log$_{10}$ CFU/ml

| Row # | Group/Level | Mean Rank | C.I. Overlaps | |
|---|---|---|---|---|
| 1 | PMX-2-AE L | 2.3333 | 2, 3, | |
| 2 | VAN-AE Log | 6.1667 | 1, 3, | |
| 3 | PMX-1-AE L | 6.5000 | 1, 2, | P = 0.05 |
| 4 | Onset-AE L | 11.3333 | 5, | |
| 5 | CON-AE Log | 13.6667 | 4, | |

PMX-2 = VAN = PMX-1 < ONSET = CON

Microbiological Results—Intact vs. Abraded Epithelium

Two Sample T-Test and Confidence Interval − PMX-1
Two sample T for PMX-1-IE Log vs PMX-1-AE Log

| | N | Mean | StDev | SE Mean |
|---|---|---|---|---|
| PMX-1-IE | 3 | 5.82 | 1.44 | 0.83 |
| PMX-1-AE | 3 | 2.599 | 0.947 | 0.55 |

95% CI for mu PMX-1-IE − mu PMX-1-AE: (0.05, 6.39)
T-Test mu PMX-1-IE = mu PMX-1-AE (vs not =): T = 3.23 P = 0.048 DF = 3
Abraded < Intact Two Sample T-Test and Confidence Interval − PMX-2
Two sample T for PMX-2-IE Log vs PMX-2-AE Log

| | N | Mean | StDev | SE Mean |
|---|---|---|---|---|
| PMX-2-IE | 3 | 6.17 | 1.04 | 0.60 |
| PMX-2-AE | 3 | 0.90 | 1.01 | 0.59 |

95% CI for mu PMX-2-IE − mu PMX-2-AE: (2.60, 7.94)
T-Test mu PMX-2-IE = mu PMX-2-AE (vs not =): T = 6.28 P = 0.0082 DF = 3
Abraded < Intact Two Sample T-Test and Confidence Interval − VAN
Two sample T for VAN-IE Log vs VAN-AE Log

| | N | Mean | StDev | SE Mean |
|---|---|---|---|---|
| VAN-IE L | 3 | 2.7239 | 0.0641 | 0.037 |
| VAN-AE L | 3 | 2.674 | 0.323 | 0.19 |

95% CI for mu VAN-IE L − mu VAN-AE L: (−0.768, 0.87)
T-Test mu VAN-IE L = mu VAN-AE L (vs not =): T = 0.26 P = 0.82 NS DF = 2

-continued

Two Sample T-Test and Confidence Interval - CON
Two sample T for CON-IE Log vs CON-AE Log

|  | N | Mean | StDev | SE Mean |
|---|---|---|---|---|
| CON-IE L | 3 | 6.898 | 0.329 | 0.19 |
| CON-AE L | 3 | 5.961 | 0.978 | 0.56 |

95% CI for mu CON-IE L - mu CON-AE L: (−1.63, 3.50)
T-Test mu CON-IE L = mu CON-AE L (vs not =): T = 1.57 P = 0.26 NS DF = 2

Microbiological Results—Intact vs. Abraded Epithelium

Two Sample T-Test and Confidence Interval - Onset
Two sample T for Onset-IE Log vs Onset-AE Log

|  | N | Mean | StDev | SE Mean |
|---|---|---|---|---|
| Onset-IE | 3 | 6.03 | 1.67 | 0.96 |
| Onset-AE | 3 | 4.816 | 0.278 | 0.16 |

95% CI for mu Onset-IE - mu Onset-AE: (−2.99, 5.42)
T-Test mu Onset-IE = mu Onset-AE (vs not =): T = 1.24 P = 0.34 NS DF = 2

Summary of Statistical Comparisons for Microbiological Data
<=Significantly Fewer Colony Counts
Effect of Abraded Epithelium on Effectiveness of Each Test Solution or Onset Control

| PMX-1 | Abraded < Intact |
| PMX-1 | Abraded < Intact |
| Vancomycin | Abraded = Intact |
| Saline Control | Abraded = Intact |
| Onset of Therapy Control | Abraded = Intact |

Effect of Test Solutions on Corneas with Intact Epithelium
PMX-1=PMX-2
PMX-1=Saline Control
PMX-2=Saline Control
Vancomycin<Saline Control
Vancomycin<PMX-1
Vancomycin<PMX-2
Effect of Test Solutions on Corneas with Abraded Epithelium
PMX-1<Saline Control
PMX-2<Saline Control
PMX-2<PMX-1
Vancomycin<Saline Control
PMX-1=Vancomycin
PMX-2<Vancomycin
Summary of Results PMX-1 and PMX-2 were effective in reducing fluoroquinolone-resistant, methicillin-resistant *Staphylococcus aureus* colony counts in the NZW rabbit keratitis model only when the corneal epithelium was removed from the corneas. PMX-2 was more effective than 5% vancomycin in reducing colony counts fluoroquinolone-resistant, methicillin-resistant *Staphylococcus aureus* colony counts in the NZW rabbit keratitis model only when the corneal epithelium was removed from the corneas. PMX-1 was as effective as 5% vancomycin in reducing colony counts fluoroquinolone-resistant, methicillin-resistant *Staphylococcus aureus* colony counts in the NZW rabbit keratitis model only when the corneal epithelium was removed from the corneas. PMX-1 and PMX-2 induced toxicity similar to 5% vancomycin as manifested by higher Total Ocular Scores compared with the Saline treated eyes in eyes with intact corneal epithelia. Removal of the epithelium increased the Total Ocular Scores of eyes treated 1% and 0.5% Oligomer 2 compared with the Total Ocular Scores of eyes treated with of 1% and 0.5% Oligomer 2 with intact epithelia.

The biomimetic Oligomer 2 was effective in reducing the number fluoroquinolone-resistant, methicillin-resistant *Staphylococcus aureus* colony counts in the NZW rabbit keratitis model. However, Oligomer 2 was effective in reducing fluoroquinolone-resistant, methicillin-resistant *Staphylococcus aureus* colony counts only when the corneal epithelium was removed. This suggests that Oligomer 2 does not penetrate the corneal epithelium into the corneal stroma. In the current study, PMX-1 and PMX-2 induced greater toxicity in infected rabbit eyes compared with the Mildly Irritating toxicity induced in uninfected rabbit eyes in experiment PMX-Tox-1.

Example 10

Ker-2

One purpose of the following experiments was to compare the efficacy of 0.25% Oligomer 2, with and without 0.005% benzalkonium chloride, and 5% vancomycin in the treatment of a fluoroquinolone-resistant, methicillin-resistant *Staphylococcus aureus* infection in the NZW rabbit keratitis model with or without intact corneal epithelia. The 0.005% benzalkonium chloride has been added to try to increase the penetration of 0.25% Oligomer 2 through the corneal epithelium.

Fifteen rabbits were received from Myrtles' Rabbitry, Thompson Station, TN. The clinical isolate of fluoroquinolone-resistant, methicillin-resistant (MRSA) *Staphylococcus aureus* (K950) was subcultured on 5% sheep blood agar and incubated at 37° C. in 6% $CO_2$ overnight. The next morning, the MRSA strain was suspended in sterile trypticase soy broth to a 0.5 McFarland Standard, containing approximately $5 \times 10^8$ cfu/ml of bacteria. The absorbance of the suspension was measured at 650 nm using a Beckman DU-70 spectrophotometer. OD readings of 0.07 corresponded to $5 \times 10^8$ cfu/ml of bacteria. This concentration was appropriately diluted in sterile trypticase soy broth to provide the inoculum of approximately 1,000 ($1.0 \times 10^3$) cfu/eye in 25 µl. Colony counts were performed on the inoculum to determine the actual cfu inoculated. Following general anesthesia with ketamine and xylazine and topical anesthesia with proparacaine and prior to bacterial inoculation in the left eyes, 6 mm areas of the corneal epithelia was removed centrally with an Amoils epithelial scrubber. Nothing was done to the right eyes. The 15 rabbits were then inoculated intrastromally in both eyes with 25 µl of the bacterial dilution of approximately $10^3$ cfu/eye of the bacteria. The bacterial inoculation of the left eyes was directly under the epithelial defect created by the Amoils epithelial scrubber. The epithelia were removed in the left corneas in order to determine whether this layer of the cornea is a barrier for Oligomer 2 penetration when compared to the right cornea with an intact epithelium. A colony count was done on the inoculum to determine the actual cfu inoculated. The rabbits were immediately treated with analgesia in the form of and intramuscular injection of ketoprofen, 1.5 mg/kg. After 4 hours, the 15 rabbits were divided into 4 treatment groups and one untreated control group sacrificed at the onset of therapy. Both eyes of each rabbit of the treatment groups were treated with one 37 µl drop of the solutions or control Saline or 1 drop of vancomycin from its dropper bottle.

Groups:

| Group | Left Eye | Right Eye | Rx - Both Eyes | Treatment Regimen | Rabbit # |
|---|---|---|---|---|---|
| I | Abraded Epithelium | Intact Epithelium | 0.25% Oligomer 2 (PMX) | Every 15 minutes for 5 hours (21 total doses) | 1-3 |
| II | Abraded Epithelium | Intact Epithelium | 0.25% Oligomer 2 with 0.005% BAK (PMX-B) | Every 15 minutes for 5 hours (21 total doses) | 4-6 |
| III | Abraded Epithelium | Intact Epithelium | Vancomycin (50 mg/ml) (Van) | Every 15 minutes for 5 hours (21 total doses) | 7-9 |
| IV | Abraded Epithelium | Intact Epithelium | Tris-Buffered Saline (Con) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment was scheduled for every 15 minutes for 5 hours (21 total doses). The 3 rabbits in group V were sacrificed 4 hours PI and large 9.5 mm buttons were removed from the corneas. These were placed in 1 ml of PBS and kept on ice. The corneal buttons were homogenized for 25 seconds on ice using the motorized homogenizer. After homogenization, colony counts were done on the homogenates using 5% sheep blood agar plates to determine the amount of bacteria contained in the corneas at the onset of therapy. Following the completion of therapy, the eyes were examined for clinical signs of infection. One hour after the final treatment, the treated rabbits (Groups I-IV) were sacrificed and large 9.5 mm buttons were removed from the corneas. These were placed in 1 ml of PBS and kept on ice. The corneal buttons were homogenized for 25 seconds on ice using the motorized homogenizer. After homogenization, colony counts were performed on the homogenates using 5% sheep blood agar plates to determine the amount of bacteria contained in the corneas after treatment. The next morning, the plates were counted and the number of cfu/eye of *Staphylococcus aureus* was determined for each cornea.

Formulations: 1) 0.25% Oligomer 2 (PMX): Oligomer 2 Powder (Lot 8-15.1 mg), on the day of treatment, was dissolved in 6.04 ml of Tris-Buffered Saline (TBS) to yield 0.25% Oligomer 2. The solution was stored at room temperature during the 5 hours of use. 37 µl drops were instilled using a Rainin EDP electronic pipet set in the multi-dispense mode. This solution was designated PMX. 2) 0.25% Oligomer 2 with 0.005% Benzalkonium Chloride (BAK) (PMX-B): Oligomer 2 Powder (Lot 8-15.8 mg), on the day of treatment, was dissolved in 6.288 ml of Tris-Buffered Saline (TBS) before use. Then, 0.032 ml (32 µl) of 1% Benzalkonium Chloride was added to the solution to yield a total volume of 6.32 ml of 0.25% Oligomer 2. The solution was stored at room temperature during the 5 hours of use. 37 µl drops were instilled using a Rainin EDP electronic pipet set in the multi-dispense mode. This solution was designated PMX-B. 3) 5% Vancomycin (50 mg/ml): Vancomycin (50 mg/ml) eye drops were purchased from the UPMC pharmacy as the fortified preparation used in patients. Vancomycin was administered using is supplied dropper bottle. 4) Control (Tris-Buffered Saline): 37 µl drops of Tris-Buffered Saline were instilled using a Rainin EDP electronic pipet set in the multi-dispense mode.

IACUC Protocol #0701145 "The In Vivo Evaluation of Biomimetics as Topical Ocular Antibiotics".

| MIC Characterization of Fluoroquinolone-Resistant, Methicillin-Resistant *Staphylococcus aureus* Strain K950 | |
|---|---|
| Antibiotic | MIC [µg/ml] (Minimum Inhibitory Concentration) |
| Oligomer 2 | 0.25 µg/ml |
| Vancomycin | 2 µg/ml |

| Drop Schedule | | |
|---|---|---|
| Drop # | Time | Time of Day |
| 1 | 0 | 9:30 |
| 2 | :15 | 9:45 |
| 3 | :30 | 10:00 |
| 4 | :45 | 10:15 |
| 5 | 1:00 | 10:30 |
| 6 | 1:15 | 10:45 |
| 7 | 1:30 | 11:00 |
| 8 | 1:45 | 11:15 |
| 9 | 2:00 | 11:30 |
| 10 | 2:15 | 11:45 |
| 11 | 2:30 | 12:00 |
| 12 | 2:45 | 12:15 |
| 13 | 3:00 | 12:30 |
| 14 | 3:15 | 12:45 |
| 15 | 3:30 | 1:00 |
| 16 | 3:45 | 1:15 |
| 17 | 4:00 | 1:30 |
| 18 | 4:15 | 1:45 |
| 19 | 4:30 | 2:00 |
| 20 | 4:45 | 2:15 |
| 21 | 5:00 | 2:30 |

Sacrifice rabbits 1 hour after final drop (3:00).

DEFINITIONS OF ABBREVIATIONS

PMX-IE 0.25% Oligomer 2 with Intact Epithelium
PMX-AE 0.25% Oligomer 2 with Abraded Epithelium
PMX-B-IE 0.25% Oligomer 2 with 0.005% BAK with Intact Epithelium
PMX-B-AE 0.25% Oligomer 2 with 0.005% BAK with Abraded Epithelium
VAN-IE 5% Vancomycin with Intact Epithelium
VAN-AE 5% Vancomycin with Abraded Epithelium
CON-AE Tris-Buffered Saline Control with Abraded Epithelium
CON-IE Tris-Buffered Saline Control with Intact Epithelium
PMX 0.25% Oligomer 2
PMX-B 0.25% Oligomer 2 with 0.005% BAK Clinical Evaluation—Results

| Eye | Group | Conj. | Chemosis | Discharge | Iritis | Corneal Edema | Corneal Infiltrate | Total Score |
|---|---|---|---|---|---|---|---|---|
| 1R | PMX-IE | 3.0 | 3.0 | 2.5 | 1.0 | 1.5 | 2.5 | 13.5 |
| 2R | PMX-IE | 2.5 | 2.5 | 2.5 | 2.0 | 2.0 | 2.0 | 13.5 |
| 3R | PMX-IE | 2.5 | 3.0 | 2.5 | 1.5 | 1.5 | 2.5 | 13.5 |
| 1L | PMX-AE | 3.0 | 2.0 | 2.5 | 1.0 | 1.0 | 0.5 | 10.0 |
| 2L | PMX-AE | 2.5 | 2.5 | 2.0 | 2.0 | 1.5 | 0 | 10.5 |
| 3L | PMX-AE | 2.5 | 2.5 | 2.5 | 0.5 | 0.5 | 0 | 8.5 |
| 4R | PMX-B-IE | 3.0 | 3.0 | 3.0 | 1.5 | 1.5 | 2.5 | 14.5 |
| 5R | PMX-B-IE | 3.0 | 3.0 | 3.0 | 2.0 | 0.5 | 2.5 | 14.0 |
| 6R | PMX-B-IE | 3.0 | 3.0 | 3.0 | 1.0 | 1.0 | 2.5 | 13.5 |
| 4L | PMX-B-AE | 2.5 | 2.5 | 2.5 | 2.0 | 1.0 | 0 | 10.5 |
| 5L | PMX-B-AE | 2.5 | 2.5 | 2.5 | 1.0 | 1.0 | 0 | 9.5 |
| 6L | PMX-B-AE | 2.5 | 2.5 | 3.0 | 1.0 | 0.5 | 0 | 9.5 |
| 7R | VAN-IE | 2.5 | 2.5 | 3.0 | 1.0 | 0.5 | 0.5 | 10.0 |
| 8R | VAN-IE | 2.5 | 2.5 | 2.5 | 1.5 | 0.5 | 0 | 9.5 |
| 9R | VAN-IE | 2.5 | 2.5 | 2.5 | 0.5 | 0.5 | 0 | 8.5 |
| 7L | VAN-AE | 2.5 | 2.5 | 2.5 | 1.0 | 0.5 | 0.5 | 9.5 |
| 8L | VAN-AE | 2.5 | 2.5 | 2.5 | 1.0 | 1.0 | 0 | 9.5 |
| 9L | VAN-AE | 2.5 | 2.5 | 2.5 | 0.5 | 1.0 | 0 | 9.0 |
| 10R | CON-IE | 0.5 | 0 | 1.0 | 0.5 | 0.5 | 3.0 | 5.5 |
| 11R | CON-IE | 2.0 | 0.5 | 2.0 | 2.5 | 3.0 | 2.0 | 12.0 |
| 12R | CON-IE | 1.5 | 0 | 2.5 | 2.0 | 0.5 | 3.0 | 9.5 |
| 10L | CON-AE | 2.0 | 1.5 | 2.0 | 1.5 | 2.0 | 2.5 | 11.5 |
| 11L | CON-AE | 2.0 | 2.0 | 1.5 | 1.5 | 1.0 | 0.5 | 8.5 |
| 12L | CON-AE | 2.5 | 2.5 | 2.5 | 1.5 | 1.0 | 0.5 | 10.5 |

Scale
0 = Normal;
0.5 = Trace;
1.0 = Mild;
1.5 = Mild/Moderate;
2.0 = Moderate;
2.5 = Moderate/Severe;
3.0 = Severe Clinical Evaluation—Statistics Descriptive Statistics Total Ocular Score

| Variable | N | Mean | Median | TrMean | StDev | SE Mean |
|---|---|---|---|---|---|---|
| PMX-IE Score | 3 | 13.500 | 13.500 | 13.500 | 0.000 | 0.000 |
| PMX-AE Score | 3 | 9.667 | 10.000 | 9.667 | 1.041 | 0.601 |
| PMX-B-IE Score | 3 | 14.000 | 14.000 | 14.000 | 0.500 | 0.289 |
| PMX-B-AE Score | 3 | 9.833 | 9.500 | 9.833 | 0.577 | 0.333 |
| VAN-IE Score | 3 | 9.333 | 9.500 | 9.333 | 0.764 | 0.441 |
| VAN-AE Score | 3 | 9.333 | 9.500 | 9.333 | 0.289 | 0.167 |
| CON-IE Score | 3 | 9.00 | 9.50 | 9.00 | 3.28 | 1.89 |
| CON-AE Score | 3 | 10.167 | 10.500 | 10.167 | 1.528 | 0.882 |

Duncan Multiple Comparisons Test

| Row # | Group/Level | Mean Rank | Total Score C.I. Overlaps | |
|---|---|---|---|---|
| 1 | VAN-AE Sco | 7.3333 | 2, 3, 4, 5, 6, | |
| 2 | VAN-IE Sco | 8.0000 | 1, 3, 4, 5, 6, | |
| 3 | CON-IE Sco | 9.1667 | 1, 2, 4, 5, 6, | P = 0.05 |
| 4 | PMX-AE Sco | 10.1667 | 1, 2, 3, 5, 6, | |
| 5 | PMX-B-AE S | 10.6667 | 1, 2, 3, 4, 6, | |
| 6 | CON-AE Sco | 11.6667 | 1, 2, 3, 4, 5, | |
| 7 | PMX-IE Sco | 20.5000 | 8, | |
| 8 | PMX-B-IE S | 22.5000 | 7, | |

VAN-AE = VAN-IE = CON-IE = PMX-AE = PMX-B-AE = CON AE < PMX-IE = PMX-B-IE

Median Total Ocular Score

| Treatment | Abraded (score) | Intact (score) |
|---|---|---|
| PMX | 10 | 13.5 |
| PMX-B | 9.5 | 14 |
| Vancomycin | 9.5 | 9.5 |
| Control | 10.5 | 9.5 |

Microbiological Results

Inoculum = 1371 cfu/cornea
Data Display

CFU/ml

| Row | PMX-IE | PMX-AE | PMX-B-IE | PMX-B-AE |
|---|---|---|---|---|
| 1 | 4750000 | 5 | 11000000 | 13500 |
| 2 | 4450000 | 8900 | 15350000 | 80 |
| 3 | 9650000 | 1200 | 12850000 | 190 |

| Row | VAN-IE | VAN-AE | CON-IE | CON-AE | Onset-IE | Onset-AE |
|---|---|---|---|---|---|---|
| 1 | 71000 | 550 | 5250000 | 3300000 | 100500 | 63000 |
| 2 | 2200 | 200 | 13200000 | 510000 | 77000 | 74500 |
| 3 | 350 | 600 | 14600000 | 965000 | 93500 | 44500 |

-continued

Data Display

| | $Log_{10}$ CFU/ml | | | |
|---|---|---|---|---|
| Row | PMX-IE Log | PMX-AE Log | PMX-B-IE Log | PMX-B-AE Log |
| 1 | 6.67669 | 0.69897 | 7.04139 | 4.13033 |
| 2 | 6.64836 | 3.94939 | 7.18611 | 1.90309 |
| 3 | 6.98453 | 3.07918 | 7.10890 | 2.27875 |

| Row | VAN-IE Log | VAN-AE Log | CON-IE Log | CON-AE Log |
|---|---|---|---|---|
| 1 | 4.85126 | 2.74036 | 6.72016 | 6.51851 |
| 2 | 3.34242 | 2.30103 | 7.12057 | 5.70757 |
| 3 | 2.54407 | 2.77815 | 7.16435 | 5.98453 |

| Row | Onset-IE Log | Onset-AE Log |
|---|---|---|
| 1 | 5.00217 | 4.79934 |
| 2 | 4.88649 | 4.87216 |
| 3 | 4.97081 | 4.64836 |

Descriptive Statistics

| | | | $Log_{10}$ CFU/ml | | | |
|---|---|---|---|---|---|---|
| Variable | N | Mean | Median | TrMean | StDev | SE Mean |
| PMX-IE Log | 3 | 6.770 | 6.677 | 6.770 | 0.186 | 0.108 |
| PMX-AE Log | 3 | 2.576 | 3.079 | 2.576 | 1.683 | 0.971 |
| PMX-B-IE Log | 3 | 7.1121 | 7.1089 | 7.1121 | 0.0724 | 0.0418 |
| PMX-B-AE Log | 3 | 2.771 | 2.279 | 2.771 | 1.192 | 0.688 |
| VAN-IE Log | 3 | 3.579 | 3.342 | 3.579 | 1.172 | 0.676 |
| VAN-AE Log | 3 | 2.607 | 2.740 | 2.607 | 0.265 | 0.153 |
| CON-IE Log | 3 | 7.002 | 7.121 | 7.002 | 0.245 | 0.141 |
| CON-AE Log | 3 | 6.070 | 5.985 | 6.070 | 0.412 | 0.238 |
| Onset-IE Log | 3 | 4.9532 | 4.9708 | 4.9532 | 0.0598 | 0.0345 |
| Onset-AE Log | 3 | 4.7733 | 4.7993 | 4.7733 | 0.1142 | 0.0659 |

Microbiological Results—Intact Epithelium

One-way Analysis of Variance
Analysis of Variance for Counts I      $Log_{10}$ CFU/ml

| Source | DF | SS | MS | F | P |
|---|---|---|---|---|---|
| Rx Corn | 4 | 29.162 | 7.290 | 24.69 | 0.000 |
| Error | 10 | 2.953 | 0.295 | | |
| Total | 14 | 32.115 | | | |

Individual 95% CIs For Mean Based on Pooled StDev

| Level | N | Mean | StDev | |
|---|---|---|---|---|
| CON | 3 | 7.0017 | 0.2448 | (----*---) |
| Onset | 3 | 4.9532 | 0.0598 | (----*----) |
| PMX | 3 | 6.7699 | 0.1864 | (----*----) |
| PMX-B | 3 | 7.1121 | 0.0724 | (---*----) |
| VAN | 3 | 3.5792 | 1.1717 | (----*----) |

Pooled StDev = 0.5434     3.0   4.5   6.0   7.5

Fisher's pairwise comparisons
Family error rate = 0.245
Individual error rate = 0.0500
Critical value = 2.228

Intervals for (column level mean) - (row level mean)

| | CON | Onset | PMX | PMX-B |
|---|---|---|---|---|
| Onset | 1.0600 | | | |
| | 3.0370 | | | |
| PMX | -0.7567 | -2.8052 | | |
| | 1.2203 | -0.8282 | | |
| PMX-B | -1.0989 | -3.1475 | -1.3308 | |
| | 0.8781 | -1.1705 | 0.6462 | |
| VAN | 2.4339 | 0.3854 | 2.2021 | 2.5444 |
| | 4.4110 | 2.3624 | 4.1791 | 4.5214 |

VAN < ONSET = PMX = CON = PMX-B

Microbiological Results—Intact Epithelium

Duncan Multiple Comparisons Test $Log_{10}$ CFU/ml

| Row # | Group/Level | Mean Rank | C.I. Overlaps | |
|---|---|---|---|---|
| 1 | VAN-IE Log | 2.0000 | 2, | |
| 2 | Onset-IE L | 5.0000 | 1, | |
| 3 | PMX-IE Log | 8.3333 | 4, 5, | P = 0.05 |
| 4 | CON-IE Log | 12.0000 | 3, 5, | |
| 5 | PMX-B-IE L | 12.6667 | 3, 4, | |

VAN = ONSET < PMX = CON = PMX-B

Microbiological Results—Abraded Epithelium

One-way Analysis of Variance
Analysis of Variance for Counts A      $Log_{10}$ CFU/ml

| Source | DF | SS | MS | F | P |
|---|---|---|---|---|---|
| Rx Corn | 4 | 30.226 | 7.556 | 8.38 | 0.003 |
| Error | 10 | 9.013 | 0.901 | | |
| Total | 14 | 39.238 | | | |

Individual 95% CIs For Mean Based on Pooled StDev

| Level | N | Mean | StDev | |
|---|---|---|---|---|
| CON | 3 | 6.0702 | 0.4122 | (-----*-----) |
| Onset | 3 | 4.7733 | 0.1142 | (-----*-----) |
| PMX | 3 | 2.5758 | 1.6827 | (-----*-----) |
| PMX-B | 3 | 2.7707 | 1.1923 | (-----*-----) |
| VAN | 3 | 2.6065 | 0.2652 | (-----*-----) |

Pooled StDev = 0.9493       2.0   4.0   6.0   8.0

Fisher's pairwise comparisons
Family error rate = 0.245
Individual error rate = 0.0500
Critical value = 2.228

Intervals for (column level mean) - (row level mean)

| | CON | Onset | PMX | PMX-B |
|---|---|---|---|---|
| Onset | -0.4301 | | | |
| | 3.0239 | | | |
| PMX | 1.7673 | 0.4704 | | |
| | 5.2214 | 3.9244 | | |
| PMX-B | 1.5725 | 0.2756 | -1.9219 | |
| | 5.0265 | 3.7296 | 1.5321 | |
| VAN | 1.7367 | 0.4398 | -1.7577 | -1.5628 |
| | 5.1907 | 3.8938 | 1.6963 | 1.8912 |

VAN = PMX = PMX-B < ONSET = CON

Microbiological Results—Abraded Epithelium

Duncan Multiple Comparisons Test $Log_{10}$ CFU/ml

| Row # | Group/Level | Mean Rank | C.I. Overlaps | |
|---|---|---|---|---|
| 1 | PMX-B-AE L | 4.6667 | 2, 3, 4 | |
| 2 | VAN-AE Log | 5.0000 | 1, 3, 4, | P = 0.05 |
| 3 | PMX-AE Log | 5.3333 | 1, 2, 4, | |
| 4 | Onset-AE L | 11.0000 | 1, 2, 3, 5, | |
| 5 | CON-AE Log | 14.0000 | 4, | |

PMX-B = VAN = PMX < CON;
All Groups = ONSET

Microbiological Results—Intact vs. Abraded Epithelium

Two Sample T-Test and Confidence Interval - PMX
Two sample T for PMX-IE Log vs PMX-AE Log

|          | N | Mean  | StDev | SE Mean |
|----------|---|-------|-------|---------|
| PMX-IE L | 3 | 6.770 | 0.186 | 0.11    |
| PMX-AE L | 3 | 2.58  | 1.68  | 0.97    |

95% CI for mu PMX-IE L - mu PMX-AE L: (−0.01, 8.40)
T-Test mu PMX-IE L = mu PMX-AE L (vs not =): T = 4.29 P = 0.050 DF = 2
Abraded < Intact Two Sample T-Test and Confidence Interval - PMX-B
Two sample T for PMX-B-IE Log vs PMX-B-AE Log

|          | N | Mean   | StDev  | SE Mean |
|----------|---|--------|--------|---------|
| PMX-B-IE | 3 | 7.1121 | 0.0724 | 0.042   |
| PMX-B-AE | 3 | 2.77   | 1.19   | 0.69    |

95% CI for mu PMX-B-IE - mu PMX-B-AE: (1.374, 7.31)
T-Test mu PMX-B-IE = mu PMX-B-AE (vs not =): T = 6.29 P = 0.024 DF = 2
Abraded < Intact Two Sample T-Test and Confidence Interval - VAN
Two sample T for VAN-IE Log vs VAN-AE Log

|          | N | Mean  | StDev | SE Mean |
|----------|---|-------|-------|---------|
| VAN-IE L | 3 | 3.58  | 1.17  | 0.68    |
| VAN-AE L | 3 | 2.607 | 0.265 | 0.15    |

95% CI for mu VAN-IE L - mu VAN-AE L: (−2.01, 3.96)
T-Test mu VAN-IE L = mu VAN-AE L (vs not =): T = 1.40 P = 0.30 NS DF = 2

Two Sample T-Test and Confidence Interval - CON
Two sample T for CON-IE Log vs CON-AE Log

|          | N | Mean  | StDev | SE Mean |
|----------|---|-------|-------|---------|
| CON-IE L | 3 | 7.002 | 0.245 | 0.14    |
| CON-AE L | 3 | 6.070 | 0.412 | 0.24    |

95% CI for mu CON-IE L - mu CON-AE L: (0.05, 1.81)
T-Test mu CON-IE L = mu CON-AE L (vs not =): T = 3.37 P = 0.044 DF = 3
Abraded < Intact Two Sample T-Test and Confidence Interval - Onset
Two sample T for Onset-IE Log vs Onset-AE Log

|          | N | Mean   | StDev  | SE Mean |
|----------|---|--------|--------|---------|
| Onset-IE | 3 | 4.9532 | 0.0598 | 0.035   |
| Onset-AE | 3 | 4.773  | 0.114  | 0.066   |

95% CI for mu Onset-IE - mu Onset-AE: (−0.057, 0.417)
T-Test mu Onset-IE = mu Onset-AE (vs not =): T = 2.42 P = 0.094 NS DF = 3

Microbiological Results—0.25% Oligomer 2 w/o BAK vs. w/ BAK—Intact Epithelium

Two Sample T-Test and Confidence Interval - PMX-IE vs. PMX-B-IE
Two sample T for PMX-IE Log vs PMX-B-IE Log

|          | N | Mean   | StDev  | SE Mean |
|----------|---|--------|--------|---------|
| PMX-IE L | 3 | 6.770  | 0.186  | 0.11    |
| PMX-B-IE | 3 | 7.1121 | 0.0724 | 0.042   |

95% CI for mu PMX-IE L - mu PMX-B-IE: (−0.84, 0.155)
T-Test mu PMX-IE L = mu PMX-B-IE (vs not =): T = −2.96 P = 0.097 NS DF = 2

Microbiological Results—0.25% Oligomer 2 w/o BAK vs. w/ BAK—Abraded Epithelium

Two Sample T-Test and Confidence Interval - PMX-AE vs. PMX-B-AE
Two sample T for PMX-AE Log vs PMX-B-AE Log

|          | N | Mean | StDev | SE Mean |
|----------|---|------|-------|---------|
| PMX-AE L | 3 | 2.58 | 1.68  | 0.97    |
| PMX-B-AE | 3 | 2.77 | 1.19  | 0.69    |

95% CI for mu PMX-AE L - mu PMX-B-AE: (−3.98, 3.59)
T-Test mu PMX-AE L = mu PMX-B-AE (vs not =): T = −0.16 P = 0.88 NS DF = 3

Summary of Statistical Comparisons for Microbiological Data
<=Significantly Fewer Colony Counts
Effect of Abraded Epithelium on Effectiveness of Each Test Solution or Onset Control

| PMX | Abraded < Intact |
| --- | --- |
| PMX-B | Abraded < Intact |
| Vancomycin | Abraded = Intact |
| Saline Control | Abraded < Intact |
| Onset of Therapy Control | Abraded = Intact |

Effect of Test Solutions on Corneas with Intact Epithelium
PMX=PMX-B
PMX=Saline Control
PMX-B=Saline Control
Vancomycin<Saline Control
Vancomycin<PMX
Vancomycin<PMX-B
Effect of Test Solutions on Corneas with Abraded Epithelium
PMX<Saline Control
PMX-B<Saline Control
PMX-B=PMX
Vancomycin<Saline Control
PMX=Vancomycin
PMX-B=Vancomycin
Effect of BAK on 0.25% Oligomer 2 on Corneas with Intact Epithelium
PMX=PMX-B
Effect of BAK on 0.25% Oligomer 2 on Corneas with Abraded Epithelium
PMX=PMX-B
Summary of Results 0.25% Oligomer 2 (PMX) and 0.25% Oligomer 2 with 0.005% benzalkonium chloride (BAK) (PMX-2) were effective in reducing fluoroquinolone-resistant, methicillin-resistant *Staphylococcus aureus* colony counts in the NZW rabbit keratitis model only when the corneal epithelium was removed from the corneas. There was no difference in fluoroquinolone-resistant, methicillin-resistant *Staphylococcus aureus* colony counts in the NZW rabbit keratitis model between 0.25% Oligomer 2 (PMX) and 0.25% Oligomer 2 with 0.005% benzalkonium chloride (BAK) (PMX-2) with intact or abraded corneal epithelium.

0.25% Oligomer 2 (PMX) and 0.25% Oligomer 2 with 0.005% benzalkonium chloride (BAK) (PMX-2) were as effective as 5% vancomycin in reducing colony counts fluoroquinolone-resistant, methicillin-resistant *Staphylococcus aureus* colony counts in the NZW rabbit keratitis model only when the corneal epithelium was removed from the corneas. 0.25% Oligomer 2 (PMX) and 0.25% Oligomer 2 with 0.005% benzalkonium chloride (BAK) (PMX-2) induced toxicity that was worse than 5% vancomycin as manifested by higher Total Ocular Scores compared with the vancomycin and Saline treated eyes in eyes with intact corneal epithelia.

The biomimetic Oligomer 2 was effective in reducing the number fluoroquinolone-resistant, methicillin-resistant *Staphylococcus aureus* colony counts in the NZW rabbit keratitis model. This result was achieved using a lower concentration (0.25%) than in previous studies (1% and 0.5%). As in the previous studies, Oligomer 2 was effective in reducing fluoroquinolone-resistant, methicillin-resistant *Staphylococcus aureus* colony counts only when the corneal epithelium was removed. The addition of 0.005% benzalkonium chloride (BAK) did not aid in the penetration of 0.25% Oligomer 2 through the intact corneal epithelium to the site of the infection in the corneal stroma. In the current study, 0.25% Oligomer 2 (PMX) and 0.25% Oligomer 2 with 0.005% benzalkonium chloride (BAK) (PMX-2) induced greater toxicity in infected rabbit eyes with intact corneal epithelium compared with 5% vancomycin and the Saline treated Control with intact corneal epithelium. As suggested in the previous study, additional studies using much lower concentrations of Oligomer 2 and/or different formulations should be considered in order to reduce its toxicity, yet retain efficacy in the fluoroquinolone-resistant, methicillin-resistant *Staphylococcus aureus* NZW rabbit keratitis model.

Example 11

Ker-3

One purpose of the following experiments was to determine the efficacy of 0.25% Oligomer 4, with and without 200 µM Farnesol, and 200 µM Farnesol in the treatment of a fluoroquinolone-resistant and methicillin-resistant *Staphylococcus aureus* infection in the NZW rabbit keratitis model with or without intact corneal epithelia. The 200 µM Farnesol has been added to try to increase the efficacy and penetration of 0.25% Oligomer 4 through the corneal epithelium.

Fifteen rabbits were received from Myrtles' Rabbitry, Thompson Station, TN. The clinical isolate of fluoroquinolone-resistant and methicillin-resistant (MRSA) *Staphylococcus aureus* ($K_{950}$) was subcultured on 5% sheep blood agar and incubated at 37° C. in 6% $CO_2$ overnight. The next morning, the MRSA strain was suspended in sterile trypticase soy broth to a 0.5 McFarland Standard, containing approximately $5 \times 10^8$ CFU/ml of bacteria. The absorbance of the suspension was measured at 650 nm using a Beckman DU-70 spectrophotometer. OD readings of 0.07 corresponded to $5 \times 10^8$ CFU/ml of bacteria. This concentration was appropriately diluted in sterile trypticase soy broth to provide the inoculum of approximately 1,000 ($1.0 \times 10^3$) CFU/eye in 25 µl. Colony counts were performed on the inoculum to determine the actual CFU inoculated. Following general anesthesia with ketamine and xylazine and topical anesthesia with proparacaine and prior to bacterial inoculation in the left eyes, 6 mm areas of the corneal epithelia were removed centrally from the left eyes with an Amoils epithelial scrubber. Nothing was done to the right eyes. The 15 rabbits the were then inoculated intrastromally in both eyes with 25 µl of the bacterial dilution of approximately $10^3$ cfu/eye of the bacteria. The bacterial inoculation of the left eyes was directly under the epithelial defect created by the Amoils epithelial scrubber. The epithelia were removed in the left corneas in order to determine whether this layer of the cornea is a barrier for drug penetration when compared to the right cornea with an intact epithelium. A colony count was done on the inoculum to determine the actual CFU inoculated. The rabbits were immediately treated with analgesia in the form of an intramuscular injection of ketoprofen, 1.5 mg/kg. After 4 hours, the 15 rabbits were divided into 4 treatment groups and one untreated control group sacrificed at the onset of therapy. Both eyes of each rabbit of the treatment groups were treated with one 37 µl drop of the solutions or control Saline.
Groups:

| Group | Left Eye | Right Eye | Rx - Both Eyes | Treatment Regimen | Rabbit # |
| --- | --- | --- | --- | --- | --- |
| I | Abraded Epithelium | Intact Epithelium | 0.25% Oligomer 4 (PMX) | Every 15 minutes for 5 hours (21 total doses) | 1-3 |
| II | Abraded Epithelium | Intact Epithelium | 0.25% Oligomer 4 + 200 µM Farnesol (P + F) | Every 15 minutes for 5 hours (21 total doses) | 4-6 |

-continued

| Group | Left Eye | Right Eye | Rx - Both Eyes | Treatment Regimen | Rabbit # |
|---|---|---|---|---|---|
| III | Abraded Epithelium | Intact Epithelium | 200 μM Farnesol (FARN) | Every 15 minutes for 5 hours (21 total doses) | 7-9 |
| IV | Abraded Epithelium | Intact Epithelium | Tris-Buffered Saline (CON) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment was scheduled for every 15 minutes for 5 hours (21 total doses). The 3 rabbits in group V were sacrificed 4 hours PI and large 9.5 mm buttons were removed from the corneas. These were placed in 1 ml of PBS and kept on ice. The corneal buttons were homogenized for 25 seconds on ice using the motorized homogenizer. After homogenization, colony counts were done on the homogenates using 5% sheep blood agar plates to determine the amount of bacteria contained in the corneas at the onset of therapy. Following the completion of therapy, the eyes were examined for clinical signs of infection. One hour after the final treatment, the treated rabbits (Groups I-IV) were sacrificed and large 9.5 mm buttons were removed from the corneas. These were placed in 1 ml of PBS and kept on ice. The corneal buttons were homogenized for 25 seconds on ice using the motorized homogenizer. After homogenization, colony counts were done on the homogenates using 5% sheep blood agar plates to determine the amount of bacteria contained in the corneas after treatment. The next morning, the plates were counted and the number of CFU/eye of *Staphylococcus aureus* was determined for each cornea.

Formulations: 1) 0.25% Oligomer 2 (PMX): Tube G1 of Oligomer 2 powder was stored at 4° C. until use. Upon use, the tube was removed from the refrigerator and 3.28 ml of S1 (sterile water for injection) was added and vortexed until the solid was completely dissolved. Then 3.28 ml of S2 (2×TBS) was added and vortexed for 10 seconds. This solution was designated PMX. 37 μl drops were instilled were instilled using a Rainin EDP electronic pipet set in the multi-dispense mode; 2) 0.25% Oligomer 2 with 200 μM Farnesol (P+F): Tube G2 of Oligomer 2 powder was stored at 4° C. until use. Upon use, the tube was removed from the refrigerator and 3.33 ml of S1 (sterile water for injection) was added and vortexed until the solid was completely dissolved. Then 3.33 ml of S3 (400 μM Farnesol+2% Propylene Glycol in 2×TBS) was added and vortexed for 10 seconds. This solution was designated P+F. 37 μl drops were instilled were instilled using a Rainin EDP electronic pipet set in the multi-dispense mode; 3) 200 μM Farnesol (FARN): Tube G3 containing about 8 ml of 200 μM Farnesol in 1% Propylene Glycol (PG) and TBS was stored at 4° C. until use. This solution was designated FARN. 37 μl drops were instilled using a Rainin EDP electronic pipet set in the multi-dispense mode; 4) Control (Tris-Buffered Saline, CON): Tube G4 containing about 8 ml of Tris-Buffered Saline (10 mM TRIS, 150 mM NaCl, pH=7.4) was stored at 4° C. until use. This solution was designated CON. 37 μl drops were instilled using a Rainin EDP electronic pipet set in the multi-dispense mode.

IACUC Protocol #0701145-1. "The In Vivo Evaluation of Biomimetics as Topical Ocular Antibiotics".

| MIC Characterization of Fluoroquinolone-Resistant, Methicillin-Resistant *Staphylococcus aureus* Strain K950 | |
|---|---|
| Antibiotic | MIC [μg/ml] (Minimum Inhibitory Concentration) |
| Oligomer 4 | 0.5 μg/ml |

| Drop Schedule | | |
|---|---|---|
| Drop # | Time | Time of Day |
| 1 | 0 | 9:30 |
| 2 | :15 | 9:45 |
| 3 | :30 | 10:00 |
| 4 | :45 | 10:15 |
| 5 | 1:00 | 10:30 |
| 6 | 1:15 | 10:45 |
| 7 | 1:30 | 11:00 |
| 8 | 1:45 | 11:15 |
| 9 | 2:00 | 11:30 |
| 10 | 2:15 | 11:45 |
| 11 | 2:30 | 12:00 |
| 12 | 2:45 | 12:15 |
| 13 | 3:00 | 12:30 |
| 14 | 3:15 | 12:45 |
| 15 | 3:30 | 1:00 |
| 16 | 3:45 | 1:15 |
| 17 | 4:00 | 1:30 |
| 18 | 4:15 | 1:45 |
| 19 | 4:30 | 2:00 |
| 20 | 4:45 | 2:15 |
| 21 | 5:00 | 2:30 |

Sacrifice rabbits 1 hour after final drop (3:30).

DEFINITIONS OF ABBREVIATIONS

PMX-IE 0.25% Oligomer 4 with Intact Epithelium
PMX-AE 0.25% Oligomer 4 with Abraded Epithelium
P+F-IE 0.25% Oligomer 4+200 μM Farnesol with Intact Epithelium
P+F-AE 0.25% Oligomer 4+200 μM Farnesol with Abraded Epithelium
FARN-IE 200 μM Farnesol with Intact Epithelium
FARN-AE 200 μM Farnesol with Abraded Epithelium
CON-AE Tris-Buffered Saline Control with Abraded Epithelium
CON-IE Tris-Buffered Saline Control with Intact Epithelium
Clinical Evaluation—Results

| Eye | Group | Conj. | Chemosis | Discharge | Iritis | Corneal Edema | Corneal Infiltrate | Total Score |
|---|---|---|---|---|---|---|---|---|
| 1R | PMX-IE | 2.5 | 2.5 | 2.0 | 2.0 | 1.0 | 2.0 | 12.0 |
| 2R | PMX-IE | 2.0 | 2.0 | 2.0 | 2.0 | 0.5 | 0.5 | 9.0 |
| 3R | PMX-IE | 2.0 | 2.0 | 2.0 | 2.0 | 0.5 | 1.0 | 9.5 |
| 1L | PMX-AE | 2.0 | 2.5 | 3.0 | 2.0 | 1.5 | 0 | 11.0 |
| 2L | PMX-AE | 2.0 | 2.0 | 3.0 | 2.0 | 0.5 | 0 | 9.5 |
| 3L | PMX-AE | 2.0 | 2.0 | 2.5 | 1.5 | 1.0 | 0 | 9.0 |
| 4R | P + F-IE | 1.5 | 1.5 | 1.5 | 1.0 | 0.5 | 0.5 | 6.5 |

-continued

| Eye | Group | Conj. | Chemosis | Discharge | Iritis | Corneal Edema | Corneal Infiltrate | Total Score |
|---|---|---|---|---|---|---|---|---|
| 5R | P + F-IE | 2.0 | 1.5 | 1.5 | 2.0 | 1.0 | 2.5 | 10.5 |
| 6R | P + F-IE | 2.0 | 2.0 | 2.5 | 2.0 | 1.0 | 1.5 | 11.0 |
| 4L | P + F-AE | 2.0 | 2.0 | 2.0 | 1.5 | 1.0 | 0 | 8.5 |
| 5L | P + F-AE | 2.5 | 2.5 | 2.5 | 2.0 | 1.0 | 0 | 10.5 |
| 6L | P + F-AE | 2.0 | 2.5 | 3.0 | 2.0 | 1.0 | 0 | 10.5 |
| 7R | FARN-IE | 1.5 | 1.5 | 1.5 | 1.5 | 1.0 | 2.0 | 9.0 |
| 8R | FARN-IE | 1.5 | 1.0 | 1.0 | 1.5 | 0.5 | 1.5 | 7.0 |
| 9R | FARN-IE | 1.5 | 1.5 | 1.5 | 2.0 | 1.0 | 2.0 | 9.5 |
| 7L | FARN-AE | 2.0 | 2.0 | 2.0 | 2.0 | 2.0 | 1.0 | 11.0 |
| 8L | FARN-AE | 1.5 | 1.5 | 1.5 | 1.5 | 1.0 | 0.5 | 7.5 |
| 9L | FARN-AE | 1.5 | 1.5 | 1.5 | 1.5 | 1.0 | 1.0 | 8.0 |
| 10R | CON-IE | 1.5 | 1.0 | 1.0 | 1.0 | 1.0 | 1.0 | 6.5 |
| 11R | CON-IE | 1.0 | 1.0 | 1.0 | 1.5 | 1.0 | 1.0 | 6.5 |
| 12R | CON-IE | 1.5 | 1.5 | 1.0 | 2.0 | 1.0 | 2.0 | 9.0 |
| 10L | CON-AE | 1.0 | 1.5 | 2.0 | 1.0 | 0.5 | 0 | 6.0 |
| 11L | CON-AE | 1.5 | 1.5 | 2.0 | 1.5 | 1.5 | 1.0 | 9.0 |
| 12L | CON-AE | 1.5 | 1.5 | 2.0 | 1.5 | 1.5 | 1.0 | 9.0 |

Scale
0 = Normal;
0.5 = Trace;
1.0 = Mild;
1.5 = Mild/Moderate;
2.0 = Moderate;
2.5 = Moderate/Severe;
3.0 = Severe Clinical Evaluation—Statistics

Descriptive Statistics

Total Ocular Score

| Variable | Total Count | Mean | SE Mean | StDev | Minimum | Median | Maximum |
|---|---|---|---|---|---|---|---|
| PMX-IE Score | 3 | 10.167 | 0.928 | 1.607 | 9.000 | 9.500 | 12.000 |
| PMX-AE Score | 3 | 9.833 | 0.601 | 1.041 | 9.000 | 9.500 | 11.000 |
| P + F-IE Score | 3 | 9.33 | 1.42 | 2.47 | 6.50 | 10.50 | 11.00 |
| P + F-AE Score | 3 | 9.833 | 0.667 | 1.155 | 8.500 | 10.500 | 10.500 |
| FARN-IE Score | 3 | 8.500 | 0.764 | 1.323 | 7.000 | 9.000 | 9.500 |
| FARN-AE Score | 3 | 8.83 | 1.09 | 1.89 | 7.50 | 8.00 | 11.00 |
| CON-IE Score | 3 | 7.333 | 0.833 | 1.443 | 6.500 | 6.500 | 9.000 |
| CON-AE Score | 3 | 8.00 | 1.00 | 1.73 | 6.00 | 9.00 | 9.00 |

Duncan Multiple Comparisons Test

| Row # | Group/Level | Mean Rank | Total Score C.I. Overlaps | |
|---|---|---|---|---|
| 1 | CON-IE Sco | 5.8333 | 2, 3, 4, 5, 6, 7, 8, | |
| 2 | CON-AE Sco | 8.0000 | 1, 3, 4, 5, 6, 7, 8, | |
| 3 | FARN-IE Sc | 10.8333 | 1, 2, 4, 5, 6, 7, 8, | |
| 4 | FARN-AE Sc | 11.6667 | 1, 2, 3, 5, 6, 7, 8, | P = 0.05 |
| 5 | P + F-IE Sco | 14.6667 | 1, 2, 3, 4, 6, 7, 8, | |
| 6 | P + F-AE Sco | 15.3333 | 1, 2, 3, 4, 5, 7, 8, | |
| 7 | PMX-AE Sco | 16.5000 | 1, 2, 3, 4, 5, 6, 8, | |
| 8 | PMX-IE Sco | 17.1667 | 1, 2, 3, 4, 5, 6, 7, | |

N0 Differences Among the Groups

Microbiological Results

Inoculum = 1098 CFU/cornea
Data Display

CFU/ml

| Row | PMX-IE | PMX-AE | P + F-IE | P + F-AE | FARN-IE | FARN-AE | CON-IE | CON-AE |
|---|---|---|---|---|---|---|---|---|
| 1 | 1650000 | 0 | 50 | 9500 | 45200000 | 7750000 | 115000000 | 30500 |
| 2 | 12500 | 12500 | 13600000 | 50 | 18600000 | 6650000 | 253000000 | 69000000 |
| 3 | 92000 | 350 | 5200000 | 8050 | 21400000 | 8250000 | 15000000 | 176000000 |

| Row | Onset-IE | Onset-AE |
|---|---|---|
| 1 | 75000 | 118000 |
| 2 | 59000 | 61000 |
| 3 | 55500 | 2500 |

Data Display

$Log_{10}$ CFU/ml

| Row | PMX-IE Log | PMX-AE Log | P + F-IE Log | P + F-AE Log | FARN-IE Log | FARN-AE Log |
|---|---|---|---|---|---|---|
| 1 | 6.21748 | 0.00000 | 1.69897 | 3.97772 | 7.65514 | 6.88930 |
| 2 | 4.09691 | 4.09691 | 7.13354 | 1.69897 | 7.26951 | 6.82282 |
| 3 | 4.96379 | 2.54407 | 6.71600 | 3.90580 | 7.33041 | 6.91645 |

| Row | CON-IE Log | CON-AE Log | Onset-IE Log | Onset-AE Log |
|---|---|---|---|---|
| 1 | 8.06070 | 4.48430 | 4.87506 | 5.07188 |
| 2 | 8.40312 | 7.83885 | 4.77085 | 4.78533 |
| 3 | 7.17609 | 8.24551 | 4.74429 | 3.39794 |

Descriptive Statistics

$Log_{10}$ CFU/ml

| Variable | Total Count | Mean | SE Mean | StDev | Minimum | Median | Maximum |
|---|---|---|---|---|---|---|---|
| PMX-IE Log | 3 | 5.093 | 0.616 | 1.066 | 4.097 | 4.964 | 6.217 |
| PMX-AE Log | 3 | 2.21 | 1.19 | 2.07 | 0.00 | 2.54 | 4.10 |
| P + F-IE Log | 3 | 5.18 | 1.75 | 3.02 | 1.70 | 6.72 | 7.13 |
| P + F-AE Log | 3 | 3.194 | 0.748 | 1.295 | 1.699 | 3.906 | 3.978 |
| FARN-IE Log | 3 | 7.418 | 0.120 | 0.207 | 7.270 | 7.330 | 7.655 |
| FARN-AE Log | 3 | 6.8762 | 0.0278 | 0.0482 | 6.8228 | 6.8893 | 6.9165 |
| CON-IE Log | 3 | 7.880 | 0.366 | 0.633 | 7.176 | 8.061 | 8.403 |
| CON-AE Log | 3 | 6.86 | 1.19 | 2.06 | 4.48 | 7.84 | 8.25 |
| Onset-IE Log | 3 | 4.7967 | 0.0399 | 0.0691 | 4.7443 | 4.7709 | 4.8751 |
| Onset-AE Log | 3 | 4.418 | 0.517 | 0.895 | 3.398 | 4.785 | 5.072 |

Microbiological Results—Intact Epithelium

Kruskal-Wallis ANOVA with Duncan Multiple Comparisons Test - $Log_{10}$ CFU/ml

| Row # | Group/Level | Mean Rank | C.I. Overlaps | |
|---|---|---|---|---|
| 1 | Onset-IE L | 4.0000 | 2, 3, | |
| 2 | PMX-IE Log | 5.0000 | 1, 3, | |
| 3 | P + F-IE Log | 6.0000 | 1, 2, | P = 0.05 |
| 4 | FARN-IE Lo | 12.0000 | 5, | |
| 5 | CON-IE Log | 13.0000 | 4, | |

ONSET = PMX = P + F < FARN = CON

Microbiological Results—Abraded Epithelium

Kruskal-Wallis ANOVA with Duncan Multiple Comparisons Test - $Log_{10}$ CFU/ml

| Row # | Group/Level | Mean Rank | C.I. Overlaps | |
|---|---|---|---|---|
| 1 | PMX-AE Log | 3.6667 | 2, 3, | |
| 2 | P + F-AE Log | 4.3333 | 1, 3, | |
| 3 | Onset-AE L | 7.6667 | 1, 2, | P = 0.05 |
| 4 | FARN-AE Lo | 12.0000 | 5, | |
| 5 | CON-AE Log | 12.3333 | 4, | |

PMX = P + F = ONSET < FARN = CON

Microbiological Results—0.25% Oligomer 4 w/o FARN vs. w/ FARN—Intact Epithelium

Mann-Whitney Test and CI: PMX-IE Log, P + F-IE Log

| | N | Median |
|---|---|---|
| PMX-IE Log | 3 | 4.964 |
| P + F-IE Log | 3 | 6.716 |

Point estimate for ETA1-ETA2 is −0.916
91.9 Percent CI for ETA1-ETA2 is (−3.034, 4.518)
W = 9.0
Test of ETA1 = ETA2 vs ETA1 not = ETA2 is significant at 0.6625 NS Microbiological Results—0.25% Oligomer 4 w/o FARN vs. w/ FARN—Abraded Epithelium

Mann-Whitney Test and CI: PMX-AE Log, P + F-AE Log

| | N | Median |
|---|---|---|
| PMX-AE Log | 3 | 2.544 |
| P + F-AE Log | 3 | 3.906 |

Point estimate for ETA1-ETA2 is −1.362
91.9 Percent CI for ETA1-ETA2 is (−3.977, 2.399)
W = 10.0
Test of ETA1 = ETA2 vs ETA1 not = ETA2 is significant at 1.0000 NS Microbiological Results—Intact vs. Abraded Epithelium

Mann-Whitney Test and CI: PMX-IE Log, PMX-AE Log

| | N | Median |
|---|---|---|
| PMX-IE Log | 3 | 4.964 |
| PMX-AE Log | 3 | 2.544 |

Point estimate for ETA1-ETA2 is 2.420
91.9 Percent CI for ETA1-ETA2 is (0.001, 6.218)
W = 14.5
Test of ETA1 = ETA2 vs ETA1 not = ETA2 is significant at 0.1266
The test is significant at 0.1212 NS (adjusted for ties)

Mann-Whitney Test and CI: P + F-IE Log, P + F-AE Log

| | N | Median |
|---|---|---|
| P + F-IE Log | 3 | 6.716 |
| P + F-AE Log | 3 | 3.906 |

Point estimate for ETA1-ETA2 is 2.810
91.9 Percent CI for ETA1-ETA2 is (−2.277, 5.436)
W = 12.5
Test of ETA1 = ETA2 vs ETA1 not = ETA2 is significant at 0.5127
The test is significant at 0.5066 NS (adjusted for ties)

-continued

| Mann-Whitney Test and CI: FARN-IE Log, FARN-AE Log | | |
|---|---|---|
| | N | Median |
| FARN-IE Log | 3 | 7.3304 |
| FARN-AE Log | 3 | 6.8893 |
| Point estimate for ETA1-ETA2 is 0.4467 | | |
| 91.9 Percent CI for ETA1-ETA2 is (0.3532, 0.8323) | | |
| W = 15.0 | | |
| Test of ETA1 = ETA2 vs ETA1 not = ETA2 is significant at 0.0809 NS | | |

| Mann-Whitney Test and CI: CON-IE Log, CON-AE Log | | |
|---|---|---|
| | N | Median |
| CON-IE Log | 3 | 8.061 |
| CON-AE Log | 3 | 7.839 |
| Point estimate for ETA1-ETA2 is 0.222 | | |
| 91.9 Percent CI for ETA1-ETA2 is (−1.070, 3.917) | | |
| W = 12.0 | | |
| Test of ETA1 = ETA2 vs ETA1 not = ETA2 is significant at 0.6625 NS | | |

| Mann-Whitney Test and CI: Onset-IE Log, Onset-AE Log | | |
|---|---|---|
| | N | Median |
| Onset-IE Log | 3 | 4.771 |
| Onset-AE Log | 3 | 4.785 |
| Point estimate for ETA1-ETA2 is −0.015 | | |
| 91.9 Percent CI for ETA1-ETA2 is (−0.328, 1.477) | | |
| W = 10.0 | | |
| Test of ETA1 = ETA2 vs ETA1 not = ETA2 is significant at 1.0000 NS | | |
| class = Section8> | | |

Summary of Statistical Comparisons for Microbiological Data
<=Significantly Fewer Colony Counts
Effect of Abraded Epithelium on Effectiveness of Each Test Solution or Onset Control

| PMX | Abraded = Intact |
|---|---|
| P + F | Abraded = Intact |
| FARN | Abraded = Intact |
| Saline Control | Abraded = Intact |
| Onset of Therapy Control | Abraded = Intact |

Effect of Test Solutions on Corneas with Intact Epithelium
ONSET=PMX=P+F<FARN=CON
Effect of Test Solutions on Corneas with Abraded Epithelium
PMX=P+F=ONSET<FARN=CON
Effect of Farnesol on 0.25% Oligomer 4 on Corneas with Intact Epithelium
PMX=P+F
Effect of Farnesol on 0.25% Oligomer 4 on Corneas with Abraded Epithelium
PMX=P+F
Summary of Results 0.25% Oligomer 4 (PMX) and 0.25% Oligomer 4 with 200 mM Farnesol (P+F) were effective in reducing fluoroquinolone-resistant, methicillin-resistant *Staphylococcus aureus* colony counts compared with the Saline Control in the NZW rabbit keratitis model when the corneal epithelium was intact or removed from the corneas. 0.25% Oligomer 4 (PMX) and 0.25% Oligomer 4 with 200 mM Farnesol (P+F) were not effective in reducing fluoroquinolone-resistant, methicillin-resistant *Staphylococcus aureus* colony counts compared with the Onset of Therapy Control in the NZW rabbit keratitis model when the corneal epithelium was intact or removed from the corneas. There was no difference in fluoroquinolone-resistant, methicillin-resistant *Staphylococcus aureus* colony counts in the NZW rabbit keratitis model between 0.25% Oligomer 4 (PMX) and 0.25% Oligomer 4 with 200 mM Farnesol (P+F) with intact or abraded corneal epithelium. 200 mM Farnesol alone was NOT effective in reducing colony counts fluoroquinolone-resistant, methicillin-resistant *Staphylococcus aureus* colony counts compared with the Saline Control in the NZW rabbit keratitis model. 0.25% Oligomer 4 (PMX) and 0.25% Oligomer 4 with 200 mM Farnesol (P+F) and 200 mM Farnesol alone did not induce statistically greater toxicity (as manifested by higher Total Ocular Scores) compared with the Saline treated eyes in eyes with intact or abraded corneal epithelia.

The biomimetic Oligomer 4 alone or in combination with 200 mM Farnesol were effective in reducing the number fluoroquinolone-resistant, methicillin-resistant *Staphylococcus aureus* colony counts in the NZW rabbit keratitis model compared with the Saline Control compared with the Saline Control. However, Oligomer 4 alone or in combination with 200 mM Farnesol were not effective in reducing fluoroquinolone-resistant, methicillin-resistant *Staphylococcus aureus* colony counts whether when the corneal epithelium was intact or removed compared with the Onset of Therapy Control in the fluoroquinolone-resistant, methicillin-resistant *Staphylococcus aureus* NZW rabbit keratitis model indicating the compounds did not significantly reduce the bacterial load present at the onset of therapy. The addition of 200 mM Farnesol did not appear aid in the penetration of 0.25% Oligomer 4 through the intact corneal epithelium to the site of the infection in the corneal stroma nor enhance its antibacterial efficacy in the fluoroquinolone-resistant, methicillin-resistant *Staphylococcus aureus* NZW rabbit keratitis model. In the current study, Oligomer 4 alone or in combination with 200 mM Farnesol did not induced significantly greater toxicity in infected rabbit eyes compared with the Saline treated Control in the fluoroquinolone-resistant, methicillin-resistant *Staphylococcus aureus* NZW rabbit keratitis model. The results from this study essentially reproduce those obtained in previous studies.

Example 12

Ker-4

DEFINITIONS OF ABBREVIATIONS

PMX-IE 0.25% Oligomer 4 with Intact Epithelium
PMX-AE 0.25% Oligomer 4 with Abraded Epithelium
P+F-IE 0.25% Oligomer 4+200 μM Farnesol with Intact Epithelium
P+F-AE 0.25% Oligomer 4+200 μM Farnesol with Abraded Epithelium
FARN-IE 200 μM Farnesol with Intact Epithelium
FARN-AE 200 μM Farnesol with Abraded Epithelium
CON-AE Tris-Buffered Saline Control with Abraded Epithelium
CON-IE Tris-Buffered Saline Control with Intact Epithelium Clinical Evaluation—Statistics

Data Display

Total Ocular Score

| Row | PMX-IE | PMX-AE | P + F-IE | P + F-AE | FARN-IE | FARN-AE | CON-IE | CON-AE | |
|---|---|---|---|---|---|---|---|---|---|
| 1 | 6.5 | 9.5 | 13.0 | 9.5 | 10.0 | 11.0 | 9.5 | 10.0 | |
| 2 | 13.0 | 10.5 | 8.0 | 8.5 | 10.0 | 8.5 | 11.0 | 14.0 | Ker-3 |
| 3 | 16.5 | 12.0 | 12.5 | 10.0 | 8.5 | 8.5 | 9.5 | 10.5 | |
| 4 | 12.0 | 11.0 | 6.5 | 8.5 | 9.0 | 11.0 | 6.5 | 6.0 | |
| 5 | 9.0 | 9.5 | 10.5 | 10.5 | 7.0 | 7.5 | 6.5 | 9.0 | Ker-4 |
| 6 | 9.5 | 9.0 | 11.0 | 10.5 | 9.5 | 8.0 | 9.0 | 9.0 | |

Descriptive Statistics

Total Ocular Score

| Variable | Total Count | Mean | SE Mean | StDev | Minimum | Median | Maximum |
|---|---|---|---|---|---|---|---|
| PMX-IE Score | 6 | 11.08 | 1.43 | 3.51 | 6.50 | 10.75 | 16.50 |
| PMX-AE Score | 6 | 10.250 | 0.461 | 1.129 | 9.000 | 10.000 | 12.000 |
| P + F-IE Score | 6 | 10.25 | 1.04 | 2.54 | 6.50 | 10.75 | 13.00 |
| P + F-AE Score | 6 | 9.583 | 0.375 | 0.917 | 8.500 | 9.750 | 10.500 |
| FARN-IE Score | 6 | 9.000 | 0.465 | 1.140 | 7.000 | 9.250 | 10.000 |
| FARN-AE Score | 6 | 9.083 | 0.625 | 1.530 | 7.500 | 8.500 | 11.000 |
| CON-IE Score | 6 | 8.667 | 0.738 | 1.807 | 6.500 | 9.250 | 11.000 |
| CON-AE Score | 6 | 9.75 | 1.06 | 2.60 | 6.00 | 9.50 | 14.00 |

Duncan Multiple Comparisons Test

| Row # | Group/Level | Mean Rank | Total Score C.I. Overlaps | |
|---|---|---|---|---|
| 1 | CON-IE Sco | 18.5833 | 2, 3, 4, 5, 6, 7, 8, | |
| 2 | FARN-AE Sc | 19.5833 | 1, 3, 4, 5, 6, 7, 8, | |
| 3 | FARN-IE Sc | 19.7500 | 1, 2, 4, 5, 6, 7, 8, | |
| 4 | P + F-AE Sco | 24.2500 | 1, 2, 3, 5, 6, 7, 8, | $P = 0.05$ |
| 5 | CON-AE Sco | 24.4167 | 1, 2, 3, 4, 6, 7, 8, | |
| 6 | P + F-IE Sco | 29.0833 | 1, 2, 3, 4, 5, 7, 8, | |
| 7 | PMX-IE Sco | 30.1667 | 1, 2, 3, 4, 5, 6, 8, | |
| 8 | PMX-AE Sco | 30.1667 | 1, 2, 3, 4, 5, 6, 7, | |

No Differences Among the Groups

Microbiological Results

Data Display

CFU/ml

| Row | PMX-IE | PMX-AE | P + F-IE | P + F-AE | FARN-IE | FARN-AE | |
|---|---|---|---|---|---|---|---|
| 1 | 0 | 0 | 11950000 | 255 | 15200000 | 7500000 | |
| 2 | 16750000 | 0 | 415000 | 1100000 | 18150000 | 1285000 | Ker-3 |
| 3 | 5800000 | 995000 | 16650000 | 35500 | 30100000 | 1400000 | |
| 4 | 1650000 | 0 | 50 | 9500 | 45200000 | 7750000 | |
| 5 | 12500 | 12500 | 13600000 | 50 | 18600000 | 6650000 | Ker-4 |
| 6 | 92000 | 350 | 5200000 | 8050 | 21400000 | 8250000 | |

| Row | CON-IE | CON-AE | Onset-IE | Onset-AE | |
|---|---|---|---|---|---|
| 1 | 467000000 | 1650000 | 15000 | 1635000 | |
| 2 | 221500000 | 23500000 | 107000 | 130000 | PMX-Ker-3 |
| 3 | 202000000 | 5400000 | 132500 | 133000 | |
| 4 | 115000000 | 30500 | 75000 | 118000 | |
| 5 | 253000000 | 69000000 | 59000 | 61000 | PMX-Ker-4 |
| 6 | 15000000 | 176000000 | 55500 | 2500 | |

Data Display

$Log_{10}$ CFU/ml

| Row | PMX-IE Log | PMX-AE Log | P + F-IE Log | P + F-AE Log | FARN-IE Log | FARN-AE Log | |
|---|---|---|---|---|---|---|---|
| 1 | 0.00000 | 0.00000 | 7.07737 | 2.40654 | 7.18184 | 6.87506 | |
| 2 | 7.22401 | 0.00000 | 5.61805 | 6.04139 | 7.25888 | 6.10890 | K-3 |

-continued

| | | | | | | | |
|---|---|---|---|---|---|---|---|
| 3 | 6.76343 | 5.99782 | 7.22141 | 4.55023 | 7.47857 | 6.14613 | |
| 4 | 6.21748 | 0.00000 | 1.69897 | 3.97772 | 7.65514 | 6.88930 | |
| 5 | 4.09691 | 4.09691 | 7.13354 | 1.69897 | 7.26951 | 6.82282 | K-4 |
| 6 | 4.96379 | 2.54407 | 6.71600 | 3.90580 | 7.33041 | 6.91645 | |

| Row | CON-IE Log | CON-AE Log | Onset-IE Log | Onset-AE Log | |
|---|---|---|---|---|---|
| 1 | 8.66932 | 6.21748 | 4.17609 | 6.21352 | |
| 2 | 8.34537 | 7.37107 | 5.02938 | 5.11394 | PMX-Ker-3 |
| 3 | 8.30535 | 6.73239 | 5.12222 | 5.12385 | |
| 4 | 8.06070 | 4.48430 | 4.87506 | 5.07188 | |
| 5 | 8.40312 | 7.83885 | 4.77085 | 4.78533 | PMX-Ker-4 |
| 6 | 7.17609 | 8.24551 | 4.74429 | 3.39794 | |

Descriptive Statistics

| | | $Log_{10}$ CFU/ml | | | | | |
|---|---|---|---|---|---|---|---|
| Variable | Total Count | Mean | SE Mean | StDev | Minimum | Median | Maximum |
| PMX-IE Log | 6 | 4.88 | 1.08 | 2.66 | 0.00 | 5.59 | 7.22 |
| PMX-AE Log | 6 | 2.11 | 1.04 | 2.55 | 0.00 | 1.27 | 6.00 |
| P + F-IE Log | 6 | 5.911 | 0.876 | 2.147 | 1.699 | 6.897 | 7.221 |
| P + F-AE Log | 6 | 3.763 | 0.632 | 1.548 | 1.699 | 3.942 | 6.041 |
| FARN-IE Log | 6 | 7.3624 | 0.0712 | 0.1744 | 7.1818 | 7.3000 | 7.6551 |
| FARN-AE Log | 6 | 6.626 | 0.158 | 0.388 | 6.109 | 6.849 | 6.916 |
| CON-IE Log | 6 | 8.160 | 0.212 | 0.520 | 7.176 | 8.325 | 8.669 |
| CON-AE Log | 6 | 6.815 | 0.554 | 1.356 | 4.484 | 7.052 | 8.246 |
| Onset-IE Log | 6 | 4.786 | 0.136 | 0.333 | 4.176 | 4.823 | 5.122 |
| Onset-AE Log | 6 | 4.951 | 0.370 | 0.906 | 3.398 | 5.093 | 6.214 |

Microbiological Results—Intact Epithelium

| Kruskal-Wallis ANOVA with Duncan Multiple Comparisons Test - $Log_{10}$ CFU/ml | | | | |
|---|---|---|---|---|
| Row # | Group/Level | Mean Rank | C.I. Overlaps | |
| 1 | Onset-IE L | 6.8333 | 2, 3, | |
| 2 | PMX-IE Log | 9.6667 | 1, 3, | |
| 3 | P + F-IE Log | 12.6667 | 1, 2, | P = 0.05 |
| 4 | FARN-IE Lo | 22.1667 | 5, | |
| 5 | CON-IE Log | 26.1667 | 4, | |

ONSET = PMX = P + F < FARN = CON

Microbiological Results—Abraded Epithelium

| Kruskal-Wallis ANOVA with Duncan Multiple Comparisons Test - $Log_{10}$ CFU/ml | | | | |
|---|---|---|---|---|
| Row # | Group/Level | Mean Rank | C.I. Overlaps | |
| 1 | PMX-AE Log | 6.5000 | 2, | |
| 2 | P + F-AE Log | 9.3333 | 1, | |
| 3 | Onset-AE L | 14.3333 | | P = 0.05 |
| 4 | FARN-AE Lo | 23.5000 | 5, | |
| 5 | CON-AE Log | 23.8333 | 4, | |

PMX = P + F < ONSET < FARN = CON

Microbiological Results—0.25% Oligomer 4 w/o FARN vs. w/ FARN—Intact Epithelium

| Mann-Whitney Test and CI: PMX-IE Log, P + F-IE Log | | |
|---|---|---|
| | N | Median |
| PMX-IE Log | 6 | 5.591 |
| P + F-IE Log | 6 | 6.897 |

Point estimate for ETA1-ETA2 is −0.757
95.5 Percent CI for ETA1-ETA2 is (−3.124, 1.607)
W = 34.0
Test of ETA1 = ETA2 vs ETA1 not = ETA2 is significant at 0.4712 NS Microbiological Results—0.25% Oligomer 4 w/o FARN vs. w/ FARN—Abraded Epithelium

| Mann-Whitney Test and CI: PMX-AE Log, P + F-AE Log | | |
|---|---|---|
| | N | Median |
| PMX-AE Log | 6 | 1.272 |
| P + F-AE Log | 6 | 3.942 |

Point estimate for ETA1-ETA2 is −1.822
95.5 Percent CI for ETA1-ETA2 is (−4.549, 1.690)
W = 32.0
Test of ETA1 = ETA2 vs ETA1 not = ETA2 is significant at 0.2980
The test is significant at 0.2946 NS (adjusted for ties)

Microbiological Results—Intact vs. Abraded Epithelium

| Mann-Whitney Test and CI: PMX-IE Log, PMX-AE Log | | |
|---|---|---|
| | N | Median |
| PMX-IE Log | 6 | 5.591 |
| PMX-AE Log | 6 | 1.272 |

Point estimate for ETA1-ETA2 is 3.400
95.5 Percent CI for ETA1-ETA2 is (0.001, 6.764)
W = 50.0
Test of ETA1 = ETA2 vs ETA1 not = ETA2 is significant at 0.0927
The test is significant at 0.0864 NS (adjusted for ties)

| Mann-Whitney Test and CI: P + F-IE Log, P + F-AE Log | | |
|---|---|---|
| | N | Median |
| P + F-IE Log | 6 | 6.897 |
| P + F-AE Log | 6 | 3.942 |

Point estimate for ETA1-ETA2 is 2.705
95.5 Percent CI for ETA1-ETA2 is (−0.423, 4.727)
W = 50.5
Test of ETA1 = ETA2 vs ETA1 not = ETA2 is significant at 0.0782
The test is significant at 0.0776 NS (adjusted for ties)

-continued

| Mann-Whitney Test and CI: FARN-IE Log, FARN-AE Log | | |
|---|---|---|
| | N | Median |
| FARN-IE Log | 6 | 7.3000 |
| FARN-AE Log | 6 | 6.8489 FARN-AE < FARN-IE |
| Point estimate for ETA1-ETA2 is 0.5964 | | |
| 95.5 Percent CI for ETA1-ETA2 is (0.3588, 1.1843) | | |
| W = 57.0 | | |
| Test of ETA1 = ETA2 vs ETA1 not = ETA2 is significant at 0.0051 | | |

| Mann-Whitney Test and CI: CON-IE Log, CON-AE Log | | |
|---|---|---|
| | N | Median |
| CON-IE Log | 6 | 8.325 |
| CON-AE Log | 6 | 7.052 CON-AE < CON-IE |
| Point estimate for ETA1-ETA2 is 1.003 | | |
| 95.5 Percent CI for ETA1-ETA2 is (0.100, 2.691) | | |
| W = 53.0 | | |
| Test of ETA1 = ETA2 vs ETA1 not = ETA2 is significant at 0.0306 | | |

| Mann-Whitney Test and CI: Onset-IE Log, Onset-AE Log | | |
|---|---|---|
| | N | Median |
| Onset-IE Log | 6 | 4.823 |
| Onset-AE Log | 6 | 5.093 |
| Point estimate for ETA1-ETA2 is −0.218 | | |
| 95.5 Percent CI for ETA1-ETA2 is (−1.091, 0.778) | | |
| W = 32.0 | | |
| Test of ETA1 = ETA2 vs ETA1 not = ETA2 is significant at 0.2980 NS | | |

Summary of Statistical Comparisons for Microbiological Data
<=Significantly Fewer Colony Counts
Effect of Abraded Epithelium on Effectiveness of Each Test Solution or Onset Control

| PMX | Abraded = Intact |
|---|---|
| P + F | Abraded = Intact |
| FARN | Abraded < Intact |
| Saline Control | Abraded < Intact |
| Onset of Therapy Control | Abraded = Intact |

Effect of Test Solutions on Corneas with Intact Epithelium
ONSET=PMX=P+F<FARN=CON
Effect of Test Solutions on Corneas with Abraded Epithelium
PMX=P+F<ONSET<FARN=CON
Effect of Farnesol on 0.25% Oligomer 4 on Corneas with Intact Epithelium
PMX=P+F
Effect of Farnesol on 0.25% Oligomer 4 on Corneas with Abraded Epithelium
PMX=P+F
Summary of Results 0.25% Oligomer 4 (PMX) and 0.25% Oligomer 4 with 200 mM Farnesol (P+F) were effective in reducing fluoroquinolone-resistant, methicillin-resistant *Staphylococcus aureus* colony counts compared with the Saline Control in the NZW rabbit keratitis model when the corneal epithelium was intact or removed from the corneas. 0.25% Oligomer 4 (PMX) and 0.25% Oligomer 4 with 200 mM Farnesol (P+F) were effective in reducing fluoroquinolone-resistant, methicillin-resistant *Staphylococcus aureus* colony counts compared with the Onset of Therapy Control in the NZW rabbit keratitis model when the corneal epithelium was removed but not when the epithelium was intact. There was no difference in fluoroquinolone-resistant, methicillin-resistant *Staphylococcus aureus* colony counts in the NZW rabbit keratitis model between 0.25% Oligomer 4 (PMX) and 0.25% Oligomer 4 with 200 mM Farnesol (P+F) with intact or abraded corneal epithelium. 200 mM Farnesol alone was not effective in reducing colony counts fluoroquinolone-resistant, methicillin-resistant *Staphylococcus aureus* colony counts compared with the Saline Control in the NZW rabbit keratitis model. Eyes treated with 200 mM Farnesol alone and Saline demonstrated significantly fewer colony counts in eyes with the corneal epithelium removed compared to those with intact epithelium. 0.25% Oligomer 4 (PMX) and 0.25% Oligomer 4 with 200 mM Farnesol (P+F) and 200 mM Farnesol alone did not induce statistically greater toxicity (as manifested by higher Total Ocular Scores) compared with the Saline treated eyes in eyes with intact or abraded corneal epithelia.

The biomimetic Oligomer 4 was effective in significantly reducing colony counts in a fluoroquinolone-resistant, methicillin-resistant *Staphylococcus aureus* NZW rabbit keratitis model. Oligomer 4 formulations were effective when the corneal epithelium was removed suggesting that epithelium appears to be barrier for penetration of Oligomer 4 to the site of infection in the corneal stroma. The addition of 200 mM Farnesol did nothing to promote penetration Oligomer 4 through intact corneal epithelium, nor did it enhance its antibacterial efficacy. In fact, a trend toward antagonism was observed. Mechanical abrasion of the corneal epithelium alone reduced the bacterial colony counts in the control eyes. Therefore, the lower colony counts observed in the Oligomer 4-treated abraded eyes does not necessarily indicate greater drug efficacy. No significant ocular toxicity was observed for any formulation in this rabbit keratitis model.

Having now fully described this invention, it will be understood to those of ordinary skill in the art that the same can be performed within a wide and equivalent range of conditions, formulations, and other parameters without affecting the scope of the invention or any embodiment thereof. All documents, e.g., scientific publications, patents, patent applications, and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document. Various modifications of the invention, in addition to those described herein, will be apparent to those skilled in the art from the foregoing description. Such modifications are also intended to fall within the scope of the appended claims.

What is claimed is:
1. A compound having the formula:

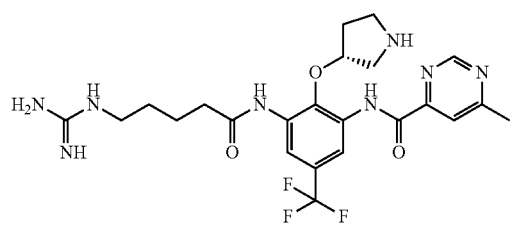

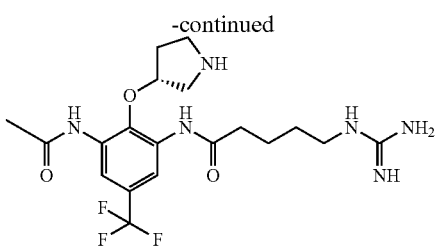

or a pharmaceutically acceptable salt thereof.

2. A composition comprising the compound of claim 1, or a pharmaceutically acceptable salt thereof.

3. The composition of claim 2 which is in the form of a powder.

4. The composition of claim 2 further comprising an additional medicament.

5. The composition of claim 4 wherein the additional medicament is chosen from an antibiotic, an anti-inflammatory agent, an anesthetic agent, an anti-allergic agent, an acetylcholine blocking agent, an adrenergic agonist, a beta-adrenergic blocking agent, an anti-glaucoma agent, and an antihypertensive agent.

6. The composition of claim 5 wherein the antibiotic is chosen from an aminoglycoside, a cephalosporin, a diaminopyridine, a fluoroquinolone, a sulfonamide, and a tetracycline.

7. The composition of claim 5 wherein the antibiotic is chosen from amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin, and trimethoprim.

8. The composition of claim 5 wherein the anti-inflammatory agent is a steroidal agent or a non-steroidal agent.

9. The composition of claim 8 wherein the steroidal agent is chosen from dexamethasone, rimexolone, prednisolone, fluorometholone, and hydrocortisone, and wherein the non-steroidal agent is chosen from a cyclooxygenase type I or type II inhibitor, a PAF antagonist, a PDE IV inhibitor, and an inhibitor of cytokine production.

10. The composition of claim 9 wherein the cyclooxygenase type I or type II inhibitor is chosen from diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, tenoxicam, carprofen, vioxx, celecoxib, and etodolac.

11. The composition of claim 9 wherein the PAF antagonist is chosen from apafant, bepafant, minopafant, nupafant, and modipafant.

12. The composition of claim 9 wherein the PDE IV inhibitor is chosen from ariflo, torbafylline, rolipram, filaminast, piclamilast, cipamfylline, and roflumilast.

13. The composition of claim 5 wherein the anti-allergic agent is pemirolast or olopatadine.

14. The composition of claim 5 wherein the anti-allergic agent is a corticosteroid.

15. The composition of claim 14 wherein the corticosteroid is chosen from prednisolone, fluorometholone, loteprenol, and dexamethasone.

16. A method of treating a bacterial infection of the eye in a mammal comprising administering to the mammal in need thereof an effective amount of the compound of claim 1, or a pharmaceutically acceptable salt thereof, or a composition comprising the compound of claim 1, or a pharmaceutically acceptable salt thereof.

17. A composition comprising a compound having the formula:

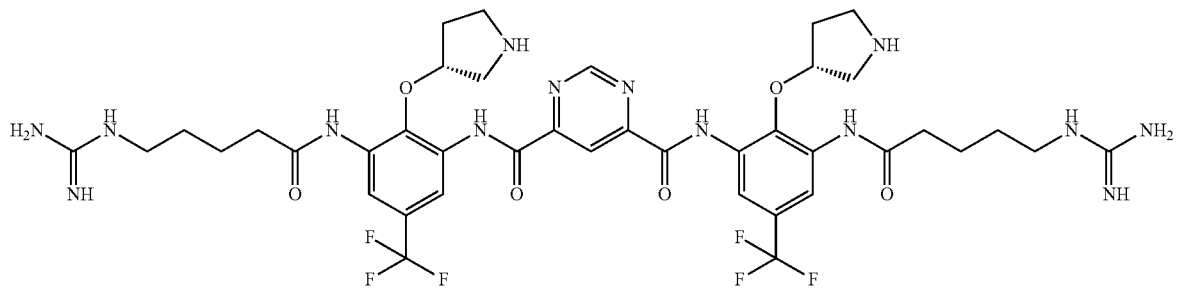 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3O[C@@H]3CCNC3)ncn2)c1O[C@@H]1CCNC1]

or a pharmaceutically acceptable salt thereof, and an aminoglycoside, a cephalosporin, or a fluoroquinolone.

18. The composition of claim 17 wherein the aminoglycoside is gentamicin, the cephalosporin is ceftazidime or ceftriaxone, and the fluoroquinolone is ciprofloxacin.

19. The composition of claim 2 further comprising a cyclodextrin.

20. The method of claim 16 wherein the bacterial infection is chosen from *Pseudomonas aeruginosa, Klebsiella pneumonia, Enterococcus faecalis, Eschericia coli, Staphylococcus aureus, Streptococcus viridans*, and *Streptococcus pneumonia*.

21. The composition of claim 2, wherein the pharmaceutically acceptable salt thereof is in the form of a hydrochloride acid addition salt.

* * * * *